US012708647B2

(12) United States Patent
Pena et al.

(10) Patent No.: US 12,708,647 B2
(45) Date of Patent: Aug. 18, 2026

(54) DELIVERY OF NUCLEIC ACIDS, PROTEINS AND SMALL MOLECULES IN VITREOUS VESICULAR BODIES

(71) Applicant: CORNELL UNIVERSITY, Ithaca, NY (US)

(72) Inventors: John TG Pena, New York, NY (US); Mrinali Patel Gupta, New York, NY (US); Donald J. D'Amico, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 1402 days.

(21) Appl. No.: 16/332,315

(22) PCT Filed: Sep. 9, 2017

(86) PCT No.: PCT/US2017/050854
§ 371 (c)(1),
(2) Date: Mar. 11, 2019

(87) PCT Pub. No.: WO2018/049284
PCT Pub. Date: Mar. 15, 2018

(65) Prior Publication Data
US 2019/0216857 A1 Jul. 18, 2019

Related U.S. Application Data

(60) Provisional application No. 62/385,711, filed on Sep. 9, 2016.

(51) Int. Cl.

| | |
|---|---|
| ***A61K 35/12*** | (2015.01) |
| ***A61K 9/00*** | (2006.01) |
| ***A61K 35/30*** | (2015.01) |
| ***A61K 38/00*** | (2006.01) |
| ***A61K 38/38*** | (2006.01) |
| ***A61K 48/00*** | (2006.01) |
| ***C12N 15/11*** | (2006.01) |
| ***C12N 15/113*** | (2010.01) |
| ***C12N 15/88*** | (2006.01) |

(52) U.S. Cl.
CPC ............ *A61K 35/30* (2013.01); *A61K 9/0048* (2013.01); *A61K 38/00* (2013.01); *A61K 38/385* (2013.01); *C12N 15/11* (2013.01); *C12N 15/1137* (2013.01); *C12N 15/88* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 5,468,253 | A | 11/1995 | Bezwada | |
| 6,627,246 | B2 | 9/2003 | Mehta | |
| 6,899,863 | B1 | 5/2005 | Dhellin | |
| 9,376,679 | B2 * | 6/2016 | Zhang | A61P 1/00 |
| 9,629,929 | B2 | 4/2017 | Lotvall et al. | |
| 9,958,448 | B2 | 5/2018 | Halbert | |
| 2002/0002185 | A1 | 1/2002 | Reed | |
| 2004/0029184 | A1 | 2/2004 | Gourevitch | |
| 2007/0009497 | A1 | 1/2007 | Steinman | |
| 2007/0172954 | A1 | 7/2007 | Ismagilov | |
| 2008/0004657 | A1 | 1/2008 | Obermiller | |
| 2008/0070324 | A1 | 3/2008 | Floyd | |
| 2008/0128341 | A1 | 6/2008 | Jang | |
| 2009/0239792 | A1 | 9/2009 | Vaara | |
| 2009/0318512 | A1 | 12/2009 | Yu | |
| 2010/0075315 | A1 | 3/2010 | Pieterzkowski | |
| 2010/0233706 | A1 | 9/2010 | Tuschl | |
| 2011/0177047 | A1 | 7/2011 | Liu | |
| 2013/0184318 | A1 | 7/2013 | Russell | |
| 2013/0288375 | A1 | 10/2013 | Zhang | |
| 2013/0302856 | A1 | 11/2013 | Yoo | |
| 2014/0038221 | A1 | 2/2014 | Bergkvist | |
| 2014/0056807 | A1 | 2/2014 | Divizio | |
| 2014/0081012 | A1 | 3/2014 | Desimone | |
| 2014/0220574 | A1 | 8/2014 | Tuschl | |
| 2014/0257075 | A1 | 9/2014 | Kagemann | |
| 2014/0349306 | A1 | 11/2014 | Chung | |
| 2014/0356382 | A1 | 12/2014 | Wood | |
| 2015/0037422 | A1 | 2/2015 | Kaplan et al. | |
| 2015/0038335 | A1 | 2/2015 | Skog | |
| 2015/0050328 | A1 | 2/2015 | Feinstein et al. | |

(Continued)

FOREIGN PATENT DOCUMENTS

| | | | |
|---|---|---|---|
| JP | 2016211925 | A | 12/2016 |
| RU | 2576778 | C1 | 3/2016 |

(Continued)

OTHER PUBLICATIONS

Sato et al, Engineering hybrid exosomes by membrane fusion with liposomes, Scientific Reports, 2016, pp. 1-11.*
Dismuke et al,Human Aqueous Humor Exosomes, Exp Eye Res. Mar. 2015 ; 132: pp. 1-12.*
Rene et al, Bioengineering extracellular vesicle cargo for optimal therapeutic efficiency, Molecular Therapy: Methods & Clinical Development vol. 32 Jun. 2024, pp. 1-15.*
Elsharkasy et al, Extracellular vesicles as drug delivery systems: Why and how?,Advanced Drug Delivery Reviews 159 (2020) 332-343.*
Camras, Advances in glaucoma management: risk factors, diagnostic tools, therapies and the role of prostaglandin analogs, Foreword. Surv Ophthalmol, vol. 53 (Suppl1), pp. S1-2 (2008).

(Continued)

*Primary Examiner* — Maria Marvich
(74) *Attorney, Agent, or Firm* — FisherBroyles, LLP; Andrew K. Gonsalves

(57) ABSTRACT

The present invention relates to compositions of aqueous humor and/or vitreous humor derived extracellular vesicles and their use for the delivery of therapeutic agents to ocular tissues for the treatment of ophthalmic diseases. Further disclosed are methods of making the compositions. Methods of treating and diagnosing an ocular condition are also disclosed.

11 Claims, 18 Drawing Sheets

(56) References Cited

U.S. PATENT DOCUMENTS

2015/0216899 A1 8/2015 Pusic et al.
2015/0306236 A1 10/2015 Linder et al.
2016/0040212 A1 2/2016 Lieberman-Aiden
2016/0206780 A1 7/2016 Wang
2016/0216253 A1 7/2016 Balaj
2016/0245809 A1 8/2016 Connor
2016/0313306 A1 10/2016 Ingber
2017/0051050 A1 2/2017 Pereira Martins
2017/0121685 A1 5/2017 De La Rosa et al.
2017/0137469 A1 5/2017 Li
2017/0183686 A1* 6/2017 Khvorova .......... C12N 15/1137
2017/0229043 A1 8/2017 Huh
2017/0258320 A1 9/2017 Abreu
2017/0284975 A1 10/2017 Zhong
2017/0304368 A1* 10/2017 Marban ................ C12N 5/0656
2017/0362649 A1 12/2017 Lieberman-Aiden
2018/0085065 A1 3/2018 Haffner
2018/0104186 A1 4/2018 Badiavas
2018/0105552 A1 4/2018 Herdwijn
2018/0178142 A1 6/2018 Gjerde
2018/0305682 A1 10/2018 Craighead
2019/0008902 A1* 1/2019 Anderson ............. C07K 14/71
2019/0094115 A1 3/2019 Bhakdi
2019/0112666 A1 4/2019 Barbie
2019/0216857 A1 7/2019 Pena
2020/0121724 A1 4/2020 Pena
2020/0264076 A1 8/2020 Pena

FOREIGN PATENT DOCUMENTS

WO 2001082958 A2 11/2001
WO 2003093801 A1 11/2003
WO 2003102585 A2 12/2003
WO 2004077057 A1 9/2004
WO 2009100029 A1 8/2009
WO 2010119256 A1 10/2010
WO 2011044216 A1 4/2011
WO 2011090731 A1 7/2011
WO 2011143540 A1 11/2011
WO 2012021891 A1 2/2012
WO 2012021891 A2 2/2012
WO 2013016712 A2 1/2013
WO 2013084000 A2 6/2013
WO 2013106852 A1 7/2013
WO WO-2013158258 A1 * 10/2013 .......... A61K 35/545
WO 2014028493 A2 2/2014
WO WO-2014054588 A1 * 4/2014 .......... A61K 31/713
WO 2014068408 A2 5/2014
WO 2014159662 A1 10/2014
WO 2014205374 A1 12/2014
WO 2015002975 A1 1/2015
WO 2015080758 A1 6/2015
WO 2015143113 A1 9/2015
WO 2015171736 A2 11/2015
WO 2016176396 A1 11/2016
WO 2016201064 A1 12/2016
WO 2017087940 A1 5/2017
WO 2017130178 A2 8/2017
WO 2017136430 A1 8/2017
WO WO-2017160884 A1 * 9/2017 ............ A61K 35/34
WO 2017190142 A1 11/2017
WO 2018049284 A1 3/2018
WO 2019109077 A1 6/2019

OTHER PUBLICATIONS

Stone et al., Missense Variations in the Fibulin 5 Gene and Age-Related Macular Degeneration, N Engl J Med 351, 346-353 (2004).
Shen et al., A Human Opsin-Related Gene That Encodes a Retinaldehyde-Binding Proteint, Biochemistry 33, 13117-13125 (1994).
Conde-Vancells, Characterization and Comprehensive Proteome Profiling of Exosomes Secreted by Hepatocytes, J et al. J Proteome Res 7, 5157-5166 (2008).
Thery, C. et al., Molecular Characterization of Dendritic Cell-derived Exosomes: Selective Accumulation of the Heat Shock Protein hsc73, J Cell Biol 147, 599-610 (1999).
Vlassov, A et al.. Exosomes: Current knowledge of their composition, biological functions, and diagnostic and therapeutic potentials, Biochim Biophys Acta 1820, 940-948 (2012).
Higashiyama, S. et al., The Membrane Protein CD9/DRAP 27 Potentiates the Juxtacrine Growth Factor Activity of the Membrane-anchored Heparin-binding EGF-like Growth Factor, J Cell Biol 128, 929-938 (1995).
Keerthikumar, S. et al., ExoCarta: A web-based compendium of exosomal cargo, J Mal Biol 428, 688-692 (2016).
Nickells, Under pressure: cellular and molecular responses during glaucoma, a common neurodegeneration with axonopathy, Annu Rev Neurosci, vol. 35, pp. 153-179 (2012).
Collaborative Normal-Tension Glaucoma Study Group, Comparison of glaucomatous progression between untreated patients with normal-tension glaucoma and patients with therapeutically reduced IOPs, Am J Ophthalmol, vol. 126, pp. 487-497 (1998).
Drance, The Collaborative Normal-Tension Glaucoma Study and some of its lessons, Can J Ophthalmol, vol. 34, pp. 1-6 (1999).
Sommer, Collaborative normal-tension glaucoma study, Am J Ophthalmol, vol. 128, pp. 776-777 (1999).
Dvorak, Tumor Shedding and Coagulation, Science, vol. 212, pp. 923-924 (1981).
Brubaker, Mechanism of action of bimatoprost (Lumigan), Surv Ophthalmol, vol. 45 (Suppl 4), pp. S347-S351 (2001).
Nicoletti, Molecular characterization of the human gene encoding an abundant 61 kDa protein specific to the retinal pigment epithelium, Hum. Mol. Genetic vol. 4, pp. 641-649 (1995).
Morimura et al., Mutations in RGR, encoding a light-sensitive opsin homologue, in patients with retinitis pigmentosa, Nat Genet 23, 393-394 (1999).
Lamichhane et al., "Exogenous DNA Loading into Extracellular Vesicles via Electroporation is Size-Dependent and Enables Limited Gene Delivery," Molecular Pharmaceutics 12(10):3650-3657 (2015).
Dismuke et al., "Human Aqueous Humor Exosomes," Experimental Eye Research 132:73-77 (2015).
Ohno et al., "Focus on Extracellular Vesicles: Development of Extracellular Vesicle-Based Therapeutic Systems," International Journal of Molecular Sciences 17(2):1-19 (2016).
Tanaka et al., "Profiles of Extracellular miRNAs in the Aqueous Humor of Glaucoma Patients Assessed with a Microarray System," Scientific Reports 4:1-7 (2014).
Lerner et al., "Extracellular Vesicles Mediate Signaling Between the Aqueous Humor Producing and Draining Cells in the Ocular System," PLOS One 12(2):E017-1153 (2017).
Gygory et al., "Analysis of Extracellular Vesicles in Vitreous Samples," Investigative Ophthalmology & Visual Science 54:3148 (2013) abstract only.
Ragusa et al., "miRNA Profiling in Vitreous Humor, Vitreal Exosomes and Serum from Uveal Melanoma Patients: Pathological and Diagnostic Implications, " Cancer biology & Therapy 16(9):1387-1396 (2015).
PCT International Search Report and Written Opinion for corresponding PCT/US2017/050854, mailed Feb. 5, 2018.
Griffith, Epithelial-mesenchymal transformation during palatal fusion: carboxyfluorescein traces cells at light and electron microscopic levels, Development vol. 116, pp. 1087-1099 (1992).
Dragovic, Sizing and phenotyping of cellular vesicles using Nanoparticle Tracking Analysis, Nanomedicine vol. 7, pp. 780-788 (2011).
Van Der Pol, Recent developments in the nomenclature, presence, isolation, detection and clinical impact of extracellular vesicles, J Thromb Haemost vol. 14, pp. 48-56 (2016).
Suzuki, DNA staining for fluorescence and laser confocal microscopy, J Histochem Cytochem vol. 45, pp. 49-53 (1997).
Thakur, Double-stranded DNA in exosomes: a novel biomarker in cancer detection, Cell Res vol. 24, pp. 766-769 (2014).
Skog, Glioblastoma microvesicles transport RNA and proteins that promote tumour growth and provide diagnostic biomarkers, Nat Cell Biol vol. 10, pp. 1470-1476 (2008).

(56) References Cited

OTHER PUBLICATIONS

Mallawaaratchy, Comprehensive proteome profiling of glioblastoma-derived extracellular vesicles identifies markers for more aggressive disease, J. Neurooncol. vol. 131, pp. 233-244 (2017).
Keerthikumar, Proleogenomic analysis reveals exosomes are more oncogenic than ectosomes, Oncolarget vol. 6, pp. 15375-15396 (2015).
Vargas, Neutrophil-derived exosomes: a new mechanism contributing to airway smooth muscle remodeling, Am. J. Respir. Cell and Mol. Biol. vol. 55, pp. 450-461 (2015).
Saari, Photochemistry and stereoselectivity of cellular retinaldehyde-binding protein from bovine retina, J. Biol. Chem vol. 262, pp. 7618-7622 (1987).
Crabb, Structural and functional characterization of recombinant human cellular retinaldehyde-binding protein, Protein Sci. vol. 7, pp. 746-757 (1998).
Li, Secretory defect and cytotoxicity: the potential disease mechanisms for the retinitis pigmentosa {RP)-associated interphotoreceptor retinoid-binding protein (IRBP), J. Biol. Chem. vol. 288, pp. 11395-11406 (2013).
Den Hollander, A homozygous missense mutation in the IRBP gene {RBP3) associated with autosomal recessive retinitis pigmentosa, Invest. Ophthalmol. Vis. Sci. vol. 50, pp. 1864-1872 (2009).
Friedman, Protein localization in the human eye and genetic screen of opticin, Hum. Mol. Genet. vol. 11, pp. 333-1342 (2002).
Reardon, Identification in vitreous and molecular cloning of opticin, a novel member of the family of leucine-rich repeat proteins of the extracellular matrix, J. Biol. Chem. vol. 275, pp. 2123-2129 (2000).
Van Pelt-Verkuil, The Use of a Carbodiimide-Containing Fixative for the Immunohistochemical Demonstration of Coagulation Factor VIII in Rat Vascular Tissue, Histochemistry, vol. 71, pp. 187-194 (1981).
Aran, Microfiltration platform for continuous blood plasma protein extraction from whole blood during cardiac surgery, Lab Chip, vol. 11, pp. 2858-2868 (2011).
Thery, Isolation and Characterization of Exosomes from Cell Culture Supernatants and Biological Fluids, Current Protocols in Cell Biology, Supplement 30, vol. 3.22.1-3.22.29, pp. 1-29 (2006).
Bergamaschi, Extracellular matrix signature identifies breast cancer subgroups with different clinical outcome, J. Pathol., vol. 214, pp. 357-367 (2008).
Hollands, Do findings on routine examination identify patients at risk for primary open-angle glaucoma? The rational clinical examination systematic review, JAMA, vol. 309, pp. 2035-2042 (2013).
Zode, Bone morphogenetic protein 4 inhibits TGF-β stimulation of extracellular matrix proteins in optic nerve head cells: role of gremlin in ECM modulation, Glia, vol. 57, pp. 755-766 (2009).
Faivre, In frame fibrillin-1 gene deletion in autosomal dominant Weill-Marchesani syndrome, J. Med. Genet. vol. 40, pp. 34-36 (2003).
Hubmacher, Human eye development is characterized by coordinated expression of fibrillin isoforms, Invest. Ophthalmol. Vis. Sci. vol. 55, pp. 7934-7944 (2014).
Sakuma, Isolation and characterization of the human X-arrestin gene, Gene vol. 224, pp. 87-95 (1998).
Dryja, Mutations within the rhodopsin gene in patients with autosomal dominant retinitis pigmentosa. N. Eng. J. Med. vol. 323, pp. 1302-1307 (1990).
Liden, Biochemical defects in 11-cis retinol dehydrogenase mutants associated with fundus albipunctatus, J. Biol. Chem. vol. 276, pp. 49251-49257 (2001).
Moiseyev, RPE65 is the isomerohydrolase in the retinoid visual cycle, Proc. Natl. Acad. Sci. vol. 102, pp. 12413-12418 (2005).
Merdes, The 47-kDa lens-specific protein phakinin is a tailless intermediate filament protein and an assembly partner of filensin, J. Cell. Biol. vol. 123, pp. 1507-1516 (1993).
Schindelin, Fiji: an open-source platform for biological-image analysis, Nat. Methods vol. 9, pp. 676-682 (2012).
Schneider, NIH Image to ImageJ: 25 years of image analysis, Nat. Methods vol. 9, pp. 671-675 (2012).
Siegel, Cancer Statistics, 2017, CA Cancer J Clin vol. 67, pp. 7-30, (2017).
Luga, Exosomes mediate stromal mobilization of autocrine Wnt-PCP signaling in breast cancer cell migration, Cell vol. 151, pp. 1542-1556, (2012).
Cho, Exosomes from breast cancer cells can convert adipose tissue-derived mesenchymal stem cells into myofibroblast-like cells, Int J Oncol vol. 40, pp. 130-138, (2012).
Lee, Exosomes derived from mesenchymal stem cells suppress angiogenesis by down-regulating VEGF expression in breast cancer cells, PLoS One, vol. 8, pp. e84256 (2013).
Nilsson, Prostate cancer-derived urine exosomes: a novel approach to biomarkers for prostate cancer, Br J Cancer vol. 100, pp. 1603-1607, (2009).
Wysoczynski, Lung cancer secreted microvesicles: underappreciated modulators of microenvironment in expanding tumors, Int J Cancer vol. 125, pp. 1595-1603, (2009).
Janowska-Wieczorek, Microvesicles derived from activated platelets induce metastasis and angiogenesis in lung cancer, Int J Cancer vol. 113, pp. 752-760, (2005).
Silva, Expression and cellular localization of microRNA-29b and RAX, an activator of the RNA-dependent protein kinase (PKR), in the retina of streptozotocin-induced diabetic rats, Mol Vis vol. 17, pp. 2228-2240 (2011).
Weidle, The Emerging Role of New Protein Scaffold-based Agents for the Treatment of Cancer, Cancer Genomics & Proteomics, vol. 10, pp. 155-168 (2013).
Klingeborn, Roles of Exosomes in the Normal and Diseased Eye, Progress in Retinal and Eye Research, vol. 59, pp. 158-177 (2017).
Keller, The Juxtacanalicular Region of Ocular Trabecular Meshwork: A Tissue with a Unique Extracellular Matrix and Specialized Function, J Ocular Biology, vol. 1, pp. 1-15 (2013).
Gyorgy, Membrane vesicles, current state-of-the-art: emerging role of extracellular vesicles, Cell Mol Life Sci vol. 68, pp. 2667-2688 (2011).
Trams, Exfoliation of membrane ecto-enzymes in the form of micro-vesicles, Biochim Biophys Acta vol. 645, pp. 63-70 (1981).
Hristov, Apoptotic bodies from endothelial cells enhance the number and initiate the differentiation of human endothelial progenitor cells in vitro, Blood vol. 104, pp. 2761-2766 (2004).
Raposo, Extracellular vesicles: exosomes, microvesicles, and friends. J Cell Biol vol. 200, pp. 373-383 (2013).
Gatti, Microvesicles derived from human adult mesenchymal stem cells protect against ischaemia-reperfusion-induced acute and chronic kidney injury, Nephrol Dial Transplant vol. 26, pp. 1474-1483 (2011).
Zomer, In Vivo imaging reveals extracellular vesicle-mediated phenocopying of metastatic behavior, Cell vol. 161, pp. 1046-1057 (2015).
Becker, Extracellular Vesicles in Cancer: Cell-to-Cell Mediators of Metastasis, Cancer Cell vol. 30, pp. 836-848 (2016).
Zappulli, Extracellular vesicles and intercellular communication within the nervous system, J Clin Invest vol. 126, pp. 1198-1207 (2016).
D'Souza-Schorey, Tumor-derived microvesicles: shedding light on novel microenvironment modulators and prospective cancer biomarkers, Genes Dev vol. 26, pp. 1287-1299 (2012).
Bellingham, Exosomes: vehicles for the transfer of toxic proteins associated with neurodegenerative diseases? Front Physiol vol. 3, article 124, pp. 1-12 (2012).
Lai, Visualization and tracking of tumour extracellular vesicle delivery and RNA translation using multiplexed reporters, Nat Com mun vol. 6, pp. 7029 (2015).
Ridder, Extracellular vesicle-mediated transfer of functional RNA in the tumor microenvironment, Oncoimmunology vol. 4, pp. e1008371 (2015).
Tkach, Communication by Extracellular Vesicles: Where We Are and Where We Need to Go, Cell vol. 164, pp. 1226-1232 (2016).
Le Goff, Adult vitreous structure and postnatal changes, Eye (Lond) vol. 22, pp. 1214-1222 (2008).
Ragusa, miRNA profiling in vitreous humor, vitreal exosomes and serum from uveal melanoma patients: Pathological and diagnostic implications, Cancer Biol Ther vol. 16, pp. 1387-1396 (2015).

(56) References Cited

OTHER PUBLICATIONS

Shi, Antigen retrieval in formalin-fixed, paraffin-embedded tissues: an enhancement method for immunohistochemical staining based on microwave oven heating of tissue sections, J Histochem Cytochem vol. 39, pp. 741-748 (1991).
Ikeda, Extraction and analysis of diagnostically useful proteins from formalin-fixed, paraffin-embedded tissue sections, J Histochem Cytochem vol. 46, pp. 397-403 (1998).
Pena, miRNA in situ hybridization in formaldehyde and EDC-fixed tissues, Nat Methods vol. 6, pp. 139-141 (2009).
Raposo, B lymphocytes secrete antigen-presenting vesicles, J Exp Med vol. 183, pp. 1161-1172 (1996).
Hoboro et al. An evaluation of fixation methods: Spatial and compositional cellular changes observed by Raman imaging Jul. 2017. Vibrational Spectroscopy 91: 31-45 (Year: 2017).
Bronner-Fraser, Alterations in neural crest migration by a monoclonal antibody that affects cell adhesion, J Cell 3iol vol. 101, pp. 610-617 (1985).
Rowland, The Effects of Crosslinking of Scaffolds Engineered from Cartilage ECM on the Chrondrogenic Differentiation of MSCs, Biomaterials, vol. 34, pp. 5802-5812 (2013).
Lamichhane, Exogenous DNA Loading into Extracellular Vesicles via Electroporation is Size-Dependent and nables Limited Gene Delivery, Mol Pharm. vol. 12(10), pp. 3650-3657 (2015).
Dismuke, Human aqueous humor exosomes, Exp Eye Res., vol. 132, pp. 73-77 (2015).
Ohno, Focus on Extracellular Vesicles: Development of Extracellular Vesicle-Based Therapeutic Systems, Int J Mol, Sci. vol. 17(2), pp. 1-19 (2016).
Tanaka, Profiles of Extracellular miRNAs in the Aqueous Humor of Glaucoma Patients Assessed with a Microarray System, Sci Rep. vol. 4, pp. 5089 (2014).
Lerner, Extracellular vesicles mediate signaling between the aqueous humor producing and draining cells in the ocular system, PloS One, vol. 12(2), pp. e0171153 (2017).
Abu-Hassan, The Trabecular Meshwork: A Basic Review of Form and Function, J Ocul Biol, vol. 2(1), pp. 1-22 (2014).
Zhou, Discovery of a Potential Plasma Protein Biomarker Panel for Acute-on-Chronic Liver Failure Induced by Hepatitis B Virus, Frontiers in Physiology, vol. 8, pp. 1-12 (2017).
Chen, Development and validation of a panel of five proteins as blood biomarkers for early detection of colorectal cancer, Clinical Epidemiology, vol. 9, pp. 517-526 (2017).
Kim, Protein immobilization techniques for microfluidic assays, Biomicrofluidics, vol. 7, pp. 1-47 (2013).
Rusling, Measurement of biomarker proteins for point-of-care early detection and monitoring of cancer, analyst, vol. 135. pp. 2496-2511 (2010).
Naba, The matrisome: in silica and in vivo characterization by proteomics of normal and tumor extracellular matrices, Mol. Cell. Proteomics, vol. 11, pp. 1-18 (2012).
Provenzano, Enzymatic targeting of the stroma ablates physical barriers to treatment of pancreatic ductal adenocarcinoma, Cancer Cell, vol. 21, pp. 418-429 (2012).
Barsky, Increased content of type V collagen in desmoplasia of human breast carcinoma, Am. J. Pathol., vol. 108, pp. 276-283 (1982).
Riaz, High TWIST1 mRNA expression is associated with poor prognosis in lymph node-negative and estrogen receptor-positive human breast cancer and is co-expressed with stromal as well as ECM related genes, Breast Cancer Res., vol. 14, pp. 1-15 (2012).
Weinreb, The pathophysiology and treatment of glaucoma: a review, JAMA, vol. 311, pp. 1901-1911 (2014).
Quigley, The number of people with glaucoma worldwide in 2010 and 2020, Br J Ophthalmol, vol. 90, pp. 262-267 (2006).
Zha, Extracellular vesicles: An overview of biogenesis, function, and role in breast cancer, Tumour Biol, vol. 39, pp. 1-7 (2017).
Stradleigh, Fixation strategies for retinal immunohistochemistry, Progress in retinal and eye research, vol. 48, pp. 181-202 (2015).
European Search Report EP17849694.9 (dated Apr. 15, 2020).
Wheatley, Immunohistochemical localization of fibrillin in human ocular tissues Relevance to the Marfan syndrome, Arch. Ophthalmol. vol. 113, pp. 103-109 (1996).
Wald, The light reaction in the bleaching of rhodopsin, Science vol. 111, pp. 179-181 (1950).
Dryja, A point mutation of the rhodopsin gene in one form of retinitis pigmentosa, Nature vol. 343, pp. 354-366 (1990).
Yamamoto, Mutations in the gene encoding 11-cis retinol dehydrogenase cause delayed dark adaption and fundus albipunctatus, Nat. Genet. vol. 22, pp. 188-191 (1999).
Carter, Mapping of the human CP49 gene and identification of an intragenic polymorphic marker to allow genetic linkage analysis in autosomal congenital cataract, Biochem. Biophys. Res. Commun. vol. 270, pp. 432-436 (2000).
Rabinowits, Exosomal microRNA: a diagnostic marker for lung cancer, Clin Lung Cancer vol. 10, pp. 42-46, (2009).
Consortium, Ev-Track: transparent reporting and centralizing knowledge in extracellular vesicle research, Nat Methods vol. 14, pp. 228-232 (2017).
Anand, "Mechanism of Corneal Permeation of L-valyl Ester of Acyclovir: Targeting the Oligopeptide Transporter on the Rabbit Cornea", Pharm Res, vol. 19, pp. 1194-1202 (2002).
Anand, "Amino Acid Prodrugs of Acyclovir as Possible Antiviral Agents against Ocular HSV-1 Infections: Interactions with the Neutral and Cationic Amino Acid Transporter on the Corneal Epithelium", Curr Eye Res, vol. 29, pp. 153-166 (2004).
Dalpiaz, et al., "Molecular Mechanism Involved in the Transport of a Prodrug Dopamine Glycosyl Conjugate", Int J Pharm., vol. 336, pp. 133-139 (2007).
Dun, et al., "Functional and Molecular Analysis of D-serine Transport in Retinal Muller Cells", Exp Eye Res., vol. 84, pp. 191-199 (2007).
Gunda, et al., "Corneal Absorption and Anterior Chamber Pharmacokinetics of Dipeptide Monoester Prodrugs of Ganciclovir (GCV): In vivo Comparative Evaluation of these Prodrugs with Val-GCV and GCV in Rabbits", J Ocul Pharmacol and Ther, vol. 22, pp. 465-476 (2006).
Janoria, et al., "Vitreal Pharmacokinetics of Biotinylated Ganciclovir: Role of Sodium-dependent Multibitamin Transporter Expressed on Retina", J Ocul Pharmacol and Ther, vol. 25, pp. 39-49 (2009).
Kaiser, et al., "RNAi-based treatment for neovascular age-related macular degeneration by SiRNA-027", Am J Ophthalmol., vol. 150, pp. 33-39 (2010).
Kansara, et al., "Dipeptide Monoester Ganciclovir Prodrugs for Transscleral Drug Delivery: Targeting the Oligopeptide Transporter on Rabbit Retina", J Ocul Pharmacol and Ther., vol. 23, pp. 321-334 (2007).
Katragadda, et al., "Modulation of P-glycoprotein-mediated Efflux by Prodrug Derivatization: an Approach Involving Peptide Transporter-mediated Influx across Rabbit Cornea", J Ocul Pharmacol and Ther., vol. 22, pp. 110-120 (2006).
Kim, et al., "Genome Surgery Using Cas9 Ribonucleoproteins for the Treatment of Age-Related Macular Degeneration", Genome Research, vol. 27, pp. 419-426 (2017).
Liu, et al., "Gene Therapy for Ocular Diseases", Postgrad. Med. J., vol. 87, at 487-495 pp. 1-16 (2011).
Majumdar, et al., "Dipeptide Monoester Ganciclovir Prodrugs for Treating HSV-1-induced Corneal Epithelial and Stromal Keratitis: In vitro and In vivo Evaluations", J Ocul Pharmacol and Ther., vol. 21, pp. 463-474 (2005).
Majumdar, et al., "Transcorneal Permeation of L- and D-aspartate Ester Prodrugs of Acyclovir: Delineation of Passive Diffusion Versus Transporter involvement", Pharm Res., vol. 26, pp. 1261-1269 (2009).
Malecaze, et al., "Detection of Vascular Endothelial Growth Factor Messenger RNA and Vascular Endothelial Growth Factor-like Activity in Proliferative Diabetic Retinopathy", Arch Ophthalmol, vol. 112, pp. 1476-1482 (1994).
Nguyen, et al., "Dose-ranging evaluation of intravitreal siRNA PF-04523655 for diabetic macular edema (the DEGAS Study)", Invest Ophthalmol & Vis Sci., vol. 53, pp. 7666-7674 (2012).

(56) References Cited

OTHER PUBLICATIONS

Nguyen, et al., "Phase 1 dose-escalation study of a siRNA targeting the RTP801 gene in age-related macular degeneration patients", Eye (Lond), vol. 26, pp. 1099-1105 (2012).
O'Reilly, et al., "RNA interference-mediated suppression and replacement of human rhodopsin in vivo", Am J Hum Genet., vol. 81, pp. 127-135 (2007).
Rosca, et al., "Anti-angiogenic Peptides for Cancer Therapeutics", Curr. Pharm. Biotechol., vol. 12, at 1101-1116 pp. 1-31 (2011).
Tyanova, et al., "The Perseus Computational Platform for Comprehensive Analysis of (Prote)omics Data", Nat Methods, vol. 13, pp. 731-740 (2016).
Zhu, et al., "Gene and Mutation Independent Therapy via CRISPR-Cas9 Mediated Cellular Reprogramming in Rod Photoreceptors", Cell Res., vol. 27, pp. 830-833 (2017).
Ausubul, et al., Informatics for Molecular Biologists, Current Protocols in Molecular Biology, Supplement 33, Unit 19.0.3, pp. 1-2 (1996).
Cox, et al., "MaxQuant Enables High Peptide Identification Rates, Individualized p.p.b.-Range Mass Accuracies and Proteome-Wide Protein Quantification", Nat Biotechnol vol. 26, pp. 1367-1372 (2008).
Debruijn, "Glycogen, Its Chemistry and Morphologic Appearance in the Electron Microscope. I. A Modified OsO4 Fixative Which Selectively Contrasts Glycogen", J Ultrastruct Res, vol. 42, pp. 29-50 (1973).
Fox, Formaldehyde Fixation, J Histochem. Cytochem, vol. 33, pp. 845-853 (1985).
Fraenkel-Conrat, Reaction of Formaldehyde with Proteins, VI. Cross-Linking of Amino Groups with Phenol, Imidazole, and Indole Groups, J Biol. Chem, vol. 174, pp. 827-843 (1948).
Fraenkel-Conrat, et al., The Reaction of Formaldehyde with Proteins, IV. Participation of Indole Groups, J. Biol. Chem. vol. 168, pp. 99-118 (1947).
Ishihama, et al., "Modular Stop and go Extraction Tips with Stacked Disks for Parallel and Multidimensional Peptide Fractionation in Proteomics", J Proteome Res, vol. 5, pp. 988-994 (2006).
Ji, et al., "Proteome Profiling of Exomones Derived from Human Primary and Metastatic Colorectal Cancer Cells Reveal Differential Expression of Key Metastatic Factors and Signal Transduction Components", Proteomics, vol. 13, pp. 1672-1686 (2013).
Jones, "Reactions of Aldehyde with Unsaturated Fatty Acids During Histological Fixation", Histochemical J, vol. 4, pp. 421-465 (1972).
Kunkel, Contact-site cross-linking agents, Mol. Cell. Biochem, vol. 34, pp. 3-13 (1981).
Luga, et al., "Exosomes Mediate Stromal Mobilization of Autocrine Wnt-PCP Signaling in Breast Cancer Cell Migration", Cell, vol. 151, pp. 1542-1556 (2012).
McPhail et al., "Stage at Diagnosis and Early Mortality from Cancer in England", Br J Cancer, vol. 112, pp. S108-S115 (2015).
Renwick, et al., "Multiplexed miRNA Fluorescence in situ Hybridization for Formalin-Fixed Paraffin-Embedded Tissues", Methods Mol Biol, vol. 1211, pp. 171-187 (2014).
Schwanhausser, et al., "Global Quantification of Mammalian Gene Expression Control", Nature vol. 473, pp. 337-342 and Correction vol. 495, pp. 126-127 (2011).
Sung, et al., "Directional Cell Movement Through Tissues Is Controlled by Exosome Secretion", Nat Commun, vol. 6, at 7164, pp. 1-14 (2015).
Torre, et al., "A Global Cancer Incidence and Mortality Rates and Trends—An Update", Cancer Epidemiol Biomarkers & Prevention, vol. 25, pp. 16-27 (2016).
UniProt C, UniProt: A Hub for Protein Information:, Nucleic Acids Res, vol. 43, pp. D204-D212 (2014).
Venable, et al., "A Simplified Lead Citrate Stain for Use in Electron Microscopy", J Cell Biol, vol. 25, pp. 407-408 (1965).
Voloboueva, et al., "(R)-Alpha-Lipoic Acid Protects Retinal Pigment Epithelial Cells from Oxidative Damage", Invest Ophthalmol Vis Sci, vol. 46, at 4302-4310, pp. 1-24 (2005).
Valadi, Exosome-mediated transfer of mRNAs and microRNAs is a novel mechanism of genetic exchange between cells, Nat Cell Biol vol. 9, pp. 654-659 and S1-S11 (2007).
Peinado, The secreted factors responsible for pre-metastatic niche formation: Old sayings and new thoughts, Semin Cancer Biol vol. 21, pp. 139-146 (2011).
Pulaski, Mouse 4T1 breast tumor model, Curr Protoc Immunol Chapter 20, Unit 20 22 (2001).
Ji, Proteome profiling of exosomes derived from human primary and metastatic colorectal cancer cells reveal differential expression of key metastatic factors and signal transduction components, Proteomics vol. 13, pp. 1672-1686 (2013).
Koppen, Proteomics analyses of microvesicles released by Drosophila Kc167 and S2 cells, Proteomics vol. 11, pp. 4397-4410 (2011).
Baietti, Syndecan-syntenin-ALIX regulates the biogenesis of exosomes, Nat. Cell Biol. vol. 14, pp. 677-685 and S1-S18 (2012).
Kim, Proteomic analysis of microvesicles derived from human mesenchymal stem cells, J. Proteome Res. vol. 11, pp. 839-849 (2012).
Inui, Annexin VI binds to a synaptic vesicle protein, synapsin I, J. Neurochem. vol. 63, pp. 1917-1923 (1994).
Wolfers, Tumor-derived exosomes are a source of shared tumor rejection antigens for CTL cross-priming, Nature Med. vol. 7, pp. 297-303 (2001).
Maw, Mutation of the gene encoding cellular retinaldehyde binding protein in autosomal recessive retinitis pigmentosa, Nat. Genet. vol. 17, pp. 198-200 (1997).
Brodeur, Neuroblastoma: Biological Insights Into a Clinical Enigma, Nature Reviews, vol. 3, pp. 203-216 (2003).
Drolet, Fit for the Eye: Aptamers in Ocular Disorders, Nucleic Acid Therapeutics, vol. 26, pp. 127-146 (2016).
Guzman-Aranguez, Small-interfering RNAs (siRNAs) as a Promising Tool for Ocular Therapy, British Journal of Pharmacology, vol. 170, pp. 730-747 (2013).
Harris, American Society of Clinical Oncology 2007 Update of Recommendations for the Use of Tumor Markers in Breast Cancer, Journal of Clinical Oncology, vol. 25, pp. 5287-5312 (2007).
Ito, Formaldehyde-Glutaraldehyde Fixatives Containing Trinitro Compounds, The Journal of Cell Biology, Abstract 418, vol. 39, pp. 168a-169a (1968).
Linares et al. High-speed centrifugation induces aggregation of extracellular vesicles 2015. Journal of Extracellular Vesicles 2015, 4: 29509 (Year: 2015).
Perkumas et al. Myocilin-associated exosomes in human ocular samples Experimental Eye Research 84 (2007) 209-212 (Year: 2007).
Hoboro et al. An evaluation of fixation methods: Spatial and compositional cellular changes observed by Raman maging Jul. 2017. Vibrational Spectroscopy 91: 31-45 (Year: 2017).
Lavik et al. Novel drug delivery systems for glaucoma Eye (2011) 25, 578-586 (Year: 2011).
Batrakova et al. Using exosomes, naturally-equipped nanocarriers, for drug delivery. J Control Release, 219, pp. 396-405, Aug. 1, 2015.
Bouremel, Arvo Annual Meeting, Jul. 1, 2018.
Narumi, M. et al., A survey of vitreous cell components performed using liquid-based cytology, Acta Ophtalmologica, vol. 93, Issue 5, pp. e386-e390, Mar. 9, 2015.
Wu, et al., Exosomes: Improved methods to characterize their morphology, RNA content, and surface protein biomarkers, Analyst, vol. 140, pp. 6631-6642; 2015.
Hoffman, Regulation of Myocilin-Associated Exosome Release from Human Trabecular Meshwork Cells, 2009, Investigative Ophthalmology & Visual Science, vol. 50, pp. 1313-1318.
Stamer, Protein Profile of Exosomes from Trabecular Meshwork Cells, 2011, J Proteomics, vol. 74, pp. 796-804.
Burnouf, An overview of plasma fractionation, Annals of Blood, vol. 3, pp. 1-10 (2018).
Skubitz, Simultaneous Measurement of 92 Serum Protein Biomarkers for the Development of a Multiprotein Classifier for Ovarian Cancer Detection, Cancer Prev Res, vol. 12, pp. 171-184 (2019).
Chang, LXII Edward Jackson lecture: Open angle glaucoma after vitrectomy, 2006, American Journal of Ophthalmology, vol. 141, pp. 1033-1043.

(56) References Cited

OTHER PUBLICATIONS

Dismuke, Mechanism of fibronectin binding to human trabecular meshwork exosomes and its modulation by dexamethasone, 2016, PLOS One, vol. 11(10), code e0165326, pp. 1-18.
Ozcimen, Ocular penetration of intravenously administered colistin in rabbit uveitis model, 2014, Journal of Ocular Pharmacology and Therapeutics: The Official Journal of the Association for Ocular Pharmacology and Therapeutics, vol. 30(8), pp. 681-685.
Moreno-Montanes, Phase I Clinical Trial of SYL040012, a Small Interfering RNA Targeting β-Adrenergic Receptor 2, for Lowering Intraocular Pressure, 2014, Molecular Therapy, vol. 22, pp. 226-232.
Kanada et al., Differential fates of biomolecules delivered to target cells via extracellular vesicles, PNAS, Feb. 23, 2015, E1433-E1442.
Yellon et al., Exosomes, Nanoparticles Involved in Cardioprotection?, Circ Res., 2014, vol. 114, pp. 325-332.
Hoen et al., Extracellular vesicles and viruses: Are they close relatives?, PNAS, Aug. 16, 2016, vol. 113, pp. 9155-9161.
Paggetti et al., Exosomes released by chronic lymphocytic leukemia cells induce the transition of stromal cells into cancer-associated fibroblasts, Blood, 2014, vol. 126, pp. 1106-1117.
Crescitelli, Distinct RNA profiles in subpopulations of extracellular vesicles: apoptotic bodies, microvesicles and exosomes, Journal of Extracellular Vesicles, 2013, vol. 2, pp. 20677.
Azaro-Ibanez, Different gDNAContent inthe Subpopulations of Prostate Cancer ExtracellularVesicles: Apoptotic Bodies, Microvesicles, and Exosomes, 2014, The Prostate, vol. 74, pp. 1379-1390.
Paneda, 11th Scientific AOPT Meeting Abstracts, 2013, pp. 1-118, Abstract 08-02 pp. 61, Abstract P1-06 pp. 83, Abstrat P2-03 pp. 96.

* cited by examiner

DELIVERY OF NUCLEIC ACIDS, PROTEINS AND SMALL MOLECULES IN VITREOUS VESICULAR BODIES

This application is a national stage application under 35 U.S.C. § 371 of PCT International Application Serial No. PCT/US2017/050854, filed Sep. 9, 2017, which claims the benefit of U.S. Provisional Patent Application Ser. No. 62/385,711 filed Sep. 9, 2016, which are hereby incorporated by reference in their entirety.

This invention was made with government support under grant number UL1 TR000457-06 from the National Institutes of Health. The government has certain rights in this invention.

FIELD OF THE INVENTION

The present invention relates to methods and compositions for delivery of therapeutic agents to ocular tissues for the treatment of ophthalmic diseases.

BACKGROUND OF THE INVENTION

Therapies involving the delivery of nucleic acids (such as genes, mRNA, DNA, siRNA, miRNA, or other noncoding RNA), proteins, and/or small molecules to the intraocular structures have tremendous therapeutic potential in disease, including ocular disease. However, the inability to deliver biologically active molecules directly to their target site is a major limitation in treatment of eye disease. The blood-retinal barrier prevents penetration of most molecules into the retina. Similar limitations exist for other ocular tissues.

For example, a number of retinal degenerative conditions are due to single gene mutations. Delivery of a normal copy of the mutated gene or the protein encoded by the gene, has the potential to prevent progression of such diseases. Direct delivery of these genes is limited by a number of factors including instability of free genetic material in the extracellular milieu. Direct delivery of proteins can likewise be limited by instability in the extracellular tissues, as well limitations to penetration of the blood-retinal and other natural barriers. Development of a process to bring nucleic acids, proteins or small molecules into cells could transform ocular therapeutics.

Similarly, a number of retinal diseases such as wet age-related macular degeneration, diabetic retinopathy, macular edema from a number of causes, and others have been linked to elevated vascular endothelial growth factor (VEGF) levels. Intravitreal injection of antibodies or small molecules that inhibit VEGF is an effective therapy for these diseases; however, frequent injections are often required. A number of approaches have been attempted to reduce VEGF through alternative approaches, such as gene therapy using genes encoding naturally occurring anti-VEGF proteins such as sFLT-1. These gene therapy approaches have historically used viral vectors such as adenoviral vectors (or adeno-associated viral (AAV) vectors) for gene delivery. AAV vector-based delivery of genes for retinal disease is limited due to the potential toxicity or immunogenicity of the viral vector itself. Moreover, recent clinical trial attempted to utilize this technology and the trials were stopped due to failure.

The present invention is directed at overcoming this and other deficiencies of the art.

SUMMARY OF THE INVENTION

A first aspect of the present invention is directed to a composition comprising one or more aqueous humor and/or vitreous humor extracellular vesicular bodies. The aqueous humor and vitreous vesicular bodies of the composition are modified to contain one or more exogenous agents.

Another aspect of the present invention is directed to a method of delivering a therapeutic agent to select cells or tissue of a subject. This method involves providing a composition comprising one or more aqueous humor and/or vitreous humor vesicular bodies, where the vesicular bodies of the composition are modified to contain one or more therapeutic agents. The method further involves administering the composition to the subject under conditions effective to deliver the composition comprising the one or more aqueous humor and/or vitreous humor extracellular vesicular bodies modified to contain the therapeutic agent(s) to the select cells or tissue of the subject.

Another aspect of the present invention is directed to a method of making a composition comprising one or more aqueous humor and/or vitreous humor vesicular bodies, where the vesicular bodies of the composition are modified to contain one or more exogenous agents. This method involves providing a mammalian ocular fluid sample comprising vitreous and/or aqueous humor fluids, and isolating vesicular bodies from said ocular fluid sample. The method further involves inserting the one or more exogenous agents into the isolated vesicular bodies.

Described here in are compositions and methods of using vesicular bodies present in the vitreous humor and/or aqueous humor of the eye to deliver genes, proteins, or small molecules for therapeutic purposes. These vesicular bodies can be safely collected from the eye, emptied of their natural contents, and then filled with therapeutic substance (nucleic acid, protein, or small molecule). They can then be administered to the patient through a number of routes including intravenously or through intraocular injection. The vesicular bodies are taken up by the target cell, and the payload is released in a form suitable to exert therapeutic effects. Targeting molecules on the cell surface of the vesicular bodies can be modified to allow targeting of the vesicular body directly to the site of disease, thereby reducing toxicity to bystander tissues. Most importantly, because these vesicular bodies are endogenous, physiologic bodies that are already present in the vitreous, their harvesting, loading, and re-administration for therapeutic purposes can be performed with little toxicity or immunogenicity to the delicate neural structures of the eye.

BRIEF DESCRIPTION OF THE DRAWINGS

FIG. 1A is a schematic diagram showing formalin-fixed vitreous (Vit) tissue immersed in wash buffer (supernatant) and heated to 37° C. results in escape of EVs (arrowhead) and vitreous collagen (C, closed arrow) into the supernatant. FIGS. 1B-1C are representative transmission electron microscopy (TEM) photomicrographs of supernatant collected from formalin-fixed bovine vitreous tissue after incubation at 37° C. and uranyl acetate (UA) and lead citrate staining show evidence of collagen strands (C, closed arrow) and numerous EVs (arrowhead) that are lost to the wash buffer. FIG. 1D is a schematic diagram showing EDC-formalin-fixed vitreous tissue immersed in wash buffer and heated to 37° C. resulted in retention of EVs in the tissue, with no loss of EVs and minimal loss of vitreous collagen strands into the supernatant. FIG. 1E shows representative TEM photomicrographs of supernatant from EDC-formalin-fixed vitreous tissue after incubation at 37° C. and UA and lead citrate staining showing few collagen strands (C, closed arrow) and no EVs in the supernatant. FIG. 1F shows representative TEM photographs of specificity control, PBS alone, which shows no collagen fibers nor EVs in the supernatant, but does show non-specific punctate staining of electron dense foci measuring less than 20 nm (NS, open arrow). FIG. 1G shows a western blot detecting exosome marker TSG-101 in supernatant (wash buffer) of formalin-fixed vitreous tissue (left lane) and vitreous sample (right lane). Scale bars are (FIG. 1B) 2.5 μm, (FIG. 1C), 500 nm, (FIGS. 1E-1F), and 200 nm.

FIG. 2A is a gross image of bovine vitreous placed on a vision testing card that demonstrates the highly transparent, gel-like structure. FIG. 2B shows representative MPM photomicrographs of whole mount bovine vitreous specimens fixed with formalin alone and stained with CFSE to mark protein (orange) and Hoechst to mark nuclei (purple). CFSE signal is observed surrounding the nuclei (FIG. 2B, left panel, open arrow), but not in the extracellular space. Nuclei staining shows no extracellular signal (FIG. 2B, left panel, purple, open arrow). FIG. 2C shows representative MPM photomicrographs of EDC-formalin-fixed vitreous stained with CFSE (orange) and Hoechst (purple). Overlay of image shows positive signal consistent with cell bodies (denoted with open arrow) and foci of extracellular protein signal (arrowheads) consistent in size and shape with EVs. FIG. 2D is an inset of FIG. 2C (white box), which shows multiple round intracellular foci (FIG. 2D, left panel, open arrowhead, orange) surrounding the area of nuclear stains (FIG. 2D, right panel, open arrowhead, purple). Numerous focal extracellular protein signals are observed (FIG. 2D, left panel, closed arrowheads, orange), consistent in size and shape with EVs, and no extracellular DNA is observed. FIG. 2E is a graph representing the mean±standard deviation number of EVs per vitreous cell and shows that EDC-formalin-fixed vitreous exhibit significantly more EVs than formalin-fixed vitreous. FIG. 2F is a graphical representation of frequency distribution of bovine vitreous EV diameter imaged by MPM. EV sizes was measured for 4,000 EVs and the frequency of EVs were plotted against the diameter of the EV. The lower limit of multiphoton microscopy is 200 nm and EVs up to 6000 nm were measured. EVs were distinguished from cells and defined as containing extracellular protein or RNA without extracellular DNA. p-values are <0.05. Scale bars are (FIG. 2A) 1 cm, (FIG. 2B) 40 μm, (FIG. 2C) 50 μm and (FIG. 2D) 10 μm.

FIGS. 3A-3C shows representative confocal fluorescent photomicrographs of whole mount bovine vitreous specimens crosslinked with EDC-formalin (FIGS. 3A and 3B) or formalin alone (FIG. 3C), stained with propidium iodide (PI, red) to mark DNA and RNA, Hoechst (blue) to visualize DNA and nuclei, and carboxyfluorescein succinimidyl ester (CFSE, green) to stain for protein. FIG. 3A is an overlay of images from EDC-formalin-fixed bovine vitreous and shows positive signal consistent with cell bodies (FIG. 3A, denoted with open arrow) and foci of extracellular RNA (closed arrowhead) and extracellular protein (closed arrowhead) consistent in size and shape with EVs. FIG. 3B shows representative confocal fluorescent photomicrographs of EDC-formalin-fixed vitreous and shows multiple round cellular foci (FIG. 3B, all panels, open arrowhead) and numerous focal signals of extracellular RNA (FIG. 3B, left panel, PI stain, red) and extracellular protein (FIG. 3B, right panel, CFSE stain, green) between the cells. FIG. 3C shows representative photomicrographs of whole mount bovine vitreous fixed with formalin alone and shows signal for RNA (FIG. 3C, left panel, PI, red) in the nucleus, similar to nuclei staining (FIG. 3C, middle panel, Hoechst, blue). Formalin-only fixed vitreous show no foci of extracellular RNA signal (FIG. 3C, left panel). CFSE stain shows cellular signal (open arrow), but no EV-shaped extracellular protein signal (FIG. 3C, right panel, green, no punctate staining observed between open arrows). The cell size appears smaller in the formalin only fixation, presumably due to EDC-formalin retaining more cytoplasmic RNAs and protein as compared to formalin alone. Scale bars are (FIG. 3A) 25 μm and (FIGS. 3B-3C) 50 μm.

FIG. 4A shows low-power wide-field fluorescent photomicrographs of whole mount bovine vitreous specimens crosslinked with EDC-formalin and stained with PI (FIG. 4A, top panel, red) and shows signal in the extracellular environment of vitreous tissue (denoted with closed arrowhead, inset), nuclei labeled (FIG. 4A, middle panel, Hoechst, blue) and merged images are shown (FIG. 4A, bottom panel). Vitreous cell nuclei stain positive with PI and Hoechst; colocalized signals are shown in green (FIG. 4A, bottom panel, inset). Cells are denoted with an open arrow and foci of extracellular PI signal are marked with a closed arrowhead (FIG. 4A, top and middle panel, inset). Nuclei were stained, and no extracellular DNA signal is observed (FIG. 4A, bottom panel). FIG. 4B shows photomicrographs of whole mount bovine vitreous fixed with EDC-formalin and treated with RNAse A. Samples stained with PI (FIG. 4B, top panel, red), Hoechst (FIG. 4B, middle panel), and merged images are shown (FIG. 4B, bottom panel). RNAse A treated samples show no evidence of extracellular RNAs as demonstrated by the lack of signal between the cell bodies (FIG. 4B, top and middle panel) and show no signal between two cell nuclei (open arrows). The PI signal for cytoplasmic RNA in RNAse A treated samples (FIG. 4B, top panel) appear smaller than pre-RNAse treated samples (FIG. 4A, top panel), presumably due to EDC-formalin retaining more cytoplasmic RNA. FIG. 4C is a graphical representation of mean±standard deviation foci of extracellular signal for EDC-formalin fixed tissues stained with PI pre-RNAase treatment and after RNAse treatment show significantly fewer EVs after RNAse treatment. Mean+/−standard error for EVs per cell were 60.7+/−35.1 pre-RNAse treatment and 0.03+/−0.04 post RNAse treatment, with significantly more EVs per cell noted pre-RNAse treatment ($p<0.001$) (FIG. 4C). Scale bars are (FIGS. 4A-4B) 50 μm and (4A inset, 4B inset) 20 μm.

FIGS. 5A-5B show low-power wide field fluorescent photomicrographs of whole mount bovine vitreous specimens crosslinked with EDC-formalin (FIG. 5A) or formalin alone (FIG. 5B). FIG. 5A shows representative photomicrographs of bovine vitreous fixed with EDC-formalin and stained with CFSE to label protein (FIG. 5A, top and middle panel, white) and Hoechst to label nuclei (FIG. 5A, bottom panel, blue) and shows multiple round cellular foci (FIG. 5A, all panels, open arrowhead) with numerous extracellular protein signals (top and middle panels, CSFE, white) consistent with EVs. FIG. 5B shows photomicrographs of whole mount bovine vitreous fixed with formalin only show nuclear stain (FIG. 5B, middle and bottom panels, Hoechst, blue) co-localizing with CFSE (FIG. 5B, top and middle panel, white), consistent with cellular DNA and nucleic acid, respectively. There is no evidence of extracellular protein signal (FIG. 5B, top and middle panel, CSFE, white). The CFSE stained cell size appears smaller in the formalin only fixation (FIG. 5B, middle panel) as compared to EDC-formalin fixation (FIG. 5A, middle panel), presumably due to EDC-formalin retaining more small protein as compared to formalin fixation alone. Scale bars are (FIGS. 5A-5B) 100 μm.

FIG. 6A shows representative transmission electron microscopy (TEM) photomicrographs of bovine vitreous tissue sections stained with uranyl acetate (UA) and lead citrate and shows a substantial number of EVs that are pleomorphic in size (arrowheads) and that contact collagen strands (marked with a "C" and arrow). The inset (upper right corner) is an enlargement of the area-enclosed box in the lower right corner and shows an EV associated with a collagen strand. FIG. 6B shows representative TEM photomicrograph of EVs isolated from bovine vitreous and stained with the electron dense protein stain, CSFE, which depict EV morphology and show numerous EVs pleomorphic in size (smaller EV marked with arrowhead, larger EV with double arrowhead). FIG. 6C shows representative TEM photomicrograph of EVs isolated from bovine vitreous and electron dense nucleic acid stain acridine orange (AO) staining and shows large EVs (double arrowhead) positive nucleic acid signal. FIG. 6D shows multiple EVs (arrowheads) in a network of collagen within whole mounted bovine vitreous stained with ethidium bromide (EtBr), an electron dense and nucleic acid stain. FIG. 6E shows a graphical representation of the mean (black line)+standard error (red bars) concentration EVs according to EV diameter, based on nanoparticle tracking analysis of EVs isolated from bovine vitreous. FIG. 6F shows representative TEM photomicrographs of postmortem human eye sections stained with UA and lead citrate show a substantial number of EVs at the vitreous base (Vit), adjacent to the non-pigmented epithelium (NPE) of the ciliary body (smaller EVs marked with arrowhead, larger EVs with double arrowhead). The EVs (FIGS. 6F-6G, arrowheads) contact with collagen strands (arrows). FIG. 6H shows representative TEM photomicrographs of EVs isolated from human vitreous and stained with AO show EVs (arrowhead) with positive nucleic acid signal. FIG. 6I is a graphical representation of frequency distribution of human vitreous EV diameter. Scale bars are (FIG. 6A, FIG. 6G) 100 nm, (FIG. 6B) 50 nm, (FIG. 6C-6D, FIG. 6H) 200 nm, and (FIG. 6F) 2 μm.

FIG. 7A shows representative wide-field fluorescent photomicrographs of whole mount bovine vitreous specimens fixed with formalin and processed at cold temperatures and demonstrates immunohistochemical stain for the EV-associated protein, TGS-101, in the extracellular space (FIG. 7A, top and middle panels, arrowhead, Alexa 488, Green). The inset (FIG. 7A, all panels, top right) is a higher magnification image of the box in the middle (FIG. 7A, all panels). Nuclei are marked with Hoechst counterstain (FIG. 7A, top and bottom, blue, open arrow). Hundreds of punctate extracellular signals were observed (FIG. 7A, top and middle). No evidence of extracellular DNA was observed (FIG. 7A, bottom). FIG. 7B shows representative photomicrographs from specificity controls for TSG-101 immunohistochemistry: whole mount normal bovine vitreous labeled with non-specific IgG antibody (green). The inset (FIG. 7B, all panels, top right) is a higher magnification image of the box in the middle (FIG. 7B, all panels). Signal was observed surrounding the nuclei (FIG. 7B, top and middle, Alexa 488, green). Images show no evidence of extracellular signal (FIG. 7B, top and bottom, Hoechst, blue). FIG. 7C is a graphical representation of mean+/−standard error for TSG-101 signal in extracellular and intracellular spaces, *$p<0.05$ by Student's unpaired t-tests. FIG. 7D shows positive signal for TSG-101 is observed in the extracellular space of the formalin-fixed vitreous (FIG. 7D, left, green). Nuclei are labeled with Hoechst (FIG. 7D, left, blue) and PI (FIG. 7D, right, red). There is no evidence of extracellular RNA in formalin-fixed samples (FIG. 7D, right, red). Scale bars are (FIGS. 7A-7B) 40 μm and (FIG. 7A inset, FIG. 7B inset and FIG. 7D) 10 μm.

FIG. 8A shows representative low power light microscopy photomicrographs of whole mount bovine vitreous after low-speed centrifugation followed by hematoxylin and eosin staining. These images show eosinophilic signal consistent with vitreous collagen (pink, arrow) without evidence of hematoxylin stained cellular nuclei. FIG. 8B shows images of whole mount vitreous prior to centrifugation. These images show eosinophilic signal consistent with vitreous collagen (pink, arrow) with evidence of hematoxylin stained cellular nuclei (purple, open arrow). Scale bars are (FIGS. 8A-8B) 50 μm.

FIGS. 9A-9C show representative confocal photomicrograph images of a human retinal pigment epithelial cells (ARPE-19) after 24 h treatment with a bolus of bovine vitreous EVs that were pre-labeled with the nucleic acid stain acridine orange (AO). Images show uptake of EV-labeled RNA in ARPE-19 cells (FIG. 9A, green). Nuclei are labeled (FIG. 9B, Hoechst, purple) and a merged image (FIG. 9C) shows transfection of ARPE-19 cells, with AO signal in the cytoplasm. FIG. 9D is a graphical representation of transfection efficiency (% of cells transfected) for ARPE-19 cells treated with bovine vitreous EVs (error bars represent standard deviation, n=3, $p<0.05$). FIGS. 9E-9F show representative confocal photomicrographs of human embryonic kidney (HEK) cells treated with a 24 h bolus of bovine EVs bodies pre-labeled with AO and show staining in the cytoplasm (FIG. 9E). Nuclei were labeled and a merged image is shown (FIG. 9F). FIGS. 9G and 9H are representative low-power fluorescent photomicrograph images of ARPE-19 cells treated for 3 h with a bolus of EVs that were isolated from post-mortem human vitreous and pre-labeled with AO. The image of FIG. 9G shows transfection of cells (FIG. 9G, AO, green). Nuclei were marked (FIG. 9H, Hoechst, blue). FIG. 9I is a graphical representation of transfection efficiency (% of cells transfected) for ARPE-19 cells treated with human vitreous EVs (error bars represent standard deviation, n=3, $p<0.05$). Scale bars are (FIGS. 9A-9C) 50 μm, (FIGS. 9E-9F) 15 μm, and (FIGS. 9G-9H) 100 μm.

FIG. 10A are representative photomicrographs of ARPE-19 cells treated with a bolus of bovine vitreous EVs that had been pre-loaded with 1 μg BSA conjugated to fluorescein by electroporation at 300 V. The left image of FIG. 10A shows fluorescein staining (yellow)

in the cytoplasm. FIG. 10A, middle image shows nuclei labelled with Hoechst stain (blue), and a merged image (FIG. 10A, right) shows substantial number of cells transfected. FIG. 10B are representative photomicrographs of ARPE-19 cells treated with a bolus of bovine vitreous EVs that had been mixed with BSA-fluorescein without electroporation (0 V, control). FIG. 10B, left image show no fluorescein staining, while FIG. 10B, right image shows nuclei labeling with Hoechst stain (blue). FIG. 10C is a graphical representation of mean±standard deviation transfection efficiency (% of cells transfected) of ARPE-19 cells treated with vitreous EVs loaded with 3 μg, 1 μg, or 0.5 μg BSA-fluorescein by electroporation at 300 V, with EVs loaded with 0.5 μg BSA-fluorescein without electroporation (0 V, control), or with PBS alone without electroporation (0 V, control). $p<0.001$ for all BSA-fluorescein dosages loaded at 300 V vs. controls at 0 V. FIG. 10D shows representative photomicrographs of ARPE-19 cells after application of a bolus of bovine vitreous EVs that had been pre-loaded with 1 μg of recombinant GFP by electroporation at 300 V. FIG. 10D, left image, shows positive GFP staining (green) in the cytoplasm. FIG. 10D, middle image, shows nuclei labelled with Hoechst stain (blue), and a merged image (FIG. 10D, right) shows substantial number of cells transfected. FIG. 10E, right image, shows no fluorescein staining in a representative photomicrograph of ARPE-19 cells after application of a bolus of bovine vitreous EVs that had been mixed with GFP without electroporation (0 V, control). Nuclei labeling with Hoechst stain (blue) in the control sample is shown FIG. 10E, right image. FIG. 10F is a graphical representation of mean±standard deviation transfection efficiency (% cells transfected) of ARPE-19 cells after application of EVs loaded with 1 μg, 0.5 μg, or 0.25 μg GFP by electroporation at 300 V or 1 μg GFP without electroporation (0 V, control). $p<0.05$ for all GFP dosages loaded at 300 V vs. control at 0 V. Scale bars (FIGS. 10A-10E) 50 μm.

FIG. 11A are representative wide-field fluorescent photomicrographs of mouse retina tissue sections after injection of a dilute amount of bovine EVs loaded with recombinant bovine serum albumin (BSA) conjugated to fluorescein on day 3 post injection. FIG. 11A, left image shows BSA fluorescein only, FIG. 11A, middle image, shows nuclei staining with Hoeschst only, and FIG. 11A, right image, shows a merged image. The images of FIG. 11A show signal in vitreous that does not penetrate the inner limiting membrane (ILM). FIG. 11B are representative confocal photomicrographs of mouse retina tissues section 3 weeks after injection of BSA-fluorescein showing expression in the retinal outer plexiform layer (OPL) and inner plexiform layer (IPL, arrow). FIG. 11B, left image, shows BSA fluorescein only, FIG. 11B, middle image, shows nuclei staining only, and FIG. 11B, right image, shows a merged image. FIG. 11C are images showing signal in cells traversing the IPL and OPL, as well as, ganglion cells (marked with inset box). The inset box from (FIG. 11C) is shown in higher power in (FIG. 11D) demonstrating positive stain in a cluster of cells in ganglion cell layer (GCL) and retinal nerve fiber layer. FIGS. 11C-D, left image, shows BSA fluorescein only, FIGS. 11C-D, middle, image, show nuclei staining only, and FIGS. 11C-D, right images, show a merged view. Scale bars are 30 μm (FIG. 11A), 50 μm (FIGS. 11B-11C) and 25 μm (FIG. 11D). Photoreceptor segments (ph segments), outer nuclear layer (ONL), inner nuclear layer (ONL).

FIG. 12A are representative confocal fluorescent photomicrographs of mouse eye tissue sections after injection of bovine EVs loaded by electroporation (300 V) with recombinant bovine serum albumin (BSA) conjugated to fluorescein (BSA-fluorescein) at 3-weeks post injection showing signal in cornea from endothelial cells and corneal keratocytes (FIG. 12A, left image shows BSA fluorescein only, FIG. 12A, middle image, shows nuclei staining with Hoeschst only, and FIG. 12A, right image, shows a merged image). FIG. 12B are images from control group of bovine EV mixed with BSA-fluorescein without electroporation (0 V) after 3-week injection showing no expression in endothelial cells nor corneal keratocytes, but does show non-specific staining of the corneal epithelium (FIG. 12B, left image shows BSA fluorescein only, FIG. 12B, middle image, shows nuclei staining with Hoeschst only, and FIG. 12B, right image, shows a merged image). FIG. 12C are representative confocal fluorescent photomicrographs from mouse eyes at 3-week post injection of EVs loaded by electroporation (300 V) with BSA-fluorescein that show signal in non-pigmented ciliary epithelial cells (FIG. 12A, left image shows BSA fluorescein only, FIG. 12C, middle image, shows nuclei staining with Hoeschst only, and FIG. 12C, right image, shows a merged image). FIG. 12D are images showing robust expression of BSA-Fluorescein in the photoreceptors, inner plexiform layer (IPL), retinal pigment epithelial (RPE) cells, and choroid (FIG. 12D, left image shows BSA fluorescein only, FIG. 12D, middle image, shows nuclei staining with Hoeschst only, and FIG. 12D, right image, shows a merged image). FIG. 12E are images of the mouse retina photoreceptors and retinal pigment epithelium (RPE) that are transfected with recombinant BSA protein that was delivered by EVs. Scale bars are 25 μm (FIGS. 12A-12E). Corneal epithelium (Epi), corneal endothelium (endo), outer plexiform layer (OPL), outer nuclear layer (ONL), inner plexiform layer (ONL).

FIGS. 13A-13C are low-power fluorescent photomicrographs of human retinal pigment epithelial (ARPE-19) cells that show transfection of anti-GAPDH siRNA conjugated to cyanine 3 dye (siRNA-Cy3) after electroporation with bovine vesicular bodies at 350 V (FIG. 13A, yellow, Cy3), nuclei marked with Hoechst dye (FIG. 13B, blue), and merge image of FIG. 13A and FIG. 13B shows substantial number of cells transfected (FIG. 13C). FIGS. 13D-13F are low-power photomicrographs of ARPE-19 cells treated with bovine vitreous vesicular bodies containing siRNA-Cy3 after electroporation at 200 V. FIG. 13D shows siRNA-Cy3 staining in the cytoplasm (yellow). Nuclei were labeled with Hoescht stain (FIG. 13E, blue), and the merged image of FIG. 13F show staining in the cytoplasm with reduced cell staining when compared to 350 V. FIGS. 13G-13H are images showing ARPE-19 cells treated with a bolus of bovine vesicular bodies and anti-GAPDH siRNA-Cy3 without electroporation (0 V). FIG. 13G shows no siRNA-Cy3 staining in ARPE-19 cells, and FIG. 13H shows nuclei marked with Hoechst stain (blue). The graph of 13I shows the percent of cells transfected with siRNA-GAPDH-Cy3 by electroporation voltage. Scale bars are 50 μm (FIGS. 13A-13H).

FIGS. 14A-14C are TEM photomicrograph images from bovine sections of ciliary body nonpigmented epithelium (NPE) stained with uranyl acetate showing multiple vesicular bodies (FIG. 14A, arrowheads) within the lumen of enlarged intercellular spaces (ISP) and budding from the NPE surface (FIG. 14A, asterisk). The orientation of the image is such that the base of the NPE and vitreous base marked (VIT) and internal limiting membrane (ILM) are shown. FIG. 14B is the inset from FIG. 14A, upper box, and shows vesicular bodies within ISP. FIG. 14C shows the lower inset from FIG. 14A and shows a NPE cell with a vesicular body budding into the lumen of the ISP (FIG. 14C, asterisk). FIG. 14D is a TEM photomicrograph of NPE showing electron dense bodies within the cell (FIG. 14D, wedge) and in vesicular bodies in the ISP lumen (FIG. 14D, arrowheads). FIG. 14E is a TEM photomicrograph of ciliary body pigmented epithelium (PE) showing no evidence of budding vesicles. FIG. 14F is a TEM image of bovine vitreous base attached to the ciliary body showing collagen fibers with several vitreous bodies (FIG. 14F, arrow-heads) within the collagen matrix (FIG. 14F, arrows). Scale bars are 1 μm (FIG. 14A), 200 nm (FIG. 14B and FIG. 14F), 250 nm (FIG. 14C), and 500 μm (FIGS. 14D-14E).

FIGS. 15A-15C are low-power fluorescent photomicrographs of human retinal pigment epithelial (ARPE-19) cells showing uptake of exogenous bovine serum albumin. Bovine vitreous humor vesicular bodies were electroporated at 350 V with BSA-fluorescein and then a bolus given to ARPE-19 cells which showed substantial staining in the cytoplasm (FIG. 15A, yellow). Nuclei were labeled with Hoechst stain (FIG. 15B, blue), and a merged image of FIG. 15A and FIG. 15B shows a substantial number of ARPE-19 cells stain for fluorescein (FIG. 15C). ARPE-19 cells treated with bovine vitreous vesicular bodies containing BSA-fluorescein (electroporated at 200 V) also show staining in the cytoplasm (FIG. 15D). Nuclei of these cells were labeled with Hoechst stain (FIG. 15E, blue), and the merged images (FIG. 15F) shows a decrease in cytoplasm cytoplasmic staining, which means fewer transfected cells as compared to cells exposed to EV electoporated with 300 V. FIGS. 15G-15H are photomicrographs showing ARPE-19 cells treated with bovine vesicular bodies and BSA-fluorescein without electroporation. No BSA-fluorescein staining in ARPE-19 cells was observed as shown in FIG. 15G). Nuclei were marked with Hoechst stain (FIG. 15H, blue). FIG. 15I is a graph showing protein transfection efficiency (error bars standard deviation of measurements, n=3). Scale bars are 50 μm (FIGS. 15A-15H).

FIG. 16A are TEM photomicrographs of whole mount bovine aqueous labeled with acridine orange showing multiple vesicular shaped bodies of various sizes (FIG. 16A, single arrowheads, double arrowheads, and arrow marks small, medium and large vesicle, respectively). FIG. 16B is a TEM photomicrograph depicting vesicular bodies stained with CFSE (FIG. 16B, arrowheads) associated with a collagen stand (FIG. 16B, arrow). FIGS. 16C-16D are TEM photomicrographs of bovine anterior chamber exosomes after isolation by differential ultracentrifugation stained with uranyl acetate (FIG. 16C) and acridine orange (FIG. 16D) showing a cluster of vesicular bodies of various sizes (FIG. 16C). FIG. 16E is an averaged Finite Track Length Adjustment Size/Concentration graph from nanoparticle tracking analysis of ultracentrifuge-isolated exosomes (error bars indicating+/−1 standard error of the mean). The data had a concentration of 1.10 e 8, a mean of 140.8 nm, a standard deviation of 127.9 nm, and peaks at 15 nm, 35 nm, 65 nm, 115 nm, 185 nm, 205 nm, 225 nm, 275 nm, 415 nm, 505 nm, and 615 nm (FIG. 16E). Scale bars, 200 nm (FIG. 16A, FIGS. 16C-16D) 500 nm (FIG. 16B).

FIGS. 17A-17C are low power wide-field photomicrographs of human skin cells PAM-212 that were transfected with bovine vitreous RNA that was labeled with acridine orange (AO) after 3 h of transfection. FIGS. 17D-17F show PAM-212 cells transfected with AO labeled EVs 24 hours after transfection. Images show a robust transfer of bovine EV RNA to human skin cells. The images of FIGS. 17G-17I show PAM-212 cells transfected bovine vitreous EVs that were previously labeled for all protein using CFSE, EVs were isolated again and then exposed to a bolus of EV-labeled protein to PAM 212 cells. After transfection of 3 h (FIGS. 17G-17I) and 24 hours (FIGS. 17J-17L) cells show robust uptake of bovine EV protein. Negative controls show no transfection at 3 h (FIGS. 17M-17O) and 24 h (FIGS. 17P-17Q). Scale bar is 100 μm for all images.

DETAILED DESCRIPTION OF THE INVENTION

Figures 1A, 1B, 1C, 1D, 1E, 1F, 1G:
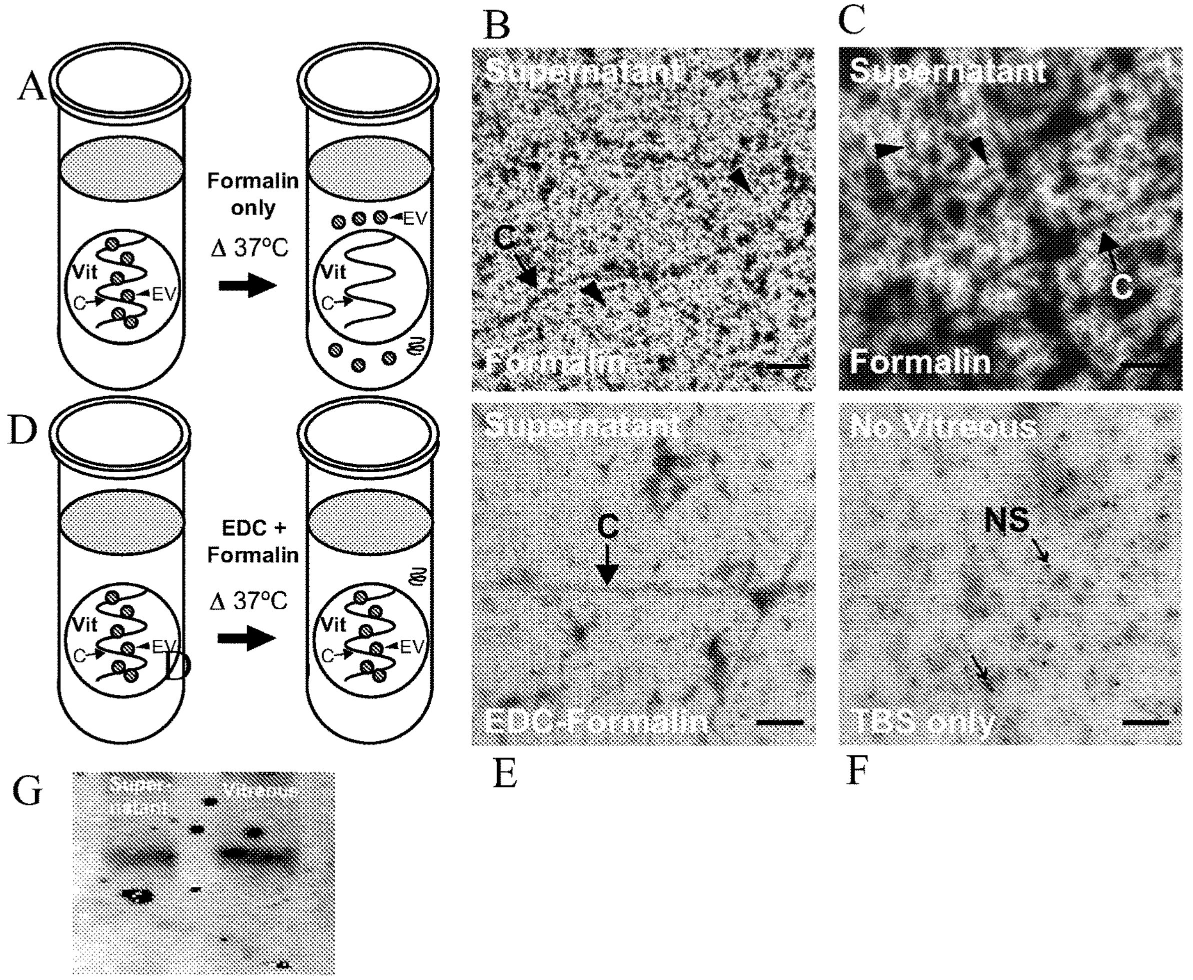
FIGS. 1A-1G show extracellular vesicles (EV) escape from formalin-fixed bovine vitreous tissues and are retained with 1-ethyl-3-(3-dimethylaminopropyl) carbodiimide (EDC)-formalin fixation.

The present invention is based on the unexpected discovery of a vesicular network in the vitreous and aqueous humor of the healthy human and bovine eyes. The vesicles of this network are loaded with a cargo of diverse proteins and coding and non-coding RNAs that they transport short and long distances to other ocular tissues. As described and demonstrated herein, these vesicle bodies can be safely isolated from ocular fluids of healthy individuals and modified to serve as therapeutic delivery vehicles.

Accordingly, a first aspect of the present invention is directed to a composition comprising one or more aqueous humor and/or vitreous humor extracellular vesicle bodies. The aqueous humor and/or vitreous extracellular vesicle bodies of the composition are modified to contain one or more exogenous agents.

The term “extracellular vesicle” as used herein refers to a nanosized membranous particle secreted by a cell. Extracellular vesicles, which are also referred to as EVs, multivesicular bodies, and ectosomes, are natural transport nanovesicles that have been implicated in intercellular communication via transfer of biomolecules such as proteins, lipids, and RNA from one cell to another. Extracellular vesicles differ from other secreted vesicles, e.g., exosomes and apoptotic bodies, based on their size, i.e., exosomes are typically about 40-100 nm in diameter, extracellular vesicles are typically 100-1000 nm in size, and apoptotic bodies are typically 1-5 μm in size.

In accordance with the present disclosure, the extracellular vesicles of the vitreous and aqueous humor are characterized by their size, i.e., their diameter. The term “diameter” refers to the maximum dimension of the vesicle, it being understood that the vesicle is not necessarily spherical. Vesicle diameter can be measured using conventional techniques for measuring nanoparticle size, such as microscopy techniques (e.g., transmission electron microscopy or light scattering techniques). In another embodiment, the vesicle diameter is measured using Nanoparticle Tracking Analysis (see WO03/093801 to Carr and Geddess, which is hereby incorporated by reference in its entirety).

The vesicular bodies of the vitreous humor are heterogenous in size, having a diameter ranging from 100 nm to 6000 nm. In one embodiment, the extracellular vesicles of the composition derived from the vitreous humor have a diameter ranging from 100 nm to 1000 nm. In another embodiment, the extracellular vesicles of the composition derived from the vitreous humor have a diameter of about 150 to 500 nm. In another embodiment, the extracellular vesicles of the composition derived from the vitreous humor have a diameter of about 150 to 300 nm.

The vesicular bodies of the aqueous humor are also heterogenous in size and generally smaller than the vitreous vesicular bodies. In one embodiment, the extracellular vesicles of the composition derived from the aqueous humor have a diameter ranging from 50 nm to 600 nm. In another embodiment, the extracellular vesicles of the composition derived from the aqueous humor have a diameter of about 50-400 nm. In another embodiment, the extracellular vesicles of the composition derived from the aqueous humor have a diameter of about 50-200 nm.

In one embodiment, the composition comprising aqueous humor and/or vitreous humor extracellular vesicle bodies comprises a population of vesicle bodies. A "population" of vesicles refers to a set of at least 2 vesicle bodies, at least 5 vesicle bodies, at least 10 vesicle bodies, at least 50 vesicle bodies, at least 100 vesicle bodies, at least 500 vesicle bodies, at least 1000 vesicle bodies, at least 10000 vesicle bodies, at least 100,000 vesicle bodies, at least 1,000,000 vesicle bodies, or more.

In another embodiment, the vesicle bodies of the vitreous and aqueous humor are characterized by their proteomic signature. For example, the vesicles of the vitreous humor express several known exosome markers, including CD-9, Hsp-90β, annexin-II, and TSG-101 proteins. The full list of exosome marker proteins present and enriched in vitreous extracellular vesicles is provided in Table 1 infra. In one embodiment, the composition comprises a population of vitreous humor extracellular vesicles expressing one or more exosome markers listed in Table 1. In another embodiment, the composition comprises a population of vitreous humor extracellular vesicles expressing two, three, four, five, six, seven, eight, nine, or all ten of the exosome markers listed in Table 1.

The vitreous humor vesicles of the composition of the present disclosure also possess a diverse proteomic signature of eye specific proteins as described in the Examples herein, see Table 2 infra. In one embodiment, the composition comprises a population of vitreous humor extracellular vesicles expressing one or more of the eye specific proteins listed in Table 2. In another embodiment, the composition comprises a population of vitreous humor extracellular vesicles expressing two, three, four, five, six, seven, eight, nine, ten or all eleven of the eye specific proteins listed in Table 2.

The entire protein signature of the vitreous extracellular vesicles is provided in Table 3 infra. Table 3 indicates the differential expression of the listed protein between the extracellular vesicle fraction of the vitreous humor and the cell free fraction of the vitreous humor. Accordingly, in one embodiment, the composition described herein comprises a population of extracellular vesicles expressing one or more of the proteins listed in Table 3. IN another embodiment, the composition described herein comprises a population of extracellular vesicles expressing one or more of the proteins enriched for in the extracellular fraction of the vitreous fraction. In another embodiment, the composition described herein comprises a population of extracellular vesicles expressing one or more of the proteins identified in Table 3 as being expressed only in the extracellular vesicle fraction. The population of extracellular vesicles described herein can be defined by the expression of any combination of proteins identified as being differentially expressed in only the extracellular vesicle fraction.

In one embodiment, the aqueous humor and/or vitreous humor vesicular bodies of the composition are isolated vesicular bodies. As used herein, the term "isolated" refers to vesicular bodies that have been removed from a human or animal body, i.e., from ocular fluids of the animal or human, and substantially separated from cell or cellular debris with which they are normally associated in vivo. In one embodiment, the composition comprising the extracellular vesicles is >75%, >80%, >85%, >90%, >95% free of cell or cellular debris normally associated with said vesicle bodies in vivo.

The extracellular vesicles of the composition may be isolated and/or purified using several techniques. These include filtration, centrifugation, ion-chromatography, or concentration, either alone or in combinations. An exemplary isolation method is described herein and involves a series of low-speed centrifugations. Other exemplary methods of isolating or purifying extracellular vesicles that are known in the art and suitable for use in accordance with the present invention include, without limitation, those disclosed by, e.g., van der Pol et al., "Recent Developments in the Nomenclature, Presence, Isolation, Detection and Clinical Impact of Extracellular Vesicles," *J Thromb Haemost* 14:48-56 (2016), U.S. Patent Application Publication No. 2016/0216253 to Balaj, WO2015/143113 to Cohen, WO2000/44389 to Dhellin, and WO2001/82958 to Lamparski, which are hereby incorporated by reference in their entirety.

In one embodiment, the composition as disclosed herein comprises extracellular bodies from the vitreous humor. The vitreous humor or vitreous body is located between the lens and the retina. It is an optically clear, mostly acellular, and gel-like structure with little known biological function. In one embodiment, the extracellular vesicles are obtained from a healthy, normal vitreous body, i.e., from a healthy subject. In another embodiment, the extracellular vesicles are obtained from a vitreous of a subject having an ocular disease. In another embodiment, the composition comprises extracellular bodies from the aqueous humor. The aqueous humor is the clear liquid filling the anterior chamber of the eye, located between the lens and the cornea. In one embodiment, the extracellular vesicles are obtained from a healthy, normal aqueous humor, i.e., from a healthy subject. In another embodiment, the extracellular vesicles are obtained from an aqueous humor of a subject having an ocular disease. In another embodiment, the composition comprises a mixture of extracellular bodies obtained from the aqueous humor and the vitreous humor.

In one embodiment, the extracellular vesicles as described herein are secreted by the ciliary body, e.g., the ciliary epithelium. In another embodiment, the extracellular vesicles as described herein are secreted by the pigmented ciliary epithelium, non-pigmented ciliary epithelium, ciliary processes. In another embodiment, the extracellular vesicles as described herein are secreted by retinal cells including Müller cells, ganglion cells, amacrine cells, horizontal cells, photoreceptors (rods and cones) bipolar cells, retinal pigment epithelium or retinal endothelial cells. In another embodiment, the extracellular vesicles as described herein are secreted by cells of cornea including corneal epithelium, corneal stroma (keratocytes), corneal endothelium, or limbal stem cells. In another embodiment, the extracellular vesicles as described herein are secreted by cells of iris including pigmented or non-pigmented cells, spindle shaped fibroblasts, macrophages (clump cells of Koganei), smooth muscle of the sphincter muscle, or posterior epithelium. In another embodiment, the extracellular vesicles as described herein are secreted by the trabecular meshwork cells including trabecular meshwork cells or endothelial cell lining of Schlemm's canal. In another embodiment, the extracellular vesicles as described herein are secreted by cells of the lens including lens epithelium, lens fibers, or lens capsule. In another embodiment, the extracellular vesicles as described herein are secreted by cells of choroid including cuboidal epithelial cells, ependymal cell layer, choroid plexus epithelial cells, or choroidal endothelial cells. In another embodiment, the extracellular vesicles as described herein are secreted by cells of the optic nerve including oligodendrocytes, retinal ganglion cell axons; or glial cells. In another embodiment, the extracellular vesicles as described herein are secreted by stem and progenitor cells including mesenchymal stem cells, limbal stem cells, retina stem cells.

The vitreous and/or aqueous humor extracellular vesicles of the composition as described herein can be any mammalian vitreous or aqueous humor extracellular vesicles. In one embodiment, the composition comprises bovine vitreous and/or aqueous humor extracellular vesicles. In another embodiment, the composition comprises human vitreous and/or aqueous humor extracellular vesicles. In another embodiment, the composition comprises vitreous and/or aqueous humor extracellular vesicles derived from non-human primates, dogs, cats, rodents (e.g., mouse, rat, and guinea pig), horses, cervids, sheep, or pigs.

As demonstrated herein, the extracellular vesicles of the vitreous and aqueous humor can be isolated, modified to contain one or more exogenous agents, and utilized as a delivery vehicle to delivery the one or more exogenous agents to a target tissue or cell. The exogenous agent can be a therapeutic agent or a diagnostic agent. Suitable therapeutic and diagnostic agents include, without limitation, nucleic acid molecules, proteins and polypeptides, small molecules, hormones, and any combination thereof.

In one embodiment, the exogenous agent is a therapeutic nucleic acid molecule. The nucleic acid molecule can be single-stranded or double-stranded nucleic acid. Single-stranded nucleic acids include those with phosphodiester, 2'O-methyl, 2' methoxy-ethyl, phosphoramidate, methylphosphonate, and/or phosphorothioate backbone chemistry. In one embodiment, the nucleic acid molecule is a therapeutic nucleic acid molecule selected from a ribonucleic acid molecule (RNA), a deoxyribonucleic acid molecule (DNA), an RNA-DNA hybrid, a modified RNA molecule, modified DNA molecule, or a modified RNA/DNA molecule thereof.

In one embodiment, the therapeutic nucleic acid molecule is an RNA molecule, such as a small RNA molecule, complementary RNA, a non-coding RNA molecule, siRNA, a pi-RNA molecule, a micro-RNA molecule, a sno-RNA molecule, long non-coding RNA molecule, messenger RNA molecule, ribosomal RNA molecule, an antisense nucleic acid molecule, Locked Nucleic Acid (LNA), antagomir, RNA aptamer, miRNA mimic, miR sponges, CRISPR/Cas gene editing RNA, trans-activating crRNA (tracrRNA), short synthetic RNA composed of a "scaffold" sequence (gRNA), Small Cajal body-specific RNAs (scaRNA), natural cis-antisense siRNAs (cis-nat-siRNAs), trans-acting siRNA (tasiRNA), repeat associated small interfering RNA (rasiRNA), 7SK, transfer-messenger RNA (tmRNA), transfer RNA (tRNA), 7SL RNA, signal recognition particle RNA (SRP), and any combination thereof.

In one embodiment, the extracellular vesicles are modified to contain a therapeutic RNA that is suitable for the treatment of an ocular disease or condition. Therapeutic RNAs suitable for the treatment of an ocular disease include, without limitation, siRNA targeting the β2-adrenoreceptor (SYL040012) for the treatment of glaucoma (Pañeda et al., "Development of SYL040012, a siRNA for treating increased intraocular pressure associated to glaucoma," AOPT 2013 Scientific Meeting 1:96 (2013), which is hereby incorporated by reference in its entirety), siRNA targeting VEGF (bevasiranib) for the treatment of age related macular degeneration (AMD), siRNA targeting VEGF receptor (siRNA-027) for the treatment of AMD (Kaiser et al., "RNAi-based treatment for neovascular age-related macular degeneration by SiRNA-027," *Am J Ophthalmol.* 150:33-39 (2010), which is hereby incorporated by reference in its entirety), and siRNA targeting RTP801 (PF-655) for the treatment of AMD and diabetic retinopathy (Nguyen et al., "Phase 1 dose-escalation study of a siRNA targeting the RTP801 gene in age-related macular degeneration patients," *Eye* (Lond) 26:1099-1105 (2012) and Nguyen et al., "Dose-ranging evaluation of intravitreal siRNA PF-04523655 for diabetic macular edema (the DEGAS Study)," *Invest Ophthalmol Vis Sci.* 53:7666-7674 (2012), which are hereby incorporated by reference in their entirety). Other therapeutic RNA molecules suitable for the treatment of ocular diseases that can be introduced to the extracellular vesicles of the composition described herein are described in Guzman-Aranguez et al., "Small-interfering RNAs (siRNAs) as a Promising Tool for Ocular Therapy," *Br. J. Pharmacol.* 170 (4): 730-747 (2013), which is hereby incorporated by reference in its entirety).

In another embodiment, the isolated extracellular vesicles of the vitreous and/or aqueous humor obtained using the methods described herein, are modified to express or incorporate an mRNA. The mRNA may encode a therapeutic agent that inhibits, down-regulates, reduces a protein expression and/or activity, the excess level of which is associated with an ocular disease, disorder or condition. Such a therapeutic agent may be a peptide, an antibody or other polypeptides or proteins, including any of those described herein. In one embodiment, the mRNA encodes an antibody, a soluble receptor or other binding protein. Typically, a suitable mRNA encodes an antibody that inhibits, down-regulates, or reduces a protein that is present in excess in amount and/or activity in an ocular disease, disorder or condition. In some embodiments, a suitable mRNA encodes an antibody that activates, up-regulates or increases a protein activity that is deficient in an ocular disease, disorder or condition. Exemplary antibodies encoded by mRNAs that can be introduced into the extracellular vesicles of the vitreous and/or aqueous humor as described herein include, but are not limited to, antibodies against VEGF, TNFα, IL-6, ICAM-1, VCAM-1, or soluble receptors such as VEGF receptors (e.g., VEGFR1).

Other mRNA molecules that are suitable for the treatment of an ocular disease or condition using the extracellular vesicles as described herein, include for example, and without limitation, mRNA molecules encoding the protein or biologically active fragments of endostatin, angiostatin, tissue inhibitor of metalloproteinase 3 (TIMP3), pigment epithelium derived factor (PEDF), or soluble vascular endothelial growth factor receptor (sFlt-1) for the reduction of neovascularization; mRNA molecules encoding the protein or biologically active fragments of Prph2, Rho, cGMP phosphodiesterase β-subunit (BPDE), Bcl2, PEDF, fibroblast growth factor (FGF-2), ciliary neurotrophic factor (CNTF), and c-mer proto-oncogene tyrosine kinase (Mertk) for the treatment of retinitis pigmentosa; mRNA molecules encoding the protein or biologically active fragments of brain-derived neurotrophic factor (BDNF), CNTF, and GDNF for the treatment of glaucoma; mRNA molecules encoding the protein or biologically active fragments of IL-10 and interleukin-1 receptor agonist (IL-1Ra) for the treatment of uveitis; and mRNA molecules encoding the protein or biologically active fragments of IFN-β and thymidine kinase (TK) for the treatment of retinoblastoma.

In one embodiment, the extracellular vesicles as described herein are modified to carry one or more of the following mRNA therapeutics, mRNA-1440, mRNA-1851, mRNA MRK-1777, mRNA-1388, mRNA-1325, mRNA-1706, mRNA-1647, mRNA-1653, mRNA-4157, mRNA-2416, mRNA-2905, mRNA AZD-8601, MRG-106, MIR-155, MRG-201, MRG-107, and MRG-110.

In another embodiment, the mRNA molecule loaded into the extracellular vesicles as described herein encodes a vaccine antigen. The mRNA directs the cells to produce and express the antigenic proteins, either secreted or on the cell surface, much like a native infection would do but without the ability to cause disease or spread. For therapeutic vaccines, using the extracellular vesicles described herein to deliver mRNA-based personalized cancer vaccines to prime the immune system to recognize cancer cells and mount a strong, tailored response to each individual patient's cancer. The extracellular vesicle includes a mRNA that encodes a patient's specific neoantigens, or unique mutations present in that specific patient's tumor.

In another embodiment, the RNA molecule is catalytic RNA. Ribozymes are catalytic RNAs that function as enzymes and do not require proteins for catalysis. Most known natural ribozymes are self-processing RNAs that catalyze RNA cleavage and ligation reactions. Suitable ribozymes therapeutics that can be delivered using the extracellular vesicles as described herein include, but are not limited to angiozyme, Heptazyme, MY-2, RRz1, OZ1 (RRz1), CCR5 ribozyme, L-TR/Tatneo.

Other RNA therapeutic molecules that are suitable for the treatment of a disease or condition using the extracellular vesicles as described herein, include for example, and without limitation SPC3649 (LNA), Bevasiranib, AGN-745, PF-655, QPI-1007, TD101, SYL040012, SYL1001, Excellair™, ALN-RSV01, CEQ508, siG12D LODER, TKM-ApoB, TKM-PLK1, ALN-VSP02, ALN-TTR01, Bcr-Abl siRNA, Atu027, 15NP, CALAA-01, FANG vaccine, iPsiRNA, Tat/Rev shRNA, siRNA-EphA2-DOPC, TD101, Atu027, ND-L02-s0201, DCR-PH1, STP705, ALN-GO1, Fitusiran (ALN-AT3SC), ALN-CC5, ALN-AS1, DCR-MYC, TKM 080301, siG12D-LODER, Inclisiran (ALN-PCSSC), PF-655, SYL1001, Bamosiran (SYL040012), QPI-1007, QPI-1002, Patisiran (ALN-TTR02), ISTH0036, EZN-2968 (RO7070179), LErafAON-ETU, AKCEA-APOCIII-LRx, BIIB067 (IONIS-SOD1Rx), AZD5312, Cenersen, IONIS-HTT Rx, IONIS ANGPTL3-LRx, AZD9150, QR-010, SB012, AEG35156, DS-5141b, AKCEA-APO(a)-LRx, Apatorsen (OGX-427), IONIS-HBV Rx, IONIS-GCGR Rx, ASM8, SB010, SB011, G4460, Prexigebersen (BP1001), IONIS-FXI Rx, Aganirsen (GS-101), Eteplirsen (AVI-4658), Alicaforsen, Volanesorsen, IONIS-TTRRx, Custirsen (OGX-011), Lipo-MERIT, IVAC mutanome/warehouse, TNBC-MERIT, CV7201, CV8102, mRNA-1851, mRNA-1440, mRNA MRK-1777, mRNA AZD-8601, mRNA-1325, CV9103, AGS-004, AGS-003-LNG, iHIVARNA-01, AGS-003.

In one embodiment, isolated extracellular vesicles of the vitreous and/or aqueous humor obtained using the methods described herein, are modified to express or incorporate a nuclease genome editing system useful to edit the genome. Genome editing as described herein may include gene insertions, deletions, modifications (e.g. nucleotide transitions, transversions, insertions or deletions of one or more nucleotides or duplications of any nucleotide sequence), gene activation and gene silencing. As will be appreciated by one of skill in the art, genome editing may be for the purpose of correcting an undesirable gene mutation, introducing a gene mutation, altering a gene sequence (e.g. to improve, enhance or inhibit gene function), inserting a gene sequence (e.g. to activate or inhibit gene expression), and the like. Examples of nuclease genome editing systems include, but are not limited to, Clustered Regularly Interspaced Short Palindromic Repeats (CRISPR) nuclease system, e.g. including a targeting gRNA and a CRISPR-associated (Cas) gene, such as CRISPR-Cas9, Transcription Activator-Like Effector Nucleases (TALEN) and mito-TALEN, Zinc-Finger Nucleases (ZFN), and other therapeutic nucleic acids, e.g. small interfering RNA, micro RNA, anti-microRNA, antagonist, small hairpin RNA, and aptamers (RNA, DNA or peptide based (including affimers)).

In one embodiment, the extracellular vesicles of the composition described herein are genetically modified to express or incorporate a CRISPR nuclease system, such as a CRISPR/Cas9 Type II genome editing system, including a Cas nuclease, and a guide RNA (gRNA), which comprises a fusion of trans-activating RNA (tracrRNA) and CRISPR RNA (crRNA). CRISPR RNA includes a targeting RNA sequence and a distinctive array of non-coding direct RNA repeats. The crRNA and tracrRNA are related to the selected Cas nuclease. As one of skill in the art will appreciate, the crRNA and tracrRNA (components of the gRNA) and the Cas nuclease are indicated to be "related" which means that the crRNA and tracrRNA are specific for and recognized by one or more particular Cas nucleases.

In one embodiment, the CRISPR nuclease system is designed to edit one or more gene defects associated with an ocular condition. For example, and without limitation, the CRISPR nuclease system may be designed to edit the VEGF gene that is overexpressed in age-related macular degeneration as described in Kim et al., "Genome Surgery Using Cas9 Ribonucleoproteins for the Treatment of Age-Related Macular Degeneration," *Genome Research* 27:419-426 (2017), which is hereby incorporated by reference in its entirety. In another embodiment, the CRISPR nuclease system may be designed to inactivate the Nrl or NR2e3 genes for the purpose of preventing degeneration associated with retinitis pigmentosa as described by Zhu et al., "Gene and Mutation Independent Therapy via CRISPR-Cas9 Mediated Cellular Reprogramming in Rod Photoreceptors," Cell Res. 27:830-833 (2017), which is hereby incorporated by reference in its entirety.

In another embodiment, the nucleic acid molecule is a DNA molecule. Suitable DNA molecules include, without limitation, a small DNA molecule, a cDNA molecule, an oligonucleotide, a locked Nucleic Acid (LNA), a deoxyribonucleic acid aptamer, a deoxyribonucleic acidzyme (DNAzymes), and any combination thereof.

In one embodiment, the therapeutic nucleic acid includes genomic sequences, e.g., cDNA sequences and smaller engineered gene segments that express, or may be adapted to express, proteins, polypeptides, fusion proteins, antibodies, and protein/peptide variants. The nucleic acid may comprise a contiguous nucleic acid sequence of about 5 to about 12000 or more nucleotides, nucleosides, or base pairs. Therapeutic nucleic acid molecules in accordance with this aspect of the invention may encode cytokines, enzymes, hormones, natural agonists and antagonists of proteins involved in disease, etc. Therapeutic nucleic acid molecules also include biologically functional equivalents of a therapeutic nucleic acid proven to benefit in the treatment or prevention of a disease or health-related condition. Accordingly, sequences that have about 70% to about 99% sequence identity to a known nucleic acid molecule are suitable therapeutic nucleic acid molecules in accordance with this aspect of the present invention.

In one embodiment, the extracellular vesicles are modified to contain a therapeutic DNA molecule that is suitable for the treatment of an ocular disease or condition. Suitable therapeutic DNA molecules include for example, and without limitation, DNA molecules encoding the protein or biologically active fragments of endostatin, angiostatin, tissue inhibitor of metalloproteinase 3 (TIMP3), pigment epithelium derived factor (PEDF), or soluble vascular endothelial growth factor receptor (sFlt-1) for the reduction of neovascularization; DNA molecules encoding the protein or biologically active fragments of Prph2, Rho, cGMP phosphodiesterase β-subunit (BPDE), Bcl2, PEDF, fibroblast growth factor (FGF-2), ciliary neurotrophic factor (CNTF), and c-mer proto-oncogene tyrosine kinase (Mertk) for the treatment of retinitis pigmentosa; DNA molecules encoding the protein or biologically active fragments of brain-derived neurotrophic factor (BDNF), CNTF, and GDNF for the treatment of glaucoma; DNA molecules encoding the protein or biologically active fragments of IL-10 and interleukin-1 receptor agonist (IL-1Ra) for the treatment of uveitis; and DNA molecules encoding the protein or biologically active fragments of IFN-β and thymidine kinase (TK) for the treatment of retinoblastoma. Other suitable DNA therapeutics that can be introduced into the extracellular vesicles of the composition as described herein are known in the art, see Liu et al., "Gene Therapy for Ocular Diseases," *Postgrad. Med. J.* 87 (1029): 487-95 (2011), which is hereby incorporated by reference in its entirety.

In another embodiment the therapeutic DNA molecule suitable for treatment of an ocular disease which is loaded into the extracellular vesicles of the composition described herein is an aptamer. Suitable aptamers include, for example and without limitation, Macugen/pegaptanib (NX1838) targeting the activity of VEGF for the treatment of ocular neovascular diseases, Fovista/pegpleranib (NX1975) targeting the activity of PDGF B-chain for the treatment of age-related macular degeneration, and Zimura/ARC1905 targeting the activity of complement component 5 (C5) for the treatment of age-related macular degeneration (see Drolet et al., "Fit for the Eye: Aptamers in Ocular Disorders," *Nucleic Acid Ther.* 26 (3): 127-146 (2016), which is hereby incorporated by reference in its entirety). Other suitable aptamers include RNA aptamer (RB006 or pegnivacogin), ARC19499 (BAX499), REG1 (RB006 & RB007), ARC1905, TAR decoy, RRE decoy.

In one embodiment, a combination of therapeutic RNA and DNA molecules are introduced into the extracellular vesicles of the composition described herein. In one embodiment, the combination of therapeutic RNA and DNA molecules work in concert for the treatment of an ocular disease. For example, and without limitation, siRNA molecules capable of silencing the expression of mutant rhodopsin expression can be administered in combination with a DNA molecule encoding the wildtype rhodopsin gene for the treatment of retinitis pigmentosa (O'Reilly et al., "RNA interference-mediated suppression and replacement of human rhodopsin in vivo," *Am J Hum Genet.* 81:127-135 (2007), which is hereby incorporated by reference in its entirety).

In another embodiment, the nucleic acid is a diagnostic nucleic acid. A diagnostic nucleic acid is a nucleic acid that can be applied in the diagnosis of a disease or health-related condition. A diagnostic nucleic acid sequence that encodes one or more reporter proteins. A "reporter protein" refers to an amino acid sequence that, when present in a cell or tissue, is detectable and distinguishable from other genetic sequences or encoded polypeptides present in cells. In some embodiments, a therapeutic nucleic acid molecule may be fused to the diagnostic nucleic acid encoding a reporter protein. For example, the two nucleic acid molecules may be linked to the same promoter by, for example, an internal ribosome entry site, or a bi-directional promoter. Using such techniques, expression of the therapeutic nucleic acid and diagnostic nucleic acid correlate. Thus, when the composition is used in the methods as described herein, one may gauge the location, amount, and duration of expression of a therapeutic nucleic acid.

Preferably, a reporter sequence encodes a protein that is readily detectable either by its presence, its association with a detectable moiety, or by its activity that results in the generation of a detectable signal. In certain aspects, a detectable moiety may include a radionuclide, a fluorophore, a luminophore, a microparticle, a microsphere, an enzyme, an enzyme substrate, a polypeptide, a polynucleotide, a nanoparticle, and/or a nanosphere, all of which may be coupled to an antibody or a ligand that recognizes and/or interacts with a reporter. Exemplary diagnostic nucleic acid molecules include, without limitation, nucleic acid molecules encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, G-protein coupled receptors (GPCRs), somatostatin receptors, CD2, CD4, CD8, the influenza hemagglutinin protein, symporters (such as NIS) and others well known in the art.

In one embodiment, the extracellular vesicles of the composition described herein are modified to include a naked nucleic acid molecule, e.g. naked DNA or naked RNA. In another embodiment, the nucleic acid is packaged in an expression vector suitable for expression in prokaryotes or eukaryotes or both, preferably for expression in mammalian cells. Suitable expression vectors include viral vectors (e.g., adenoviral vector, adeno-associated viral vector, lentiviral vector, vaccina viral vector, retroviral vector, herpes viral vector), bacterial vectors, plasmid vectors, artificial chromosomes, bacteriophages, or any combination thereof. Expression vectors generally contain regulatory sequences and other necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters. Depending on the vector system and host utilized, any number of suitable transcription and translation elements may be used. In mammalian cell systems, promoters from mammalian genes or from mammalian viruses are preferably used.

Methods of constructing expression vectors containing the desired nucleic acid molecules and appropriate transcriptional and translational control elements are well known in the art. These methods include in vitro recombinant DNA techniques, synthetic techniques, and in vivo genetic recombination. Such techniques are described in Sambrook et al., Molecular Cloning, A Laboratory Manual (Cold Spring Harbor Press, Plainview, N. Y., 1989), and Ausubel et al, Current Protocols in Molecular Biology (John Wiley & Sons, New York, N.Y., 1989), which are hereby incorporated by reference in their entirety.

The extracellular vesicles can be loaded with the nucleic acid or nucleic acids of interest using techniques known in the art, such as, for example, electroporation. Electroporation involves introducing pores into the vesicles using a pulse of electricity (e.g., 100-400 V/cm), where the nucleic acid(s) enter the vesicles through the pores. The extracellular vesicles can alternatively be loaded with nucleic acid(s) of interest using microinjection or particle bombardment. Alternatively, the extracellular vesicles can be loaded using lipofection or transfection using commercially available kits and reagent, or by transformation using heat shock.

In another embodiment, the vitreous and/or aqueous humor vesicles are loaded with a therapeutic protein and/or peptide for delivery. In one embodiment, the therapeutic protein is an exogenous protein or peptide. Exogenous refers to a protein or peptide with which the vesicle is not normally associated.

The protein and/or peptide to be loaded into the vesicles is chosen based the desired effect of that protein and/or peptide on the target cell. A single protein or peptide may be incorporated into the vesicles. Alternatively, more than one protein and/or peptide may be incorporated into the vesicles. The more than one protein and/or peptide may act on the same or different targets to bring about the desired therapeutic and/or preventative effect.

In one embodiment, the protein and/or peptide to be loaded into the vesicles is an antibody or antibody fragment. The term "antibody" as referred to herein includes whole antibodies (i.e., two heavy chains and two light chains), antibody binding fragments thereof, e.g., single chain antibodies (scFv), single domain antibodies (e.g., nanobodies or Fv), Fab, Fab', F(ab')2, and, variants thereof, e.g., tandem scFv, Fd fragments, diabodies, triabodies. These antibody fragments may be obtained using conventional techniques known to those of skill in the art, and the fragments may be screened for utility in the same manner as intact antibodies Antibody and antibody fragments disclosed herein can be mono-valent, bi-valent, or tri-valent with regard to binding domains, and the binding domains may be mono-specific, bi-specific, or tri-specific in binding specificity by design. Suitable antibodies include monoclonal antibodies or a polyclonal antibody mixture. The antibody may be a chimeric antibody, a CDR-grafted antibody, a humanized antibody or an antigen binding portion of any of the foregoing thereof. Therapeutic antibodies may be derived from a variety of species, including, without limitation, mouse, human, camel, llama, goat, rabbit, bovine, and cartilaginous fish.

In one embodiment, the antibody or antigen binding fragment thereof is one that is suitable for the treatment of an ocular disease or condition. Suitable antibodies or antigen binding fragments thereof include, without limitation, those that bind to and preferentially block or reduce the activity of integrins associated with disease, such as an anti-$\alpha_v\beta_3$ integrin antibody and an anti-$\alpha_4\beta_1$ integrin antibody. Other suitable antibodies that can be introduced into the extracellular vesicles of the compositions described herein include, for example and without limitation, an anti-epidermal growth factor receptor antibody, anti-vascular endothelial growth factor (VEGF) receptor antibody, anti-VEGF antibodies, e.g., bevacizumab, ranibizumab, anti-TNFα antibodies, e.g., infliximab and adalimumab, an anti-fibroblast growth factor antibody, an anti-epidermal growth factor antibody, an anti-CD20 antibody, an anti-CD52 antibody, an anti-CD11a antibody, and anti-IL-2 antibody.

Other suitable antibodies that can be introduced into the extracellular vesicles of the compositions described herein include, for example and without limitation, abciximab (Reopro), adalimumab (Humira, Amjevita), alefacept (Amevive), alemtuzumab (Campath), basiliximab (Simulect), belimumab (Benlysta), bezlotoxumab (Zinplava), canakinumab (Ilaris), certolizumab pegol (Cimzia), cetuximab (Erbitux), daclizumab (Zenapax, Zinbryta), denosumab (Prolia, Xgeva), efalizumab (Raptiva), golimumab (Simponi, Simponi Aria), inflectra (Remicade), ipilimumab (Yervoy), ixekizumab (Taltz), natalizumab (Tysabri), nivolumab (Opdivo), olaratumab (Lartruvo), omalizumab (Xolair), palivizumab (Synagis), panitumumab (Vectibix), pembrolizumab (Keytruda), rituximab (Rituxan), tocilizumab (Actemra), trastuzumab (Herceptin), secukinumab (Cosentyx), ustekinumab (Stelara). Additional anti-angiogenesis protein/peptide therapeutics include, without limitation, ramucirumab, axitinib, axitinib, MGCD516, cediranib, olaparib, lestaurtinib, olaparib, cediranib, pazopanib, docetaxel, pazopanib hydrochloride, TRC105, pazopanib, X4p-001, nivolumab, eribulin mesylate, ketoconazole, therapeutic hydrocortisone, antibody J591, docetaxel, plinabulin, SF1126, carfilzomib, hydroxychloroquine, aldesleukin, bevacizumab, erlotinib, sorafenib, vandetanib, durvalumab, olaparib, cediranib, sapanisertib, ziv-aflibercept, bevacizumab, LY2157299 monohydrate (LY2157299), temozolomide, SGT-53, cediranib maleate, olaparib, bevacizumabosimertinib, regorafenib, itraconazole.

In another embodiment, the therapeutic protein is an antibody mimetic.

An "antibody mimetic" encompasses any organic compound, e.g., a peptide or polypeptide, that can specifically bind an antigen like an antibody and is about 3-20 kDa. In one embodiment, the antibody mimetic comprises a scaffold which binds its target antigen via amino acids in exposed loops similar to the CDR loops of an antibody. These antibody mimetics include, without limitation, adnectins, lipocalins, Kunitz domain-based binders, avimers, knottins, fynomers, atrimers, and cytotoxic T-lymphocyte associated protein-4 (CTLA4)-based binders (reviewed in Weidle et al., "The Emerging Role of New Protein Scaffold-based Agents for the Treatment of Cancer," *Cancer Genomics & Proteomics* 10:155-168 (2013), which is hereby incorporated by reference in its entirety).

In another embodiment, the therapeutic protein is a protein or peptide inhibitor. Protein or peptide inhibitors can be full-length proteins or biologically active peptide fragments thereof which naturally antagonize or inhibit the action or activity of one or more receptors, enzymes, hormones, proteases, kinases, growth factors, signal transduction pathways, transcription factors, etc. that are associated with a disease or condition to be treated. The protein or peptide inhibitor may act as a dominant negative receptor or ligand, or a decoy receptor or ligand.

In one embodiment, the extracellular vesicles of the composition as described herein are modified to contain a protein or peptide inhibitor that is suitable for the treatment of an ocular disease. For example, the protein or peptide inhibitor may be an inhibitor of angiogenesis. Suitable protein/peptide inhibitors of angiogenesis include, without limitation, angiostatin, including full-length angiostatin and biologically active fragments and analogs thereof, and endostatin, including full-length endostatin and biologically active fragments and analogs thereof; other collagen derived peptides, such as tumstatin peptide, tumstatin fragment, and pentastatin; RGD containing peptides, such as Cilengitide, and other fibronectin derived peptides; and peptides derived from laminin, such as C16Y and C16S (see Rosca et al., "Anti-angiogenic Peptides for Cancer Therapeutics," *Curr. Pharm. Biotechol.* 12 (8): 1101-1116 (2011), which is hereby incorporated by reference in its entirety).

Other suitable protein or peptide inhibitors that can be loaded into the extracellular vesicles include, without limitation, integrin antagonists, e.g., LFA-1, VLA-4, Mac-1, ICAM-1, ICAM-2, VCAM antagonists, chemokine antagonists, e.g., MCP-1, MCP-5, MCP-3, MIP1α, CCR5, RANTES antagonists, and selectin antagonists, e.g., E-selectin, P-selectin, and L-selectin antagonists.

Other suitable protein or peptide inhibitors that can be loaded into the extracellular vesicles include, without limitation, anti-VEGF agents, Ranibizumab (Lucentis, Genentech, South San Francisco), aflibercept (Eylea, Regeneron Pharmaceuticals, Tarrytown, N.Y.), Lucentis, Bevacizumab (Avastin, Genentech), Corticosteroids, Intravitreal steroids, sustained-release biodegradable dexamethasone implant, Ozurdex (Allergan, Irvine, Calif.), Vitreolytics including Ocriplasmin (Jetrea, ThromboGenics, Leuven, Belgium), anti-PDGF therapies, RTH258, a small, humanized anti-VEGF antibody fragment that inhibits all isoforms of VEGF-A, anti-VEGF DARPin (abicipar pegol), the anti-PDGF agent Fovista (Ophthotech, New York), and Iluvien, a non-biodegradable implant indicated for DME that elutes the steroid fluocinolone acetonide.

The exogenous protein and/or peptide can be introduced into the vesicles by a number of different techniques. In one embodiment, the vesicles are loaded by electroporation or the use of a transfection reagent. Electroporation conditions may vary depending on the charge and size of the therapeutic cargo. Typical voltages are in the range of 20 V/cm to 1000 V/cm, such as 20 V/cm to 100 V/cm with capacitance typically between 25 μT and 250 μT, such as between 25 μT and 125 μT. A voltage in the range of 150 mV to 250 mV, particularly a voltage of 200 mV is preferred for loading vesicles with an antibody.

Alternatively, the vesicles may be loaded with exogenous protein and/or peptide using a transfection reagent. Despite the small size of the vesicles, conventional transfection agents may be used for transfection of vesicles with protein and/or peptide. Preferred transfection reagents for use in accordance with the present invention include cationic liposomes.

In another embodiment, extracellular vesicles may also be loaded by transforming or transfecting a host cell with a nucleic acid construct which expresses therapeutic protein or peptide of interest, such that the therapeutic protein or peptide is taken up into the extracellular vesicles as the vesicles are produced from the cell.

In another embodiment, the vitreous and/or aqueous humor vesicles are loaded with a therapeutic small molecule for delivery. In one embodiment, the small molecule is a small molecule used to treat ocular disease. Suitable ophthalmic therapeutic agents that can be loaded into the vitreous and/or aqueous humor extracellular vesicles included, without limitation, a carbonic anhydrase inhibitor, e.g., brinzolamide; a β adrenergic blocker, such as betaxolol, carteolol, levobunolol, metipranolol, timolol maleate, and timolol hemihydrate; an α2 adrenergic agonists, such as Apraclonidine, Lopindine, Brimonidine, and Alphagan; a prostaglandin, such as bimatoprost, loteprednol, and bromfenac; anti-infective agents such as antibiotics, anti-fungal agents, and anti-viral agents; T-cell immune suppression agents like cyclosporine, lipophilic steroids, and antibiotic and steroid combinations; small molecule tyrosine kinase inhibitors (TKI) such as sunitinib and sorafenib.

Additional therapeutics that can be loaded into the extracellular vitreous and/or aqueous humor vesicles for delivery to ocular tissues as described herein include, without limitation, Iquix (generic name: levofloxacin), natacyn (generic name: natamycin), tobrex (generic name: tobramycin), polytrim (generic name: polymyxin b/trimethoprim), ciloxan (generic name: ciprofloxacin), viroptic (generic name: trifluridine), moxeza (generic name: oxifloxacin), zymar (generic name: gatifloxacin), besivance (generic name: besifloxacin), vigamox (generic name: moxifloxacin), zirgan (generic name: ganciclovir), azasite (generic name: azithromycin), ak-chlor (generic name: chloramphenicol), ak-polybac (generic name: bacitracin/polymyxin b), ak-tob (generic name: tobramycin), betadine ophthalmic solution (generic name: povidone iodine), bleph-10 (generic name: sulfacetamide sodium), chloromycetin ophthalmic (generic name: chloramphenicol), chloroptic (generic name: chloramphenicol), dendrid (generic name: idoxuridine), eyemycin (generic name: erythromycin), garamycin ophthalmic (generic name: gentamicin), genoptic (generic name: gentamicin), gentacidin (generic name: gentamicin), gentak (generic name: gentamicin), gentasol (generic name: gentamicin), ilotycin (generic name: erythromycin), isopto cetamide (generic name: sulfacetamide sodium), neo-polycin (generic name: bacitracin/neomycin/polymyxin b), neocidin (generic name: acitracin/neomycin/polymyxin b), neocidin ophthalmic solution (generic name: gramicidin/neomycin/polymyxin b), neosporin ophthalmic (generic name: gramicidin/neomycin/polymyxin b), ocu-chlor (generic name: chloramphenicol), ocu-mycin (generic name: gentamicin), ocu-spore-b (generic name: bacitracin/neomycin/polymyxin), ocu-spore-g (generic name: gramicidin/neomycin/polymyxin b), ocu-tracin (generic name: bacitracin), ocuflox (generic name: ofloxacin), polycin-b (generic name: bacitracin/polymyxin b), quixin (generic name: levofloxacin), roymicin (generic name: erythromycin), sulf-10 (generic name: sulfacetamide sodium), terramycin with polymyxin b sulfate (generic name: oxytetracycline/polymyxin b), tobrasol (generic name: tobramycin), tomycine (generic name: tobramycin), vira-a (generic name: vidarabine), vitrasert (generic name: ganciclovir), zymaxin, atropine, azopt, bacitracin, betadine, betaxolol, betoptic, brinzolamide, bss (balanced salt solution), carbachol, cefazolin, celluvisc, chloramphenicol, ciloxan, ciprofloxacin, cosopt, demecarium, dexamethasone, dipivefrin, dorzolamide, epinephrine, fluorescein, flurbiprofen, physostimine, gentamicin, pilocarpine, goniosol, polymyxin b, gramicidin, prednisolone, humorsol, proparacaine, hylartin, propine, hypertonic nacl, puralube, indocycanine green, rose bengal, itraconazole, sodium hyaluronate, latanoprost, suprofen, mannitol, terramycin, methazolamide, timolol, miconazole, tobramycin, miostat, triamcinolone, muro 128, trifluridine, neomycin, tropicamide, neptazane trusopt, ocuflox, vidarabine, ofloxacin, vira-a, oxytetracycline, viroptic, phenylephrine, xalatan, NVC-422, FST-100, Luveniq, ESBA105, Mapracorat (ZK 245186/BOL-303242-X), Nepafenac 0.3%, DexaSite (or ISV-305), AzaSite Plus (or ISV-502), CF101, and Lifitegrast (SAR 1118).

Additional therapeutics that can be loaded into the extracellular vitreous and/or aqueous humor vesicles for delivery to ocular tissues for the treatment of glaucome as described herein include, without limitation, prostaglandin analogs include Xalatan® (latanoprost), Lumigan® (bimatoprost), travatan Z® (travoprost), and Zioptan™ (tafluprost), beta blockers such as timolol, alpha agonists [Alphagan®p (brimonidine), Iopidine®], carbonic anhydrase inhibitors inculding [Trusopt® (dorzolamide), Azopt® (brinzolamide)] as well as diamox (acetazolamide) and Neptazane® (methazolamide) and brinzolamide, combined medications including Cosopt®, and also as a preservative-free formulation (Cosopt® pf), combigan, Simbrinza®, Iopidine®, apraclonidine hydrochloride 0.5%, 1%, Alphagan®, brimonidine tartrate 0.1%, 0.15%, timolol maleate usp, timolol maleate 0.5%, Betoptic®, betaxolol hydrochloride 0.25%, 0.5%, Betagan®, levobunolol hydrochloride ophthalmic solution, usp 0.25%, 0.5%, Optipranolol®, metipranolol 0.3% Istalol® timolol maleate ophthalmic solution 0.5%, Timoptic-XE®, timolol maleate ophthalmic gel forming solution 0.25%, 0.5%, Betimol®, timolol hemihydrate 0.25%, 0.5%, Azopt®, brinzolamide ophthalmic suspension 1%, Neptazane®, methazolamide, Trusopt®, dorzolamide hydrochloride 2%, Diamox® Sequels®, acetazolamide, Isopto® carpine, pilocarpine hydrochloride 1%, 2%, 4%, Isopto® carbachol, 0.75%, 1.5%, 3%, pilopine HS® hydrochloride gel 4%, pilocarpine hydrochloride ophthalmic solution usp, pilocarpine hydrochloride 1%, 2%, 4%, Combigan™, brimonidine tartrate & timolol maleate, Cosopt®, dorzolamide hydrochloride & timolol maleate, Simbrinza® suspension, brinzolamide/brimonidine tartrate ophthalmic suspension 1%/0.2%, Travatan Z®, travaprost 0.004%, Lumigan®, bimatoprost 0.01%, 0.03%, Zioptan™, tafluprost ophthalmic solution 0.0015%, Xalatan®, latanoprost 0.005%, ROCK inhibitor, Y-27632, ATS907, ATS8535, AR-12286, AR-13324, AMA0076, BOL-303259-X.

Additional therapeutics that can be loaded into the extracellular vitreous and/or aqueous humor vesicles for delivery to ocular tissues for the treatment of dry eye include, without limitation, restasis ophthalmic, lacrisert ophthalmic, systane ultra ophthalmic, carboxymethylcellulose sodium ophthalmic, soothe xp ophthalmic, systane (propylene glycol) ophthalmic, freshkote ophthalmic, refresh optive advanced ophthalmic, genteal gel ophthalmic, retaine MGD (pf) ophthalmic, clear eyes itchy eye relief, systane balance ophthalmic, refresh tears, refresh liquigel ophthalmic, hypotears, clear eyes redness relief, bion tears (pf), peg 400-propylene glycol ophthalmic, refresh optive sensitive (pf) ophthalmicm, refresh plus ophthalmic, tears naturale free (pf), liquitears, cyclosporine ophthalmic, genteal pm ophthalmic, systane nighttime ophthalmic, genteal severe ophthalmic, systane gel ophthalmic, refresh lacri-lube ophthalmic, refresh p.m. ophthalmic, eye drops, isopto tears, puralube ophthalmic, theratears, polyvinyl alcohol ophthalmic, polyethylene glycol-polyvinyl alcohol eye, tears naturale pm, tears naturale forte, dextran 70-hypromellose ophthalmic, lubrifresh pm ophthalmic, lubricant eye drops, refresh celluvisc ophthalmic, carboxymethylcellulose-glycerin (pf) ophthalmic, lubricant eye (pg-peg 400), systane liquid gel ophthalmic, soothe hydration ophthalmic, refresh classic (pf) ophthalmic, refresh optive ophthalmic, systane ultra (pf) ophthalmic, systane (pf) ophthalmic, soothe lubricant ophthalmic, clear eyes complete ophthalmic, retaine pm ophthalmic, eye drops (with povidone), artificial tears (polyvinyl alcohol), visine totality ophthalmic, opti-clear ophthalmic, tetrahydrozoline-peg ophthalmic, moisture drops ophthalmic, tears again, tears pure, goniosoft ophthalmic, gonak ophthalmic, lubricating drops ophthalmic, polyvinyl alcohol-povidone ophthalmic, white petrolatum-mineral oil ophthalmic, artificial tears (hypromellose), genteal mild ophthalmic, goniotaire ophthalmic, tearfair for the eye, nature's tears, sterile eye drops, ultra fresh ophthalmic, ultra fresh pm ophthalmic, peg 400-hypromellose-glycerin ophthalmic, naphazoline-peg 300 ophthalmic, naphazoline-hypromellose ophthalmic, propylene glycol ophthalmic, all clear AR ophthalmic, propylene glycol-glycerin ophthalmic, pure and gentle eye, for sty relief ophthalmic, artificial tears (dextran-hypromellose-glycerin), sterile lubricant ophthalmic, hydroxypropyl cellulose ophthalmic, eye drops advanced relief, lubricant eye, light mineral oil-mineral oil ophthalmic, dry eye relief, redness relief ophthalmic, tetrahydralazine-dextran70-peg400-povdn ophthalmic, artificial tears with lanolin, eye lubricant combination no. 1, carboxymethylcellulose sod-hypromell ophthalmic, advanced eye relief, naphazoline-glycerin ophthalmic, genteal mild to moderate ophthalmic, artificial tears (hypromellose) (pf), carboxymethylcellulose-glycerin ophthalmic, lubricant redness reliever ophthalmic, artificial tears (glycerin/propylene glycol), naphazoline-zinc sulfate-glycerin ophthalmic, lubricant eye drops (glycerin-propylene glycol), redness reliever lubricant ophthalmic, goniovisc ophthalmic, advanced eye relief (mo-wpet) ophthalmic, refresh contacts ophthalmic, dextran 70-hypromellose (pf) ophthalmic, artificial tears (pf), natural tears (pf), tetrahydrozoline-peg 400-hypromglyc ophthalmic, lubricant eye (dextran 70/hypromellose), artificial tears (petrolatum/mineral oil), eye drop tears, povidone ophthalmic, peg 400-propylene glycol (pf) ophthalmic, polyvinyl alcohol-povidone (pf) ophthalmic, advanced formula eye drops, retaine cmc ophthalmic, light mineral oil-mineral oil (pf) ophthalmic, carboxymethylcellulose-glycerin-polysorb 80 ophthalmic, maximum redness relief ophthalmic, lubricant dry eye relief, eq gentle ophthalmic, carboxymethyl-glycerin-polysorb 80-pf ophthalmic, ultra lubricant eye, moisturizing lubricant ophthalmic, lubricating plus ophthalmic, revive plus ophthalmic, naphazo hcl-hyprome-ps 80-zn sulf ophthalmic, akwa tears (polyvinyl alcohol) ophthalmic, visine tears, visine tired eye relief, visine max redness relief, visine advanced redness relief, refresh optive advanced (pf) ophthalmic, tetrahydrozoline-zinc-peg 400-hypromello-glycerin ophthalmic, retaine hpmc ophthalmic, lubricant eye (propylene glycol) ophthalmic, lubricant eye (carboxymethylcellulose-glycerin) ophthalmic, lubricant eye (cmc-glycerin) (pf) ophthalmic, lubricant eye (pg-peg 400) (pf) ophthalmic, lubricating relief ophthalmic, lubricant gel ophthalmic, restore tears ophthalmic, lubricant plus ophthalmic, natural balance tears ophthalmic, clear eyes cooling comfort ophthalmic, clear eyes maximum redness relief ophthalmic, genteal tears ophthalmic, tears again (pva) ophthalmic, artificial tears (dextran 70-hypromellose) ophthalmic, artificial tears (polyvinyl alcohol/povidone) ophthalmic, artificial tears (pg400-hypromellose-glycerin) ophthalmic, genteal tears (dxtrn-hpm-gly) ophthalmic and Xiidra® (lifitegrast ophthalmic solution) 5% or any other percentage or combination.

In one embodiment, the vitreous and/or aqueous humor extracellular vesicles of the composition are further modified to express or display a eukaryotic cell-specific targeting molecule or moiety on the outer surface of the vesicular body. In one embodiment, the targeting moiety is a peptide which is expressed as a fusion protein with a transmembrane protein typically expressed on the surface of the extracellular vesicle. Suitable peptides are those which bind to cell surface moieties such as receptors or their ligands found on the cell surface of the cell to be targeted. Examples of suitable targeting moieties are short peptides (typically less than 100 amino acids in length, for example less than 50 amino acids in length, less than 30 amino acids in length, to a minimum length of 10, 5, 3, 2, or 1 amino acid(s)), full-length proteins, antibodies or antigen binding fragments and derivatives thereof (e.g., Fab, Fab', $F(ab')_2$, scFv, Fv, etc.), and complete proteins, so long as the targeting moiety can be expressed on the surface of the extracellular vesicle and does not interfere with insertion of the membrane protein into the extracellular vesicle. Typically the targeting peptide is heterologous to the transmembrane extracellular vesicle protein.

Targeting moieties can be selected to target the extracellular vesicle to a particular tissue type such as, for example, ocular, muscle, brain, liver, pancreas, lung, etc., or to target a diseased tissue such as a tumour. In a one embodiment of the present invention, the extracellular vesicles are targeted to ocular tissue.

In one embodiment, extracellular vesicles can be targeted to ocular tissues by expressing moieties or ligands recognized by ocular tissue influx transporters on the outer body surface of the extracellular vesicles. Several amino acid and peptide transporters are expressed on ocular tissue and cells. For example, the amino acid transporter ASCT1 (SLC1A4) is expressed in the cornea and primary corneal epithelial cells, and the amino acid transporter ASCT2 (SLC1A5) is expressed on retinal Muller cells. $B^{0,+}$ (SLC6A14) is a neutral and cationic amino acid transporter with broad substrate specificity expressed in corneal epithelium. Lat1 (SLC7A5) is expressed in human cornea, and LAT2 (SLC7A8) is expressed in retinal pigment epithelial cells. The peptide transporters, PEPT1 and PEPT2 are expressed in corneal epithelium and retinal Muller cells. Other than amino acid and peptide transporters, organic cation/anion (SLC22), monocarboxylate (SLC16), and nucleoside transporters (SLC 28 and 29) have also been identified on various ocular tissues. Accordingly, extracellular vesicles can be decorated with transporter-specific targeting moieties to direct delivery of the therapeutic cargo carried by the extracellular vesicle. Suitable targeting moieties include, without limitation, L-aspartate, gamma-glutamate, and phenylalanine to direct delivery via the $B(^{0,+})$ amino acid transporter (see e.g., Majumdar et al., "Transcorneal Permeation of L- and D-aspartate Ester Prodrugs of Acyclovir: Delineation of Passive Diffusion Versus Transporter involvement," *Pharm Res.* 26 (5): 1261-9 (2009), Anand et al., "Amino Acid Prodrugs of Acyclovir as Possible Antiviral Agents against Ocular HSV-1 Infections: Interactions with the Neutral and Cationic Amino Acid Transporter on the Corneal Epithelium," *Curr Eye Res.* 29 (2-3): 153-66 (2004), and Dun et al., "Functional and Molecular Analysis of D-serine Transport in Retinal Muller Cells," *Exp Eye Res.* 84 (1): 191-9 (2007), which are hereby incorporated by reference in their entirety); L-valine, Glycine-Valine, Valine-Valine, Tyrosine-Valine moieties to target delivery via oligopeptide transporters on the retina and cornea (see e.g., Anand and Mitra, "Mechanism of Corneal Permeation of L-valyl Ester of Acyclovir: Targeting the Oligopeptide Transporter on the Rabbit Cornea," *Pharm Res.* 19 (8): 1194-202 (2002), Gunda et al., "Corneal Absorption and Anterior Chamber Pharmacokinetics of Dipeptide Monoester Prodrugs of Ganciclovir (GCV): In vivo Comparative Evaluation of these Prodrugs with Val-GCV and GCV in Rabbits," *J Ocul Pharmacol Ther.* 22 (6): 465-76 (2006), Majumdar et al. "Dipeptide Monoester Ganciclovir Prodrugs for Treating HSV-1-induced Corneal Epithelial and Stromal Keratitis: In vitro and In vivo Evaluations," *J Ocul Pharmacol Ther.* 21 (6): 463-74 (2005), Katragadda et al., "Modulation of P-glycoprotein-mediated Efflux by Prodrug Derivatization: an Approach Involving Peptide Transporter-mediated Influx across Rabbit Cornea," *J Ocul Pharmacol Ther.* 22 (2): 110-20 (2006), Kansara et al., "Dipeptide Monoester Ganciclovir Prodrugs for Transscleral Drug Delivery: Targeting the Oligopeptide Transporter on Rabbit Retina," *J Ocul Pharmacol Ther.* 23 (4): 321-34 (2007), which are hereby incorporated by reference in their entirety), biotin to target delivery via the sodium-dependent multiple vitamin transporter on the retina (see e.g., Janoria et al., "Vitreal Pharmacokinetics of Biotinylated Ganciclovir: Role of Sodium-dependent Multivitamin Transporter Expressed on Retina," *J Ocul Pharmacol Ther.* 25 (1): 39-49 (2009), which is hereby incorporated by reference in its entirety) and glucose to target delivery to GLUT1 receptor on retinal pigment epithelial cells (see e.g., Dalpiaz et al., "Molecular Mechanism Involved in the Transport of a Prodrug Dopamine Glycosyl Conjugate," *Int J Pharm.* 336 (1): 133-9 (2007), which is hereby incorporated by reference in its entirety).

The peptide targeting moiety is expressed on the surface of the extracellular vesicles by expressing it as a fusion protein with an extracellular vesicle transmembrane protein. A number of proteins are known to be associated with extracellular vesicles; that is they are incorporated into the extracellular vesicle as it is formed. The preferred proteins for use in targeting the extracellular vesicles of the present invention are those which are transmembrane proteins. Examples include but are not limited to Lamp-1, flotillin, Syntaxin-3, CD9, CD63, CD81, HLA-DM (MHC II), immunoglobulins, MHC-I or MHC-II components, and tetraspanins.

In other embodiments, a specific targeting moiety does not need to be included in the extracellular vesicle. For example, extracellular vesicles may be administered directly to the site where therapy is required. Alternatively, delivery by, for example, periocular or intraocular administration may be sufficient to generate the desired response.

In some embodiments, particularly, where the extracellular vesicles of the composition are modified to contain an exogenous therapeutic agent, the composition further comprises a pharmaceutically acceptable carrier. A "pharmaceutically acceptable carrier" (excipient) is a pharmaceutically acceptable solvent, suspending agent or any other pharmacologically inert vehicle for delivering the extracellular vesicles of the composition to a subject. Typical pharmaceutically acceptable carriers include, but are not limited to, binding agents (e.g., pregelatinised maize starch, polyvinylpyrrolidone or hydroxypropyl methylcellulose, etc); fillers (e.g., lactose and other sugars, microcrystalline cellulose, pectin, gelatin, calcium sulfate, ethyl cellulose, polyacrylates or calcium hydrogen phosphate, etc); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc); disintegrates (e.g., starch, sodium starch glycolate, etc); or wetting agents (e.g., sodium lauryl sulphate, etc).

The compositions provided herein may additionally contain other adjunct components conventionally found in pharmaceutical compositions. Thus, for example, the compositions may contain additional compatible pharmaceutically-active materials or may contain additional materials useful in physically formulating various dosage forms of the composition of present invention, such as dyes, flavouring agents, preservatives, antioxidants, thickening agents and stabilizers. However, such materials, when added, should not unduly interfere with the biological activities of the components of the compositions provided herein.

In one embodiment, the composition of vitreous and/or aqueous humor extracellular vesicles is formulated in a slow or sustained release material. For example, in one embodiment, the composition can be formulated to include a thin film coating that slowly releases the extracellular vesicles of the composition to the target area or target tissue. The methods and materials that can be used to prepare coatings suitable for slow or sustained release coatings are well known to those skilled in the art. Suitable coatings should be both biocompatible and compatible with the extracellular vesicular composition. In one embodiment, the thin film is composed of bioabsorbable polymer(s). Examples of suitable bioabsorbable elastomers are described in U.S. Pat. No. 5,468,253 to Bezwada and 6,627,246 to Mehta. Useful polymers include mixtures of L-lactide, D-lactide, epsilon-caprolactone, and glycolide. The relative composition of these mixtures can be used to control the rate of coating hydrolysis and adsorption, the rate of extracellular vesicle release, and the strength of the film. Other polymeric materials that can be used to prepare thin films suitable for slow release include (but are not limited to) polyamides, polyalkylenes oxalates, poly(amino acids), copoly(ether-esters), poly(iminocarbonates), polyorthoesters, poly(anhydrides), and blends thereof. Naturally occurring polymers that can be degraded in the eye for slow release ocular compositions include hyaluronic acid, absorbable biocompatible polysaccharides such as chitosan or starch, fibrin, elastin, fibrinogen, collagen, and fatty acids (and esters thereof). In one embodiment, polymers containing the composition of extracellular vesicles can be applied to, for example, an implant, by spraying solutions containing dissolved polymer containing the composition of extracellular vesicles, to the surface to be coated or by dipping a portion of the implant in these solutions. Thin films typically provide sustained delivery for a few weeks until the therapeutic in the film is exhausted. The thickness will depend on how long delivery is desired and the concentration of extracellular vesicle loading. Typically, the thickness is 5-30 microns or less, though other thicknesses are allowed.

Another aspect of the present disclosure is directed to a method of delivering a therapeutic agent to select cells or tissue of a subject. This method involves providing the composition of vitreous humor extracellular vesicles and/or aqueous humor extracellular vesicles modified to contain a therapeutic agent, and administering the composition to the subject under conditions effective to deliver the composition comprising the vitreous and/or aqueous humor extracellular vesicles modified to contain the therapeutic agent to the select cells or tissue of the subject.

In accordance with this aspect of the present invention, suitable subjects include any mammalian subject. Typically, the subject is human, however, non-human mammals amenable to receiving the composition of extracellular vesicles as described herein include non-human primates, dogs, cats, rodents (e.g., mouse, rat, guinea pig), horses, cervids, cattle and cows, sheep, and pigs.

In one embodiment, the composition of extracellular vesicles is an autologous composition, i.e., the extracellular vesicles of the composition were isolated from ocular fluids, i.e., vitreous humor and/or aqueous humor of the same subject being administered the composition. In another embodiment, the composition is an allogenic composition where the donor subject that provided the ocular fluids containing the extracellular vesicles and the recipient subject to be treated are the same species but different individuals. In an alternative embodiment, the composition may be xenogenic. In this embodiment, the vitreous and/or aqueous humor vesicles are obtained from a donor subject that is a different species then the recipient species. For example, bovine extracellular vesicles may be isolated and modified to produce a composition suitable for treating a human subject.

In one embodiment, the subject being administered the composition of extracellular vesicles described herein is a subject having an ocular disease, and the administration of the composition delivers the therapeutic agent to the subject's ocular cells or tissue as a treatment for the ocular disease.

Ocular diseases that can be treated via administration of the compositions described herein include, without limitation, ocular degenerative diseases, such as dry macular degeneration, macular edema secondary to vascular disorders, retinitis pigmentosa, and wet macular degeneration; all forms of glaucoma, open-angle glaucoma (e.g., low tension and normal tension glaucoma), angle-closure glaucoma, congenital glaucoma, secondary glaucoma, neovascular glaucoma, pigmentary glaucoma, primary juvenile glaucoma, pseudoexfoliation glaucoma, irido corneal endothelial syndrome, and glaucoma of miscellaneous origin (e.g., glaucoma associated with intraocular tumors, retinal detachments, chemical burns, iris atrophy, and toxic glaucoma); inflammatory diseases, such as birdshot retinopathy, diabetic retinopathy, Harada's and Vogt-Koyanagi-Harada syndrome, iritis, multifocal choroiditis and panuveitis, pars planitis, posterior scleritis, sarcoidosis, retinitis due to systemic lupus, erythematosus, sympathetic ophthalmia, subretinal fibrosis, uveitis syndrome, white dot syndrome; ocular disorders associated with neovascularization, including age-related macular degeneration, angioid streaks, branch retinal vein occlusion, choroiditis, corneal trauma-related disorders, diabetes-related iris neovascularization, diabetic retinopathy, idiopathic choroidal neovascularization, pathologic myopia, retinal detachment, retinal tumors, retinopathy of prematurity, and sickle cell retinopathy; ocular infections associated with the choroids, retina, or cornea, such as, cytomegalovirus retinitis, histoplasma, retinochoroiditis, toxoplasma, retinochoroiditis, and tuberculous choroiditis; neoplastic diseases such as abnormal tissue growth in the retina, choroid, uvea, vitreous or cornea, choroidal melanoma, intraocular lymphoma of the choroids, vitreous, or retina, metastatic lesions, retinoblastoma, and vitreous seeding from retinoblastoma; and trauma, such as trauma resulting from injury or surgery or retinal damage resulting from exposure to laser or intense light.

Particular disorders of the corneal that are suitable for treatment using the methods and compositions described herein include corneal abrasion, corneal dystrophy, corneal ulcer, corneal neovascularization, fuchs' dystrophy, keratitis, keratoconus, allergic conjunctivitis, dry eye syndrome, dry eye, rheumatoid arthritis, sjögren's syndrome, problems following keratoplasty, corneal injury, allergies, bacterial keratitis, viral keratitis, herpes simplex virus (hsv) infections, and the varicella-zoster virus (vzv) causing herpes zoster, ophthalmicus, fungal keratitis (keratomycosis), protozoal keratitis, *acanthamoeba*, megalocornea, microcornea, cornea plana, keratoglobus, corneal opacities, marginal keratitis, rosacea, keratitis, ulcerative keratitis, pterygium, mooren's ulcer, dellen, phlyctenulosis, terrien's marginal degeneration, arcus *senilis*, vogt's limbal girdle, cornea guttata, lipid keratopathy, band keratopathy, spheroidal degeneration, salzmann's nodular degeneration, crocodile shagreen, fuchs' endothelial dystrophy, lattice dystrophy, map-dot-fingerprint dystrophy, pellucid marginal degeneration, keratoglobus, iridocorneal endothelial (ice) syndrome, exposure keratopathy, astigmatism, drug-induced keratopathies, thygeson's superficial punctate keratopathy, cystinosis, immunoprotein deposits, mucopolysaccharidoses, and wilson's disease.

Disorders of the conjunctiva that are suitable for treatment using the methods and compositions described herein include, but are not limited, to acute conjunctivitis, acute atopic conjunctivitis, acute chemical conjunctivitis, chronic allergic conjunctivitis, other chronic allergic conjunctivitis, adenoviral conjunctivitis, viral conjunctivitis, conjunctivochalasis, conjunctival hemorrhage, pingueculum, pingueculitis, serous conjunctivitis.

Corneal dystrophies that are suitable for treatment using the methods and compositions described herein include, but are not limited, endothelial (fuchs), granular, lattice, macular, other hereditary corneal dystrophies such as anterior basement membrane dystrophy and posterior polymorphous corneal dystrophy, avellino corneal dystrophy, macular corneal dystrophy, gelatinous drop-like dystrophy, schnyder corneal dystrophy, francois-neetans fleck dystrophy, congenital hereditary stromal dystrophy. Also included is corneal edema/opacity/degeneration, bullous keratopathy, corneal edema secondary to contact lens, diopathic corneal edema, secondary corneal edema, rupture in descemet's membrane, central corneal opacity, peripheral corneal opacity, other corneal scars and opacities, minor corneal opacity, arcus *senilis*, band keratopathy, keratomalacia, nodular corneal degeneration, peripheral corneal degeneration, keratoconus stable, keratoconus unstable, corneal ectasia, descemetocele, corneal transplant, corneal transplant rejection, corneal transplant failure, corneal transplant infection, other complications of corneal transplant. Also suitable for treatment using the methods and compositions described herein include, corneal foreign body/injury/laceration, corneal foreign body, conjunctival foreign body, burn of cornea and conjunctival sac, injury of conjunctiva and corneal abrasion without foreign body, ocular laceration and rupture with prolapse or loss of intraocular tissue, ocular laceration and rupture without prolapse or loss of intraocular tissue, contusion of eyeball and periocular tissues (e.g. traumatic hyphema), herpes simplex, herpes viral keratitis, herpes viral conjunctivitis, other herpes viral diseases, herpes zoster, zoster conjunctivitis, zoster keratitis, zoster scleritis, other herpes zoster, keratitis, central corneal ulcer, ring corneal ulcer, corneal ulcer with hypopyon, marginal corneal ulcer, mooren's corneal ulcer, mycotic corneal ulcer, perforated corneal ulcer, corneal abscess, filamentary, photokeratitis, punctate exposure keratoconjunctivitis keratoconjunctivitis, keratoconjunctivitis sicca, neurotrophic keratoconjunctivitis, sicca syndrome with keratoconjunctivitis, phlyctenular keratoconjunctivitis, interstitial keratitis (e.g. cogan syndrome), localized vascularization of cornea, dry eye, recurrent erosion of cornea, corneal disorder due to contact lens, sjogren's syndrome, sicca syndrome, pterygium, peripheral pterygium, stationary pterygium, progressive pterygium, recurrent pterygium.

Disorders of the lens including cataracts can also be treated with the methods and compositions described herein.

Neuro-ophthalmic conditions that can be treated with the methods and compositions described herein include, without limitation, blepharospasm, cranial nerve palsy, facial dystonias, giant cell/temporal arteritis, intracranial hypertension, ischemic optic neuropathy, multiple sclerosis, optic nerve tumors, optic neuritis. optic neuropathy, visual field defects and non-arteritic anterior ischemic optic neuropathy (naion).

Retinal diseases that can be treated with the methods and compositions described herein include, but are not limited to branch retinal vein occlusion, central retinal vein occlusion, central serous chorioretinopathy, choroidal detachment, complex retinal detachment, congenital x-linked retinoschisis, epiretinal membranes, familial exudative vitreoretinopathy, idiopathic juxtafoveal telangiectasis, infectious retinitis, intraocular lens dislocation, macular edema, macular hole, persistent fetal vasculature, polypoidal choroidal vasculopathy, posterior vitreous detachment, presumed ocular histoplasmosis syndrome, retained lens fragments, retinal artery occlusion, retinitis pigmentosa and retinal prosthesis, retinopathy of prematurity, river blindness/onchocerciasis, vitreomacular traction syndrome, retinoblastoma, macular pucker, macular hole, floaters, bietti's crystalline dystrophy, histoplasmosis, retinoblastoma, usher's syndrome.

Retinal disorders that can be treated with the methods and compositions described herein include, without limitation, diabetic retinopathy from diabetes mellitus type 1 with or without the following complications; without mention of complication, with mild non-proliferative retinopathy, with macular edema, with mild non-proliferative retinopathy, without macular edema, with moderate non-proliferative retinopathy, with macular edema, with moderate non-proliferative retinopathy, without macular edema, with severe non-proliferative retinopathy, with macular edema; with severe non-proliferative retinopathy, without macular edema, with proliferative retinopathy, with macular edema; with proliferative retinopathy, without macular edema. Diabetic retinopathy from diabetes mellitus type 2; without mention of complication, with mild non-proliferative retinopathy, with macular edema, with mild non-proliferative retinopathy, without macular edema, with moderate non-proliferative retinopathy, with macular edema, with moderate non-proliferative retinopathy, without macular edema, with severe non-proliferative retinopathy, with macular edema, with severe non-proliferative retinopathy, without macular edema, with proliferative retinopathy, with macular edema, with proliferative retinopathy, without macular edema. Other disorders of the retina include degeneration of macula and posterior pole type, nonexudative macular degeneration (dry), exudative macular degeneration (wet) macular cyst, hole, or pseudohole, central serous chorioretinopathy, cystoid macular degeneration (cme), puckering of macula (erm), drusen (degenerative) of macula, vitreomacular traction, cystoid macular edema following cataract surgery, degeneration of vitreous body type including vitreous hemorrhage, vitreous degeneration (e.g., pvd) vitreomacular adhesion (vmt), crystalline deposits in vitreous body, other vitreous opacities (e.g., vitreous oaters), other disorders of vitreous body, disorders of optic nerve type including, coloboma of optic disc, drusen of optic disc, ischemic optic neuropathy, optic papillitis, other optic atrophy, papilledema associated with increased intracranial pressure, primary optic atrophy, retrobulbar neuritis, endophthalmitis, other endophthalmitis, panophthalmitis (acute), panuveitis, purulent endophthalmitis, sympathetic uveitis. Hereditary retinal dystrophies, dystrophies primarily involving the retinal pigment epithelium, other dystrophies primarily involving the sensory retina (e.g., staargardt's disease), pigmentary (e.g., retinitis pigmentosa) dystrophies, vitreoretinal dystrophy, iridocyclitis, chronic iridocyclitis, lens induced iridocyclitis, primary iridocyclitis, recurrent acute iridocyclitis, secondary infectious iridocyclitis, secondary noninfectious iridocyclitis, amaurosis fugax, atrophy of globe (e.g., phthisis bulbi), cataract (lens) fragments in eye following cataract surgery degenerative myopia (e.g. malignant), diplopia (double vision), migraine with aura, not intractable; with status migrainosus migraine with aura, not intractable; without status migrainosus migraine with aura, intractable; with status migrainosus migraine with aura, intractable; without status migrainosus, ocular pain, ophthalmoplegic migraine, not intractable, ophthalmoplegic migraine, intractable, other abnormal glucose (e.g., prediabetes) other migraine, not intractable; with status migrainosus, other migraine, not intractable; without status migrainosus other migraine, intractable; with status migrainosus, other migraine, intractable; without status migrainosus, other long term (current) drug therapy, other visual disturbance (blurred vision), other subjective visual disturbances (e.g., visual halos) rheumatoid arthritis, sudden visual loss, transient visual loss, lupus erythematosus. macula scars of posterior pole (postin ammatory) (post-traumatic), solar retinopathy, chorioretinal inflammation, choroidal hemorrhage, choroidal rupture, benign neoplasm of choroid, chorioretinal scars after surgery for detachment, serous choroidal detachment, hemorrhagic choroidal detachment, hypertensive retinopathy, exudative retinopathy, retinal micro-aneurysms, unspecified retinal neovascularization, unspecified other non-diabetic proliferative retinopathy retinal hemorrhage, retinal edema (e.g., cotton wool spots) retinal ischemia, peripheral retinal degeneration type, lattice degeneration of retina, microcystoid degeneration of retina pavingstone, degeneration of retina, age-related reticular degeneration of retina, secondary vitreoretinal degeneration, retinal detachments, retinal detachment with single break, retinal detachment with multiple breaks, retinal detachment with giant retinal tear, retinal detachment with retinal dialysis, total retinal detachment, other retinal detachments, traction detachment of retina (e.g., PVR w/retinal detachment) unspecified, retinoschisis, other retinoschisis and retinal cysts, serous retinal detachment, serous retinal detachment, retinal tear type, retinal break, horseshoe tear of retina without detachment, round hole of retina without detachment, multiple defects of retina without detachment.

All types of retinal vascular occlusions can also be treated with the methods and compositions described herein, including central retinal artery occlusion (crao), retinal artery branch occlusion (brao), central retinal vein occlusion (crvo), tributary (branch) retinal vein occlusion (brvo), retinopathy of prematurity (ROP) type retinopathy of prematurity, ROP stage 0, retinopathy of prematurity, stage 1, retinopathy of prematurity stage 2, retinopathy of prematurity stage 3, retinopathy of prematurity stage 4, retinopathy of prematurity stage 5. Separation of retinal layers, including central serous chorioretinopathy (csr), serous detachment of retinal pigment epithelium, and hemorrhagic detachment of retinal pigment epithelium can also be treated in accordance with the methods and compositions described herein.

Disorders of choroid and retina that can be treated with the methods and EV compositions described herein include, without limitation, chorioretinal inflammation, focal chorioretinal inflammation, focal chorioretinitis, choroiditis, retinitis, retinochoroiditis, disseminated chorioretinal inflammation disseminated: chorioretinitis, choroiditis, retinitis, retinochoroiditis, exudative retinopathy, posterior cyclitis, pars planitis, other chorioretinal inflammations, harada's disease, chorioretinal inflammation, unspecified; chorioretinitis, choroiditis, retinitis, retinochoroiditis, chorioretinal scars, macula scars of posterior pole (postinflammatory) (post-traumatic), solar retinopathy, choroidal degeneration, choroidal atrophy, choroidal sclerosis, angioid streaks, hereditary choroidal dystrophy, choroideremia, dystrophy, choroidal (central areolar) (generalized) (peripapillary), gyrate atrophy, choroid ornithinaemia, choroidal haemorrhage and rupture, choroidal haemorrhage not otherwise specified, expulsive choroidal detachment, other specified disorders of choroid, chorioretinal disorders in diseases classified elsewhere, chorioretinal disorders in diseases classified elsewhere, chorioretinal inflammation in infectious and parasitic diseases classified elsewhere, chorioretinitis: syphilitic, late, toxoplasma, tuberculous, other chorioretinal disorders in diseases classified elsewhere, retinal detachments and breaks, retinal detachment, retinoschisis (including x-linked retinoschisis), retinal artery occlusion, retinal vein occlusion, hypertensive retinopathy, age-related macular degeneration, macular degeneration, epiretinal membrane, peripheral retinal degeneration, hereditary retinal dystrophy, retinitis pigmentosa, central serous retinopathy, retinal detachment, detachment of retinal pigment epithelium, other specified retinal disorders, macular edema, retinal disorder, unspecified, retinal disorders in diseases classified elsewhere.

Disorders of eyelid and lacrimal system and orbit that can also be treated with the methods and compositions as described herein include, without limitation, ectropion, lagophthalmos, blepharochalasis, ptosis, chalazion, hordioloum, xanthelasma of eyelid, parasitic infestation of eyelid in diseases classified elsewhere, dermatitis of eyelid due to demodex species, parasitic infestation of eyelid including, leishmaniasis, loiasis, onchocerciasis, phthiriasis, involvement of eyelid in other infectious diseases classified elsewhere. Involvement of eyelid in herpesviral (herpes simplex) infection, leprosy, molluscum contagiosum, tuberculosis, herpes zoster, involvement of eyelid in other diseases classified elsewhere, involvement of eyelid in impetigo, acryoadenitis, epiphora, dysthyroid exophthalmos, thyroid eye disease, Glaucoma disorders that can be treated with the methods and compositions as described herein include, but are not limited to, preglaucoma open angle with borderline findings, open angle, low risk, anatomical narrow angle primary angle closure suspect, steroid responder, ocular hypertension, primary angle closure without glaucoma damage (pas or high iop with no optic nerve or visual field loss), unspecified open-angle glaucoma, primary open-angle glaucoma, chronic simple glaucoma, low-tension glaucoma, pigmentary glaucoma, capsular glaucoma with pseudo-exfoliation of lens, residual stage of open-angle glaucoma, unspecified primary angle-closure glaucoma, acute angle-closure glaucoma attack, chronic angle-closure glaucoma, intermittent angle-closure glaucoma, residual stage of angle-closure glaucoma, glaucoma secondary to eye trauma, glaucoma secondary to eye inflammation, glaucoma secondary to other eye disorders including, retinal vascular occlusions, diabetes type 1 complicated, diabetes type 2 complicated, disorders of lens, disorders of intraocular lens, disorders after other ocular symptoms, neoplasms, benign neoplasms, or malignant. Also included is glaucoma secondary to drugs, glaucoma with increased episcleral venous pressure, hypersecretion glaucoma, aqueous misdirection malignant glaucoma, glaucoma in diseases classified elsewhere, congenital glaucoma, axenfeld's anomaly, buphthalmos, glaucoma of childhood, glaucoma of newborn, hydrophthalmos, keratoglobus, congenital glaucoma macrocornea with glaucoma, macrophthalmos in congenital glaucoma, megalocornea with glaucoma, absolute glaucoma. Also included are adverse effect of ophthalmological drugs and preparations, acute follicular conjunctivitis, adverse effect of carbonic anhydrase inhibitors, and adverse effect of under dosing of ophthalmological drugs and preparations.

Disorders of optic nerve that can be treated with the methods and compositions as described herein include, but are not limited to, glaucomatous optic atrophy, optic papillitis, retrobulbar neuritis, unspecified optic atrophy, primary optic atrophy, unspecified optic neuritis, other optic neuritis, pseudopapilledema of optic disc, unspecified papilledema, papilledema, ischemic optic neuropathy, disorders of optic chiasm, disorders of optic chiasm associated with other neoplasms, disorders of optic chiasm associated with vascular disorders, disorders of optic chiasm associated with inflammatory disorders, other disorders of optic nerve, compression of optic nerve, toxic optic neuropathy, nutritional optic neuropathy, hereditary optic atrophy, cortical blindness, granuloma of orbit (e.g. pseudotumor (inflammatory) of orbit), tonic pupil, benign neoplasm of pituitary gland, benign neoplasm of unspecified site of orbit, anisocoria, conversion disorder with sensory symptom, benign neoplasm of cerebral meninges, ocular pain, thyrotoxicosis with diffuse goiter with thyrotoxic crisis or storm (e.g. graves' disease, exophthalmic or toxic goiter not otherwise specified), thyrotoxicosis with diffuse goiter without thyrotoxic crisis or storm (e.g. graves' disease, exophthalmic or toxic goiter not otherwise specified), mydriasis, anisocoria, other specified disorders of binocular movement (e.g. skew deviation), convergence insufficiency internuclear ophthalmoplegia, other giant cell arteritis, tonic pupil, other subjective visual disturbances (e.g. visual halos), elevated erythrocyte sedimentation rate, cerebral infarction, (e.g. stroke) transient cerebral ischemic attack, malignant neoplasm of orbit, progressive external ophthalmoplegia, focal chorioretinal inflammation, juxtapapillary, acquired color vision deficiency, scotoma of blind spot, partial retinal artery occlusion (e.g. hollenhorst's), palsy (spasm) of conjugate gaze, diplopia (double vision) other strabismus type, esophoria, exophoria, vertical strabismus (e.g. hypertropia), palsies type, third ocular motor nerve, fourth ocular motor nerve, sixth ocular motor nerve, ptosis, congenital ptosis, mechanical ptosis, myogenic ptosis, paralytic ptosis, visual field disturbances, transient visual loss (e.g. scintillating scotoma), homonymous bilateral visual field defects, heteronymous bilateral field defects.

Disorders of the nervous system that can be treated with the methods and compositions as described herein include, but are not limited to, amaurosis fugax, horner's syndrome, blepharospasm, multiple sclerosis, transient cerebral ischemic attack, benign intracranial hypertension, ophthalmoplegic migraine, not intractable, ophthalmoplegic migraine, intractable, myasthenia gravis without (acute) exacerbation, myasthenia gravis with (acute) exacerbation, clonic hemifacial spasm.

Other conditions amenable to treatment with the composition of vitreous and/or aqueous humor extracellular vesicles modified to contain a therapeutic agent include as described herein, without limitation, hematological malignancies, cutaneous T-cell lymphoma, adult T-cell lymphoma/leukemia, pathologic fibrosis, cutaneous fibrosis, idiopathic pulmonary fibrosis, other fibrotic indications, neurodegeneration, ischemia, acute intermittent porphyria, solid cancer, liver cancer, adrenocortical carcinoma, pancreatic cancer, hypercholesterolemia, diabetic macular edema, acute nonarteritic anterior ischemic optic neuropathy, prevention of acute kidney injury, delayed graft function in kidney transplant recipients, familial amyloid polyneuropathy, advanced cancer, elevated triglycerides, amyotrophic lateral sclerosis, prostate cancer, myelodysplastic syndrome, Huntington's disease, elevated triglycerides/familial hypercholesterolemia, solid cancer, cystic fibrosis, ulcerative colitis, solid cancer, duchenne muscular dystrophy, hyperlipoproteinemia(a), hepatitis B infection, type 2 diabetes, allergen-induced asthma, asthma, atopic dermatitis, liquid cancer, myeloid leukemia, clotting disorders, pouchitis, familial chylomicronemia syndrome, familial partial lipodystrophy, familial amyloid polyneuropathy, prostate cancer, non small cell lung cancer, melanoma, triple negative breast cancer, rabies, RSV, HIV, influenza A, cardiovascular disease, zika, prostate cancer, multiple myeloma, acute myeloid leukemia, non-small cell lung cancer, renal cell carcinoma, solid cancer, Pachyonychia congenita, liver fibrosis, Primary hyperoxaluria type 1, hypertrophic scarring, severe hemophilia A or B, paroxysmal nocturnal hemoglobinuria, liver and lung disease, hemophilia and rare bleeding disorders, hypercholesterolemia, acutes hepatic porphyrias, complement mediated diseases, primary hyperoxaluria type 1, hereditary ATTR amyloidosis, hepatitis B and C virus infection, HCV, AMD/DME, AMD, NAION, Pachyonychia Congenita, FAP/colon cancer, PDAC, CML, AKI and DGF.

In accordance with this embodiment of the present disclosure, the extracellular vesicles of the composition are modified to contain one or more therapeutic agents that are suitable for treating the ocular disease. Suitable therapeutic agents, i.e., nucleic acid molecules (therapeutic RNAs and DNAs), protein and peptide therapeutics, and small molecule therapeutics are described supra. The selection of a suitable therapeutic for a particular ocular disease is well within the level of skill of a person of skill in the field of ophthalmology.

In accordance with this aspect of the present disclosure, the composition containing the vitreous and/or aqueous humor extracellular vesicles can be administered to a subject in need thereof using topical administration, systemic administration, periocular administration, or intraocular administration. The particular route of administration selected is dependent on the condition being treated and formulation of the composition.

In one embodiment, the composition is administered systemically. Systemic administration can be achieved via intravenous administration, oral administration, intraarterial administration, inhalation, intranasal administration, intraperitoneal administration, intra-abdominal administration, subcutaneous administration, intra-articular administration, intrathecal administration, transdural administration, transdermal administration, submucosal administration, sublingual administration, enteral administration, parenteral administration, percutaneous administration, periarticular administration, or intraventricular administration.

In another embodiment, the composition is administered locally. In one embodiment, the composition is administered locally to ocular tissue. As referred to herein, ocular tissue refers to the eye, including tissues within the sclera (e.g., the retina) and outside the sclera (e.g., ocular muscles within the orbit). Ocular tissue also includes tissues neurologically connected to (but distinct from) the eye, such as the optic nerve, the *geniculate* nucleus and the visual cortex. Local administration to ocular tissue can be achieved via intraocular administration. In accordance with this embodiment, intraocular administration can be carried out via intracameral administration, intravitreal administration, or subretinal administration.

In another embodiment, local administration to ocular tissue can be achieved via periocular administration. Periocular administration can be carried out via sub-conjunctival injection, sub-Tenon's injection, direct periocular injection, or depot periocular injection.

The target cells and/or tissue of the extracellular vesicles can include any desired cell and/or tissue type. In one embodiment, the target cells are ocular cells. Suitable ocular cells for delivery of the therapeutic agent via the extracellular vesicles as described herein include, without limitation, ciliary epithelium, pigmented ciliary epithelium, non-pigmented ciliary epithelium, ciliary processes, retinal cells including Müller cells, ganglion cells, amacrine cells, horizontal cells, photoreceptors (rods and cones) bipolar cells, retinal pigment epithelium or retinal endothelial cells, cells of the cornea including corneal epithelium, corneal stroma (keratocytes), corneal endothelium, or limbal stem cells, cells of iris including pigmented or non-pigmented cells, spindle shaped fibroblasts, macrophages (clump cells of Koganei), smooth muscle of the sphincter muscle, or posterior epithelium, trabecular meshwork cells including trabecular meshwork cells or endothelial cell lining of Schlemm's canal, cells of the lens including lens epithelium, anterior lens epithelial cell, crystallin-containing lens fiber cell, lens fibers, or lens capsule, cells of choroid including cuboidal epithelial cells, ependymal cell layer, choroid plexus epithelial cells, or choroidal endothelial cells, cells of the optic nerve including oligodendrocytes, retinal ganglion cell axons, or glial cells, stem and progenitor cells including mesenchymal stem cells, limbal stem cells, retina stem cells.

In another embodiment, the target cells and/or tissue of the extracellular vesicles carrying a therapeutic agent include non-ocular cells. Non-ocular target cells and tissue for therapeutic delivery using the extracellular vesicles as described herein include, without limitation, exocrine secretory cells and tissue including but not limited to, epithelial cells, salivary gland mucous cell (polysaccharide-rich secretion), salivary gland number 1 (glycoprotein enzyme-rich secretion), von ebner's gland cell in tongue (washes taste buds), mammary gland cell (milk secretion), lacrimal gland cell (tear secretion), ceruminous gland cell in ear (earwax secretion), eccrine sweat glandering dark cell (glycoprotein secretion), eccrine sweat gland clear cell (small molecule secretion), apocrine sweat gland cell (odoriferous secretion, sex-hormone sensitive), gland of moll cell in eyelid (specialized sweat gland), sebaceous gland cell (lipid-rich sebum secretion), bowman's gland cell in nose (washes olfactory epithelium), brunner's gland cell in duodenum (enzymes and alkaline mucus), seminal vesicle cell (secretes seminal fluid components, including fructose for swimming sperm), prostate gland cell (secretes seminal fluid components), bulbourethral gland cell (mucus secretion), bartholin's gland cell (vaginal lubricant secretion), gland of littre cell (mucus secretion), uterus endometrium cell (carbohydrate secretion), insolated goblet cell of respiratory and digestive tracts (mucus secretion), stomach lining mucous cell (mucus secretion), gastric gland zymogenic cell (pepsinogen secretion), gastric gland oxyntic cell (hydrochloric acid secretion), pancreatic acinar cell (bicarbonate and digestive enzyme secretion, paneth cell of small intestine (lysozyme secretion), type ii pneumocyte of lung (surfactant secretion), club cell of lung.

In another embodiment, the target cells and/or tissue of the extracellular vesicles carrying a therapeutic agent include hormone-secreting cells including but not limited to, anterior pituitary cells, somatotropes, lactotropes, thyrotropes, gonadotropes, corticotropes, intermediate pituitary cell, secreting melanocyte-stimulating hormone, magnocellular neurosecretory cells, nonsecreting oxytocin, secreting vasopressin, gut and respiratory tract cells, secreting serotonin, secreting endorphin, secreting somatostatin, secreting gastrin, secreting secretin, nonsecreting cholecystokinin, secreting insulin, secreting glucagon, nonsecreting bombesin, thyroid gland cells, thyroid epithelial cell, parafollicular cell, parathyroid gland cells, parathyroid chief cell, oxyphil cell, adrenal gland cells, chromaffin cells, secreting steroid hormones (mineralocorticoids and gluco corticoids), leydig cell of testes secreting testosterone, theca interna cell of ovarian follicle secreting estrogen, corpus luteum cell of ruptured ovarian follicle secreting progesterone, granulosa lutein cells, theca lutein cells, juxtaglomerular cell (renin secretion), macula densa cell of kidney, peripolar cell of kidney, mesangial cell of kidney, pancreatic islets (islets of langerhans), alpha cells (secreting glucagon), beta cells (secreting insulin and amylin), delta cells (secreting somatostatin), pp cells (gamma cells) (secreting pancreatic polypeptide), epsilon cells (secreting ghrelin).

In another embodiment, the target cells and/or tissue of the extracellular vesicles carrying a therapeutic agent include cells derived primarily from ectoderm including cells from the integumentary system, keratinizing epithelial cells, epidermal keratinocyte (differentiating epidermal cell), epidermal basal cell (stem cell), keratinocyte of fingernails and toenails, nail bed basal cell (stem cell), medullary hair shaft cell, cortical hair shaft cell, cuticular hair shaft cell; cuticular hair root sheath cell, hair root sheath cell of huxley's layer, hair root sheath cell of henle's layer, external hair root sheath cell, hair matrix cell (stem cell), wet stratified barrier epithelial cells, surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, urinary epithelium cell (lining urinary bladder and urinary ducts).

In another embodiment, the target cells and/or tissue of the extracellular vesicles carrying a therapeutic agent include nervous system cells including but not limited to sensory transducer cells, auditory inner hair cell of organ of corti, auditory inner hair cell of organ of corti, auditory outer hair cell of organ of corti, basal cell of olfactory epithelium (stem cell for olfactory neurons), cold-sensitive primary sensory neurons, heat-sensitive primary sensory neurons, merkel cell of epidermis (touch sensor), olfactory receptor neuron, pain-sensitive primary sensory neurons (various types), photoreceptor cells of retina in eye, photoreceptor rod cells, photoreceptor blue-sensitive cone cell of eye, photoreceptor green-sensitive cone cell of eye, photoreceptor red-sensitive cone cell of eye, proprioceptive primary sensory neurons (various types), touch-sensitive primary sensory neurons (various types), type i carotid body cell (blood ph sensor), type ii carotid body cell (blood ph sensor), type i hair cell of vestibular system of ear (acceleration and gravity), type ii hair cell of vestibular system of ear (acceleration and gravity), type i taste bud cell, autonomic neuron cells, cholinergic neural cell (various types), adrenergic neural cell (various types), peptidergic neural cell (various types), sense organ and peripheral neuron supporting cells, inner pillar cell of organ of corti, outer pillar cell of organ of corti, inner phalangeal cell of organ of corti, outer phalangeal cell of organ of corti, border cell of organ of corti, hensen cell of organ of corti, vestibular apparatus supporting cell, taste bud supporting cell, olfactory epithelium supporting cell, schwann cell, satellite glial cell (encapsulating peripheral nerve cell bodies), enteric glial cell, central nervous system neurons and glial cells, neuron cells (large variety of types, still poorly classified), interneurons, basket cells, cartwheel cells, stellate cells, golgi cells, granule cells, lugaro cells, unipolar brush cells, martinotti cells, chandelier cells, medium spiny neurons, cajal-retzius cells, double-bouquet cells, neurogliaform cells, spinal interneuron, renshaw cells, principal cells, spindle neuron, pyramidal cells, place cells, grid cells, speed cells, head direction cells, betz cells, stellate cells, boundary cells, astrocyte (various types), oligodendrocyte, ependymal cells, and tanycytes.

In another embodiment, the target cells and/or tissue of the extracellular vesicles carrying a therapeutic agent include cells derived primarily from mesoderm including but not limited to metabolism and storage cells, adipocytes, white fat cell, brown fat cell, liver lipocyte, barrier function cells (lung, gut, exocrine glands and urogenital tract), kidney, kidney parietal cell, kidney glomerulus podocyte, kidney proximal tubule brush border cell, loop of henle thin segment cell, kidney distal tubule cell, kidney collecting duct cell, principal cells, intercalated cells, other, type i pneumocyte (lining air space of lung cell), pancreatic duct cell (centroacinar cell), nonstriated duct cell (of sweat gland, salivary gland, mammary gland, etc.), principal cell, intercalated cell, duct cell (of seminal vesicle, prostate gland, etc.), intestinal brush border cell (with microvilli), exocrine gland striated duct cell, gall bladder epithelial cell, ductulus efferens nonciliated cell, epididymal principal cell, epididymal basal cell, endothelial cells.

In another embodiment, the target cells and/or tissue of the extracellular vesicles carrying a therapeutic agent include extracellular matrix cells including but not limited to ameloblast epithelial cell (tooth enamel secretion), planum semilunatum epithelial cell of vestibular system of ear (proteoglycan secretion), organ of corti interdental epithelial cell (secreting tectorial membrane covering hair cells), loose connective tissue fibroblasts, corneal fibroblasts (corneal keratocytes), tendon fibroblasts, bone marrow reticular tissue fibroblasts, other nonepithelial fibroblasts, pericyte, nucleus pulposus cell of intervertebral disc, cementoblast/cementocyte (tooth root bonelike ewan cell secretion), odontoblast/odontocyte (tooth dentin secretion), hyaline cartilage chondrocyte, fibrocartilage chondrocyte, elastic cartilage chondrocyte, osteoblast/osteocyte, osteoprogenitor cell (stem cell of osteoblasts), hyalocyte of vitreous body of eye, stellate cell of perilymphatic space of ear, hepatic stellate cell (ito cell), pancreatic stelle cell.

In another embodiment, the target cells and/or tissue of the extracellular vesicles carrying a therapeutic agent include contractile cells including but not limited to skeletal muscle cell, red skeletal muscle cell (slow), white skeletal muscle cell (fast), intermediate skeletal muscle cell, nuclear bag cell of muscle spindle, nuclear chain cell of muscle spindle, satellite cell (stem cell), heart muscle cells, ordinary heart muscle cell, nodal heart muscle cell, purkinje fiber cell, smooth muscle cell (various types), myoepithelial cell of iris, myoepithelial cell of exocrine glands.

In another embodiment, the target cells and/or tissue of the extracellular vesicles carrying a therapeutic agent include blood and immune system cells including but not limited to erythrocyte (red blood cell), megakaryocyte (platelet precursor), monocyte (white blood cell), connective tissue macrophage (various types), epidermal langerhans cell, osteoclast (in bone), dendritic cell (in lymphoid tissues), microglial cell (in central nervous system), neutrophil granulocyte, eosinophil granulocyte, basophil granulocyte, hybridoma cell, mast cell, helper T cell, suppressor T cell, cytotoxic T cell, natural killer T-cell, B-cell, natural killer cell, reticulocyte, stem cells and committed progenitors for the blood and immune system (various types), germ cells including but not limited to oogonium/oocyte, spermatid, spermatocyte, spermatogonium cell (stem cell for spermatocyte), spermatozoon, nurse cells including but not limited to ovarian follicle cell, sertoli cell (in testis), thymus epithelial cell, and interstitial cells including interstitial kidney cells.

In accordance with this aspect of the present disclosure, a subject is administered a therapeutically effective amount of the composition. A therapeutically effective amount is the amount effective to alleviate, inhibit, lessen, delay, and/or prevent at least one symptom or other aspect of the condition being treated. In another embodiment, a therapeutically effective amount is the amount effective to ameliorate the ocular condition being treated. The dose may be determined according to various parameters, especially according to the severity of the condition, age, and weight of the patient to be treated; the route of administration; and the required regimen. A physician will be able to determine the required route of administration and dosage for any particular patient. Optimum dosages may vary depending on the relative potency of the composition being administered, and can generally be estimated based on the half maximal effective concentration (EC50) found to be effective in in vitro and in vivo models. In general, dosage is from 0.01 mg/kg to 100 mg per kg of body weight. A typical daily dose is from about 0.1 to 50 mg per kg, preferably from about 0.1 mg/kg to 10 mg/kg of body weight, according to the potency of the specific construct, the age, weight and condition of the subject to be treated, the severity of the disease and the frequency and route of administration. Different dosages of the construct may be administered depending on whether administration is by systemic administration or local administration.

Due to therapeutic agent clearance (and breakdown of any targeted therapeutic molecule), the subject may have to be treated repeatedly, for example once or more daily, weekly, monthly or yearly. Persons of ordinary skill in the art can easily estimate repetition rates for dosing based on measured residence times and concentrations of the construct in bodily fluids or tissues. Following successful treatment, it may be desirable to have the patient undergo maintenance therapy, wherein the construct is administered in maintenance doses, ranging from 0.01 mg/kg to 100 mg per kg of body weight, once or more daily, monthly, yearly, etc.

Another aspect of the present disclosure is directed methods of making the composition comprising vitreous and/or aqueous humor extracellular vesicles as described herein. An exemplary method involves providing a mammalian ocular fluid sample comprising vitreous and/or aqueous humor fluids, and isolating vesicular bodies from the ocular fluid sample. The method further involves inserting the one or more exogenous therapeutic agents into the isolated vesicular bodies.

In one embodiment, the ocular fluid sample is a human ocular fluid sample. In another embodiment, the ocular fluid sample is a bovine ocular fluid sample. In another embodiment the ocular fluid sample is non-human mammalian ocular fluid sample, such as an ocular fluid sample obtained from a non-human primate, dog, cat, rodent, deer, sheep, pig, etc.

In one embodiment, the ocular fluid sample is a healthy, normal ocular fluid sample. In another embodiment, the ocular fluid sample is a diseased ocular fluid sample, or obtained from a subject having an ocular disease or condition. Ocular fluid samples can be obtained using methods known in the art and described herein. In one embodiment, the ocular fluid sample is obtained via vitreous biopsy or an aqueous humor biopsy or aspiration.

Suitable methods of isolating extracellular vesicles from ocular fluids are described herein. In one embodiment, the method of isolating extracellular vesicles involves a series of centrifugation steps. As referred to herein, "ocular fluid" includes, without limitation, fluid from the vitreous humor, fluid from the aqueous humor, or any ocular fluid sample comprising the vitreous and/or aqueous humor fluid.

As described herein, the extracellular vesicles isolated from the aqueous humor and/or vitreous humor are modified to contain one or more exogenous agents. Methods of inserting the exogenous agent(s) into the extracellular vesicles can be achieved as described herein using methods and techniques readily known and practiced in the art, including, without limitation, electroporation, transfection, viral-vector delivery, or any combination thereof.

In one embodiment, the endogenous contents of the isolated extracellular vesicles are removed prior to inserting the one or more exogenous agents. Methods of removing the endogenous contents of the extracellular vesicles can be achieved using ultraviolet radiation. Other methods known in the art for emptying the contents of vesicular bodies are also suitable for use in accordance with this aspect of the present disclosure.

Another aspect of the present disclosure is directed to a method of identifying, detecting, diagnosing, monitoring, or prognosing an ocular disease in a subject. This method involves providing an ocular fluid sample that comprises vitreous and/or aqueous humor fluids from the subject, and isolating extracellular vesicles from the ocular fluid sample. This method further involves analyzing at least one molecular or physical property of the isolated extracellular vesicles, and comparing the at least one analyzed molecular or physical property of the isolated vesicular bodies to the molecular or physical property in isolated vesicular bodies obtained from a reference sample. The presence or absence of an ocular disease is identified, detected, or diagnosed based on that comparison. Alternatively, the comparison provides information regarding the progression or prognosis of the ocular disease or condition. A comprehensive list of ocular conditions that can be detected, diagnosed, and monitored based on the molecular and/or physical properties of the vitreous and/or aqueous humor extracellular vesicles is provided supra.

Described herein is the discovery of an extensive extracellular vesicle network in the normal, healthy vitreous humor and aqueous humor. A comprehensive proteomic analysis has been conducted to characterize the normal, healthy proteome of this extracellular vesicular network. Changes in this proteomic signature can be utilized as a means to identify, detect, diagnose, prognose, and/or monitor changes in ocular health in an individual. Similarly, other molecular properties of the isolated extracellular vesicles, such as, gene expression and lipid content of the extracellular vesicles in the sample obtained from normal, healthy ocular fluid can also be obtained, and utilized as reference values to track changes in ocular health of an individual overtime. Changes in gene expression and/or lipid content of the extracellular vesicles can be used to identify, detect, diagnose, prognose, and/or monitor changes in ocular health in an individual.

Accordingly, in one embodiment, an ocular fluid sample comprising aqueous and/or vitreous humor fluid is obtained from a healthy subject and the extracellular vesicles contained therein are isolated or purified. A proteomic, genomic, or lipid analysis is carried out to determine the subject's baseline or reference protein or gene expression signature or lipid content. Subsequently, a second ocular fluid sample comprising the aqueous and/or vitreous humor fluid is obtained, the extracellular vesicles of the aqueous humor and/or vitreous humor are isolated, and a protein expression, gene expression, and/or lipid content profile of the extracellular vesicles is determined. The second ocular fluid sample can be collected from the subject at any time after the first sample was collected. In one embodiment, the second sample is collected at or about the time the subject is experiencing one or more symptoms of an ocular condition. In other embodiment, the second sample is collected at a time that the subject has not yet experienced or exhibited any change in ocular health. The protein expression, gene expression, and/or lipid content of the first collected sample is compared to the protein expression, gene expression and/or lipid content of the second collected sample, respectively, to detect changes to one or more factors, i.e., protein expression, gene expression, and/or lipid content. Any changes in protein expression, gene expression, or lipid content are correlated to known changes in one or more ocular conditions to identify, detect, diagnose, and/or prognose the ocular health for the individual.

In another embodiment, changes in protein expression, gene expression, and/or lipid content are monitored in extracellular vesicle samples obtained from the aqueous and/or vitreous humor of a subject over time as a means of tracking progression (or lack of progression) of an ocular condition. In another embodiment, changes in protein expression, gene expression, and/or lipid content are monitored in extracellular vesicle samples obtained from the aqueous and/or vitreous humor of a subject over time as a means of tracking or monitoring the effectiveness of a therapeutic intervention. Changes in protein or gene expression or lipid content overtime may indicate the effectiveness of the therapeutic intervention. Likewise, little or no change in protein or gene expression or lipid content over time may serve as an early indicator that the selected therapeutic intervention is ineffective in the monitored individual. Such a finding may warrant a modification to the therapeutic intervention to improve effectiveness and treatment.

In addition to tracking and/or monitoring changes in one or more molecular properties, such as protein expression, gene expression, and/or lipid content for diagnostic, prognostic, or related purposes, one or more physical properties of the extracellular vesicles derived from the vitreous and/or aqueous humor can be monitored in conjunction with or as an alternative to the one or more molecular properties. Suitable physical properties of the extracellular vesicles that can be measured and monitored include, without limitation, extracellular vesicle size, quantity, shape, and morphology. Methods of measuring such physical properties of extracellular vesicles derived from the vitreous and/or aqueous humor sample are described herein.

The time between obtaining a first ocular extracellular vesicle sample and a second, or any additional subsequent ocular extracellular vesicle samples can be any desired period of time, for example, weeks, months, years, as determined is suitable by a physician and based on the characteristics of the ocular condition. In one embodiment, the first sample is obtained before treatment and the second sample is obtained after treatment. Alternatively, both samples can be obtained after one or more therapeutic treatments; the second sample being obtained at some point in time later than the first sample.

EXAMPLES

The examples below are intended to exemplify the practice of the present invention but are by no means intended to limit the scope thereof.

Materials and Methods for Examples

Tissue preparation and processing from post mortem samples. Post-mortem human eyes without disease were obtained (The Eye-Bank for Sight Restoration, New York, NY). Bovine eyes were acquired from a local butcher shop (Green Village Packing, Green Village, New Jersey). For dissection procedures, eyes were placed in a 100 mm plastic petri dish on ice to prevent RNA and protein degradation. Using a SZX-16 stereo dissecting microscope (Olympus) orbital fat and extraocular muscles attached to the globe were removed. The globe was rinsed with 5 ml of ice-cold Tris Buffered Saline (TBS) containing 50 mM Tris-HCl, 150 mM NaCl and the pH adjusted to 8.0 for 1 minute at 4° C. Vitreous was dissected by making an sclerotomy incision 4 mm or 8 mm posterior to the limbus (human and bovine eye, respectively) using a 16g needle and then making a circumferential sagittal incision with scissors to separate the globe into an anterior and posterior cup. Scissors were used to cut and remove the formed vitreous and to sever adhesions between vitreous and ocular structures. Care was taken to avoid vitreous contamination of choroid melanocytes and the neural retina. Other ocular tissues including choroid, retina, ciliary body, lens and cornea were identified and dissected. Tissue samples were rinsed with TBS (pH 8.0) for 1 min at 4° C. Specimens collected for electron microscopy and EV isolation were processed immediately without fixation as described below. Samples used for immunohistochemistry, western blot, or EDC-formalin fixation were placed in 15 ml centrifuge tubes and immersed in 10 ml of 4% formalin (also known as formaldehyde, paraformaldehyde, or PFA) diluted in TBS (pH 8.0) for at least 24 h at 4° C. Tissues that were "formalin only," were washed three times in TBS (pH 8.0) for 5 min at 4° C. and not further processed or fixed with EDC. Formalin only tissues were used for immunohistochemistry, western blot or nucleic acid, and protein imaging. EDC-formalin fixed specimens were processed further as described below.

Human subject surgical vitreous specimen collection. Institutional Review Board (IRB) approval was obtained from Weill Cornell Medicine, and protocols were in accordance with NIH guidelines, the Healthcare Insurance Portability and Accountability Act, and the tenets put forth by the Declaration of Helsinki. Informed consent was obtained from all subjects. Subjects were patients who were undergoing vitrectomy for an existing medical condition. Methods for vitreous biopsy were previously described (Malecaze et al., "Detection of Vascular Endothelial Growth Factor Messenger RNA and Vascular Endothelial Growth Factor-like Activity in Proliferative Diabetic Retinopathy," *Arch Ophthalmol* 112:1476-1482 (1994), which is hereby incorporated by reference in its entirety). Briefly, at the beginning of pars plana vitrectomy, 0.5-1 ml of un-dilute vitreous (which is removed during vitrectomy surgery for medical purposes) was collected using the vitrectomy probe connected to a sterile 3-mL syringe for aspiration. All samples were de-identified and coded. The vitreous specimen was immediately placed on ice and transferred to the laboratory for TEM or vitreous vesicle isolation as described below.

EDC-formalin tissue fixation. Methods for EDC-formalin fixation were adapted from previous reports (Valadi et al., "Exosome-mediated Transfer of mRNAs and MicroRNAs is a Novel Mechanism of Genetic Exchange Between Cells," *Nat Cell Biol* 9:654-659 (2007); Suzuki et al., "DNA Staining for Fluorescence and Laser Confocal Microscopy," *J Histochem Cytochem* 45:49-53 (1997), which are hereby incorporated by reference in their entirety). A piece of vitreous (1 cm×1 cm) was isolated as described and examined under the microscope to ensure the sample was free of contaminating tissues like retina or choroid. The tissue was placed into a 100 mm plastic petri dish and washed two times in 5 ml of TBS (pH 8.0) for 5 min at 4° C. The sample was immersed in 5 ml of 4% formalin diluted in TBS (pH 8.0) for 24 h and stored in a humidified chamber at 4° C. The samples were washed three times in ice-cold TBS (pH 8.0) for 5 min at 4° C. To remove residual phosphate from the tissue, the sample was incubated in 10 ml of a freshly prepared 0.1 M 1-Methylimidazole buffer solution (0.1 M 1-methylimidazole, 300 mM NaCl, with an adjusted pH to 8.0 with 12 N NaOH) for 30 min at 4° C. Next, the EDC fixation solution was prepared. First, 9.6 ml of 0.1 M 1-Methylimidazole buffer solution was made and 130 mg of 5-(Ethylthio)-1H-tetrazole (ETT, Sigma Aldrich, final concentration was 0.1 M) was added. The pH was adjusted to 8.0 with 12 N NaOH. Next, 192 mg of 1-ethyl-3-(3-dimethylaminopropyl) carbodiimide (EDC) (Sigma Aldrich, final concentration 0.10 M) was added to the 1-Methylimidazole-ETT solution. The pH of the solution was readjusted as needed by addition of 12 M HCl to pH 8.0. The piece of vitreous tissue (1 cm×1 cm) was then transferred to a 35 mm plastic petri dish and 2 ml of EDC fixation solution was added. The samples were then placed in a humidified chamber and specimens were incubated for 3 h at 37° C. After incubation, the EDC-ETT solution was removed and specimens were washed in 5 ml of 0.2% (w/v) glycine diluted in TBS (pH 7.4). The samples were washed twice in TBS (pH 7.4). Finally, the samples were stained for DNA, RNA, and protein as described below.

Staining for DNA, RNA and protein. Vitreous tissues fixed with 4% formalin only or EDC-formalin as described above were stained. Tissues were then immersed with various dyes to label DNA, RNA or proteins. To mark DNA, a dissected piece of vitreous (1 cm×1 cm) was placed in a 35 mm petri dish and immersed with 1 ml of 0.5 μg/ml of Hoechst 33342 Stain Solution (Sigma Aldrich). Samples were incubated at 37° C. for 15 min at room temperature and then tissues were washed with 5 ml of 1×TBS (pH 7.4) for 3 min at room temperature. Wash steps were repeated twice. Samples were stained with secondary marker or mounted for imaging. To label both DNA and RNA with a single dye, propidium iodide (PI, Sigma Aldrich) was used, which intercalates between DNA bases and also binds to RNA, with less affinity (Le Goff and Bishop, "Adult Vitreous Structure and Postnatal Changes," *Eye* (Lond) 22:1214-1222 (2008), which is hereby incorporated by reference in its entirety). It was found that a solution of 50 μg/ml of PI diluted in TBS (pH 7.4) was the optimal concentration of PI for co-staining DNA and RNA in whole mounted vitreous samples. Therefore, tissues were placed in a 35 mm petri dish and then immersed in 1 ml solution 50 μg/ml of PI (diluted in TBS) for 24 h at 37° C. in a humidified chamber. Samples were washed with TBS (pH 7.4) three times. Samples were stained with another marker or mounted for imaging. To differentiate between DNA and RNA, all tissues were co-stained with Hoechst 33342 Stain Solution. Hoechst has a strong affinity for DNA and does not label RNA. For Hoechst and PI stained samples, the RNA signal was determined by excluding the Hoechst signal. To label cellular and extracellular proteins in whole mount vitreous, the cell permeable and electron dense stain carboxyfluorescein succinimidyl ester (CFSE, Sigma Aldrich) was used, which covalently links to intracellular amines (Ikeda et al., "Extraction and Analysis of Diagnostically Useful Proteins From Formalin-fixed, Paraffin-embedded Tissue Sections," *J Histochem Cytochem* 46:397-403 (1998), and Tkach and Thery, "Communication by Extracellular Vesicles: Where We Are and Where We Need to Go." *Cell* 164:1226-1232 (2016), which are hereby incorporated by reference in their entirety). Vitreous tissues were placed in a 35 mm plastic petri dish and then tissues were immersed in 1 ml of 500 μM CFSE diluted in TBS (pH 7.4) and samples were incubated at 37° C. for 24 h in a humidified chamber. After incubation, the CFSE solution was removed and the tissues were placed in a 100 mm plastic petri dish. The tissues were washed in 5 ml of 0.2% (w/v) glycine diluted in TBS (pH 7.4) for 30 min at room temperature. Next, tissues were washed in 10 ml of TBS (pH 7.4) for 5 min at room temperature and wash steps were repeated twice. Finally, samples were counter-stained with Hoescht and or PI as described. After staining with the respective dye(s), the samples were then mounted in custom chambers for imaging on the multiphoton, confocal or wide-field fluorescent microscope as described below.

RNAse digestion of extracellular RNA in situ. Vitreous tissues were fixed with EDC-formalin and immersed with 2 ml of RNAse buffer (consisting of 50 mM Tris-Cl, pH 8.0, 10 mM EDTA) containing 100 μg/mL RNase A (Sigma Aldrich), and then incubated at 42° C. for 16 hr. Next, the RNAse solution was removed, samples washed, and stained with PI (described above), and imaged with wide-field fluorescent microscopy.

Light microscopy, confocal microscopy, and image processing. Color bright field images were captured on a Nikon eclipse an upright e600 microscope (Nikon) equipped with an Axiocam 105 color camera (Zeiss), and images were processed with Zen software (Zeiss, version 4.3). Tissues were mounted on a 60 mm glass bottom dish (20 mm viewing area, MatTek) for fluorescent imaging studies. An Axio Observer Z1 inverted microscope (Zeiss) was used with the following filter sets: Ziess filter set 49 (Ziess) for Hoechst; Ziess filter set 38 (Ziess) for Alexa 488, green fluorescent protein (GFP), and fluorescein; and Ziess filter set 45 (Ziess) for PI. Confocal imaging was conducted with Zeiss LSM880 microscope using the 25×/0.8 NA lens. Images were captured and processed using imageJ software.

Multiphoton imaging. Bovine eyes were dissected as described above and vitreous was cut into sections that were approximately 1 cm×1 cm. Tissues were fixed with EDC-formalin or formalin only as described. DNA, RNA, and/or protein were labeled with Hoechst, PI and/or CSFE as described above. Whole mount vitreous tissue was mounted on a specialized chamber made of silicone and a glass coverslip, and was placed on top of the chamber. The coverslip was immersed in 1 ml of 1×TBS and then imaged using MPM (Olympus FV1000MPE, using a specialized 25×/1.05 NA water immersion objective, Weill-Cornell Medicine Imaging Core Facility). The vitreous was then imaged in sectors. The images were captured, z-stacks were assembled, and a 2-dimensional reconstruction was constructed (Fiji software (Schneider et al., "NIH Image to ImageJ: 25 years of image analysis," *Nat Methods* 9:671-675 (2012), which is hereby incorporated by reference in its entirety) and Imaris software (Bitplane), 6-regions imaged per vitreous, n=3). The data was analyzed for staining of extracellular protein. EVs and vitreous cells were measured and counted.

Defining vitreous cells and extracellular vessels. The goal was to identify extracellular vesicles (EV) and extracellular RNA in the vitreous tissue. To do this, vitreous cells (presumed hyalocytes) and EVs were differentiated by the following method. Multiphoton or confocal images of EDC-formalin fixed bovine vitreous co-stained with Hoechst and CFSE were obtained as described above. Using these images, vitreous cells were identified by identifying the nuclei using the Hoechst signal and then the cell bodies were identified by using the CFSE signal. The diameter of the cell bodies was then measured from over 100 cell diameters (n=3 biological samples, 6 image frames per sample) using ImageJ software (Schneider et al., "NIH Image to ImageJ: 25 years of image analysis," *Nat Methods* 9:671-675 (2012), which is hereby incorporated by reference in its entirety). The average vitreous cell body diameter and standard deviation (SD) was calculated and the data was presented graphically. It was found that the average vitreous cell size was 10.5 μm±1.77 μm and normally distributed. Thus, an upper limit diameter of 2 SD above the mean (14 μm) would encompass approximately 97.5% of cells. Therefore, in ImageJ software, a 14 μm circle centered on the nuclei was drawn, and considered positive signal within this circle as intracellular protein. Signal outside this 14 μm circle was considered to be extracellular. Two independent and blinded research assistants were used to count EVs. The criteria for counting EVs included round shape, location outside of the cell radius, and size larger than 100 nm and smaller than cells. The data was normalized by dividing the number of EVs counted per frame, by the number of cells in the frame. The data is represented graphically. The size of bovine vitreous EVs was also measured using similar techniques (n=4, and 3 biological replicates).

Electron microscopy of vitreous humor, aqueous human, and ocular tissues. Human or bovine vitreous tissue was obtained as above. Samples were cleared of cells with low speed centrifugation and whole mount specimens tested with H and E staining and imaging as described below. For vitreous, 2 μL was pipetted onto a block and fixed in a solution of 2.5% glutaraldehyde, 4% paraformaldehyde, 0.02% picric acid in 0.1M sodium cacodylate buffer and incubated at room temperature for 60 min (Raposo et al., "B Lymphocytes Secrete Antigen-presenting Vesicles," *J Exp Med* 183:1161-1172 (1996), which is hereby incorporated by reference in its entirety). Specimens were washed with excess volume of buffer (pH 7.3) for 5 minutes each at room temperature. Samples were post-fixed with 1% $OsO_4$-1.5% K-ferricyanide (aqueous) for 60 min at room temperature (Griffith and Hay, "Epithelial-mesenchymal Transformation During Palatal Fusion: Carboxyfluorescein Traces Cells at Light and Electron Microscopic Levels," *Development* 116:1087-1099 (1992), which is hereby incorporated by reference in its entirety). Samples were washed with buffer 3 times for 5 min each at room temperature. Samples were set en bloc and stained with 1.5% uranyl acetate for 60 min at room temperature. Samples were dehydrated through graded ethanol series and transitioned through acetonitrile. Specimens were infiltrated and embedded in Embed 812 resin (Electron Microscopy Sciences). Tissue sections cut at 60-65 nm using a Diatome diamond knife (Diatome) on Leica Ultracut T ultramicrotome (Leica Microsystems). Sections were contrasted with lead citrate (Dragovic et al., "Sizing and Phenotyping of Cellular Vesicles Using Nanoparticle Tracking Analysis," *Nanomedicine* 7:780-788 (2011), which is hereby incorporated by reference in its entirety) and viewed on a JEM 1400 electron microscope (JEOL, USA, Inc) operated at 100 kV. Digital images were captured on a Veleta 2K×2K CCD camera (Olympus-SIS). Electron microscopy images were recorded and analyzed for size and frequency using ImageJ software.

For TEM visualization of whole mounts of extracellular vesicles from human or bovine vitreous were obtained after ultracentrifugation, re-suspended in formaldehyde, loaded on Formwar/carbon-coated EM grids, postfixed in 1% glutaraldehyde, and contrasted successively in 2% uranyl acetate, pH 7, and 2% methylcellulose/0.4% uranyl acetate, pH 4, or acridine orange or CFSE.

Extracellular vesicle isolation and purification. Methods for isolating extracellular vesicles from fluids (van der Pol et al., "Recent Developments in the Nomenclature, Presence, Isolation, Detection and Clinical Impact of Extracellular Vesicles,". *J Thromb Haemost* 14:48-56 (2016), which is hereby incorporated by reference in its entirety) were adapted. For this study, the goal was to have vitreous specimens free of cells. The vitreous was therefore cleared with a series of low-speed centrifugations. Approximately 8 ml of vitreous was placed in 15 ml tubes and centrifuged in Sorvall legend RT Swinging bucket (Sorvall) at 2,000 g (2500 rpm) at 4° C. for 30 minutes. The supernatant was then transferred to a new 15 ml tube. Then the centrifugation step was repeated. The supernatant was then transferred to new tube and centrifuged at 10,000 g in a Sorvall RC-58 centrifuge (Sorvall) using an SS-34 rotor (DuPont) for 30 min at 4° C. For each aliquot of vitreous or aqueous humor, whole mount hematoxylin and eosin staining (H and E) was conducted to survey for cells as described below (FIG. 11). Whole mount slides were then imaged and all cell free samples were further processed. The supernatant was then transferred and the step was repeated. The sample was transferred to an ultracentrifuge tube (Beckman) and in a swinging bucket rotor (SW-41, Beckman) and centrifuged at 100,000 g in an L7-55 ultracentrifuge (Beckman) at 4° C. for 1 hour. The supernatant was transferred to a new tube. The step was repeated. Samples were resuspended in 50 μl of sterile phosphate buffered saline (PBS, pH 7.5) and placed in a siliconized tube. Samples for imaging were immediately processed, and remaining sample was frozen at −80° C.

Vitreous histochemical staining to confirm acellularity of samples. To optimize vitreous EV isolation techniques, histochemical stains were applied after low-speed centrifugation to exclude vitreous samples contaminated by cells. Vitreous samples were dissected and collected as above. Acellularity was confirmed by whole mounting centrifuged vitreous onto glass slides and then subjecting the specimen to histochemical staining with hematoxylin and eosin (H and E). Approximately 1 ml of vitreous supernatant was placed on SuperFrost Plus glass slides (Thermo Fisher Scientific) and then dried in a chamber for 16 hours at 4° C. The dried slides were rinsed with 5 mls of 1×TBS for 3 min at room temperature, and then washed again. The slides were then stained with H and E using standard procedures. Slides were preserved by mounting glass coverslips and then sealed. Samples were analyzed with light microscopy as described below. Specimens with hematoxylin-stained cells were subjected to repeat centrifugation or discarded. Therefore, all extracellular fractions used for further experiments were free from contaminating vitreous cells.

Nanoparticle tracking analysis. The NanoSight NS300 system (Malvern) was used to perform nanoparticle tracking analysis to characterize particles from 30-800 nm in solution. Extracellular vesicles isolated from bovine vitreous were resuspended in 100 μl of phosphate buffered saline (PBS, pH 7.0) at a concentration of approximately 2.5 μg of protein per ml, and then the sample was diluted to a final volume of 2 ml in PBS for analysis. Particles were loaded, the camera was focused, and 5 videos were captured for 60 sec each. Videos were recorded and then analyzed using NanoSight software (Version 3.0) to determine the size distribution and particle concentration of EVs. Graphs were created. The Brownian motion of each particle is tracked between frames, ultimately allowing calculation of the size through application of the Stokes-Einstein equation.

Extracellular vesicle isolation from formalin-fixed tissue. Whole bovine vitreous microdissected as described above was placed in a 50 ml conical tube and then submerged in 10 ml of 4% formalin diluted in TBS (pH 7.4) and incubated for 24 h at 4° C. After fixation, tissues were dissected on ice into approximately 1 cm×1 cm sections and the weight of vitreous section was recorded. The tissues were then placed in 15 ml centrifuge tubes. The tissues were immersed in 250 μl of TBS and the sample and overlying wash buffer (or supernatant) was incubated at 37° C. for 30 min, 1 hr, 3 hr, 6 hr and 24 hr (n=3). The vitreous tissue and supernatant were collected and placed in separate 1.5 ml tubes for further protein studies. For the formalin fixed vitreous tissue, the specimen was homogenized at 4° C. and then lysed in equal volume of NP-40 lysis buffer. The lysate was transferred to a 1.5 ml tube and centrifuged for 15 min at 12,000 g at 4° C. The aqueous phase was transferred to a new tube without the white pellet. The protein pellet was collected by centrifugation for 15 min at 4° C. at 12,000 g and the supernatant removed. The pellet was then dissolved in 30 μl water and used for Western blotting. For the supernatant, the samples were cleared of cellular debris by centrifugation at 12,000 g for 15 min at 4° C. The protein supernatant was collected lysed with equal volume of NP-40 lysis buffer. The lysate was used for Western blotting.

Western blotting. Vitreous tissue or vitreous supernatant (250 μl) was collected after incubation at designated times and temperatures. Vitreous supernatant was pre-cleared with centrifugation at 12,000 g for 30 min at 4° C. and then lysed in buffer (50 mM Tris pH 8.0, 250 mM NaCl, 0.5% NP-40, protease inhibitors, Sigma Aldrich). An equal amount of protein (determined by BIO-RAD protein assay) from each sample was separated on SDS-PAGE gels, transferred to protein blotting membrane (Hybond, Amersham GE Healthcare), and blotted following standard procedures. The primary antibodies used included: rabbit monoclonal anti-TSG101 (Systems Bioscience). The monoclonal antibodies were blotted with a secondary antibody, IRDye 680LT Goat anti-Rabbit (LI-COR Inc.), followed by detection with fluorescent imaging system (Odyssey CLx, Li-Cor) according to manufacturers' recommendations.

Immunohistochemistry of exosome marker proteins in vitreous. Immunohistochemistry was performed on whole mounted 4% formalin-fixed bovine vitreous. To prevent formalin crosslinks from reverting and thus reduce the rate of EV loss, all were conducted at 4° C. for the duration of the experiment, except for microscopic imaging. The bovine vitreous humor was cut into approximately 1 cm×1 cm pieces and then the specimen was rinsed in 5 ml of ice-cold TBS (pH 7.4) for 3 minutes at 4° C. Wash steps were repeated twice. Specimens were then examined with a dissecting microscope (SZX-16 Olympus) to remove potentially contaminating tissues. Samples were then immersed in 500 μl of blocking buffer (10% goat serum diluted in TBS)

for 1 h at 4° C. The samples were briefly washed in 5 ml of TBS for 3 min at 4° C. The antibody to TSG-101 (System Biosciences, diluted 1:500) was used to immunostain the bovine vitreous overnight at 4° C. The samples were washed in 5 ml of TBS for 3 min at 4° C. Wash steps were repeated twice. IHC staining was visualized using a secondary antibody, goat anti-rabbit IgG conjugated to Alexa Fluor 488 (Abcam). Samples were washed three times. Bovine vitreous was counterstained with Hoechst stain (as described above) to mark nuclei and then washed twice in 5 ml of TBS for 5 min at 4° C. The vitreous was then immediately imaged and photomicrographs were recorded. For negative controls, normal goat serum (1:1000 dilution) was substituted for the primary antibody (secondary antibody only). Antibodies were verified to be specific for TSG101 using western blotting and the expected 45 kD protein band was observed.

Vitreous proteome analysis. Bovine vitreous samples were cleared of cells using the above protocol and whole mount samples were determined to be cell free by whole mount H and E staining and subsequent imaging as described above. Samples free of cells were then selected for proteomic analysis. Protein from extracellular vesicle fraction or cell free vitreous fraction was denatured in 8M urea, and cysteines were reduced with dithiothreitol (Sigma Aldrich) prior to alkylation with iodoacetamide (Sigma Aldrich). Proteins were digested with LysC (Wako Chemicals) followed by trypsin (Promega) and desalted with Empore C18 STaGETips (3M) (Skog et al., "Glioblastoma Microvesicles Transport RNA and Proteins That Promote Tumour Growth and Provide Diagnostic Biomarkers" *Nat Cell Biol* 10:1470-1476 (2008), which is hereby incorporated by reference in its entirety). One μg of total protein was injected for nano-LC-MS/MS analysis (Q-Exactive Plus, Thermo Scientific). Peptides were separated using a 12 cm×75 μm C18 column (Nikkyo Technos Co., Ltd. Japan) at a flow rate of 200 nL/min, with a 5-40% gradient over 160 minutes (buffer A 0.1% formic acid, buffer B 0.1% formic acid in acetonitrile). The Q-Exactive Plus was operated in data-dependent mode, with a top 20 method. Nano-LC-MS/MS data were analyzed using MaxQuant (version 1.5) and Perseus software (version 1.4) (Tyanova et al., "The Perseus Computational Platform for Comprehensive Analysis of (Prote)omics Data," *Nat Methods* 13 (9): 731-740 (2016), which is hereby incorporated by reference in its entirety), searching against a Uniprot *Bos taurus* database (downloaded July 14), allowing oxidation of methionine and protein N-terminal acetylation, and filtering at a 1% false discovery rate at the peptide and protein level. Proteins were quantified using iBAQ values. Protein enrichment was compared between vitreous extracellular vesicle fraction and cell free vitreous fraction.

Cell culture. Human retinal pigmented epithelial cells, ARPE-19 (ATCC) were cultured in DMEM:F12 medium (ThermoFisher Scientific) supplemented with 10% fetal bovine serum, penicillin, and streptomycin. All cells were incubated at 37° C. in 95% air and 5% $CO_2$ and maintained using standard sterile techniques.

Loading recombinant proteins into EVs. Bovine vitreous EVs were obtained as described above and the total protein concentration was measured (Pierce™ BCA Protein Assay Kit, Thermo Fisher Scientific). 4 μg of vitreous EVs was used for in vitro treatments and 0.025 μg of bovine vitreous EVs was used for in vivo injections along with the following concentrations of BSA-fluorescein (3 μg, 1 μg, and 0.5 μg) or GFP (0.25 μg, 0.5 μg, and 1 μg). Recombinant protein and EVs were mixed in 300 μl of electroporation buffer (BioRad) and electroporated in a 4 mm cuvette. Electroporation was performed on the EVs using a square wave program under the following conditions; voltage at 300 V, pulse length time of 35 ms, with the number of pulses at 2, and pulse interval of 0.1 sec. For in vitro experiments, 100 μl of the electroporated solution was added to 300 μl of warm media, and the solution was transferred into each well of a 12-well plate (n=3) with APRE-19 cells plated at 70% confluence. Cultures were incubated for 24 h and the media was then replaced with complete media. Cells were fixed with 4% paraformaldehyde and imaged at 48 h after treatment. For in vivo studies, electroporation was performed in 300 μl of electroporation buffer (BioRad) and electroporated in a 4 mm cuvette at 300 V. Samples were desalted after resuspension in balanced salt solution 5 volumes and then concentrated with centrifugal size exclusion filters (Amicon, Millipore Sigma). The re-suspension volume in balanced salt solution (BSS) was 75 μl and 0.5 μl was used per injection.

In vitro application of EVs to cultured cells. Bovine or post-mortem human vitreous EVs were isolated and loaded with recombinant protein via electroporation as described above. ARPE-19 cells were cultured on a 12-well plate and approximately 70% confluent at the time of EV treatment. Then, 100 μl of the electroporated EV solution was added to 1 ml of complete media. The cells were incubated for 16 h under standard culture conditions and then the media was removed and replaced with complete media. At 48 h post-treatment, cell media was removed and cultures immersed with 1 ml of Hoechst stain and incubated for 15 min at 37° C. The stain was removed and cells were washed with 2 ml of phosphate buffered saline and fixed with 2 mls of 4% formalin diluted in PBS for 10 min at room temperature. Cells were washed with 2 ml of PBS for 5 min. The wash was repeated twice. Cells were evaluated for transfection efficiency with using wide-field fluorescent microscopy.

In vivo injection of vitreous EVs. All procedures were performed in accordance with NIH guidelines and approved by Weill Cornell Medicine's Institutional Animal Care and Use Committee (IACUC). Male, 6-week-old C57BL/6J mice (Jackson Labs) were maintained on a 12-h light/dark cycle at Weill Cornell Medical College's Research Animal Resource Center (RARC). Intravitreal injections of mouse eyes occurred at 8 weeks of age in all experimental variables (n≥3). Animals were sedated with a ketamine and xylazine cocktail in accordance with NIH Animal Welfare guidelines. Pupils were dilated with 1 drop of 2.5% phenylephrine, 1 drop of 1% tropicamide, and then a lubricating ophthalmic ointment was applied. After 15 min, animals were prepared for injection. Ophthalmic ointment was removed using a cotton swab and eyes were rinsed with 10 drops of 1×TBS. Under a dissecting stereo microscope (Olympus SZX50), a guide track was made in the eye by positioning a 32-gauge needle at the limbus and then traversing from the sclera and into the posterior chamber. Care was taken to avoid disrupting the crystalline lens. Next, the guide needle was withdrawn and the micro-injector (Pneumatic picopump, PV830, World Precision Instruments) was positioned into the guide needle track and the glass pipette tip was inserted into the posterior chamber avoiding the retina. 500 nl of EV solution or control solutions was injected. After completion of the injection, a 10 sec interval was maintained before removing the glass pipette. The glass pipette was removed and ophthalmic antibiotic ointment applied to the injected eye immediately after the intravitreal injection procedure. The animals were then monitored for recovery from anesthesia and then returned to the Weill Cornell Medicine's RARC Facility.

Evaluation of bio-distribution of intravitreally injected EVs or controls in rodent eyes. The bio-distribution of EV intravitreal injection was analyzed at post injection day 3, week 1, and weeks 2 (n≥3). Animals were sedated and euthanized in accordance with NIH Animal Welfare guidelines. The eyes were enucleated and placed in 5 ml of 4% formalin in 1×TBS for 16-hr at 4° C. and then immersed in 5 ml of 0.5 M sucrose diluted in TBS for 12 h at 4° C. The tissues were mounted in OCT Compound (Tissue-Tek), frozen in a dry-ice/ethanol bath in a Cryomold (Tissue-Tek), immediately serial sectioned from 5 to 40 μm with a cryostat (Leica 3050 S, Leica) and mounted on SuperFrost Plus glass slides (Thermo Fisher Scientific). Specimens were counterstained with 1 ml of Hoechst stain for 15 min at room temperature. The slides were rinsed in 5 ml of TBS (pH 7.4) for 5 min at room temperature. Wash steps were repeated twice. 300 μl of mounting media was then added and a cover-slip (VWR International LLC) was placed. Slides were imaged with wide field fluorescent microscopy for BSA-fluorescein or bright-field microscopy for H and E stained samples. Unprocessed specimen or mounted slides were stored at −80° C.

Aqueous EV isolation. Aqueous humor was collected by paracentesis. Briefly, an 18-gauge needle was inserted in the cornea approximately 2 mm anterior to the limbus and then 250 μL of fluid was removed into a 1 ml syringe. The fluid was immediately transferred to a 1.5 ml siliconized microfuge tube and samples placed on ice. EVs were isolated as described for vitreous EVs.

Statistical analyses. Graph visualization, calculations were performed using Excel (version 2011, Microsoft). All experiments, unless otherwise stated, were performed with n of ≥3. For nanoparticle tracking analysis particle size, concentration, and distribution was calculated using Stokes-Einstein equation. All error bars are standard deviation and p values <0.05 for all studies.

Example 1—Extracellular Vesicles (EV) Escape from Formalin-Fixed Bovine Vitreous Tissues and are Retained with 1-Ethyl-3-(3-Dimethylaminopropyl) Carbodiimide (EDC)-Formalin Fixation The studies described herein focused on optimizing tissue fixation to retain EVs in the extracellular space. To preserve the histological and morphological structures of tissues, conventional fixation methods employ 10% formalin to create protein-protein crosslinks. The fixation process generally involves processing steps or incubations at or above room temperature; however, elevated temperatures are known to revert formalin protein-protein crosslinks (Shi et al., "Antigen Retrieval in Formalin-fixed, Paraffin-embedded Tissues: An Enhancement Method for Immunohistochemical Staining Based on Microwave Oven Heating of Tissue Sections," *J Histochem Cytochem* 39:741-748 (1991); Ikeda et al., "Extraction and Analysis of Diagnostically Useful Proteins From Formalin-fixed, Paraffin-embedded Tissue Sections," *J Histochem Cytochem* 46:397-403 (1998), which are hereby incorporated by reference in their entirety) and RNA-protein crosslinks (Pena et al., "miRNA In Situ Hybridization in Formaldehyde and EDC-fixed Tissues," *Nat Methods* 6:139-141 (2009), which is hereby incorporated by reference in its entirety). It was hypothesized that the nanometer-sized EVs are lost from formalin-fixed tissue specimens during wash steps at or above room temperature, as shown in a schematic diagram in FIG. 1A. To examine the extent of EV loss from formalin-fixed tissues, formalin-fixed bovine vitreous tissue was immersed in wash buffer at 37° C. for various time points and then the supernatant was collected. The ultrastructural content of the supernatant was imaged using transmission electron microscopy (TEM) and it was found that a substantial number of EVs were present in the wash buffer and had leaked from the formalin-fixed tissue (FIGS. 1B-1C), as early as 30 minutes. Exposure to temperatures above 4° C. also resulted in RNA escape (Pena et al., "miRNA In Situ Hybridization in Formaldehyde and EDC-fixed Tissues," *Nat Methods* 6:139-141 (2009), which is hereby incorporated by reference in its entirety), and likely protein escape. To permanently retain these nanometer-sized EVs within the tissue and surrounding extracellular space, an additional fixation step was added, in which the water-soluble carbodimide, EDC, creates a non-reversible crosslink between positively charged amino group side chains and carboxyl groups of EV proteins. Thus, two-step fixation was conducted that involves first fixing samples in formalin and then subsequent cross-linking with EDC. After EDC-formalin fixation, vitreous tissues were placed in wash buffer at various temperatures and the supernatant was imaged with TEM (FIG. 1D). EVs were not detected in the supernatant (FIG. 1E). Particulate matter was observed in the EDC-formalin supernatant, as well as the wash buffer control (FIG. 1F); hence EVs did not escape the EDC-formalin-fixed tissue. To quantitate EV loss from vitreous tissue, Western blotting was used to detect a known exosome marker TSG-101. The supernatant of formalin-fixed vitreous showed significant amount of TSG-101 signal in the supernatant (FIG. 1G). These data suggest that formalin fixed tissues lose a substantial amount of EVs to the wash buffer.

Figures 2A, 2B, 2C, 2D, 2E:
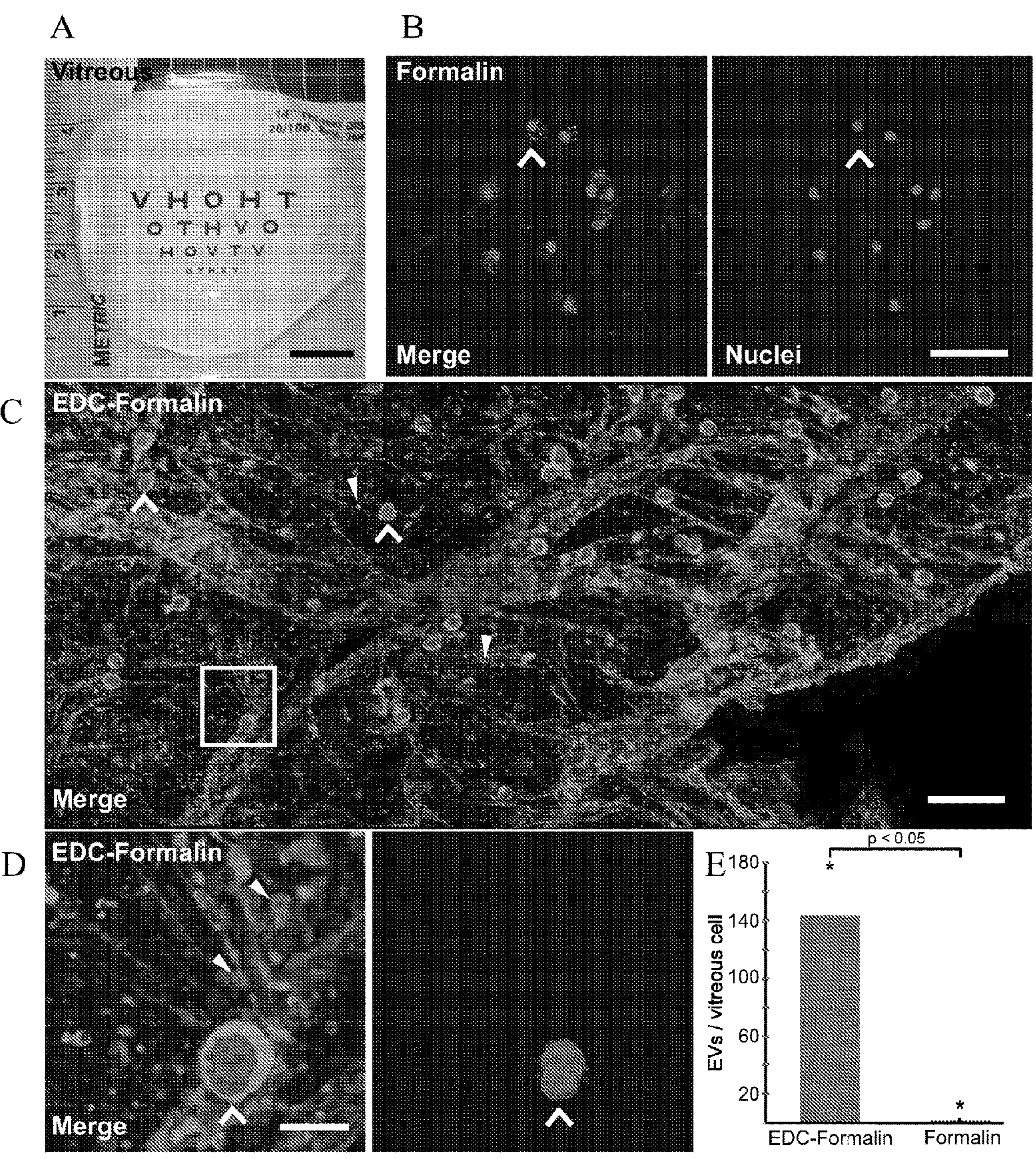
FIGS. 2A-2F show EDC-formalin fixation of bovine vitreous retains EVs imaged by multifocal microscopy (MPM), when compared to formalin fixation alone.

Example 2—EDC-Formalin Fixation of Bovine Vitreous Retains EVs Imaged by Multifocal Microscopy (MPM), when Compared to Formalin Fixation Alone The goal was to visualize the structural relationship of EVs in the extracellular space of normal vitreous tissue (FIG. 2A), therefore conventional fixation of bovine vitreous (formalin alone) was compared to EDC-formalin, and then an attempt was made to visualize EVs in situ. EVs are known to contain proteins; thus, total protein was labeled in whole mounted samples and then imaged with multiphoton microscopy (FIGS. 2B-2D). To label proteins, a cell permeable fluorescent dye, carboxyfluorescein succinimidyl ester (CFSE) (Bronner-Fraser, M., "Alterations in Neural Crest Migration by a Monoclonal Antibody That Affects Cell Adhesion," *J Cell Biol* 101:610-617 (1985), which is hereby incorporated by reference in its entirety), was used which covalently links to amines. It was found that formalin-fixed tissues showed positive protein signal near or within the vitreous cells but showed no evidence of extracellular protein signal (FIGS. 2A-2B, n=4). These data suggested that EVs were either not present in vitreous tissue or were lost during processing of formalin-fixed vitreous specimen. In contrast, EDC-formalin fixed samples showed robust signals for protein in the extracellular matrix consistent in size and shape with EVs (FIGS. 2C-2D). Moreover, EDC-formalin fixed tissues stained with CFSE consistently illuminated significantly more EVs (120 fold), when compared to formalin alone (FIG. 2E, p<0.05).

Figure 2F:
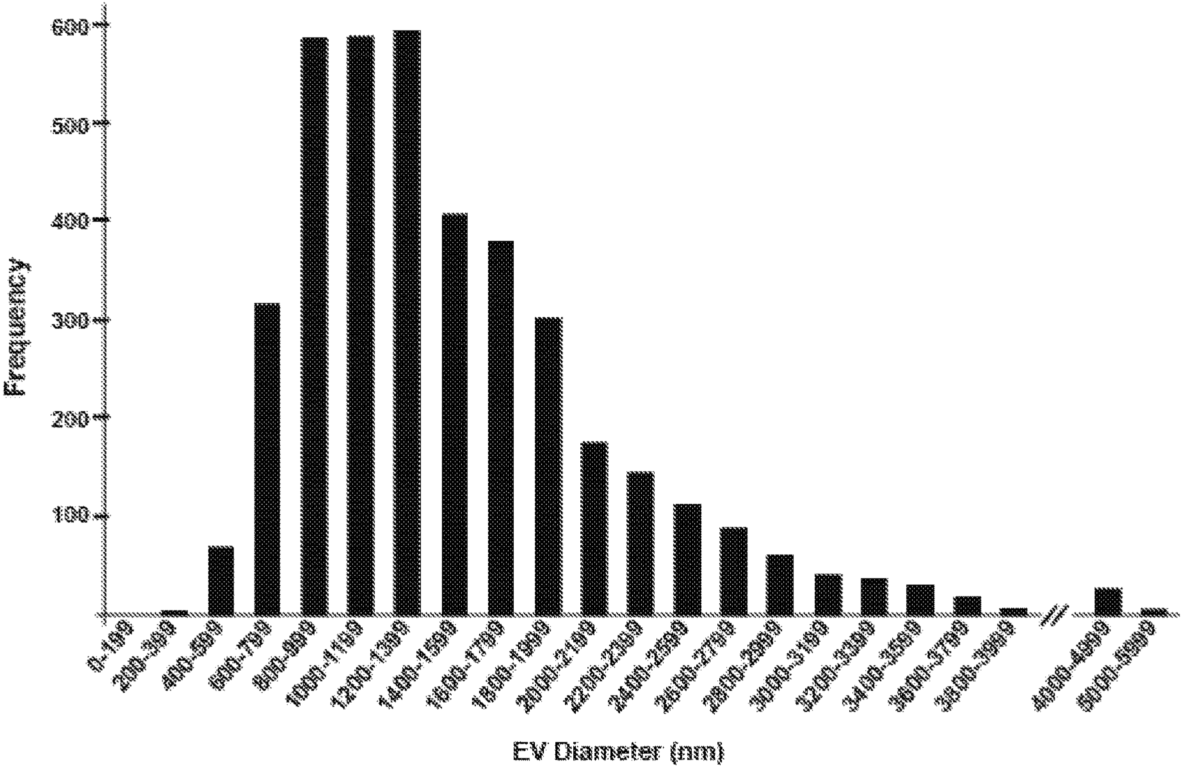

Bovine EVs imaged by MPM were pleomorphic in size, ranging from approximately 200 to 6000 nm in size, with mean diameter 1513.0 nm (standard error 708.8 nm), and modal size of 800-1400 nm (FIG. 2F). The lower limit of resolution of the multiphoton microscope limited ability to resolve EVs smaller than 200 nm.

Figures 3A, 3B, 3C:
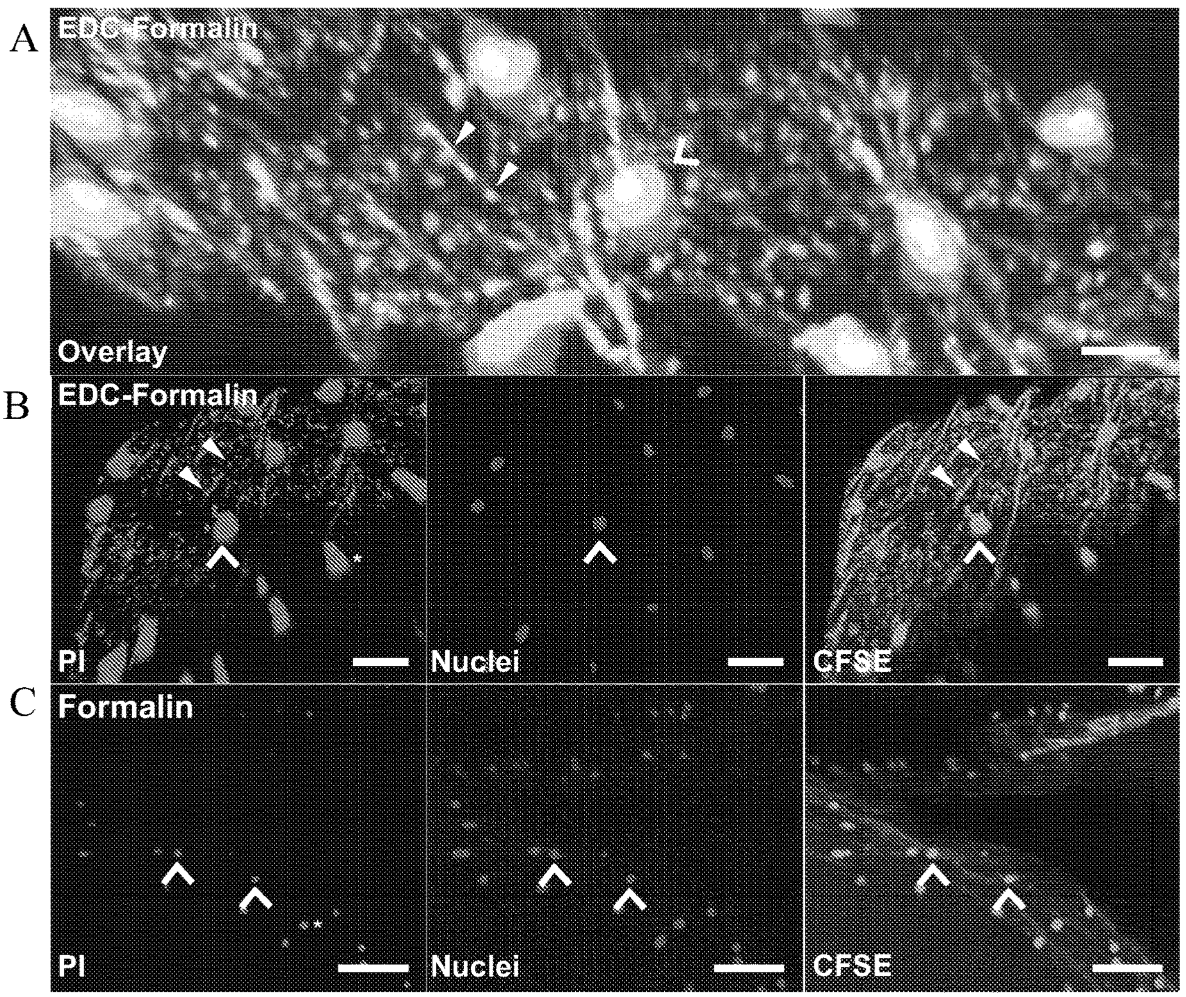
FIGS. 3A-3C show fixation of bovine vitreous with EDC-formalin retains EVs and extracellular RNA in situ.
Figures 4A, 4B, 4C:
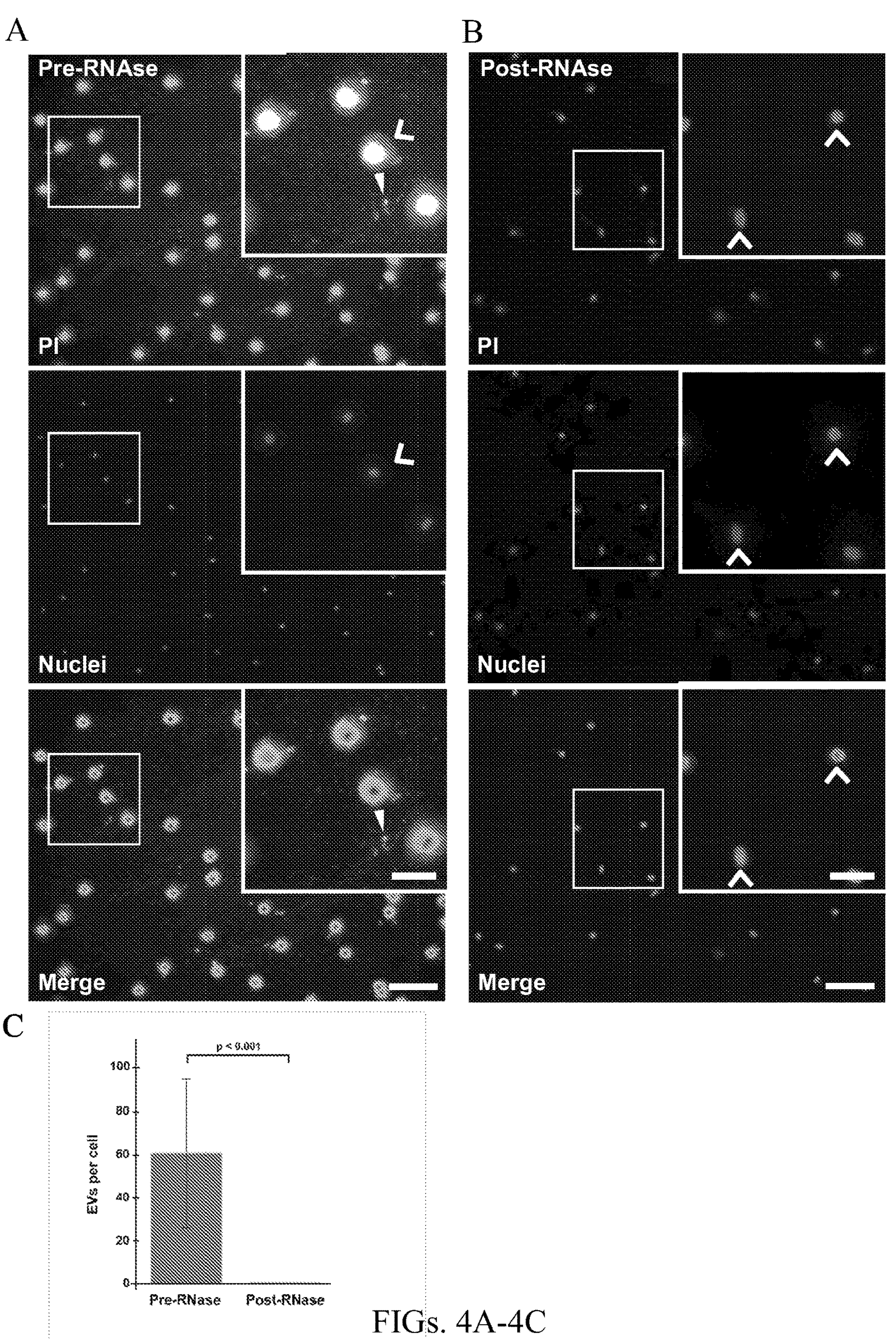
FIGS. 4A-4C show RNAse treatment of EDC-formalin-fixed bovine vitreous stained with PI show reduced extracellular signal.
Figures 5A, 5B:
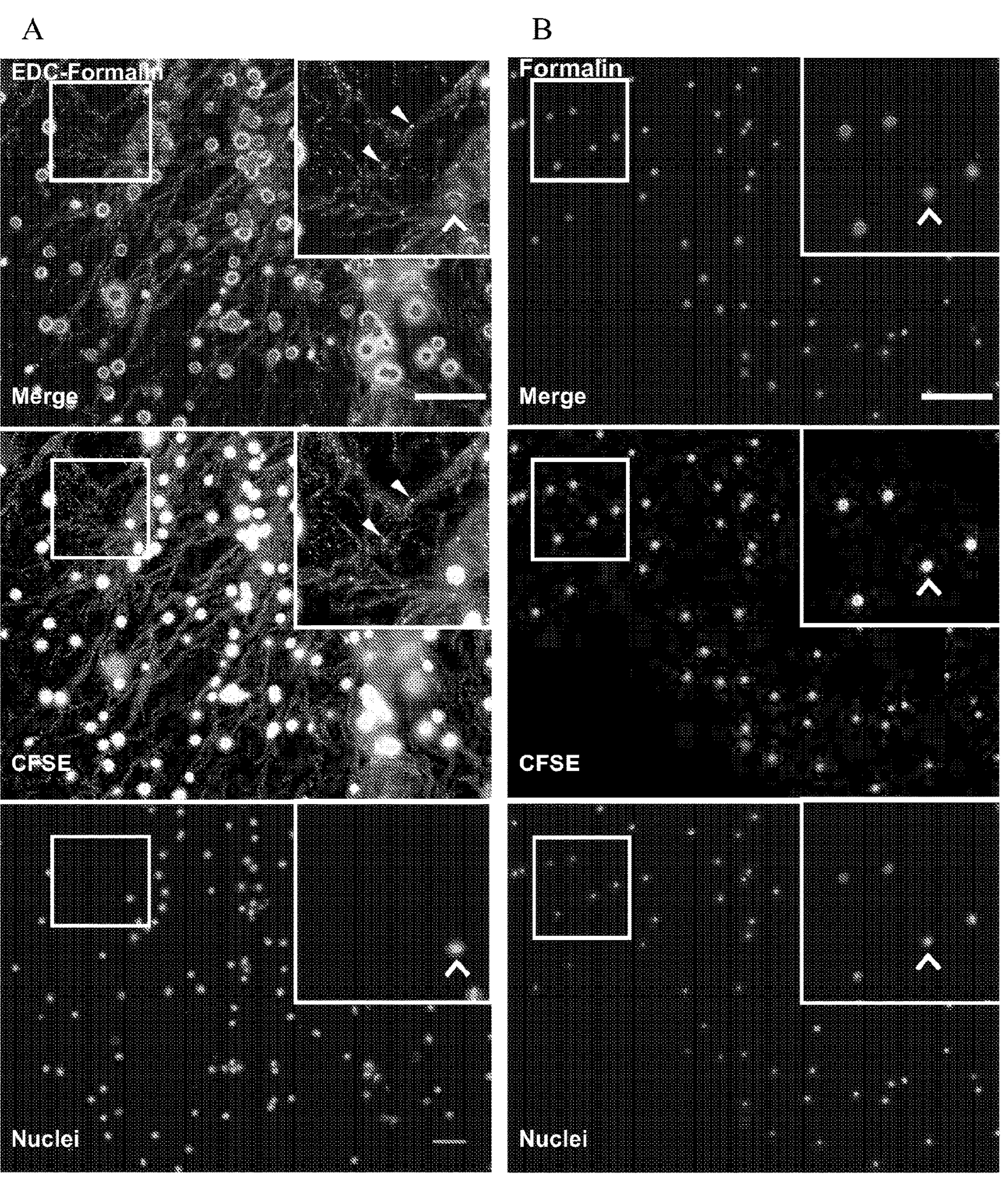
FIGS. 5A-5B show EDC-formalin fixation of bovine vitreous retains EVs imaged with photomicroscopy.

Example 3—Fixation of Bovine Vitreous with EDC-Formalin Retains EVs and Extracellular RNA In Situ EVs are also known to contain extracellular RNA (Valadi et al., "Exosome-mediated Transfer of mRNAs and MicroRNAs is a Novel Mechanism of Genetic Exchange Between Cells," *Nat Cell Biol* 9:654-659 (2007), which is hereby incorporated by reference in its entirety), therefore, it was sought to visualize extracellular RNA in vitreous tissues. Bovine vitreous nucleic acids were labeled with propidium iodide (PI), which stains DNA as well as RNA (Suzuki et al., "DNA Staining for Fluorescence and Laser Confocal Microscopy," *J Histochem Cytochem* 45:49-53 (1997), which is hereby incorporated by reference in its entirety), albeit with a lower affinity. Imaging EDC-formalin fixed tissues with confocal microscopy showed signals positive for extracellular RNA and extracellular protein, however no extracellular DNA was detected (FIGS. 3A-3B). Signals for extracellular RNA were found to co-localize within the EV protein signal (FIG. 3A), suggesting that extracellular RNA is within the vesicle. In contrast, fixation with formalin alone resulted in substantially less extracellular RNA and protein signal (FIG. 3C). It was also noted that substantially more RNA was retained within the cytoplasm of vitreous cells in EDC-formalin fixed tissues when compared to conventional fixation. To verify that extracellular PI signal was indeed RNA, EDC-formalin fixed samples were treated with RNAse and a significant reduction in extracellular signal was noted (FIGS. 4A-4B). To determine if improvements in EV signals could be observed using a standard fluorescent microscope, images from formalin and EDC-formalin-fixed vitreous samples that were stained with CFSE and PI and then captured with a wide-field fluorescent microscope were compared. The data show EDC-formalin fixed samples demonstrated a strong signal for extracellular protein and RNA, while formalin-fixed specimens failed to show extracellular protein signal (FIGS. 5A-5B). Taken together, these data suggest that EDC-formalin fixation is superior to formalin fixation alone for retaining EV proteins and extracellular RNAs in tissues. Moreover, this technique allows one to determine the spatial relationship of EVs within the vitreous tissue in situ.

Example 4—Bovine and Human Vitreous Humor Contains EVs

Figures 6A, 6B, 6C, 6D, 6E, 6F, 6G, 6H, 6I:
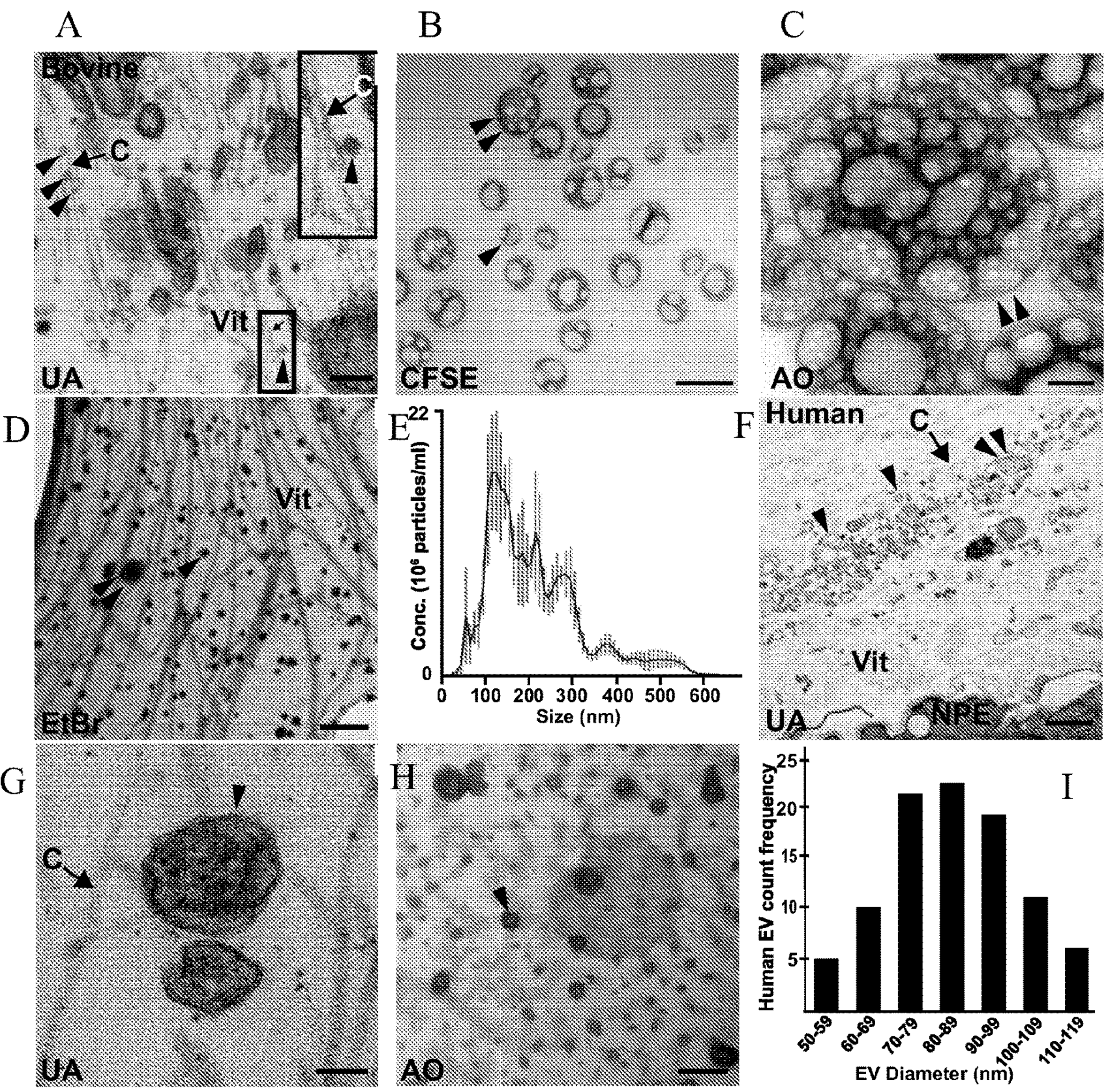
FIGS. 6A-6I show bovine and human vitreous humor contains EVs.

To correlate the findings observed in the micrographs from EDC-formalin fixed tissues with other methods used to visualize EVs, the ultrastructure of vitreous EVs was studied with TEM (Raposo et al., "B Lymphocytes Secrete Antigen-presenting Vesicles," *J Exp Med* 183:1161-1172 (1996), which is hereby incorporated by reference in its entirety). Bovine vitreous specimens were negatively stained with uranyl acetate and lead citrate, and the images showed a substantial amount of EVs that were pleomorphic in size (FIG. 6A). Next, EVs isolated from bovine vitreous were labeled with CFSE, an electron dense dye that covalently links to protein amines (Raposo et al., "B Lymphocytes Secrete Antigen-presenting Vesicles," *J Exp Med* 183:1161-1172 (1996), which is hereby incorporated by reference in its entirety), and images showed an abundance of EVs with dense intra-vesicular staining (FIG. 6B). Since EVs are known to contain RNAs (Valadi et al., "Exosome-mediated Transfer of mRNAs and MicroRNAs is a Novel Mechanism of Genetic Exchange Between Cells," *Nat Cell Biol* 9:654-659 (2007), which is hereby incorporated by reference in its entirety), EVs isolated from bovine vitreous were imaged after staining with an electron dense and nucleic acid selective dye, acridine orange (AO), that showed positive signal within the EVs (FIG. 6C). Staining whole mount bovine vitreous with ethidium bromide, another electron dense nucleic acid stain, also showed positive signal within the EVs (FIG. 6D). To determine the concentration and size distribution of bovine vitreous EVs, nanoparticle-tracking analysis (NTA) (Dragovic et al., "Sizing and Phenotyping of Cellular Vesicles Using Nanoparticle Tracking Analysis," *Nanomedicine* 7:780-788 (2011), which is hereby incorporated by reference in its entirety) was used, and it was found that the concentration of extracellular vesicles was at least $2.98\times10^{7}$ particles per ml (s.e.m$\pm8.98\times10^{6}$ particles per ml), corresponding to over 2 billion EVs per bovine eye (FIG. 6E). The data show a heterogeneous extracellular vesicle size, with a mean of 212 nm (s.e.m±10 nm), mode of 143 nm (s.e.m±20.4 nm), peaks at 125 nm and 215 nm, and some extracellular vesicles measuring up to 550 nm (FIG. 6E). EV size measured by NTA differed from EV size observed by multiphoton microscopy, which is likely the result of ultracentrifugation-based isolation methods that removed larger EVs (van der Pol et al., "Recent Developments in the Nomenclature, Presence, Isolation, Detection and Clinical Impact of Extracellular Vesicles,". *J Thromb Haemost* 14:48-56 (2016), which is hereby incorporated by reference in its entirety). To determine the distribution of vitreous EVs in the whole eye, TEM was performed on post-mortem human eyes and demonstrated numerous vitreous EVs in high concentrations near the vitreous base and ciliary body (FIG. 6F-6G). EVs purified from post-mortem human vitreous specimens and stained with AO also revealed size and shape consistent with EVs (FIG. 6H-6I). These data show that the vitreous EVs are indeed present, are abundant in number and heterogeneous in size, and positively stain with CFSE and nucleic acid selective dyes.

Example 5—Immunohistochemistry Staining of EV-Specific Protein TGS-101 in Normal Bovine Vitreous To determine if vitreous EVs expressed EV-associated proteins, proteomic analysis was conducted using liquid chromatography mass spectrometry (LC-MS) and bovine vitreous (cleared of cells with low-speed centrifugation) was compared with the EV isolated fraction (n=6 of bovine vitreous, samples were pooled). The vitreous and EV isolated fraction showed a total of 1686 protein in the combined proteomic inventory, with 682 and 464 proteins enriched in whole vitreous fraction or EV fraction, respectively, and 540 proteins that were similar in abundance for both. A comprehensive listing of the 1779 proteins detected in the EV and whole vitreous fraction is provided in Table 3, infra. The listing of Table 3 identifies the proteins by their protein name (column 1) and protein identifier, which includes their UniProtKB Accession number and name. For each protein listed in Table 3, the log 2 difference in protein amount in the EV fraction compared to cell-free vitreous fraction is listed in column 5, which is based on the amount of protein quantified by label free quantification (LFQ) intensity in the EV-enriched fraction (column 3) and in the cell-free vitreous fraction (column 4). Proteins with enrichment in the EV-fraction are denoted as "EV fraction only" (column 5). The proteins total intensity is represented by the iBAQ value (column 6).

Further analysis of the proteome data showed that several known EV-associated proteins are enriched in the EV fraction, including TSG-101 (iBAQ value, which represents protein abundance was 2.30 E+05), CD-9 (iBAQ value, 2.80 E+06), HSP 90-β (iBAQ value, 3.00E+08), and annexin II protein (iBAQ value, 9.40 E+05), as shown in Table 1.

TABLE 1

Exosome marker proteins present and enriched in bovine vitreous EVs when compared to cell-free vitreous.

| Protein Name | Vesicular body fraction compared to vitreous Log2 ratio | iBAQ Vitreous | iBAQ vesicular body | **Refs. |
|---|---|---|---|---|
| CD9 antigen | Vesicular body fraction | 2.80E+06 | 2.80E+06 | 1-5 |
| Annexin II | Vesicular body fraction | 9.40E+05 | 9.40E+05 | 2, 3, 5 |
| *TSG101 protein | Vesicular body fraction | 2.30E+05 | 2.30E+05 | 3, 5 |
| †HSP 90-beta | 1.755888 | 3.00E+08 | 3.00E+08 | 3, 5 |
| †HSP 90-alpha | 0.7320843 | 1.20E+09 | 1.20E+09 | 3, 5 |
| Pyruvate kinase | 0.8703709 | 1.30E+09 | 1.30E+09 | 5 |
| L-lactate dehydrogenase A chain | 1.020498 | 1.20E+09 | 1.20E+09 | 5 |
| Elongation factor 1-alpha 1 | 2.292728 | 7.20E+07 | 7.20E+07 | 2, 5 |
| Clathrin heavy chain 1 | 3.026251 | 8.60E+06 | 8.60E+06 | 5 |
| Alpha-enolase | 0.4244232 | 5.20E+09 | 5.20E+09 | 5 |

*TSG101 = Tumor Susceptibility Gene 101;

†HSP = Heat shock protein

**References for Table 1 which are hereby incorporated by reference in their entirety:

1. Conde-Vancells, J. et al. *J Proteome Res* 7, 5157-5166 (2008).

2. Thery, C. et al. *J Cell Biol* 147, 599-610 (1999).

3. Vlassov, A. et al.. *Biochim Biophys Acta* 1820, 940-948 (2012).

4. Higashiyama, S. et al. *J Cell Biol* 128, 929-938 (1995).

5. Keerthikumar, S. et al. *J Mol Biol* 428, 688-692 (2016).

The analysis also showed that several eye specific proteins are also enriched in EV as compared to the cell free vitreous fraction. These eye specific proteins are listed in Table 2 below.

TABLE 2

Eye specific proteins enriched in bovine vitreous EVs

| Protein Name | Vesicular body fraction compared to vitreous | LFQ intensity vitreous/exosome | iBaQ | References |
|---|---|---|---|---|
| Retinaldehyde-binding protein 1 | 2.08453 | 32.20889 | 1.50E+09 | 1-3 |
| Fibrillin-1 | 2.192545 | 32.26072 | 1.20E+08 | 4-6 |
| Opticin | 2.649029 | 31.54315 | 1.10E+09 | 7-8 |
| Arrestin-C | 2.369839 | 26.13197 | 1.40E+07 | 9 |
| Retinol-binding protein 3 | 2.399818 | 36.24624 | 5.40E+09 | 10-11 |
| Phakinin | Vesicular body fraction only | 22.0284 | 1.60E+05 | 12-13 |
| 11-cis retinol dehydrogenase | Vesicular body fraction only | 24.73975 | 1.60E+06 | 14-15 |
| Fibulin 5 | Vesicular body fraction only | 25.49948 | 5.00E+06 | 16 |
| RPE-retinal G-protein coupled receptor | Vesicular body fraction only | 26.91809 | 1.80E+07 | 17-18 |
| Retinoid isomerohydrolase (RPE65) | Vesicular body fraction only | 23.69232 | 6.20E+05 | 19-20 |
| Rhodopsin | Vesicular body fraction only | 23.91497 | 2.30E+06 | 21-23 |

REFERENCES FOR TABLE 2, WHICH ARE HEREBY INCORPORATED BY REFERENCE IN THEIR ENTIRETY

1. Saari J C, Bredberg D L. *J Biol Chem* 262, 7618-7622 (1987).

2. Crabb et al., *Protein Sci* 7. 746-757 (1998).

3. Maw et al., *Nat Genet* 17, 198-200 (1997).

4. Wheatley et al., *Arch Ophthalmol* 113, 103-109 (1996).

5. Faivre et al., *J Med Genet* 40, 34-36 (2003).

6. Hubmacher et al., *Invest Ophthalmol Vis Sci* 55, 7934-7944 (2014).

7. Friedman et al., *Hum Mol Genet* 11, 1333-1342 (2002).

8. Reardon et al., *J Biol Chem* 275, 2123-2129 (2000).

9. Sakuma et al., *Gene* 224, 87-95 (1998).

10. Li et al., *J Biol Chem* 288, 11395-11406 (2013).

11. den Hollander et al., *Invest Ophthalmol Vis Sci* 50, 1864-1872 (2009).

12. Merdes et al., *J Cell Biol* 123, 1507-1516 (1993).

13. Carter et al., *Biochem Biophys Res Commun* 270, 432-436 (2000).

14. Yamamoto et al., *Nat Genet* 22, 188-191 (1999).

15. Liden et al., *J Biol Chem* 276, 49251-49257 (2001).

16. Stone et al., *N Engl J Med* 351, 346-353 (2004).

17. Shen et al., *Biochemistry* 33, 13117-13125 (1994).

18. Morimura et al., *Nat Genet* 23, 393-394 (1999).

19. Nicoletti et al., *Hum Mol Genetic* 4, 641-649 (1995).

20. Moiseyev et al., *Proc Natl Acad Sci* 102, 12413-12418 (2005).

21. Wald et al., *Science* 111, 179-181 (1950).

22. Dryja et al., *Nature* 343, 354-366 (1990).

23. Dryja et al., *N Eng J Med* 323, 1302-1307 (1990).

Figures 7A, 7B, 7C, 7D:
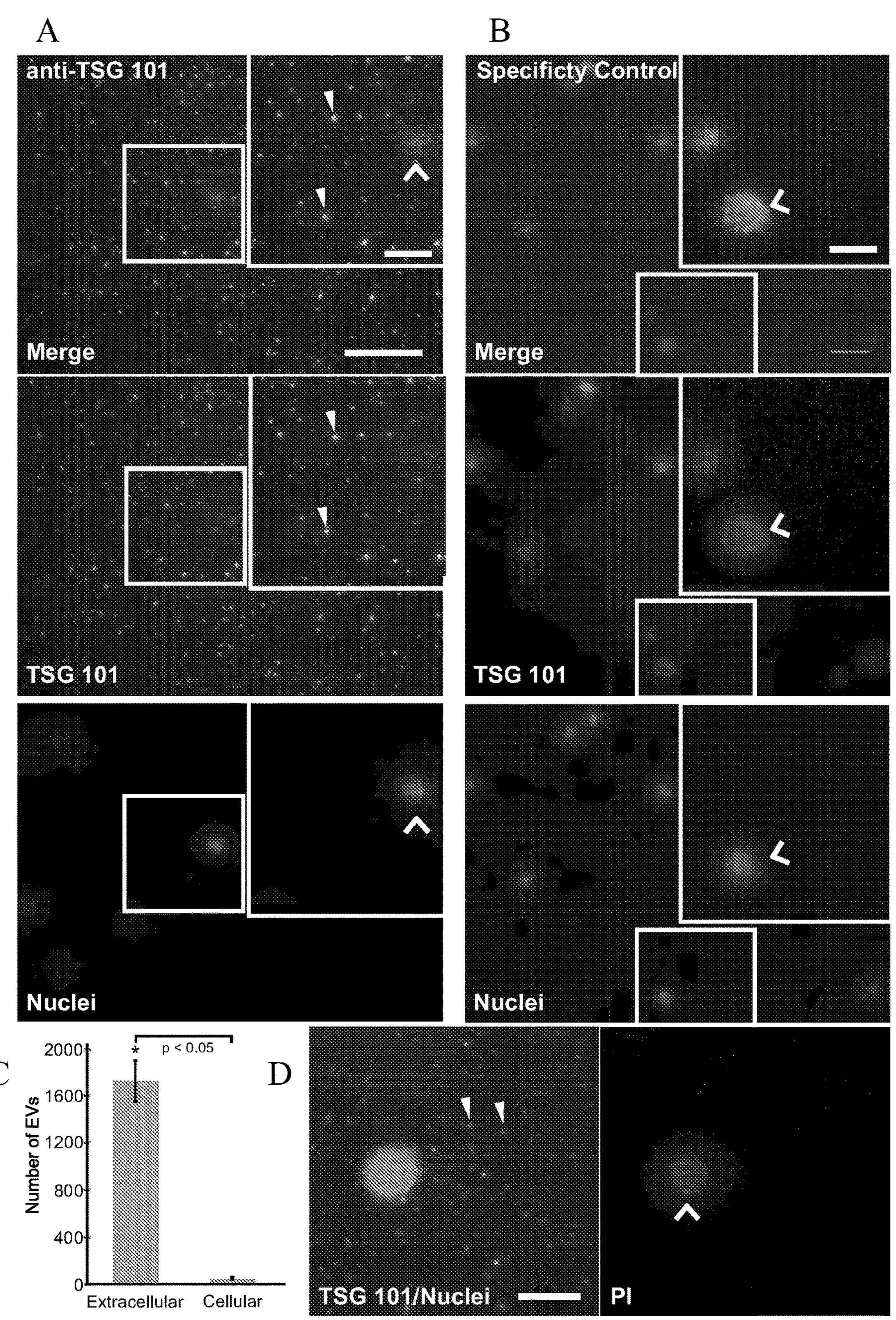
FIGS. 7A-7D show immunohistochemistry staining of EV-specific protein TGS-101 in normal bovine vitreous.

To confirm that protein signals observed in the EDC-formalin-fixed vitreous were indeed EVs, immunohistochemistry (IHC) was conducted to visualize in situ distribution of a known exosome protein, TSG-101. EDC-formalin fixation of tissues was incompatible with IHC staining. Moreover, TSG-101 signal was not reliably detectable in formalin-fixed tissues when conducting experiments at room temperature, presumably because EVs were lost to the wash buffer. However, reversal of formalin crosslinks are known to be temperature dependent (Ikeda et al., "Extraction and Analysis of Diagnostically Useful Proteins From Formalin-fixed, Paraffin-embedded Tissue Sections," *J Histochem Cytochem* 46:397-403 (1998), which is hereby incorporated by reference in its entirety) and reversion occurs at a slower rate at colder temperatures. Therefore, IHC was performed on formalin-fixed bovine vitreous specimens at 4° C. for all processing steps, except for imaging. IHC showed an abundant amount of punctate TSG-101-positive signal in the extracellular space (FIG. 7A), consistent with the EV spatial distribution in EDC-formalin-fixed tissues stained with CFSE (FIG. 2C). Specificity controls showed no extracellular signal (FIG. 7B). It was found that TSG-101 was 136-fold more likely to be found in the vitreous extracellular space than within vitreous cell bodies (FIG. 7C). Formalin-fixed IHC samples were also co-stained for RNA using PI, but extracellular RNA was unable to be detected (FIG. 7D), further suggesting that EDC-formalin fixation is necessary for retaining EV-associated RNAs. These data demonstrate that vitreous EVs contain EV protein markers and can be imaged with IHC under low temperature conditions.

Figures 8A, 8B:
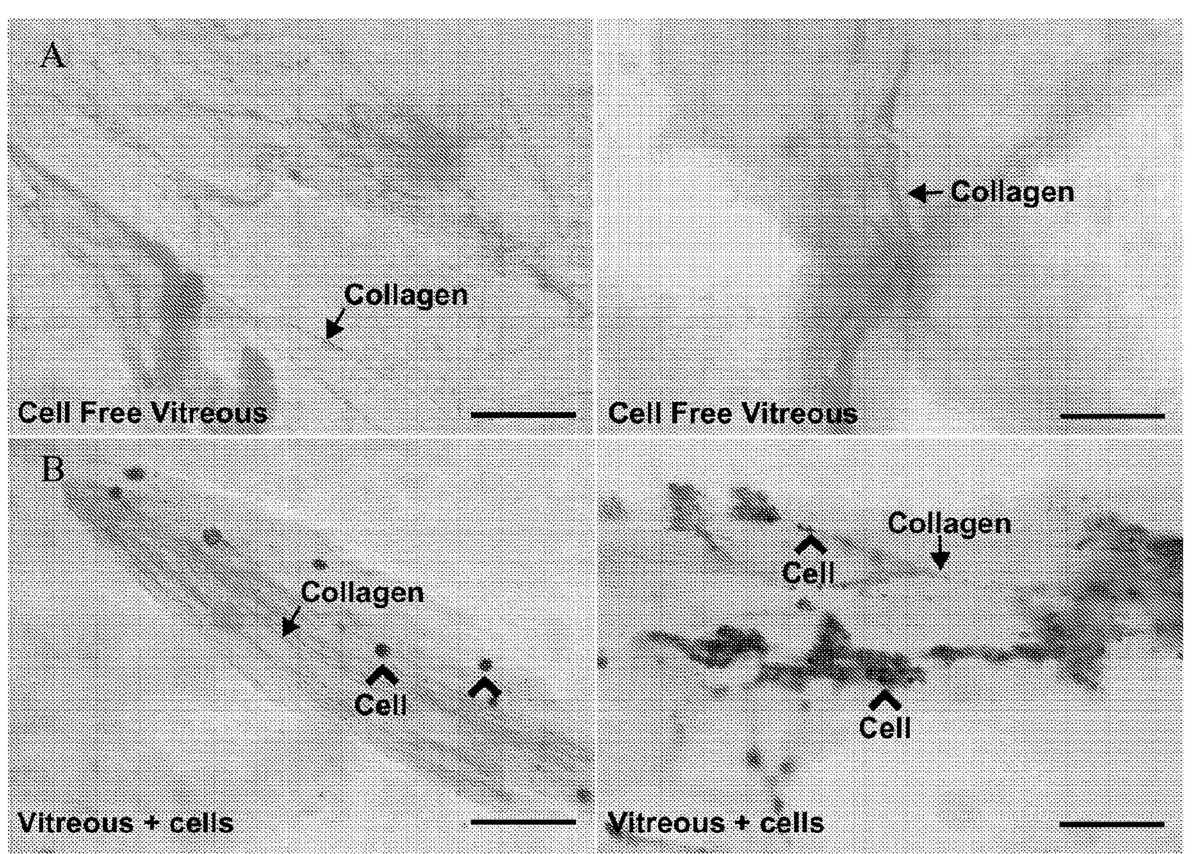
FIGS. 8A-8B show bovine vitreous is free of cells after low-speed centrifugation.
Figures 9A, 9B, 9C, 9D, 9E, 9F, 9G, 9H, 9I:
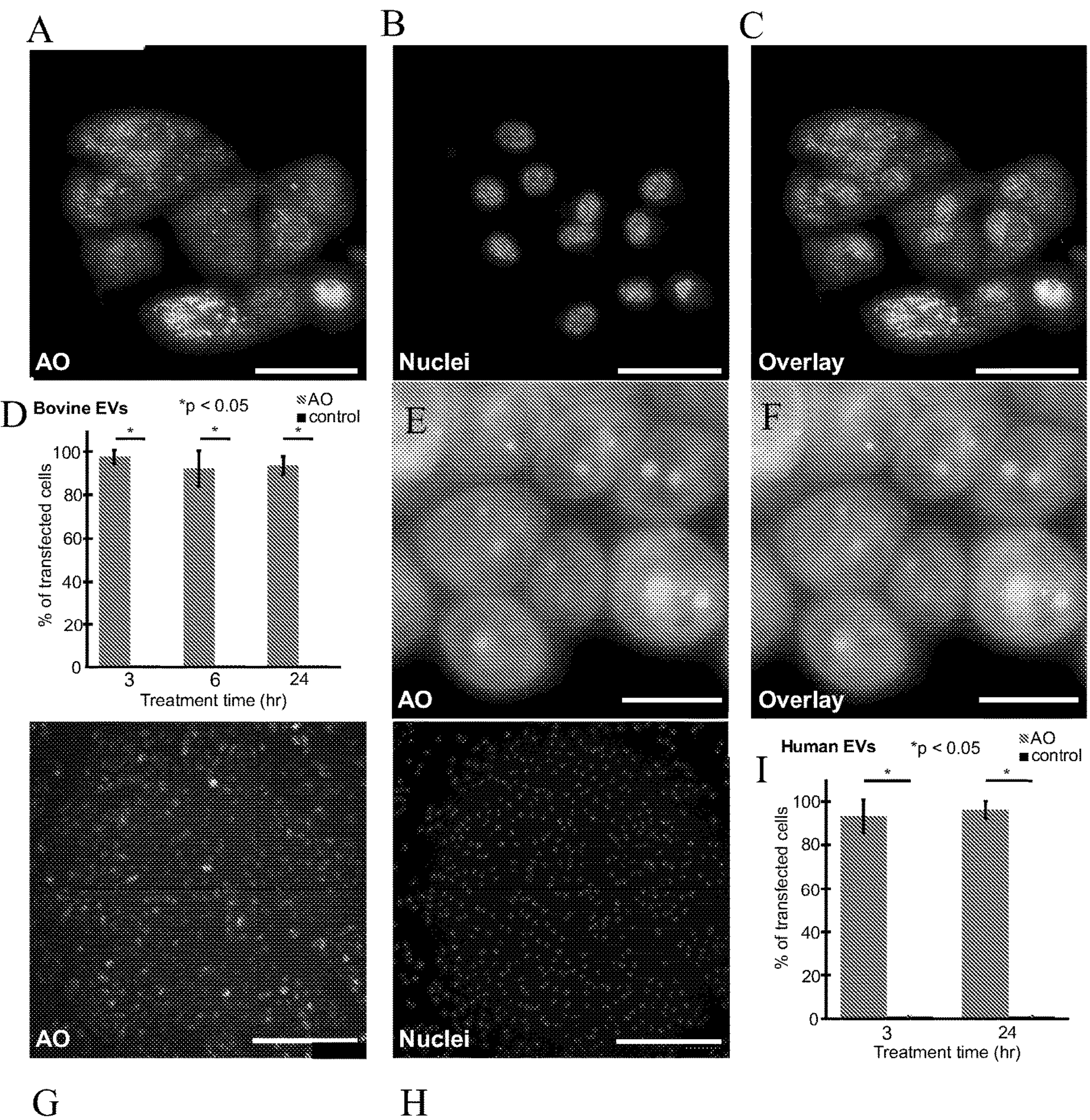
FIGS. 9A-9I show human and bovine vitreous EV transfer endogenous RNA into cultured cells.

Example 6—Vitreous EVs Transfer Endogenous RNA Recombinant Bovine Serum Albumin (BSA), and Green Fluorescent Protein (GFP) into Cultured Cells Whether vitreous EVs have biological activity similar to other EVs, which are known to transfer their RNA and protein cargo into target cells, was investigated. Early studies showed that EVs carry mRNAs and microRNAs into cells in vitro (Valadi et al., "Exosome-mediated Transfer of mRNAs and MicroRNAs is a Novel Mechanism of Genetic Exchange Between Cells," *Nat Cell Biol* 9:654-659 (2007); Skog et al., "Glioblastoma Microvesicles Transport RNA and Proteins That Promote Tumour Growth and Provide Diagnostic Biomarkers" *Nat Cell Biol* 10:1470-1476 (2008), which are hereby incorporated by reference in its entirety). Therefore, bovine and post-mortem human vitreous EVs' capacity to transfer their endogenous RNA into cultured cells was tested. Bovine or human vitreous EV RNA were labeled with AO fluorescent dye, the EV fraction was purified (FIGS. 8A-8B), and retinal pigment epithelial cells (ARPE-19) were exposed to a bolus of the labeled EVs. For bovine EV-RNA, transfection rate of up to 96.2%±01.9% was observed at 48 hours in cultured ARPE-19 cells (FIGS. 9A-9C), which was significantly more than controls. Human embryonic kidney cells were also transfected successfully (FIG. 9D-9F). Isolated post-mortem human vitreous EVs were also capable of transferring labelled EV-RNA at 96%±3.8% in ARPE-19 cells at 24 hours, significantly more when compared to the controls (FIGS. 9G-9I).

Figures 10A, 10B, 10C, 10D, 10E, 10F:
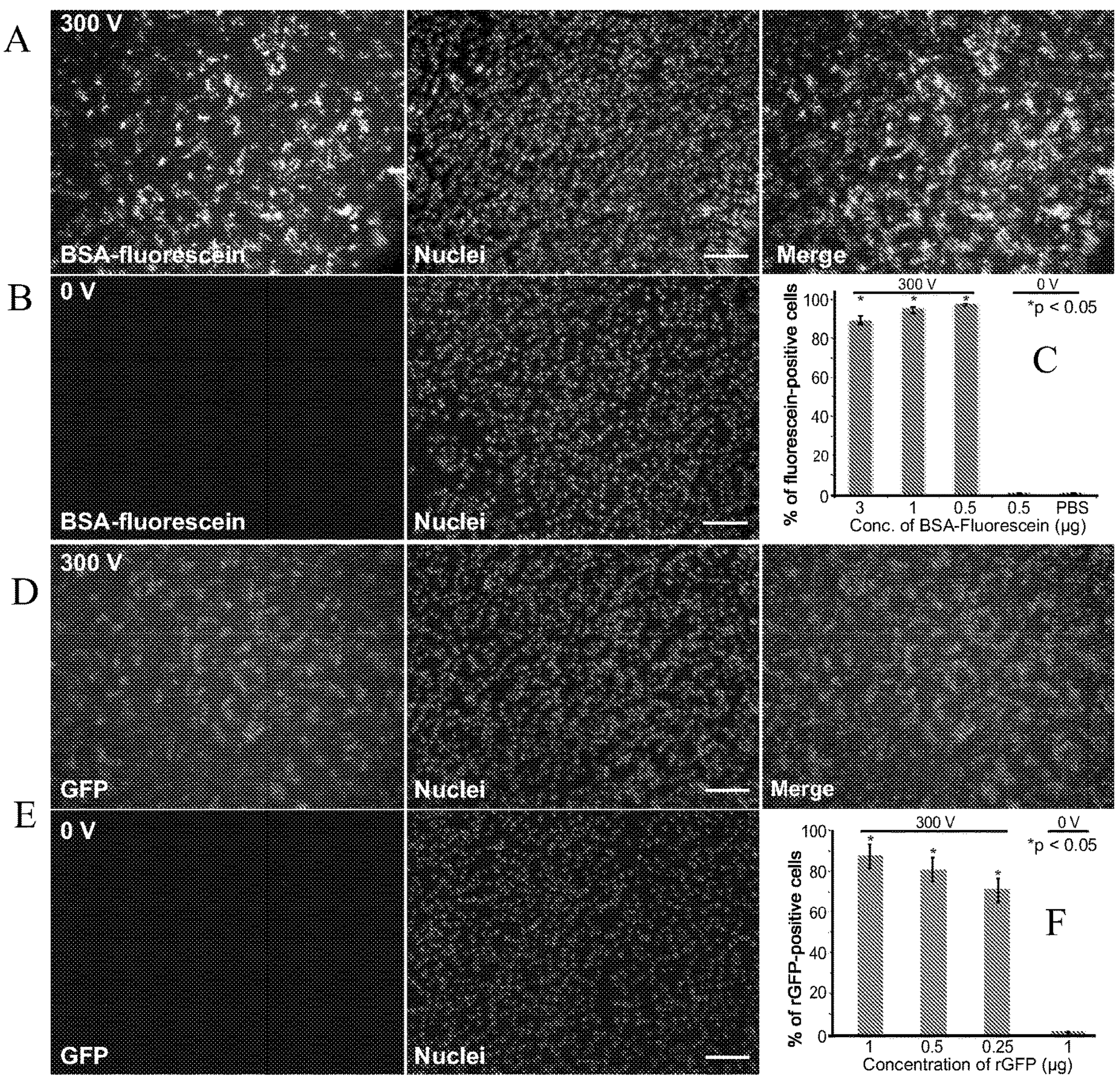
FIGS. 10A-10F show delivery of recombinant bovine serum albumin (BSA) protein and recombinant green fluorescent protein (GFP) by bovine vitreous extracellular vesicles (EV) to cultured human retinal pigment epithelial (ARPE-19) cells.

EVs are also known to be a vector capable of delivering recombinant protein to target cells. Therefore, bovine serum albumin (BSA, 66 kD protein) conjugated to fluorophore (fluorescein) was loaded into 3 μg of bovine vitreous EVs via electropermeabilization at 300 V, the BSA-fluorescein-loaded EVs were repurified, and then cultured ARPE-19 cells were treated with the vector. It was observed that cells were transfected at 97.6%±0.85%, 95.3%±2.428%, and 88.9%±1.745% for concentrations of BSA-fluorescein of 3 μg, 1 μg, and 0.5 μg, respectively. The controls, PBS alone or EVs mixed with BSA-fluorescein without electroporation, did not result in transfection of ARPE-19 cells (FIGS. 10A-10C), and these groups were statistically different than test groups ($p<0.05$, $n=3$). These control data demonstrated that the EV vector was necessary for ARPE-19 cell uptake of BSA-fluorescein. To evaluate whether vitreous EVs are capable of transfecting a functional protein, which must retain its conformational state to fluoresce, recombinant green fluorescent protein (GFP) was loaded into 3 μg vitreous EVs. The data showed that ARPE-19 cells were transfected at 88.3%±4.2%, 81.4%±4.8%, and 72.9%±3.9% for concentrations of GFP at 0.25 μg, 0.5 μg, and 1 μg, respectively (FIGS. 10D-10F). The controls showed no signal, significantly less than the test groups ($p<0.05$, $n=3$). These data show that vitreous EVs are capable of transferring their endogenous RNA as well as exogenous, recombinant protein to cells in vitro.

Bovine vitreous and aqueous EVs are capable of transferring their endogenous protein and RNA into human cells other than ocular cells, such as skin cells. Bovine vitreous EVs endogenous RNAs and endogenous proteins were labeled and transferred into human skin cells at high efficiency as shown in FIGS. 17A-17L. No transfer was observed under control conditions (FIGS. 17M-17R). These data suggest that vitreous EVs have a broad tropism, and can be used as therapeutic delivery vehicles throughout the body for a broad variety of conditions.

Figures 11A, 11B, 11C, 11D:
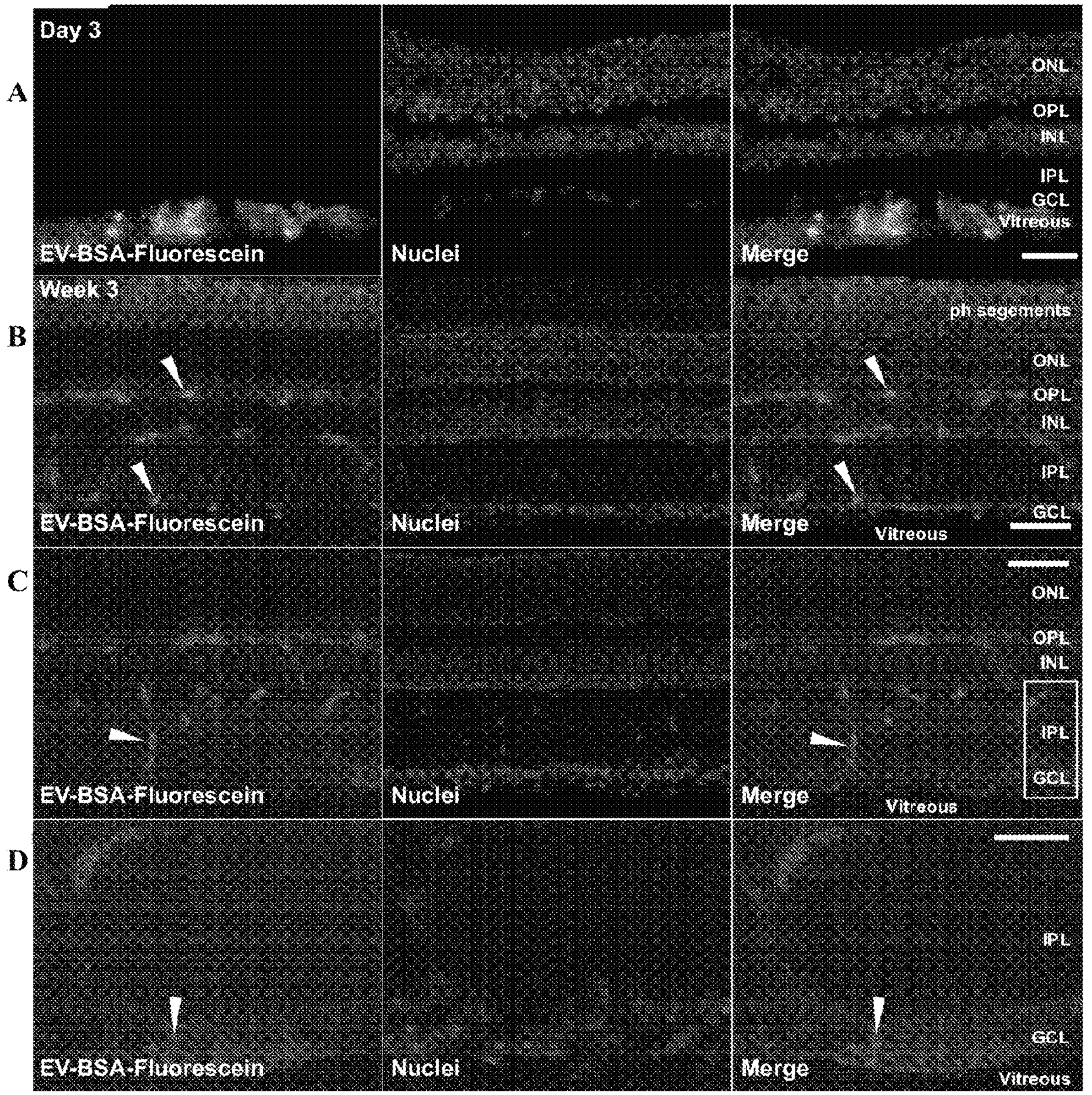
FIGS. 11A-11D show bovine vitreous EVs target the retina and deliver recombinant protein in vivo.

Example 7—Bovine Vitreous EVs Target the Retina and Deliver Recombinant Protein in Vivo An attempt was made to validate vitreous EV transfection efficiency in vivo and determine the target cells in the eye. A dilute amount of EVs (0.025 μg) that were loaded with 0.5 μg of BSA-fluorescein via electroporation were administered to rodent eyes through intravitreal injection, a common technique used for intraocular delivery. On day 3 post-treatment, EVs show no evidence of crossing into the retina and do not penetrate the inner limiting membrane (FIG. 11A). At three weeks post injection, transfection in cells of multiple retinal cell layers was noted (FIG. 11B-11D). For specificity controls, no evidence of transfection was observed with PBS alone or with EV samples mixed with BSA-fluorescein without electropermeabilization. Together, these data show that the vitreous EVs are biologically active and function as a vector to deliver recombinant proteins in vivo. Moreover, vitreous EVs target retinal cells and maintain a sustained transfection for up to 3 weeks.

Figures 12A, 12B, 12C, 12D, 12E:
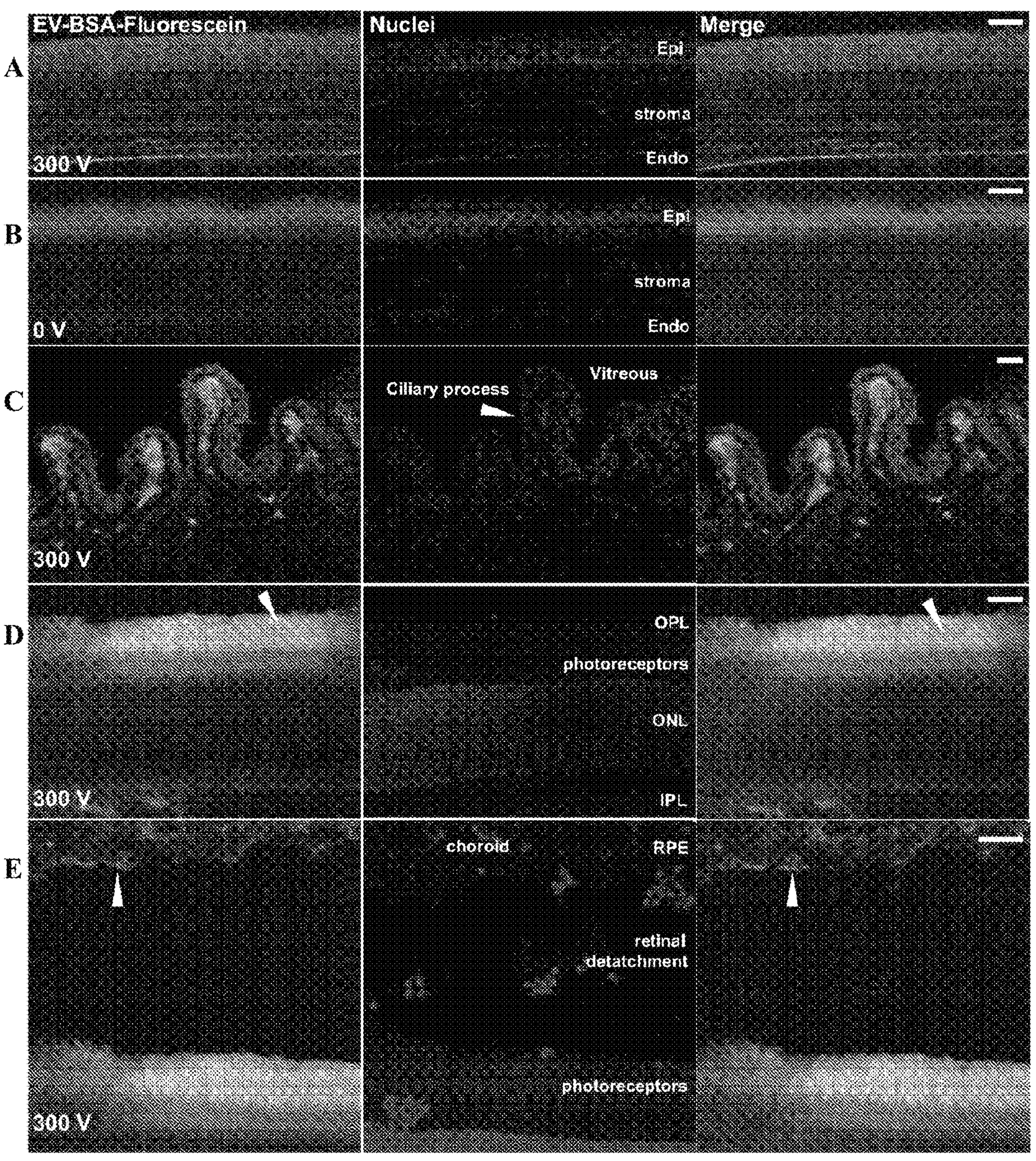
FIGS. 12A-12E show bovine vitreous EVs target the cornea, ciliary body, and retina to deliver recombinant protein in vivo.

Example 8—Bovine Vitreous EVs Target the Cornea, Ciliary Body, and Retina to Deliver Recombinant Protein In Vivo Bovine EVs loaded by electroporation (300 V) with recombinant bovine serum albumin (BSA) conjugated to fluorescein (BSA-fluorescein) were injected into mice eyes. At 3-week post injection mouse eye sections were examined for BSA-fluorescein delivery, and delivery was observed in cornea from endothelial cells and corneal keratocytes as shown in the photomicrographs of FIG. 12A. Images from the control group of bovine EV mixed with BSA-fluorescein without electroporation (0 V) after 3-week injection show no expression in endothelial cells nor corneal keratocytes, but does show non-specific staining of the corneal epithelium (FIG. 12B). FIG. 12C are representative confocal fluorescent photomicrographs from mouse eyes at 3-week post injection of EVs loaded by electroporation (300 V) with BSA-fluorescein show signal in ciliary body, in the non-pigmented ciliary epithelial cells. The images of FIG. 12D show robust expression of BSA-Fluorescein in the photoreceptors, inner plexiform layer (IPL), retinal pigment epithelial (RPE) cells, and choroid. Nuclei in all tissue sections were stained with Hoechst blue, and these are shown in the middle panels of FIGS. 12A-12D. Merged images are shown in the far left panels of FIGS. 12A-12D. The images of FIG. 12E show expression of BSA-fluorescein in the retinal pigment epithelial cells (RPE) and choroid.

Figures 13A, 13B, 13C, 13D, 13E, 13F, 13G, 13H, 13I:
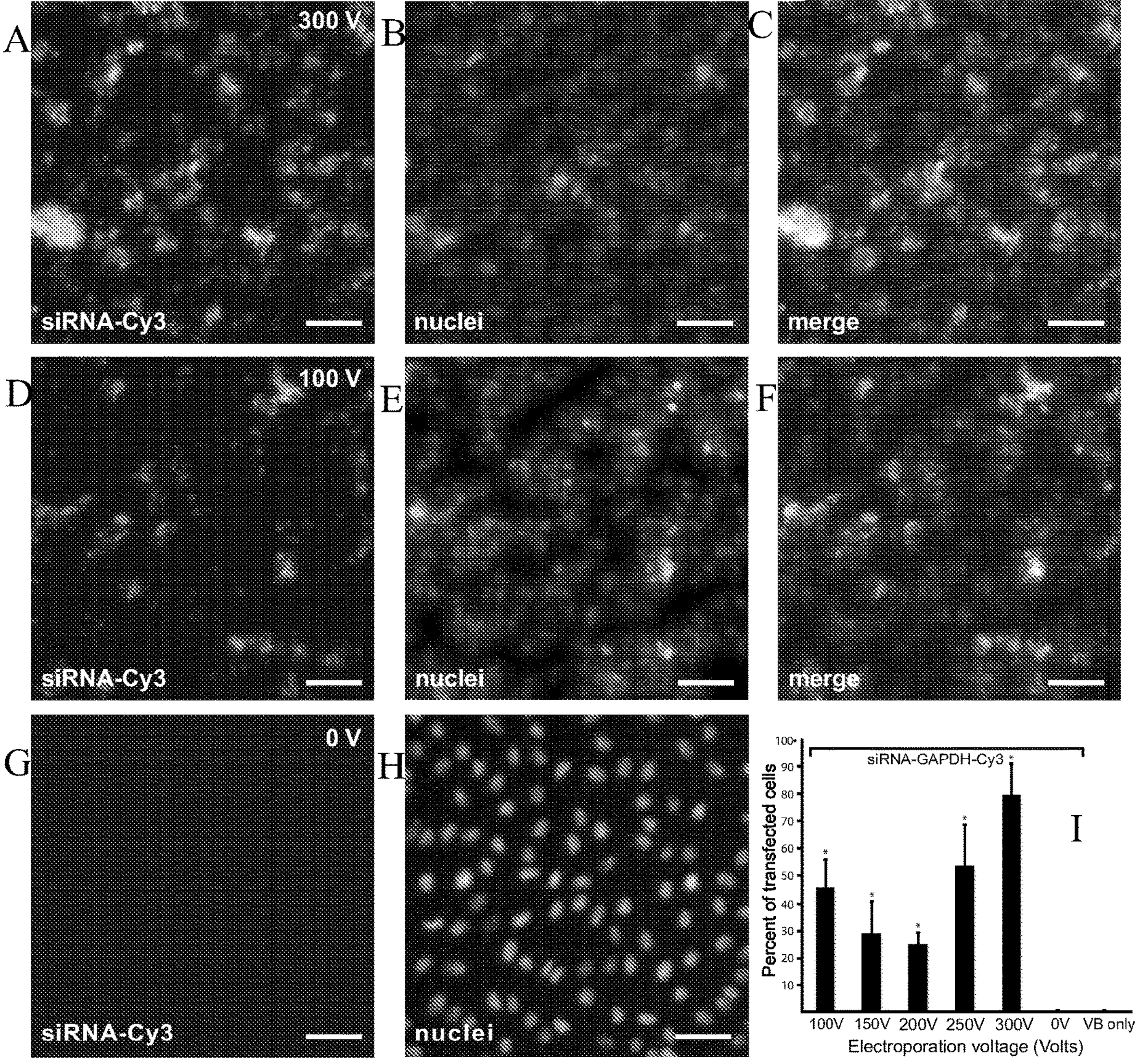
FIGS. 13A-13I show bovine vitreous vesicular bodies loaded with fluorescent labeled siRNAs transfects into human retinal pigment epithelial cells with high efficiency.

Example 9—Bovine Vitreous Vesicular Bodies Loaded with Fluorescent Labeled siRNAs Transfects into Human Retinal Pigment Epithelial Cells with High Efficiency To determine if vitreous vesicular bodies are capable of modification with exogenous small interfering RNAs, an anti-GAPDH siRNA conjugated to cyanine 3 was introduced into vesicular bodies using electroporation. ARPE-19 cells were exposed to anti-GAPDH siRNA-Cy3 loaded into vesicular bodies at various electroporation voltages and it was found that siRNA loaded vesicles transfected the cells at greater efficiency at higher voltages (FIGS. 13A-13C) and less efficiency at lower voltages (FIGS. 13D-13F), and was undetectable without electroporation (FIGS. 13G-13H). FIG. 13I is a graph showing the transfection efficiency by electroporation voltage.

Figures 14A, 14B, 14C, 14D, 14E, 14F:
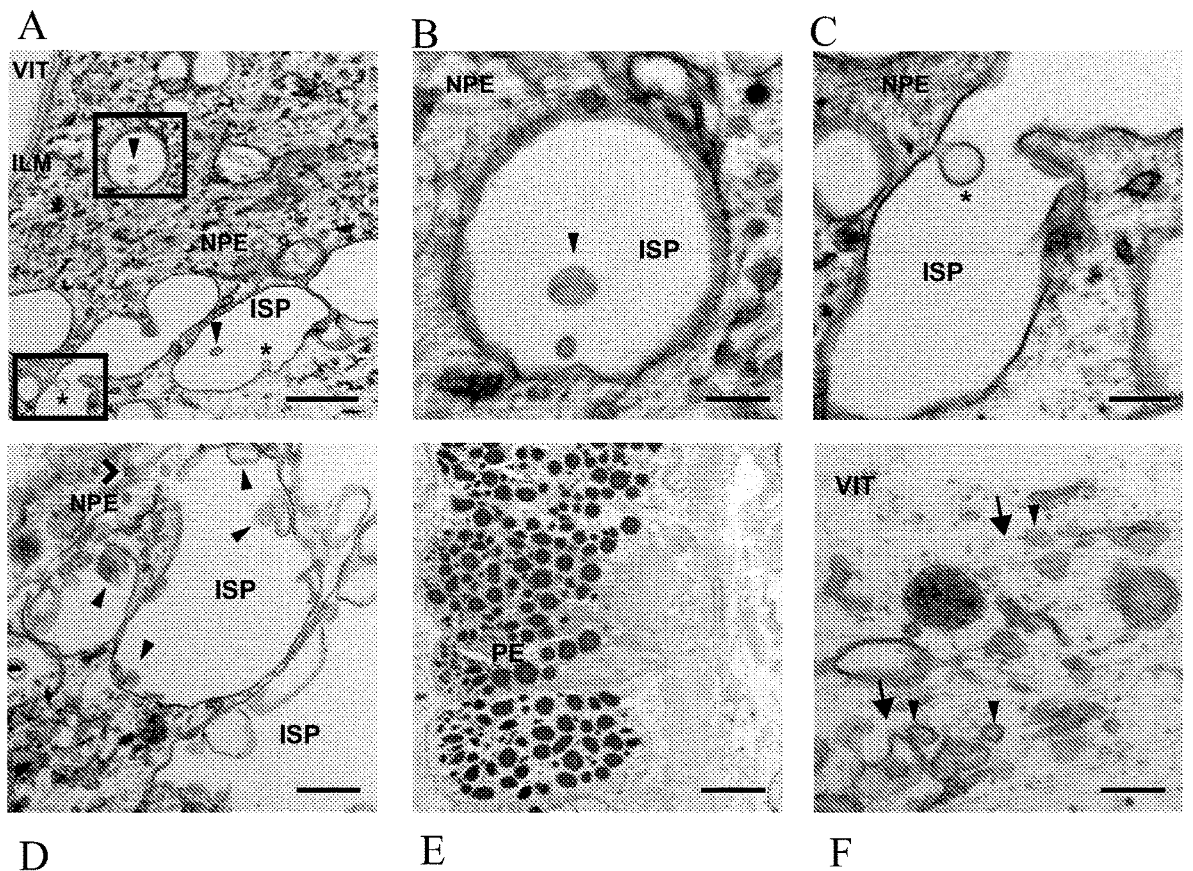
FIGS. 14A-14F show the bovine ciliary body non-pigmented epithelium produces abundant vesicular bodies and that are released into intracellular spaces.

Example 10—Bovine Ciliary Body Non-Pigmented Epithelium Produces Abundant Vesicular Bodies that are Released into Intracellular Spaces It was next sought to identify the origin of the ocular fluid vesicular bodies. It was hypothesized the vesicular bodies are produced in the ciliary body since; 1) the vitreous humor collagen fibrils are highest in concentration near the vitreous base, which is behind the lens and juxtaposed to the ciliary body and; 2) The ciliary body is known to have a high surface area and produces the aqueous humor. Therefore, TEM was conducted on tissue sections of bovine ciliary body stained with uranyl acetate and budding vesicles were found in the non-pigmented epithelium into intercellular spaces (FIGS. 14A-14D). Vesicular body budding in the pigmented epithelium was not observed (FIG. 14E). These data suggest that the ciliary body is at least in part, a source of vesicular bodies in the eye.

Figures 15A, 15B, 15C, 15D, 15E, 15F, 15G, 15H, 15I:
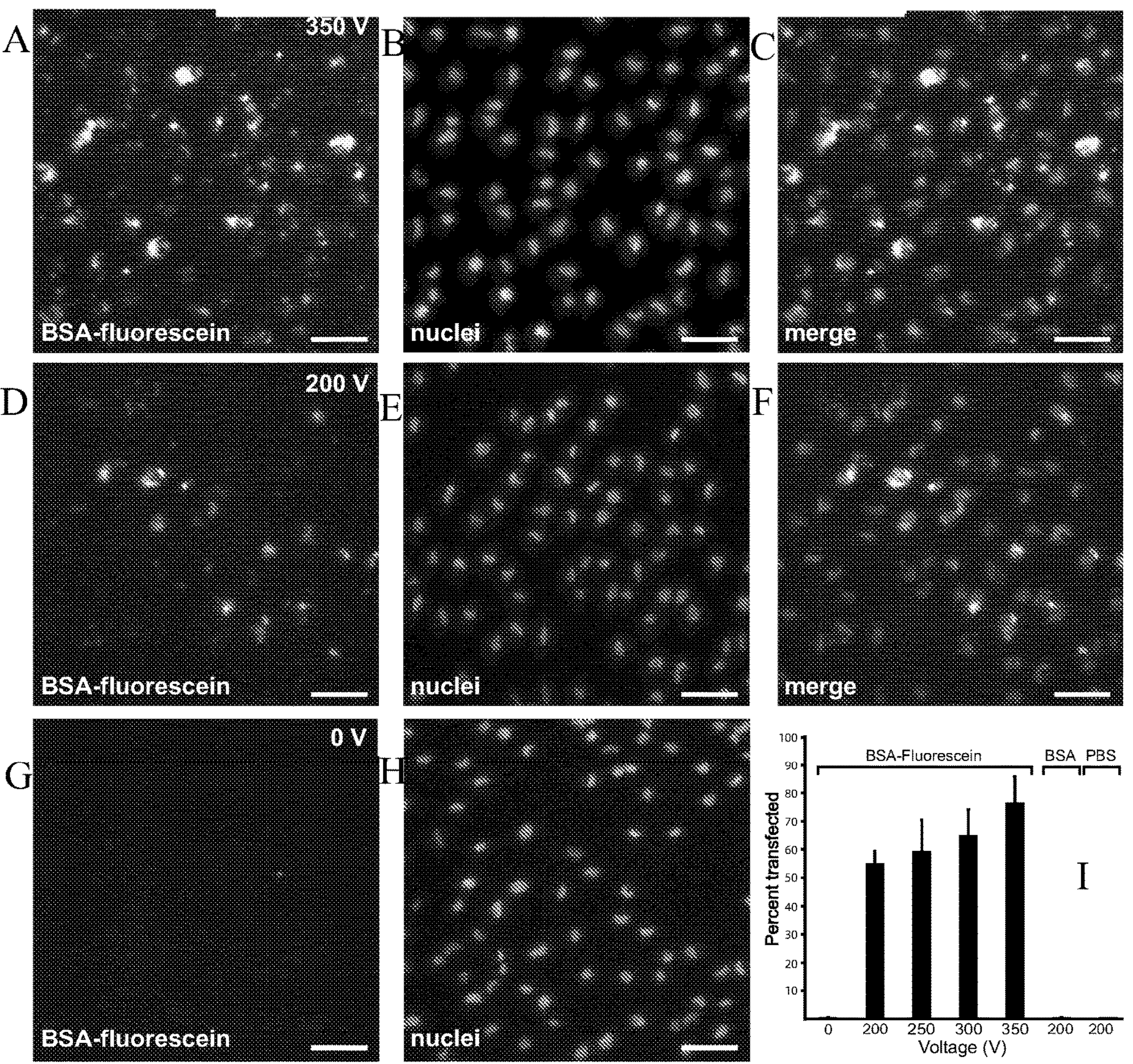
FIGS. 15A-15I show vitreous vesicular bodies loaded with exogenous protein transfects with high efficiency into human retinal pigment epithelial cells.

Example 11—Bovine Vitreous Vesicular Bodies Deliver Proteins in Human Retinal Pigment Epithelial Cells with High Efficiency at Various Voltages As discussed supra, bovine vesicular bodies contain a diverse proteome. It was reasoned these vesicles could be loaded with exogenous proteins and used as a tool to deliver proteins to target cells. Therefore, whether vitreous vesicular bodies are capable of modification with exogenous proteins was examined. Bovine serum albumin conjugated to fluorescein (BSA-fluorescein) was introduced into vesicular bodies using electroporation at various voltages and ARPE-19 cells were exposed to the loaded BSA-fluorescein vesicles. It was found that BSA-fluorescein loaded vesicles transfected ARPE-19 cells at a substantially higher efficiency when loaded with protein using 350 V (FIGS. 15A-15C) as compared to when loaded with protein using 100 V (FIGS. 15D-15F). No transfection was observed in the absence of electroporation (FIGS. 15G-15H).

Example 12—Bovine Aqueous Humor Contains Abundant Vesicular Bodies

Figures 16A, 16B, 16C, 16D, 16E:
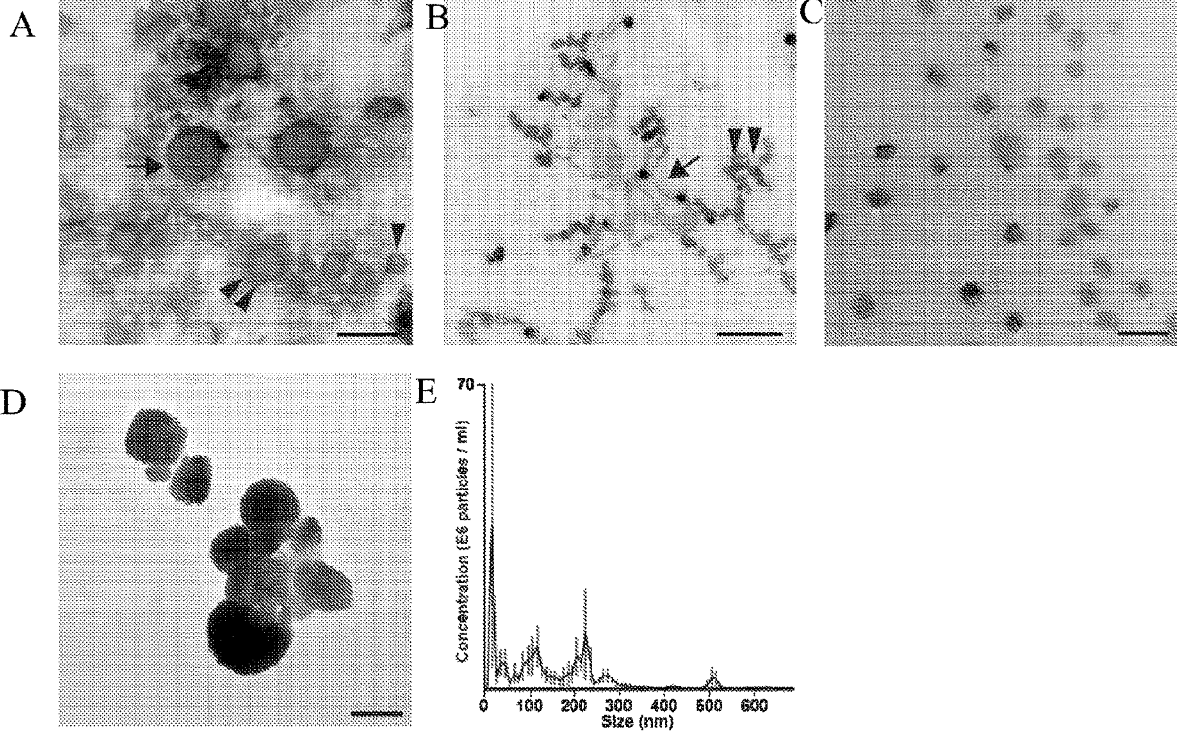
FIGS. 16A-16E show aqueous humor contains abundant vesicular bodies.
Figures 17A, 17R:
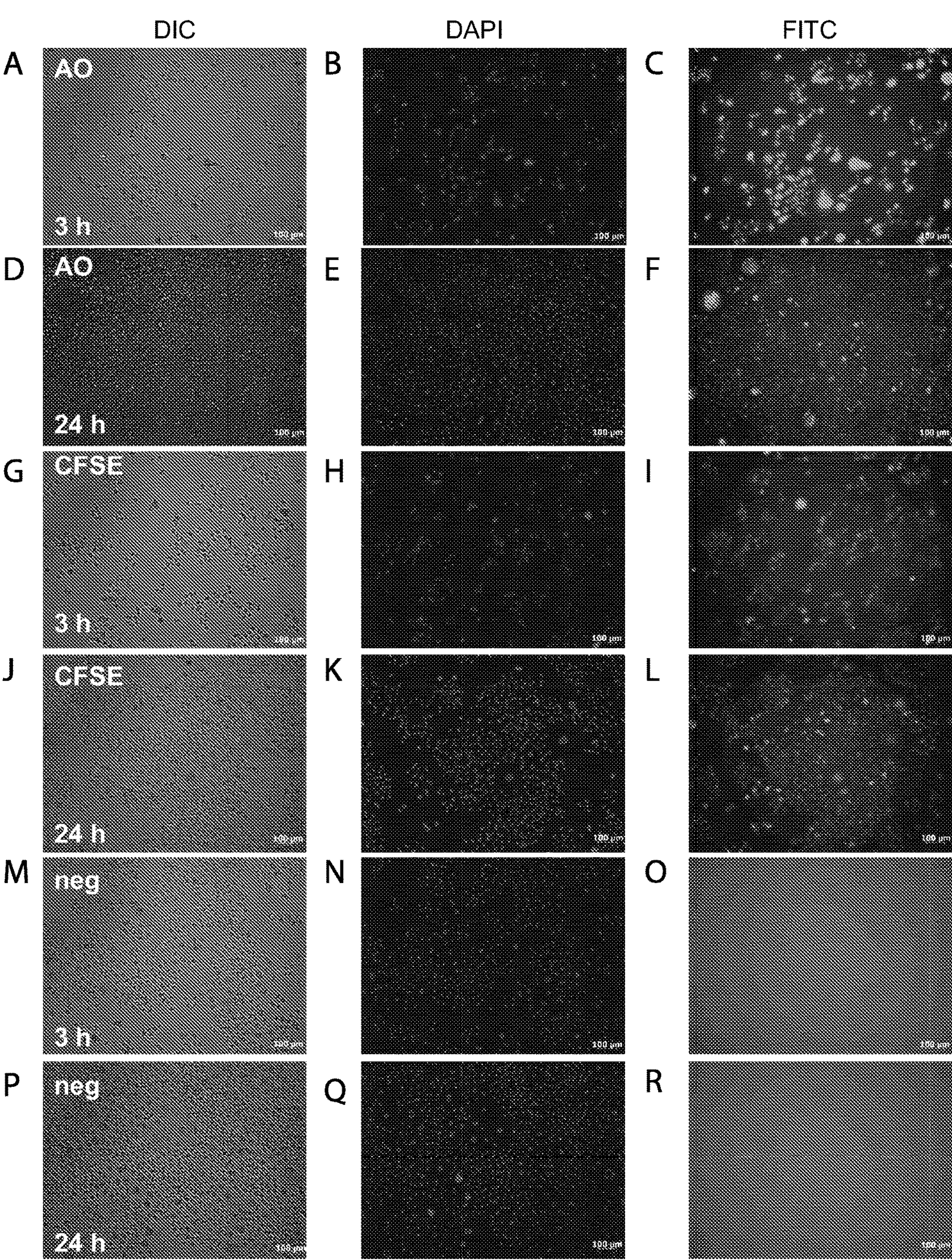
FIGS. 17A-17R show that isolated bovine EVs can transfect human skin cells. Isolated bovine EVs were labeled for endogenous proteins (CFSE) and RNA (acridine orange) and then human skin cells (PAM-212) were transfected in culture.

The high levels of vitreous vesicular bodies led to the hypothesis that vesicular bodies were also likely located in the anterior chamber of the eye within the aqueous humor. Therefore, the aqueous humor was examined with TEM imaging and a wide distribution of vesicular bodies was found (FIGS. 16A-16C). The vesicular body fraction was isolated and vesicular body size and concentration was determined with nanoparticle tracking analysis, which showed a concentration of at least $1.10\times10^8$ particles per ml (FIG. 16E, s.c.m±$9.25\times10^7$ particles per ml, n=10), and a total of $2.7\times10^8$ particles per ml per eye (FIG. 16E, n=10), with a mean size of 155 nm (s.e.m±27.9 nm) and mode of 88.7 nm (s.e.m±34.1) nm. Interestingly, the vesicular body size distribution in the aqueous humor was substantially smaller than vitreous vesicular bodies.

Discussion of Examples

In summary, conventional formalin fixation based techniques result in escape of a substantial amount of EVs from mammalian tissues, which results in inconsistent or negative visualization of EVs in situ. However, EDC-formalin fixation significantly improves retention of EVs in tissues and allows for robust EV imaging in situ. This method illuminated a previously unidentified network of EVs in the normal vitreous humor of the eye, a tissue long considered to have few biological functions. Moreover, the data presented herein demonstrates that vitreous EVs can be manipulated as a vector to deliver recombinant proteins and nucleic acids molecules in vitro and in vivo. In conclusion, this method opens up new possibilities for studying the structure and function of EVs in normal or disease tissues specimens including a wide range of diseases thought to be mediated by EVs such as ophthalmic diseases, neurological disorders, and cancers.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

TABLE 3

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Superoxide dismutase [Cu—Zn] | sp\|P00442\|SODC_BOVIN; tr\|F1MNQ4\|F1MNQ4_BOVIN | 22.602 | 30.464 | −7.862 | 2.90E+09 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Alpha-1-acid glycoprotein | tr\|Q5GN72\|Q5GN72_BOVIN; sp\|Q3SZR3\|A1AG_BOVIN; CON_Q3SZR3 | 23.646 | 31.172 | −7.526 | 2.70E+09 |
| Carbonic anhydrase 2 | sp\|P00921\|CAH2_BOVIN | 22.362 | 29.354 | −6.992 | 6.20E+08 |
| Uncharacterized protein | tr\|F1MIL3\|F1MIL3_BOVIN | 23.282 | 30.226 | −6.943 | 4.80E+08 |
| Plasminogen | tr\|E1B726\|E1B726_BOVIN; tr\|A7E350\|A7E350_BOVIN | 23.421 | 30.323 | −6.901 | 3.60E+08 |
| Beta-crystallin B2 | sp\|P02522\|CRBB2_BOVIN | 25.394 | 32.077 | −6.682 | 4.10E+09 |
| Vitamin D-binding protein | tr\|F1N5M2\|F1N5M2_BOVIN; CON_ENSEMBL: ENSBTAP00000018229; sp\|Q3MHN5\|VTDB_BOVIN; CON_Q3MHN5 | 25.276 | 31.824 | −6.548 | 2.10E+09 |
| Contactin-1 | tr\|F1MVI0\|F1MVI0_BOVIN; sp\|Q28106\|CNTN1_BOVIN | 22.155 | 28.658 | −6.503 | 1.00E+08 |
| N(G),N(G)-dimethylarginine dimethylaminohydrolase 1 | sp\|P56965\|DDAH1_BOVIN | 23.851 | 30.220 | −6.369 | 1.00E+09 |
| Beta-2-glycoprotein 1 | sp\|P17690\|APOH_BOVIN; CON_P17690 | 22.838 | 29.009 | −6.171 | 4.10E+08 |
| Isoform 2 of Prosaposin | sp\|P26779-2\|SAP_BOVIN | 24.161 | 30.297 | −6.136 | 6.40E+08 |
| Beta-crystallin A3 | sp\|P11843\|CRBA1_BOVIN; sp\|P11843-2\|CRBA1_BOVIN | 23.426 | 29.561 | −6.135 | 9.70E+08 |
| Triosephosphate isomerase | sp\|Q5E956\|TPIS_BOVIN | 25.211 | 31.324 | −6.113 | 2.20E+09 |
| Aspartate aminotransferase, cytoplasmic | sp\|P33097\|AATC_BOVIN | 37.271 | 31.166 | −6.105 | 1.30E+09 |
| Nucleoside diphosphate kinase A 2 | sp\|P52175\|NDKA2_BOVIN; sp\|P52174\|NDKA1_BOVIN; tr\|G1K1A3\|G1K1A3_BOVIN | 23.196 | 29.102 | −5.906 | 7.10E+08 |
| Beta-2-microglobulin | sp\|P01888\|B2MG_BOVIN | 22.905 | 28.765 | −5.860 | 1.00E+09 |
| Fascin | tr\|Q3MHK9\|Q3MHK9_BOVIN | 22.848 | 28.699 | −5.851 | 2.00E+08 |
| Retinol-binding protein 4 | sp\|P18902\|RET4_BOVIN; tr\|G1K122\|G1K122_BOVIN | 24.465 | 30.314 | −5.849 | 2.00E+09 |
| Ectonucleotide pyrophosphatase/phosphodiesterase family member 2 | sp\|A1A4K5\|ENPP2_BOVIN | 24.627 | 30.447 | −5.820 | 4.40E+08 |
| Uncharacterized protein (Fragment) | tr\|G5E604\|G5E604_BOVIN | 24.911 | 30.127 | −5.217 | 3.20E+09 |
| DKK3 protein | tr\|A6QL81\|A6QL81_BOVIN | 26.859 | 32.061 | −5.202 | 3.20E+09 |
| Phosphatidylethanolamine-binding protein 1 | sp\|P13696\|PEBP1_BOVIN | 26.793 | 31.988 | −5.195 | 4.50E+09 |
| 12 kDa protein | CON_ENSEMBL:ENSBTAP00000014147; tr\|G3N2D7\|G3N2D7_BOVIN | 25.722 | 30.836 | −5.115 | 4.40E+09 |
| Beta A4 crystallin | tr\|Q6DTZ8\|Q6DTZ8_BOVIN; sp\|P11842\|CRBA4_BOVIN | 23.947 | 29.042 | −5.095 | 8.30E+08 |
| SPARC-like 1 (Hevin) | tr\|Q3SYW7\|Q3SYW7_BOVIN | 25.349 | 30.359 | −5.009 | 5.80E+08 |
| Transferrin | CON_Q0IIK2; CON_Q29443; sp\|Q29443\|TRFE_BOVIN; sp\|P24627\|TRFL_BOVIN | 29.333 | 34.318 | −4.986 | 6.80E+09 |
| Secernin-1 | sp\|P83939\|SCRN1_BOVIN | 23.902 | 28.854 | −4.952 | 4.40E+08 |
| Amyloid beta (A4) protein | tr\|Q08E54\|Q08E54_BOVIN | 27.302 | 32.122 | −4.820 | 2.20E+09 |
| Protein HP-20 homolog | sp\|Q2KIT0\|HP20_BOVIN; CON_Q2KIT0 | 24.398 | 29.126 | −4.728 | 7.30E+08 |
| Fructose-bisphosphate aldolase | tr\|A6QLL8\|A6QLL8_BOVIN | 26.352 | 30.909 | −4.557 | 1.20E+09 |
| Hemopexin | sp\|Q3SZV7\|HEMO_BOVIN | 27.158 | 31.679 | −4.520 | 2.00E+09 |
| Complement factor H | sp\|Q28085\|CFAH_BOVIN; CON_Q28085; tr\|E1BFN5\|E1BFN5_BOVIN | 25.819 | 30.259 | −4.441 | 2.80E+08 |
| Ubiquitin-60S ribosomal protein L40 | sp\|P63048\|RL40_BOVIN; sp\|P62992\|RS27A_BOVIN; tr\|E1B9K1\|E1B9K1_BOVIN; sp\|P0CG53\|UBB_BOVIN; sp\|P0CH28\|UBC_BOVIN | 27.095 | 31.526 | −4.430 | 6.80E+09 |
| Prostaglandin-H2 D-isomerase | sp\|O02853\|PTGDS_BOVIN | 27.751 | 32.132 | −4.382 | 1.20E+10 |
| Uncharacterized protein | tr\|G3MYY6\|G3MYY6_BOVIN | 23.753 | 28.122 | −4.369 | 7.00E+07 |
| Peptidyl-prolyl cis-trans isomerase A | sp\|P62935\|PPIA_BOVIN; tr\|G3X8B1\|G3X8B1_BOVIN; tr\|G3MZS9\|G3MZS9_BOVIN; sp\|A4FV72\|PPIE_BOVIN | 25.766 | 30.133 | −4.367 | 1.60E+09 |
| Uncharacterized protein | tr\|G8JKW7\|G8JKW7_BOVIN | 25.222 | 29.501 | −4.279 | 5.30E+08 |
| Gamma-synuclein | sp\|Q9NZ50\|SYUG_BOVIN | 23.391 | 27.653 | −4.262 | 3.60E+08 |
| Alpha-1-antiproteinase | sp\|P34955\|A1AT_BOVIN; CON_P34955 | 26.848 | 31.033 | −4.185 | 1.50E+09 |
| Uncharacterized protein | tr\|F1N4M7\|F1N4M7_BOVIN; CON_Q32PI4 | 26.330 | 30.462 | −4.132 | 5.30E+08 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Fructose-bisphosphate aldolase | tr\|Q3ZBY4\|Q3ZBY4_BOVIN; tr\|A5PK73\|A5PK73_BOVIN; sp\|Q3T0S5\|ALDOB_BOVIN | 27.423 | 31.539 | −4.116 | 1.90E+09 |
| Serpin A3-7 | sp\|A2I7N3\|SPA37_BOVIN; CON_A2I7N3 | 26.452 | 30.558 | −4.106 | 1.20E+09 |
| Insulin-like growth factor-binding protein 6 | tr\|F1MUK3\|F1MUK3_BOVIN; sp\|Q05718\|IBP6_BOVIN | 24.771 | 28.773 | −4.002 | 5.70E+08 |
| Uncharacterized protein | tr\|E1BLM2\|E1BLM2_BOVIN | 25.797 | 29.650 | −3.852 | 1.90E+08 |
| Superoxide dismutase [Cu—Zn] | tr\|A3KLR9\|A3KLR9_BOVIN | 23.538 | 27.381 | −3.843 | 2.40E+08 |
| Serpin A3-1 | sp\|Q9TTE1\|SPA31_BOVIN; CON_Q9TTE1 | 28.309 | 32.074 | −3.766 | 3.60E+09 |
| Protein FAM3C | sp\|A5PKI3\|FAM3C_BOVIN | 25.873 | 29.552 | −3.679 | 8.50E+08 |
| Complement factor B | CON_Q3KUS7; sp\|P81187\|CFAB_BOVIN | 27.471 | 31.129 | −3.658 | 9.10E+08 |
| Fatty acid-binding protein, epidermal | sp\|P55052\|FABP5_BOVIN; tr\|G3N269\|G3N269_BOVIN | 25.962 | 29.509 | −3.547 | 1.30E+09 |
| Uncharacterized protein (Fragment) | tr\|F1N226\|F1N226_BOVIN | 28.827 | 32.351 | −3.524 | 2.40E+09 |
| Leucine-rich alpha-2-glycoprotein 1 | tr\|Q2KIF2\|Q2KIF2_BOVIN; CON_Q2KIF2 | 24.082 | 27.599 | −3.517 | 1.70E+08 |
| 44 kDa protein | CON_ENSEMBL: ENSBTAP00000024466 | 26.445 | 29.937 | −3.492 | 8.40E+08 |
| Complement component C7 | tr\|F1N045\|F1N045_BOVIN; sp\|Q29RQ1\|CO7_BOVIN; CON_Q29RQ1 | 23.540 | 26.987 | −3.447 | 3.30E+07 |
| Transketolase | tr\|A7Z014\|A7Z014_BOVIN; tr\|A7E3W4\|A7E3W4_BOVIN | 27.980 | 31.413 | −3.433 | 1.60E+09 |
| Apolipoprotein A-IV | tr\|F1N3Q7\|F1N3Q7_BOVIN; sp\|Q32PJ2\|APOA4_BOVIN; CON_Q32PJ2 | 25.676 | 29.107 | −3.431 | 3.90E+08 |
| Rho GDP-dissociation inhibitor 1 | sp\|P19803\|GDIR1_BOVIN; tr\|Q58DT6\|Q58DT6_BOVIN | 23.758 | 27.156 | −3.398 | 2.30E+08 |
| Uncharacterized protein (Fragment) | tr\|F1MW33\|F1MW33_BOVIN | 27.383 | 30.695 | −3.312 | 5.50E+08 |
| Spondin-1 | sp\|Q9GLX9\|SPON1_BOVIN | 25.918 | 29.188 | −3.270 | 2.20E+08 |
| Versican core protein | tr\|F1MZ85\|F1MZ85_BOVIN; sp\|P81282\|CSPG2_BOVIN; tr\|F1MZ83\|F1MZ83_BOVIN; sp\|P81282-3\|CSPG2_BOVIN; tr\|F1N6I5\|F1N6I5_BOVIN; sp\|P81282-2\|CSPG2_BOVIN; tr\|F1N6I7\|F1N6I7_BOVIN; sp\|P81282-4\|CSPG2_BOVIN | 25.871 | 29.079 | −3.208 | 6.00E+07 |
| Microtubule-associated protein | tr\|F1MEW3\|F1MEW3_BOVIN | 25.105 | 28.293 | −3.189 | 4.90E+07 |
| Hemoglobin subunit alpha | sp\|P01966\|HBA_BOVIN; CON_P01966; tr\|F1MMI1\|F1MMI1_BOVIN; tr\|E1BAP8\|E1BAP8_BOVIN | 28.801 | 31.916 | −3.115 | 6.30E+09 |
| Pigment epithelium-derived factor | sp\|Q95121\|PEDF_BOVIN; CON_Q95121 | 29.317 | 32.298 | −2.981 | 3.20E+09 |
| Metalloproteinase inhibitor 2 | tr\|F1N430\|F1N430_BOVIN; sp\|P16368\|TIMP2_BOVIN | 24.231 | 27.203 | −2.972 | 1.90E+08 |
| Metalloproteinase inhibitor 1 | sp\|P20414\|TIMP1_BOVIN | 24.511 | 27.440 | −2.930 | 3.20E+08 |
| Malate dehydrogenase, cytoplasmic | sp\|Q3T145\|MDHC_BOVIN | 27.167 | 30.066 | −2.899 | 1.10E+09 |
| Rab GDP dissociation inhibitor alpha | sp\|P21856\|GDIA_BOVIN | 27.525 | 30.403 | −2.879 | 8.10E+08 |
| Isoaspartyl peptidase/L-asparaginase | sp\|Q32LE5\|ASGL1_BOVIN | 23.567 | 26.410 | −2.842 | 9.40E+07 |
| Phosphoprotein enriched in astrocytes 15 | tr\|Q0VCY8\|Q0VCY8_BOVIN | 24.651 | 27.444 | −2.793 | 3.60E+08 |
| Isoform 3 of Neurexin-3-beta | sp\|Q28143-3\|NRX3B_BOVIN; sp\|Q28143\|NRX3B_BOVIN; tr\|F1MR33\|F1MR33_BOVIN; sp\|Q28143-4\|NRX3B_BOVIN; sp\|Q28143-2\|NRX3B_BOVIN; tr\|G3X794\|G3X794_BOVIN; tr\|F6RU36\|F6RU36_BOVIN | 23.933 | 26.721 | −2.788 | 1.10E+08 |
| Glucose-6-phosphate isomerase | sp\|Q3ZBD7\|G6PI_BOVIN; CON_Q3ZBD7 | 28.915 | 31.682 | −2.768 | 1.80E+09 |
| Latent-transforming growth factor beta-binding protein 2 | tr\|F1MF86\|F1MF86_BOVIN; sp\|Q28019\|LTBP2_BOVIN | 25.914 | 28.631 | −2.717 | 7.90E+07 |
| Cathepsin B | sp\|P07688\|CATB_BOVIN | 24.321 | 27.005 | −2.684 | 1.10E+08 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Macrophage migration inhibitory factor | sp\|P80177\|MIF_BOVIN | 25.576 | 28.244 | −2.668 | 8.40E+08 |
| Alpha-crystallin A chain | sp\|P02470\|CRYAA_BOVIN | 30.314 | 32.963 | −2.649 | 1.10E+10 |
| similar to endopin 2B | CON_REFSEQ: XP_001252647 | 28.386 | 31.016 | −2.630 | 1.70E+09 |
| Haptoglobin | sp\|Q2TBU0\|HPT_BOVIN; tr\|G3X6K8\|G3X6K8_BOVIN | 26.301 | 28.923 | −2.622 | 2.60E+08 |
| Uncharacterized protein | tr\|F1MI18\|F1MI18_BOVIN; tr\|F1MJK3\|F1MJK3_BOVIN | 23.474 | 26.063 | −2.589 | 1.30E+07 |
| Beta-crystallin S | sp\|P06504\|CRBS_BOVIN | 24.716 | 27.285 | −2.569 | 2.60E+08 |
| WAP, Kazal, immunoglobulin, Kunitz and NTR domain-containing protein 2 | tr\|F1MRR8\|F1MRR8_BOVIN; sp\|Q08E66\|WFKN2_BOVIN | 26.327 | 28.853 | −2.526 | 3.30E+08 |
| Histidine triad nucleotide-binding protein 1 | sp\|P62958\|HINT1_BOVIN | 25.815 | 28.317 | −2.502 | 7.60E+08 |
| Seizure protein 6 homolog | tr\|F1N649\|F1N649_BOVIN; sp\|A0JNA2\|SEZ6_BOVIN | 27.474 | 29.972 | −2.498 | 4.50E+08 |
| Glutathione S-transferase Mu 1 | tr\|A1A4L7\|A1A4L7_BOVIN | 24.255 | 26.706 | −2.451 | 1.00E+08 |
| Beta-crystallin A2 | sp\|P26444\|CRBA2_BOVIN | 24.556 | 26.966 | −2.411 | 1.60E+08 |
| Serum albumin | sp\|P02769\|ALBU_BOVIN; CON_P02769 | 33.997 | 36.325 | −2.329 | 3.20E+10 |
| Protein CutA | tr\|F1MTI7\|F1MTI7_BOVIN; tr\|F1N5T0\|F1N5T0_BOVIN; sp\|P69678\|CUTA_BOVIN | 25.272 | 27.584 | −2.312 | 4.70E+08 |
| Uncharacterized protein | tr\|F1MZ96\|F1MZ96_BOVIN; tr\|F1MH40\|F1MH40_BOVIN; CON_Q05B55 | 26.892 | 29.189 | −2.297 | 7.90E+08 |
| Apolipoprotein E | sp\|Q03247\|APOE_BOVIN; CON_Q03247 | 28.872 | 31.167 | −2.295 | 2.30E+09 |
| Neural cell adhesion molecule 1 (Fragment) | tr\|F1MMJ2\|F1MMJ2_BOVIN; sp\|P31836\|NCAM1_BOVIN | 26.725 | 28.952 | −2.227 | 2.10E+08 |
| Chondroadherin | tr\|F1MYE4\|F1MYE4_BOVIN; sp\|Q27972\|CHAD_BOVIN | 25.400 | 27.601 | −2.202 | 1.90E+08 |
| Protein DJ-1 | sp\|Q5E946\|PARK7_BOVIN | 27.638 | 29.820 | −2.182 | 1.00E+09 |
| Nucleoside diphosphate kinase B | sp\|Q3T0Q4\|NDKB_BOVIN; tr\|F1MPL4\|F1MPL4_BOVIN | 24.330 | 26.507 | −2.177 | 1.40E+08 |
| Calbindin | sp\|P04467\|CALB1_BOVIN | 25.302 | 27.430 | −2.128 | 1.70E+08 |
| Protein AMBP | tr\|F1MMK9\|F1MMK9_BOVIN; sp\|P00978\|AMBP_BOVIN; CON_P00978 | 25.095 | 27.186 | −2.090 | 1.30E+08 |
| Uncharacterized protein (Fragment) | tr\|F1MD95\|F1MD95_BOVIN | 29.489 | 31.555 | −2.066 | 1.30E+09 |
| Protein S100-A1 | sp\|P02639\|S10A1_BOVIN; tr\|H9KUV1\|H9KUV1_BOVIN | 27.359 | 29.412 | −2.053 | 3.80E+09 |
| Isoform 3 of Microtubule-associated protein 4 | sp\|P36225-3\|MAP4_BOVIN; tr\|F1MAZ3\|F1MAZ3_BOVIN; sp\|P36225-4\|MAP4_BOVIN; tr\|G3N2G7\|G3N2G7_BOVIN; tr\|F1MAZ1\|F1MAZ1_BOVIN; sp\|P36225\|MAP4_BOVIN; sp\|P36225-2\|MAP4_BOVIN; tr\|F1N0J2\|F1N0J2_BOVIN | 25.476 | 27.522 | −2.045 | 4.80E+07 |
| Uncharacterized protein | tr\|E1BBY7\|E1BBY7_BOVIN | 24.581 | 26.626 | −2.045 | 3.00E+07 |
| Poly(RC) binding protein 3 | tr\|Q17QV0\|Q17QV0_BOVIN; sp\|Q0VCU0\|PCBP4_BOVIN | 29.413 | 27.398 | 2.015 | 2.00E+08 |
| Uncharacterized protein | tr\|E1BNY5\|E1BNY5_BOVIN; tr\|G3N1P4\|G3N1P4_BOVIN; tr\|F6R352\|F6R352_BOVIN; tr\|E1BMQ2\|E1BMQ2_BOVIN; tr\|F1MEH0\|F1MEH0_BOVIN | 27.656 | 25.618 | 2.038 | 3.30E+07 |
| Uncharacterized protein | tr\|F1MZU2\|F1MZU2_BOVIN; tr\|G3N178\|G3N178_BOVIN | 30.598 | 28.541 | 2.056 | 1.30E+08 |
| Retinaldehyde-binding protein 1 | sp\|P10123\|RLBP1_BOVIN | 32.209 | 30.124 | 2.085 | 1.50E+09 |
| Cullin-associated NEDD8-dissociated protein 1 | sp\|A7MBJ5\|CAND1_BOVIN; tr\|E1BNE2\|E1BNE2_BOVIN; tr\|G3N157\|G3N157_BOVIN | 29.951 | 27.856 | 2.095 | 6.30E+07 |
| SNX12 protein | tr\|A6QR61\|A6QR61_BOVIN | 27.838 | 25.738 | 2.099 | 7.10E+07 |
| Uncharacterized protein | tr\|E1BHR3\|E1BHR3_BOVIN | 27.565 | 25.465 | 2.100 | 1.20E+08 |
| Lactadherin | sp\|Q95114\|MFGM_BOVIN; tr\|F1MXX6\|F1MXX6_BOVIN; sp\|Q95114-2\|MFGM_BOVIN; tr\|G3MYW7\|G3MYW7_BOVIN | 25.996 | 23.886 | 2.109 | 9.40E+06 |
| >P35527 SWISS-PROT: P35527 Tax_Id = 9606 | CON_P35527; tr\|G3X7W8\|G3X7W8_BOVIN; CON_Q99456; tr\|G3MX98\| | 28.971 | 26.835 | 2.136 | 7.20E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Gene_Symbol = KRT9 Keratin, type I cytoskeletal 9 | G3MX98_BOVIN | | | | |
| Dynamin-1-like protein | sp\|Q2KIA5\|DNM1L_BOVIN | 28.918 | 26.778 | 2.140 | 3.60E+07 |
| EGF-containing fibulin-like extracellular matrix protein 1 | tr\|A2VE41\|A2VE41_BOVIN | 31.663 | 29.517 | 2.146 | 6.20E+08 |
| Synaptojanin-1 | tr\|E1BD68\|E1BD68_BOVIN; tr\|F1MC12\|F1MC12_BOVIN; sp\|O18964\|SYNJ1_BOVIN | 27.268 | 25.112 | 2.156 | 8.50E+06 |
| Dynamin-1 | sp\|Q08DF4\|DYN1_BOVIN | 29.583 | 27.425 | 2.158 | 5.40E+07 |
| Fibrillin-1 | tr\|F1N4K8\|F1N4K8_BOVIN; sp\|P98133\|FBN1_BOVIN; tr\|F1MTZ4\|F1MTZ4_BOVIN | 32.261 | 30.068 | 2.193 | 1.20E+08 |
| SUB1 protein | tr\|A7YWC6\|A7YWC6_BOVIN | 26.815 | 24.615 | 2.200 | 9.50E+07 |
| Uncharacterized protein (Fragment) | tr\|F1MJ70\|F1MJ70_BOVIN; tr\|A6QLJ2\|A6QLJ2_BOVIN | 29.150 | 26.935 | 2.215 | 7.80E+07 |
| Oxidation resistance protein 1 (Fragment) | tr\|F1MR28\|F1MR28_BOVIN; sp\|A5PKL1\|OXR1_BOVIN; tr\|Q0II63\|Q0II133_BOVIN | 26.788 | 24.498 | 2.290 | 1.10E+07 |
| Elongation factor 1-alpha 1 | sp\|P68103\|EF1A1_BOVIN; tr\|E1B9F6\|E1B9F6_BOVIN; tr\|G3N0P6\|G3N0P6_BOVIN; tr\|E1BED8\|E1BED8_BOVIN; tr\|E1B7J1\|E1B7J1_BOVIN; tr\|G3N2F0\|G3N2F0_BOVIN; tr\|E1BPF4\|E1BPF4_BOVIN | 28.821 | 26.528 | 2.293 | 7.20E+07 |
| Uncharacterized protein (Fragment) | tr\|F1MPE5\|F1MPE5_BOVIN; tr\|F1N074\|F1N074_BOVIN | 27.638 | 25.338 | 2.300 | 9.30E+06 |
| Syntaxin-binding protein 1 | tr\|F6R0H3\|F6R0H3_BOVIN | 30.466 | 28.153 | 2.313 | 1.90E+08 |
| Uncharacterized protein | tr\|E1BFV0\|E1BFVO_BOVIN | 26.789 | 24.451 | 2.337 | 1.10E+07 |
| Eukaryotic initiation factor 4A-II | sp\|Q3SZ65\|IF4A2_BOVIN | 30.167 | 27.826 | 2.340 | 1.60E+08 |
| Calcyclin-binding protein | sp\|Q3T168\|CYBP_BOVIN | 27.032 | 24.684 | 2.348 | 3.90E+07 |
| Mitogen-activated protein kinase 1 | sp\|P46196\|MK01_BOVIN; tr\|F1MI27\|F1MI27_BOVIN; tr\|F1MVV5\|F1MVV5_BOVIN; tr\|G5E577\|G5E577_BOVIN | 28.682 | 26.331 | 2.350 | 8.60E+07 |
| Uncharacterized protein | tr\|F1N5F9\|F1N5F9_BOVIN | 27.727 | 25.376 | 2.351 | 3.10E+07 |
| Poly(RC) binding protein 2 | tr\|Q3SYT9\|Q3SYT9_BOVIN | 26.633 | 24.280 | 2.352 | 2.80E+07 |
| Arrestin-C | sp\|Q9N0H5\|ARRC_BOVIN; tr\|F1MCQ1\|F1MCQ1_BOVIN | 26.132 | 23.762 | 2.370 | 1.40E+07 |
| V-type proton ATPase subunit B, brain isoform | sp\|P31408\|VATB2_BOVIN; tr\|F1N688\|F1N688_BOVIN; sp\|P31407\|VATB1_BOVIN | 27.441 | 25.051 | 2.389 | 2.10E+07 |
| Retinol-binding protein 3 | sp\|P12661\|RET3_BOVIN | 36.246 | 33.846 | 2.400 | 5.40E+09 |
| Uncharacterized protein (Fragment) | tr\|F1MKZ3\|F1MKZ3_BOVIN | 29.234 | 26.796 | 2.438 | 2.70E+07 |
| Isoform Beta of V-type proton ATPase subunit H | sp\|O46563-2\|VATH_BOVIN; sp\|O46563\|VATH_BOVIN; tr\|F1MZL6\|F1MZL6_BOVIN; tr\|F1MZL8\|F1MZL8_BOVIN | 25.964 | 23.504 | 2.460 | 7.70E+06 |
| >P15636 SWISS-PROT: P15636 Protease I precursor Lysyl endopeptidase *Achromobacter lyticus*. | CON_P15636 | 33.776 | 31.310 | 2.466 | 1.60E+09 |
| Histone H3.3 | sp\|Q5E9F8\|H33_BOVIN; tr\|G3MYD7\|G3MYD7_BOVIN; sp\|A5PK61\|H3C_BOVIN; tr\|G3N2P2\|G3N2P2_BOVIN; tr\|E1BGN3\|E1BGN3_BOVIN; sp\|P84227\|H32_BOVIN; sp\|P68432\|H31_BOVIN; sp\|Q3SZB8\|H3CL_BOVIN | 27.521 | 25.025 | 2.496 | 8.70E+07 |
| ADP-ribosylation factor 4 | sp\|Q3SZF2\|ARF4_BOVIN | 27.440 | 24.914 | 2.525 | 4.80E+07 |
| Elongation factor 1-alpha 2 | sp\|Q32PH8\|EF1A2_BOVIN | 31.216 | 28.670 | 2.546 | 3.40E+08 |
| Phosphoribosylaminoimidazole carboxylase, phosphoribosylaminoimidazole succinocarboxamide synthetase | tr\|Q2HJ26\|Q2HJ26_BOVIN; tr\|F1MN04\|F1MN04_BOVIN | 27.307 | 24.756 | 2.551 | 2.70E+07 |
| ADP-ribosylation factor 3 | sp\|Q5E9I6\|ARF3_BOVIN | 30.361 | 27.800 | 2.561 | 3.60E+08 |
| Uncharacterized protein | tr\|F2Z4C1\|F2Z4C1_BOVIN; sp\|Q3ZCJ7\|TBA1C_BOVIN; tr\|F1MNF8\|F1MNF8_BOVIN; tr\|F2Z4K0\|F2Z4K0_BOVIN; | 29.832 | 27.246 | 2.586 | 1.70E+08 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| | tr\|F6RP72\|F6RP72_BOVIN; sp\|Q32KN8\|TBA3_BOVIN | | | | |
| Uncharacterized protein | tr\|F1MVT7\|F1MVT7_BOVIN | 27.080 | 24.460 | 2.620 | 1.50E+07 |
| Opticin | sp\|P58874\|OPT_BOVIN | 31.543 | 28.894 | 2.649 | 1.10E+09 |
| Uncharacterized protein | tr\|E1BMU2\|E1BMU2_BOVIN | 27.283 | 24.606 | 2.677 | 2.90E+07 |
| Uncharacterized protein | tr\|F1MQ37\|F1MQ37_BOVIN | 25.781 | 23.103 | 2.678 | 2.00E+06 |
| SERPIND1 protein | tr\|A6QPP2\|A6QPP2_BOVIN; CON_ENSEMBL: ENSBTAP00000018574 | 30.392 | 27.707 | 2.685 | 1.60E+08 |
| Uncharacterized protein (Fragment) | tr\|E1BKM4\|E1BKM4_BOVIN | 27.286 | 24.592 | 2.695 | 9.60E+06 |
| Glyceraldehyde-3-phosphate dehydrogenase | sp\|P10096\|G3P_BOVIN; sp\|Q2KJE5\|G3PT_BOVIN; tr\|E1BH84\|E1BH84_BOVIN | 34.591 | 31.867 | 2.724 | 4.90E+09 |
| cAMP-dependent protein kinase catalytic subunit beta | sp\|P05131\|KAPCB_BOVIN; tr\|E1BEN2\|E1BEN2_BOVIN; sp\|P05131-2\|KAPCB_BOVIN | 26.843 | 24.113 | 2.730 | 1.60E+07 |
| T-complex protein 1 subunit gamma | sp\|Q3T0K2\|TCPG_BOVIN; tr\|F1N5P4\|F1N5P4_BOVIN | 25.906 | 23.121 | 2.784 | 5.80E+06 |
| Spliceosome RNA helicase DDX39B | sp\|Q3T147\|DX39B_BOVIN; tr\|Q5E970\|Q5E970_BOVIN | 29.131 | 26.341 | 2.790 | 8.70E+07 |
| Acid ceramidase | sp\|Q17QB3\|ASAH1_BOVIN | 25.522 | 22.707 | 2.815 | 6.30E+06 |
| GSK3A protein | tr\|A6QLB8\|A6QLB8_BOVIN | 26.003 | 23.144 | 2.859 | 1.00E+07 |
| APPL1 protein | tr\|A5PKI0\|A5PKI0_BOVIN; tr\|Q1RMW4\|Q1RMW4_BOVIN | 25.936 | 23.025 | 2.910 | 3.70E+06 |
| T-complex protein 1 subunit eta (Fragment) | tr\|F1MWR8\|F1MWR8_BOVIN; sp\|Q2NKZ1\|TCPH_BOVIN | 25.932 | 22.997 | 2.936 | 5.20E+06 |
| Leukocyte cell-derived chemotaxin 1 | sp\|P17404\|LECT1_BOVIN | 29.516 | 26.574 | 2.942 | 1.20E+08 |
| Clathrin heavy chain 1 | sp\|P49951\|CLH1_BOVIN; tr\|F1MPU0\|F1MPU0_BOVIN | 28.006 | 24.980 | 3.026 | 8.60E+06 |
| RAB14 protein | tr\|Q3ZBG1\|Q3ZBG1_BOVIN | 26.733 | 23.664 | 3.068 | 1.70E+07 |
| Uncharacterized protein (Fragment) | tr\|E1BFD5\|E1BFD5_BOVIN; tr\|F1N3S4\|F1N3S4_BOVIN | 26.362 | 23.255 | 3.107 | 4.00E+06 |
| Uncharacterized protein | tr\|F1MQI1\|F1MQI1_BOVIN | 26.483 | 23.371 | 3.112 | 1.80E+06 |
| N-acylneuraminate cytidylyltransferase | sp\|Q3SZM5\|NEUA_BOVIN; tr\|E1B9W3\|E1B9W3_BOVIN | 28.044 | 24.454 | 3.590 | 2.50E+07 |
| Uncharacterized protein (Fragment) | tr\|F1N1S8\|F1N1S8_BOVIN | 26.724 | 23.077 | 3.647 | 9.30E+06 |
| Isoform IB of Synapsin-1 | sp\|P17599-2\|SYN_BOVIN; sp\|P17599\|SYN1_BOVIN | 27.294 | 23.644 | 3.649 | 8.80E+06 |
| Fatty acid synthase | tr\|F1N647\|F1N647_BOVIN | 29.253 | 25.490 | 3.763 | 1.10E+07 |
| Uncharacterized protein | tr\|E1BE98\|E1BE98_BOVIN | 27.384 | 23.552 | 3.831 | 6.00E+06 |
| Exportin-2 | tr\|F1MWN1\|F1MWN1_BOVIN; sp\|A5D785\|XPO2_BOVIN; tr\|Q58DL4\|Q58DL4_BOVIN | 26.849 | 22.975 | 3.874 | 4.40E+06 |
| T-complex protein 1 subunit beta | sp\|Q3ZBH0\|TCPB_BOVIN | 26.928 | 22.900 | 4.028 | 7.10E+06 |
| MGC139254 protein | tr\|A5D7E1\|A5D7E1_BOVIN; tr\|E1BJV0\|E1BJV0_BOVIN | 27.409 | 22.675 | 4.734 | 9.90E+06 |
| Platelet-activating factor acetylhydrolase | sp\|Q28017\|PAFA_BOVIN; tr\|Q1RML9\|Q1RML9_BOVIN | 28.048 | 22.764 | 5.284 | 1.80E+07 |
| Ras-related protein Rab-21 | sp\|Q17R06\|RAB21_BOVIN | 20.130 | NaN | EV fraction only | 8.80E+04 |
| Chromosome 14 open reading frame 166 ortholog | tr\|Q3T0S7\|Q3T0S7_BOVIN | 20.158 | NaN | EV fraction only | 7.30E+04 |
| Uncharacterized protein | tr\|F1MEP1\|F1MEP1_BOVIN; sp\|Q1JP73\|CI064_BOVIN | 20.318 | NaN | EV fraction only | 5.30E+06 |
| Copine I | tr\|Q08DB4\|Q08DB4_BOVIN | 20.398 | NaN | EV fraction only | 6.00E+04 |
| Uncharacterized protein | tr\|F1MVC0\|F1MVCO_BOVIN | 20.517 | NaN | EV fraction only | 1.50E+04 |
| Uncharacterized protein | tr\|G3MZK0\|G3MZK0_BOVIN | 20.538 | NaN | EV fraction only | 9.50E+04 |
| Basal cell adhesion molecule | sp\|Q9MZ08\|BCAM_BOVIN | 20.565 | NaN | EV fraction only | 5.30E+04 |
| Ubiquitin carboxyl-terminal hydrolase | tr\|Q0IIM6\|Q0IIM6_BOVIN | 20.718 | NaN | EV fraction only | 3.30E+04 |
| Uncharacterized protein | tr\|G3N3D4\|G3N3D4_BOVIN | 20.722 | NaN | EV fraction only | 1.20E+05 |
| Uncharacterized protein | tr\|E1BFB0\|E1BFB0_BOVIN | 20.766 | NaN | EV fraction only | 1.20E+04 |
| Uncharacterized protein (Fragment) | tr\|F1MLQ5\|F1MLQ5_BOVIN | 20.857 | NaN | EV fraction only | 5.40E+04 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| ATP-dependent RNA helicase DDX19A | sp\|Q3ZBV2\|DD19A_BOVIN; tr\|F1MUT6\|F1MUT6_BOVIN; tr\|Q58DE5\|Q58DE5_BOVIN | 20.898 | NaN | EV fraction only | 7.00E+04 |
| 60S ribosomal protein L24 | sp\|Q862I1\|RL24_BOVIN | 20.938 | NaN | EV fraction only | 2.50E+05 |
| Phosphomannomutase 2 | sp\|Q3SZJ9\|PMM2_BOVIN | 20.968 | NaN | EV fraction only | 1.30E+05 |
| Eukaryotic translation initiation factor 2 subunit 2 | sp\|Q5E9D0\|IF2B_BOVIN | 21.116 | NaN | EV fraction only | 1.10E+05 |
| 26S proteasome non-ATPase regulatory subunit 6 | tr\|F1MXE4\|F1MXE4_BOVIN; sp\|Q3T0B2\|PSMD6_BOVIN | 21.119 | NaN | EV fraction only | 9.10E+04 |
| Uncharacterized protein | tr\|F1MJJ9\|F1MJJ9_BOVIN | 21.148 | NaN | EV fraction only | 7.50E+04 |
| Uncharacterized protein | tr\|F1MLE8\|F1MLE8_BOVIN | 21.156 | NaN | EV fraction only | 1.80E+05 |
| RFK protein (Fragment) | tr\|Q3SZP4\|Q3SZP4_BOVIN | 21.203 | NaN | EV fraction only | 2.20E+05 |
| 40S ribosomal protein S18 | sp\|Q3T0R1\|RS18_BOVIN | 21.227 | NaN | EV fraction only | 2.70E+05 |
| Coronin | tr\|F1MK51\|F1MK51_BOVIN; tr\|H7BWW0\|H7BWW0_BOVIN | 21.237 | NaN | EV fraction only | 1.90E+05 |
| Nucleosome assembly protein 1-like 4 | tr\|F1N7X3\|F1N7X3_BOVIN; sp\|Q2TA40\|NP1L4_BOVIN | 21.250 | NaN | EV fraction only | 1.60E+05 |
| Vacuolar protein sorting-associated protein 29 (Fragment) | tr\|G3X6P5\|G3X6P5_BOVIN; sp\|Q3T0M0\|VPS29_BOVIN | 21.252 | NaN | EV fraction only | 2.50E+05 |
| 60S ribosomal protein L6 | tr\|G3N2R1\|G3N2R1_BOVIN; sp\|Q58DQ3\|RL6_BOVIN | 21.302 | NaN | EV fraction only | 2.20E+05 |
| Golgi phosphoprotein 3-like | sp\|A6H7F6\|GLP3L_BOVIN; tr\|Q1RMW9\|Q1RMW9_BOVIN | 21.370 | NaN | EV fraction only | 1.60E+05 |
| Hemoglobin fetal subunit beta | sp\|P02081\|HBBF_BOVIN; CON_Q3SX09; tr\|G3MZ21\|G3MZ21_BOVIN; tr\|G3N1Y3\|G3N1Y3_BOVIN; tr\|E1BEL8\|E1BEL8_BOVIN; sp\|P06643\|HBE4_BOVIN; sp\|IP06642\|HBE2_BOVIN | 21.380 | NaN | EV fraction only | 2.50E+05 |
| Keratin, type II cytoskeletal 5 | tr\|M0QVZ6\|M0QVZ6_BOVIN; CON_Q922U2; tr\|A5D7M6\|A5D7M6_BOVIN; sp\|Q5XQN5\|K2C5_BOVIN; CON_Q5XQN5; sp\|Q08D91\|K2C75_BOVIN; CON_Q8BGZ7; CON_P50446; tr\|G3MXL3\|G3MXL3_BOVIN | 21.381 | NaN | EV fraction only | 8.80E+04 |
| GALE protein | tr\|Q3T105\|Q3T105_BOVIN | 21.392 | NaN | EV fraction only | 1.60E+05 |
| Uncharacterized protein | tr\|E1BAB9\|E1BAB9_BOVIN | 21.399 | NaN | EV fraction only | 4.00E+05 |
| Dystrobrevin | tr\|E1BMA8\|E1BMA8_BOVIN; tr\|E1BJB8\|E1BJB8_BOVIN | 21.405 | NaN | EV fraction only | 6.20E+04 |
| Uncharacterized protein | tr\|G3X696\|G3X696_BOVIN | 21.418 | NaN | EV fraction only | 4.40E+04 |
| Dehydrogenase/reductase SDR family member 11 | sp\|Q3ZBV9\|DHR11_BOVIN | 21.497 | NaN | EV fraction only | 2.00E+05 |
| Uncharacterized protein | tr\|F1N5V9\|F1N5V9_BOVIN | 21.514 | NaN | EV fraction only | 5.00E+05 |
| IST1 homolog | tr\|F1MXJ5\|F1MXJ5_BOVIN; sp\|Q3ZBV1\|IST1_BOVIN | 21.557 | NaN | EV fraction only | 2.80E+05 |
| Methylthioribose-1-phosphate isomerase | sp\|Q2NL31\|MTNA_BOVIN | 21.568 | NaN | EV fraction only | 1.60E+05 |
| ADP-ribosylation factor 2 | sp\|P84081\|ARF2_BOVIN | 21.594 | NaN | EV fraction only | 3.20E+05 |
| PPCS protein | tr\|A6QPS1\|A6QPS1_BOVIN | 21.596 | NaN | EV fraction only | 3.20E+05 |
| Uncharacterized protein (Fragment) | tr\|F1MJZ4\|F1MJZ4_BOVIN | 21.601 | NaN | EV fraction only | 9.60E+04 |
| Eukaryotic translation initiation factor 3 subunit K | sp\|Q3T0V3\|EIF3K_BOVIN | 21.663 | NaN | EV fraction only | 3.00E+05 |
| Uncharacterized protein | tr\|F6QK60\|F6QK60_BOVIN | 21.715 | NaN | EV fraction only | 1.50E+05 |
| DnaJ homolog subfamily A member 2 | sp\|Q2HJ94\|DNJA2_BOVIN | 21.741 | NaN | EV fraction only | 1.60E+05 |
| Uncharacterized protein (Fragment) | tr\|F1N605\|F1N605_BOVIN | 21.751 | NaN | EV fraction only | 1.60E+05 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| DMD protein | tr\|A8WFL6\|A8WFL6_BOVIN | 21.753 | NaN | EV fraction only | 1.30E+05 |
| Uncharacterized protein | tr\|F1ML33\|F1ML33_BOVIN; sp\|Q08DM5\|CS012_BOVIN | 21.757 | NaN | EV fraction only | 5.10E+05 |
| Protein phosphatase 2, regulatory subunit B, alpha isoform | tr\|A2VDZ0\|A2VDZ0_BOVIN | 21.839 | NaN | EV fraction only | 1.60E+05 |
| ADP-ribosylation factor GTPase-activating protein 2 | tr\|A6QR32\|A6QR32_BOVIN; sp\|A1L520\|ARFG2_BOVIN | 21.878 | NaN | EV fraction only | 1.40E+05 |
| Uncharacterized protein (Fragment) | tr\|E1BMF5\|E1BMF5_BOVIN; tr\|A6QR52\|A6QR52_BOVIN | 21.901 | NaN | EV fraction only | 1.20E+05 |
| Isoform 2 of Cell division control protein 42 homolog | sp\|Q2KJ93-2\|CDC42_BOVIN; tr\|F1N5L2\|F1N5L2_BOVIN | 21.940 | NaN | EV fraction only | 4.50E+05 |
| Isoform B of Phosphate carrier protein, mitochondrial | sp\|P12234-2\|MPCP_BOVIN; sp\|P12234\|MPCP_BOVIN | 21.968 | NaN | EV fraction only | 2.30E+05 |
| Uncharacterized protein (Fragment) | tr\|F1MZX3\|F1MZX3_BOVIN | 21.994 | NaN | EV fraction only | 1.90E+06 |
| Uncharacterized protein (Fragment) | tr\|E1BMW2\|E1BMW2_BOVIN; tr\|G5E675\|G5E675_BOVIN; sp\|Q0VCK5\|AP2A2_BOVIN | 21.998 | NaN | EV fraction only | 1.30E+06 |
| LRRC47 protein | tr\|A6QR01\|A6QR01_BOVIN | 22.020 | NaN | EV fraction only | 1.50E+05 |
| Phakinin | sp\|Q28177\|BFSP2_BOVIN; tr\|F1MR92\|F1MR92_BOVIN | 22.028 | NaN | EV fraction only | 1.60E+05 |
| Uncharacterized protein | tr\|G3N2H3\|G3N2H3_BOVIN; tr\|F1MIK1\|F1MIK1_BOVIN; tr\|E1BLC8\|E1BLC8_BOVIN | 22.037 | NaN | EV fraction only | 5.80E+04 |
| Protein kinase C delta type | tr\|F1MZX0\|F1MZX0_BOVIN; tr\|E1BMG4\|E1BMG4_BOVIN | 22.040 | NaN | EV fraction only | 1.10E+05 |
| TSG101 protein | tr\|A3KN51\|A3KN51_BOVIN | 22.053 | NaN | EV fraction only | 2.30E+05 |
| 26S protease regulatory subunit 10B | tr\|F1MLV1\|F1MLV1_BOVIN; sp\|Q2KIW6\|PRS10_BOVIN | 22.056 | NaN | EV fraction only | 2.10E+05 |
| Uncharacterized protein | tr\|G5E6N8\|G5E6N8_BOVIN | 22.072 | NaN | EV fraction only | 1.90E+05 |
| Uncharacterized protein | tr\|E1BKE3\|E1BKE3_BOVIN; tr\|E1B999\|E1B999_BOVIN; tr\|F1N020\|F1N020_BOVIN | 22.082 | NaN | EV fraction only | 3.80E+06 |
| Uncharacterized protein | tr\|E1BIE5\|E1BIE5_BOVIN | 22.102 | NaN | EV fraction only | 2.50E+05 |
| LGI4 protein | tr\|A6QLD0\|A6QLD0_BOVIN | 22.115 | NaN | EV fraction only | 1.60E+05 |
| Very-long-chain enoyl-CoA reductase | sp\|Q3ZCD7\|TECR_BOVIN | 22.143 | NaN | EV fraction only | 3.60E+05 |
| Uncharacterized protein | tr\|E1BLS8\|E1BLS8_BOVIN | 22.162 | NaN | EV fraction only | 9.20E+04 |
| Ubiquitin-like modifier activating enzyme 3 | tr\|Q0P5I7\|Q0P5I7_BOVIN | 22.171 | NaN | EV fraction only | 2.10E+05 |
| Phosphorylase (Fragment) | tr\|F1MU24\|F1MU24_BOVIN | 22.185 | NaN | EV fraction only | 1.20E+05 |
| Uncharacterized protein (Fragment) | tr\|F1MD34\|F1MD34_BOVIN | 22.218 | NaN | EV fraction only | 1.40E+05 |
| Serine threonine kinase 39 (STE20/SPS1 homolog, yeast) | tr\|Q32LA8\|Q32LA8_BOVIN | 22.244 | NaN | EV fraction only | 5.50E+05 |
| Uncharacterized protein | tr\|E1BM26\|E1BM26_BOVIN | 22.261 | NaN | EV fraction only | 3.90E+05 |
| Similar to Immunoglobulin lambda-like polypeptide 1 | CON_Q1RMN8 | 22.314 | NaN | EV fraction only | 5.80E+05 |
| Sulfurtransferase | tr\|Q3MHG3\|Q3MHG3_BOVIN | 22.325 | NaN | EV fraction only | 3.50E+05 |
| EH-domain containing 2 | tr\|Q2KJ47\|Q2KJ47_BOVIN | 22.328 | NaN | EV fraction only | 1.80E+05 |
| Selenocysteine lyase | sp\|A2VDS1\|SCLY_BOVIN | 22.376 | NaN | EV fraction only | 2.40E+05 |
| Oxysterol-binding protein | tr\|E1BLV1\|E1BLV1_BOVIN; tr\|Q58DI6\|Q58DI6_BOVIN; tr\|F1MYP7\|F1MYP7_BOVIN; tr\|E1BL67\|E1BL67_BOVIN | 22.404 | NaN | EV fraction only | 1.10E+05 |
| Uncharacterized protein (Fragment) | tr\|F1MCY0\|F1MCY0_BOVIN | 22.444 | NaN | EV fraction only | 1.90E+05 |
| Kinesin-associated protein 3 | tr\|Q3MHI2\|Q3MHI2_BOVIN | 22.496 | NaN | EV fraction only | 1.70E+05 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Uncharacterized protein | tr\|F1MCK4\|F1MCK4_BOVIN | 22.500 | NaN | EV fraction only | 4.20E+05 |
| Calcium/calmodulin-dependent protein kinase type II subunit beta | sp\|Q3MHJ9\|KCC2B_BOVIN; tr\|F1MG86\|F1MG86_BOVIN; tr\|F1MVF1\|F1MVF1_BOVIN | 22.509 | NaN | EV fraction only | 2.20E+05 |
| Protein kinase C and casein kinase substrate in neurons 2 | tr\|Q1RMR9\|Q1RMR9_BOVIN | 22.568 | NaN | EV fraction only | 2.50E+05 |
| Alpha-soluble NSF attachment protein | tr\|A5D7S0\|A5D7S0_BOVIN; sp\|P81125\|SNAA_BOVIN | 22.585 | NaN | EV fraction only | 3.50E+05 |
| Uncharacterized protein | tr\|F1N2Y2\|F1N2Y2_BOVIN | 22.590 | NaN | EV fraction only | 8.50E+04 |
| Protein kinase C epsilon type | tr\|F1MDC9\|F1MDC9_BOVIN; tr\|F1MY82\|F1MY82_BOVIN | 22.595 | NaN | EV fraction only | 1.50E+05 |
| Oxysterol-binding protein (Fragment) | tr\|E1BPW1\|E1BPW1_BOVIN | 22.596 | NaN | EV fraction only | 1.70E+05 |
| Uncharacterized protein | tr\|F1N6X2\|F1N6X2_BOVIN | 22.606 | NaN | EV fraction only | 2.50E+05 |
| Coronin-1A | sp\|Q92176\|COR1A_BOVIN | 22.614 | NaN | EV fraction only | 3.40E+05 |
| 60S ribosomal protein L3 | sp\|P39872\|RL3_BOVIN | 22.616 | NaN | EV fraction only | 3.40E+05 |
| Transportin-1 (Fragment) | tr\|F1MMY6\|F1MMY6_BOVIN; sp\|Q3SYU7\|TNPO1_BOVIN; tr\|F1MBJ7\|F1MBJ7_BOVIN; tr\|Q2KI57\|Q2KI57_BOVIN | 22.630 | NaN | EV fraction only | 1.80E+05 |
| Vesicle-associated membrane protein-associated protein B | sp\|A2VDZ9\|VAPB_BOVIN; sp\|Q0VCY1\|VAPA_BOVIN | 22.634 | NaN | EV fraction only | 1.20E+06 |
| Protein S100-A14 | sp\|Q3MHP3\|S10AE_BOVIN | 22.636 | NaN | EV fraction only | 8.20E+05 |
| THUMP domain-containing protein 1 | sp\|Q24K03\|THUM1_BOVIN | 22.677 | NaN | EV fraction only | 3.00E+05 |
| Malate dehydrogenase, mitochondrial | sp\|Q32LG3\|MDHM_BOVIN; tr\|G1K1H1\|G1K1H1_BOVIN | 22.681 | NaN | EV fraction only | 5.10E+06 |
| Guanine nucleotide-binding protein subunit gamma | tr\|G3MYD3\|G3MYD3_BOVIN; sp\|P63217\|GBG5_BOVIN | 22.684 | NaN | EV fraction only | 1.70E+06 |
| Uncharacterized protein | tr\|F1MLD0\|F1MLD0_BOVIN | 22.692 | NaN | EV fraction only | 1.60E+05 |
| TAR DNA binding protein | tr\|Q2KJ45\|Q2KJ45_BOVIN; tr\|G3MX91\|G3MX91_BOVIN | 22.701 | NaN | EV fraction only | 5.20E+05 |
| Uncharacterized protein (Fragment) | tr\|F1N2J6\|F1N2J6_BOVIN | 22.739 | NaN | EV fraction only | 2.50E+05 |
| ADP-ribosylation factor-like protein 6 | sp\|Q0IIM2\|ARL6_BOVIN | 22.744 | NaN | EV fraction only | 5.90E+05 |
| Tubulin-specific chaperone C | sp\|Q3SZE9\|TBCC_BOVIN | 22.751 | NaN | EV fraction only | 4.20E+05 |
| Isoform 2 of 26S proteasome non-ATPase regulatory subunit 11 | sp\|Q2KI42-2\|PSD11_BOVIN; sp\|Q2KI42\|PSD11_BOVIN | 22.767 | NaN | EV fraction only | 3.00E+05 |
| LANCL2 protein | tr\|A6QPG6\|A6QPG6_BOVIN | 22.782 | NaN | EV fraction only | 3.00E+06 |
| GTP-binding protein Rheb | tr\|F2Z4I1\|F2Z4I1_BOVIN; sp\|Q56JV3\|RHEB_BOVIN | 22.784 | NaN | EV fraction only | 8.00E+05 |
| Uncharacterized protein (Fragment) | tr\|E1BG62\|E1BG62_BOVIN | 22.785 | NaN | EV fraction only | 2.30E+05 |
| Diamine acetyltransferase 2 | sp\|Q7PCJ8\|SAT2_BOVIN | 22.801 | NaN | EV fraction only | 7.30E+05 |
| ATP-dependent (S)-NAD(P)H-hydrate dehydratase | sp\|E1BNQ4\|NNRD_BOVIN | 22.802 | NaN | EV fraction only | 3.70E+05 |
| Uncharacterized protein | tr\|F1N579\|F1N579_BOVIN; tr\|F1N4F8\|F1N4F8_BOVIN; tr\|F1MYK3\|F1MYK3_BOVIN | 22.833 | NaN | EV fraction only | 2.10E+06 |
| Serine/threonine-protein phosphatase (Fragment) | tr\|F1N6B7\|F1N6B7_BOVIN | 22.835 | NaN | EV fraction only | 4.20E+05 |
| Metalloproteinase inhibitor 3 | tr\|A5PKB4\|A5PKB4_BOVIN; sp\|P79121\|TIMP3_BOVIN | 22.839 | NaN | EV fraction only | 4.60E+06 |
| Lysosome-associated membrane glycoprotein 1 | sp\|Q05204\|LAMP1_BOVIN | 22.863 | NaN | EV fraction only | 3.80E+05 |
| Syntaxin-binding protein 1 | sp\|P61763\|STXB1_BOVIN | 22.908 | NaN | EV fraction only | 2.50E+05 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Guanidinoacetate N-methyltransferase | sp\|Q2TBQ3\|GAMT_BOVIN | 22.914 | NaN | EV fraction only | 7.90E+05 |
| TNPO3 protein | tr\|A5D7C4\|A5D7C4_BOVIN | 22.920 | NaN | EV fraction only | 7.70E+05 |
| 26S proteasome non-ATPase regulatory subunit 12 | sp\|Q2KJ25\|PSD12_BOVIN | 22.921 | NaN | EV fraction only | 1.60E+06 |
| Ubiquitin-conjugating enzyme E2 H | sp\|Q32LN1\|UBE2H_BOVIN | 22.922 | NaN | EV fraction only | 1.10E+06 |
| Uncharacterized protein | tr\|F1MF68\|F1MF68_BOVIN; tr\|G3MZH4\|G3MZH4_BOVIN | 22.933 | NaN | EV fraction only | 2.90E+06 |
| Uncharacterized protein | tr\|F1MBY5\|F1MBY5_BOVIN | 22.942 | NaN | EV fraction only | 2.10E+05 |
| Uncharacterized protein | tr\|F1MXF3\|F1MXF3_BOVIN; tr\|F1MGT1\|F1MGT1_BOVIN | 22.962 | NaN | EV fraction only | 1.90E+05 |
| Uncharacterized protein | tr\|A1A4I8\|A1A4I8_BOVIN | 22.977 | NaN | EV fraction only | 1.50E+05 |
| Uncharacterized protein | tr\|F1MSJ9\|F1MSJ9_BOVIN | 22.977 | NaN | EV fraction only | 6.40E+06 |
| Cysteine and glycine-rich protein 1 | sp\|Q3MHY1\|CSRP1_BOVIN | 22.979 | NaN | EV fraction only | 6.90E+05 |
| 60S ribosomal protein L7a | sp\|Q2TBQ5\|RL7A_BOVIN | 22.985 | NaN | EV fraction only | 8.30E+05 |
| CUL2 protein | tr\|Q08DE9\|Q08DE9_BOVIN | 22.995 | NaN | EV fraction only | 2.00E+05 |
| CTP synthase 2 | sp\|Q1RMS2\|PYRG2_BOVIN; tr\|A0JNE9\|A0JNE9_BOVIN | 23.000 | NaN | EV fraction only | 2.60E+05 |
| PGRMC2 protein | tr\|A5PJQ6\|A5PJQ6_BOVIN | 23.007 | NaN | EV fraction only | 1.10E+06 |
| O-acetyl-ADP-ribose deacetylase 1 | sp\|Q1LZ74\|OARD1_BOVIN | 23.010 | NaN | EV fraction only | 8.40E+05 |
| Fibronectin type III and SPRY domain-containing protein 1 | sp\|Q051384\|FSD1_BOVIN | 23.011 | NaN | EV fraction only | 2.20E+06 |
| Uncharacterized protein | tr\|F1MYV9\|F1MYV9_BOVIN | 23.018 | NaN | EV fraction only | 3.50E+05 |
| Bisphosphoglycerate mutase | tr\|F1MX69\|F1MX69_BOVIN; sp\|Q3T014\|PMGE_BOVIN | 23.019 | NaN | EV fraction only | 2.80E+06 |
| Uncharacterized protein | tr\|F1MIC9\|F1MIC9_BOVIN | 23.021 | NaN | EV fraction only | 5.20E+06 |
| Sulfotransferase 1A1 | tr\|E1B9K8\|E1B9K8_BOVIN; sp\|P50227\|ST1A1_BOVIN | 23.026 | NaN | EV fraction only | 4.40E+06 |
| Ras-related protein Rab-4A | sp\|Q2TBH7\|RAB4A_BOVIN | 23.052 | NaN | EV fraction only | 6.20E+05 |
| Inositol-tetrakisphosphate 1-kinase | sp\|P0C0T1\|ITPK1_BOVIN | 23.066 | NaN | EV fraction only | 5.50E+05 |
| Uncharacterized protein | tr\|G3N126\|G3N126_BOVIN; tr\|G3N3E4\|G3N3E4_BOVIN; tr\|E1BB91\|E1BB91_BOVIN | 23.068 | NaN | EV fraction only | 3.30E+05 |
| Uncharacterized protein | tr\|G3X787\|G3X787_BOVIN | 23.076 | NaN | EV fraction only | 9.60E+06 |
| Uncharacterized protein | tr\|F1MYP4\|F1MYP4_BOVIN; sp\|Q0VCQ1\|CTBP2_BOVIN; tr\|F1N053\|F1N053_BOVIN; sp\|Q0VCQ1-2\|CTBP2_BOVIN | 23.079 | NaN | EV fraction only | 4.90E+05 |
| Ras-related protein Rap-1A | sp\|P62833\|RAP1A_BOVIN; sp\|P61223\|RAP1B_BOVIN | 23.080 | NaN | EV fraction only | 5.50E+06 |
| Uncharacterized protein | tr\|F1MWE0\|F1MWE0_BOVIN | 23.082 | NaN | EV fraction only | 9.50E+05 |
| 26S proteasome non-ATPase regulatory subunit 13 (Fragment) | tr\|G8JKV6\|G8JKV6_BOVIN; sp\|Q5E964\|PSD13_BOVIN | 23.091 | NaN | EV fraction only | 1.40E+06 |
| N-alpha-acetyltransferase 50 | sp\|Q0IIJ0\|NAA50_BOVIN | 23.092 | NaN | EV fraction only | 4.30E+06 |
| V-type proton ATPase subunit D | tr\|F1N270\|F1N270_BOVIN; sp\|P39942\|VATD_BOVIN | 23.094 | NaN | EV fraction only | 6.90E+05 |
| Uncharacterized protein (Fragment) | tr\|G3MXE4\|G3MXE4_BOVIN; tr\|E1BG60\|E1BG60_BOVIN | 23.097 | NaN | EV fraction only | 1.60E+05 |
| Eukaryotic translation initiation factor 4E | sp\|Q9N0T5\|IF4E_BOVIN; tr\|F1N030\|F1N030_BOVIN | 23.100 | NaN | EV fraction only | 1.10E+07 |
| Adenylyl cyclase-associated protein | tr\|F1N715\|F1N715_BOVIN | 23.114 | NaN | EV fraction only | 3.00E+05 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Inosine triphosphate pyrophosphatase | sp\|Q2KIC5\|ITPA_BOVIN | 23.152 | NaN | EV fraction only | 9.30E+05 |
| Barrier-to-autointegration factor | sp\|P61283\|BAF_BOVIN | 23.183 | NaN | EV fraction only | 1.60E+06 |
| 26S protease regulatory subunit 8 | sp\|P62194\|PRS8_BOVIN | 23.196 | NaN | EV fraction only | 4.00E+05 |
| UDP-N-acetyl-alpha-D-galactosamine:polypeptide N-acetylgalactosaminyltransferase-like 4 | tr\|Q0IIK7\|Q0IIK7_BOVIN | 23.202 | NaN | EV fraction only | 1.50E+06 |
| Putative tyrosine-protein phosphatase auxilin | tr\|F1MPP5\|F1MPP5_BOVIN; sp\|Q27974\|AUXI_BOVIN; tr\|F1MIB2\|F1MIB2_BOVIN | 23.203 | NaN | EV fraction only | 2.30E+05 |
| Uncharacterized protein | tr\|G3N0W8\|G3N0W8_BOVIN | 23.208 | NaN | EV fraction only | 5.40E+06 |
| Interferon-induced protein with tetratricopeptide repeats 5 | tr\|Q17QZ9\|Q17QZ9_BOVIN | 23.209 | NaN | EV fraction only | 4.20E+05 |
| Protein transport protein Sec23A | tr\|F1MVW5\|F1MVW5_BOVIN; sp\|A2VDL8\|SC23A_BOVIN | 23.219 | NaN | EV fraction only | 4.70E+06 |
| TP53RK protein | tr\|A5PK80\|A5PK80_BOVIN | 23.229 | NaN | EV fraction only | 7.60E+05 |
| Uncharacterized protein | tr\|F1MEW4\|F1MEW4_BOVIN | 23.245 | NaN | EV fraction only | 1.90E+06 |
| Porphobilinogen deaminase | sp\|Q2KIN5\|HEM3_BOVIN | 23.254 | NaN | EV fraction only | 1.90E+07 |
| Plastin-3 | sp\|A7E3Q8\|PLST_BOVIN; tr\|F1MSB7\|F1MSB7_BOVIN; sp\|A6H742\|PLSI_BOVIN | 23.270 | NaN | EV fraction only | 1.40E+06 |
| AP-2 complex subunit mu | sp\|Q3ZC13\|AP2M1_BOVIN | 23.281 | NaN | EV fraction only | 1.60E+06 |
| GNB5 protein | tr\|A5PJS1\|A5PJS1_BOVIN | 23.300 | NaN | EV fraction only | 2.50E+06 |
| Uncharacterized protein (Fragment) | tr\|F6RSR1\|F6RSR1_BOVIN | 23.303 | NaN | EV fraction only | 8.50E+06 |
| Ubiquitin carboxyl-terminal hydrolase (Fragment) | tr\|F1N1Z2\|F1N1Z2_BOVIN | 23.317 | NaN | EV fraction only | 1.50E+05 |
| Protein FAM160B1 | tr\|G3X6C8\|G3X6C8_BOVIN; sp\|A0JNG7\|F16B1_BOVIN | 23.326 | NaN | EV fraction only | 2.80E+05 |
| Uncharacterized protein | tr\|G3N1T2\|G3N1T2_BOVIN | 23.336 | NaN | EV fraction only | 8.10E+05 |
| Vacuolar protein-sorting-associated protein 36 | tr\|F1MT69\|F1MT69_BOVIN; sp\|A5PK00\|VPS36_BOVIN | 23.339 | NaN | EV fraction only | 4.40E+05 |
| Uncharacterized protein (Fragment) | tr\|F1MYN0\|F1MYN0_BOVIN | 23.346 | NaN | EV fraction only | 1.70E+07 |
| Proteasome inhibitor PI31 subunit | sp\|Q3SX30\|PSMF1_BOVIN | 23.357 | NaN | EV fraction only | 1.10E+06 |
| Uncharacterized protein | tr\|F1N1L4\|F1N1L4_BOVIN | 23.364 | NaN | EV fraction only | 7.50E+05 |
| Uncharacterized protein (Fragment) | tr\|E1BIU7\|E1BIU7_BOVIN | 23.370 | NaN | EV fraction only | 1.40E+05 |
| Ceramide synthase 4 | sp\|Q5E9R6\|CERS4_BOVIN | 23.371 | NaN | EV fraction only | 7.80E+06 |
| cAMP-dependent protein kinase catalytic subunit alpha | sp\|P00517\|KAPCA_BOVIN | 23.377 | NaN | EV fraction only | 6.10E+05 |
| Uncharacterized protein | tr\|F2Z4F0\|F2Z4F0_BOVIN; sp\|A4IFE3\|ACTY_BOVIN; tr\|G3N132\|G3N132_BOVIN | 23.385 | NaN | EV fraction only | 5.50E+05 |
| Isoform 1 of Aquaporin-4 | sp\|O77750-2\|AQP4_BOVIN; sp\|O77750\|AQP4_BOVIN | 23.400 | NaN | EV fraction only | 1.80E+06 |
| Uncharacterized protein (Fragment) | tr\|F1MNP9\|F1MNP9_BOVIN; tr\|G3N1N5\|G3N1N5_BOVIN | 23.401 | NaN | EV fraction only | 1.20E+06 |
| Uncharacterized protein | tr\|F1MNK0\|F1MNK0_BOVIN | 23.411 | NaN | EV fraction only | 1.00E+06 |
| Uncharacterized protein | tr\|F2Z4H6\|F2Z4H6_BOVIN | 23.412 | NaN | EV fraction only | 1.10E+07 |
| Isoform Smooth muscle of Myosin light polypeptide 6 | sp\|P60661-2\|MYL6_BOVIN; sp\|P60661\|MYL6_BOVIN | 23.419 | NaN | EV fraction only | 6.70E+06 |
| Olfactomedin-like protein 2B | sp\|A6QLD2\|OLM2B_BOVIN | 23.440 | NaN | EV fraction only | 2.70E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Adenosylhomocysteinase | tr\|A6QLP2\|A6QLP2_BOVIN | 23.441 | NaN | EV fraction only | 3.90E+05 |
| Sorting nexin-5 | sp\|Q3ZBM5\|SNX5_BOVIN | 23.441 | NaN | EV fraction only | 4.70E+05 |
| Uncharacterized protein (Fragment) | tr\|F1MIC3\|F1MIC3_BOVIN | 23.450 | NaN | EV fraction only | 1.40E+06 |
| Uncharacterized protein | tr\|E1B8Q8\|E1B8Q8_BOVIN | 23.471 | NaN | EV fraction only | 2.60E+05 |
| ERI1 exoribonuclease 3 | tr\|F1ML00\|F1ML00_BOVIN; sp\|A6QLH5\|ERI3_BOVIN | 23.482 | NaN | EV fraction only | 1.30E+06 |
| Uncharacterized protein | tr\|F1N1X8\|F1N1X8_BOVIN | 23.497 | NaN | EV fraction only | 8.50E+05 |
| Eukaryotic translation initiation factor 3 subunit M | sp\|Q3T148\|EIF3M_BOVIN; tr\|F1N5F7\|F1N5F7_BOVIN | 23.500 | NaN | EV fraction only | 3.30E+06 |
| ELAV (Embryonic lethal, abnormal vision, *Drosophila*)-like 4 (Hu antigen D) | tr\|A2VDK5\|A2VDK5_BOVIN; tr\|F1N4V6\|F1N4V6_BOVIN; tr\|G3N063\|G3N063_BOVIN | 23.502 | NaN | EV fraction only | 6.60E+05 |
| ATCAY protein | tr\|A2VE75\|A2VE75_BOVIN; tr\|F1N6R4\|F1N6R4_BOVIN | 23.510 | NaN | EV fraction only | 9.20E+05 |
| ADP-ribosylation factor-like protein 2 | sp\|Q2TA37\|ARL2_BOVIN | 23.512 | NaN | EV fraction only | 1.30E+06 |
| Cerebellin-1 | sp\|P86437\|CBLN1_BOVIN | 23.523 | NaN | EV fraction only | 1.50E+07 |
| Uncharacterized protein | tr\|F1MWB9\|F1MWB9_BOVIN | 23.548 | NaN | EV fraction only | 2.00E+07 |
| Uncharacterized protein | tr\|F1MHR4\|F1MHR4_BOVIN; tr\|F1MHT2\|F1MHT2_BOVIN | 23.555 | NaN | EV fraction only | 6.80E+05 |
| Ankyrin repeat and MYND domain-containing protein 2 | sp\|Q0VCS9\|ANKY2_BOVIN | 23.555 | NaN | EV fraction only | 5.40E+05 |
| Serine carboxypeptidase 1 | tr\|Q2NKZ9\|Q2NKZ9_BOVIN | 23.563 | NaN | EV fraction only | 1.60E+06 |
| Proteasome (Prosome, macropain) 26S subunit, ATPase, 1 | tr\|A4FUZ3\|A4FUZ3_BOVIN | 23.564 | NaN | EV fraction only | 2.00E+06 |
| Uncharacterized protein | tr\|F1N3I3\|F1N3I3_BOVIN; tr\|A3KMX3\|A3KMX3_BOVIN | 23.571 | NaN | EV fraction only | 2.30E+05 |
| Uncharacterized protein (Fragment) | tr\|F1MHQ3\|F1MHQ3_BOVIN; tr\|A7YY64\|A7YY64_BOVIN | 23.574 | NaN | EV fraction only | 1.70E+06 |
| PI-PLC X domain-containing protein 3 | tr\|F1N4B7\|F1N4B7_BOVIN; sp\|A6QNU9\|PLCX3_BOVIN | 23.579 | NaN | EV fraction only | 1.00E+06 |
| Active breakpoint cluster region-related protein | sp\|A6QNS3\|ABR_BOVIN; sp\|A6QNS3-2\|ABR_BOVIN; tr\|F1MBT5\|F1MBT5_BOVIN | 23.582 | NaN | EV fraction only | 2.90E+05 |
| 1-phosphatidylinositol 4,5-bisphosphate phosphodiesterase beta-1 | sp\|P10894\|PLCB1_BOVIN | 23.600 | NaN | EV fraction only | 6.60E+05 |
| Uncharacterized protein (Fragment) | tr\|F1MX04\|F1MX04_BOVIN | 23.613 | NaN | EV fraction only | 2.00E+05 |
| Fructose-1,6-bisphosphatase 1 | sp\|Q3SZB7\|F16P1_BOVIN | 23.615 | NaN | EV fraction only | 7.10E+05 |
| Ethanolamine-phosphate cytidylyltransferase | sp\|Q5EA75\|PCY2_BOVIN | 23.626 | NaN | EV fraction only | 5.40E+05 |
| Signal transducer and activator of transcription | tr\|E1BPP7\|E1BPP7_BOVIN | 23.631 | NaN | EV fraction only | 2.10E+05 |
| Histone H1.2 | sp\|P02253\|H12_BOVIN; sp\|G3N131\|H11_BOVIN; tr\|G3MWV5\|G3MWV5_BOVIN; sp\|A7MAZ5\|H13_BOVIN | 23.632 | NaN | EV fraction only | 1.40E+06 |
| Uncharacterized protein | tr\|E1BJP5\|E1BJP5_BOVIN | 23.636 | NaN | EV fraction only | 1.00E+07 |
| Uncharacterized protein | tr\|E1BIB4\|E1BIB4_BOVIN | 23.661 | NaN | EV fraction only | 6.60E+05 |
| MAPK10 protein | tr\|A4FV00\|A4FV00_BOVIN; tr\|Q2KI72\|Q2KI72_BOVIN; tr\|F1MM73\|F1MM73_BOVIN | 23.663 | NaN | EV fraction only | 1.50E+06 |
| Developmentally-regulated GTP-binding protein 2 | sp\|Q58D56\|DRG2_BOVIN | 23.668 | NaN | EV fraction only | 6.30E+05 |
| Calponin-3 | sp\|Q32L92\|CNN3_BOVIN; sp\|Q3SYU6\|CNN2_BOVIN | 23.678 | NaN | EV fraction only | 8.90E+05 |
| UNC45A protein | tr\|A5PKJ5\|A5PKJ5_BOVIN | 23.678 | NaN | EV fraction only | 2.50E+05 |
| Eukaryotic translation initiation factor 2 subunit 3 | sp\|Q2KHU8\|IF2G_BOVIN; tr\|G3N0A9\|G3N0A9_BOVIN; tr\|G3MWU5\|G3MWU5_BOVIN | 23.680 | NaN | EV fraction only | 2.40E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Septin-5 (Fragment) | tr\|F1MEZ1\|F1MEZ1_BOVIN; sp\|Q0VC68\|SEPT5_BOVIN | 23.688 | NaN | EV fraction only | 6.40E+05 |
| Retinoid isomerohydrolase | sp\|Q28175\|RPE65_BOVIN | 23.692 | NaN | EV fraction only | 6.20E+05 |
| COP9 signalosome complex subunit 7b | sp\|Q2KI56\|CSN7B_BOVIN | 23.696 | NaN | EV fraction only | 6.50E+06 |
| COPS8 protein | tr\|A4FV74\|A4FV74_BOVIN | 23.706 | NaN | EV fraction only | 1.70E+06 |
| Uncharacterized protein | tr\|E1BNY9\|E1BNY9_BOVIN | 23.717 | NaN | EV fraction only | 1.00E+06 |
| Uncharacterized protein | tr\|F1MU99\|F1MU99_BOVIN | 23.721 | NaN | EV fraction only | 3.50E+07 |
| Eukaryotic translation initiation factor 2 subunit 1 | sp\|P68102\|IF2A_BOVIN | 23.731 | NaN | EV fraction only | 1.00E+07 |
| Uncharacterized protein (Fragment) | tr\|F1MVZ2\|F1MVZ2_BOVIN; tr\|F1MXK4\|F1MXK4_BOVIN | 23.734 | NaN | EV fraction only | 3.60E+05 |
| Voltage-dependent anion-selective channel protein 2 | sp\|P68002\|VDAC2_BOVIN | 23.736 | NaN | EV fraction only | 8.70E+05 |
| Eukaryotic translation initiation factor 1B | tr\|Q32LJ9\|Q32LJ9_BOVIN; sp\|Q5E938\|EIF1_BOVIN | 23.740 | NaN | EV fraction only | 2.80E+06 |
| Uncharacterized protein | tr\|E1BA29\|E1BA29_BOVIN; sp\|P38409\|GNA11_BOVIN; sp\|P38408\|GNA14_BOVIN; tr\|G5E6P3\|G5E6P3_BOVIN; tr\|G3N0K2\|G3N0K2_BOVIN; tr\|E1BIL1\|E1BIL1_BOVIN | 23.747 | NaN | EV fraction only | 7.40E+05 |
| Ras suppressor protein 1 | sp\|Q5E9C0\|RSU1_BOVIN | 23.753 | NaN | EV fraction only | 1.10E+06 |
| Ubiquitin-fold modifier-conjugating enzyme 1 | sp\|Q5E953\|UFC1_BOVIN | 23.761 | NaN | EV fraction only | 9.50E+06 |
| Ubiquitin-like domain-containing CTD phosphatase 1 | sp\|Q2KJD7\|UBCP1_BOVIN | 23.772 | NaN | EV fraction only | 1.90E+06 |
| Protein O-linked mannose beta1,2-N-acetylglucosaminyltransferase | tr\|Q3T015\|Q3T015_BOVIN; sp\|Q5EAB6\|PMGT1_BOVIN | 23.772 | NaN | EV fraction only | 1.00E+06 |
| Uncharacterized protein | tr\|F1MWU9\|F1MWU9_BOVIN | 23.784 | NaN | EV fraction only | 4.00E+05 |
| Uncharacterized protein | tr\|F1MY44\|F1MY44_BOVIN; tr\|F1MYI2\|F1MYI2_BOVIN | 23.785 | NaN | EV fraction only | 3.10E+05 |
| Uncharacterized protein | tr\|G3MZE2\|G3MZE2_BOVIN | 23.790 | NaN | EV fraction only | 5.60E+05 |
| Isochorismatase domain-containing protein 1 | sp\|A6QLY4\|ISOC1_BOVIN | 23.796 | NaN | EV fraction only | 6.30E+06 |
| Uncharacterized protein | tr\|F1MSB5\|F1MSB5_BOVIN | 23.807 | NaN | EV fraction only | 1.00E+06 |
| Uncharacterized protein (Fragment) | tr\|G5E5T2\|G5E5T2_BOVIN; tr\|A4IFF4\|A4IFF4_BOVIN; tr\|F1MZW8\|F1MZW8_BOVIN | 23.808 | NaN | EV fraction only | 5.40E+05 |
| LRRC24 protein | tr\|A4IFI5\|A4IFI5_BOVIN | 23.812 | NaN | EV fraction only | 6.40E+05 |
| 60S ribosomal protein L14 | tr\|G8JKV5\|G8JKV5_BOVIN; sp\|Q3T0U2\|RL14_BOVIN | 23.815 | NaN | EV fraction only | 3.00E+06 |
| Leukocyte elastase inhibitor | sp\|Q1JPB0\|ILEU_BOVIN; tr\|G1K1L8\|G1K1L8_BOVIN; sp\|Q5BIR5\|SPB8_BOVIN; tr\|A6QPW6\|A6QPW6_BOVIN | 23.821 | NaN | EV fraction only | 2.60E+06 |
| Uncharacterized protein (Fragment) | tr\|F1MM21\|F1MM21_BOVIN; sp\|O46470\|RGS7_BOVIN | 23.822 | NaN | EV fraction only | 6.40E+05 |
| Uncharacterized protein | tr\|F6QYV9\|F6QYV9_BOVIN | 23.823 | NaN | EV fraction only | 4.90E+05 |
| Uncharacterized protein (Fragment) | tr\|F1MCI9\|F1MCI9_BOVIN | 23.835 | NaN | EV fraction only | 2.80E+05 |
| Uncharacterized protein | tr\|E1BA27\|E1BA27_BOVIN | 23.836 | NaN | EV fraction only | 1.30E+06 |
| Importin subunit alpha-7 (Fragment) | tr\|G5E536\|G5E536_BOVIN; sp\|Q0V7M0\|IMA7_BOVIN; tr\|F1N1K5\|F1N1K5_BOVIN; sp\|A2VE08\|IMA5_BOVIN | 23.866 | NaN | EV fraction only | 6.60E+05 |
| Uncharacterized protein | tr\|F1N1G7\|F1N1G7_BOVIN | 23.904 | NaN | EV fraction only | 6.40E+05 |
| Protein kinase C alpha type | sp\|P04409\|KPCA_BOVIN; tr\|F1MJX9\|F1MJX9_BOVIN; sp\|P05126\|KPCB_BOVIN; sp\|P05126-2\|KPCB_BOVIN | 23.908 | NaN | EV fraction only | 4.80E+05 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Ras-related protein Rab-3C | tr\|E1BF18\|E1BF18_BOVIN; sp\|P10949\|RAB3C_BOVIN | 23.910 | NaN | EV fraction only | 1.40E+06 |
| ACSS2 protein | tr\|A7YWF1\|A7YWF1_BOVIN | 23.914 | NaN | EV fraction only | 4.80E+05 |
| Rhodopsin | sp\|P02699\|OPSD_BOVIN | 23.915 | NaN | EV fraction only | 2.30E+06 |
| Uncharacterized protein | tr\|F1N4V5\|F1N4V5_BOVIN | 23.924 | NaN | EV fraction only | 5.10E+05 |
| UBX domain-containing protein 6 | tr\|F1MES6\|F1MES6_BOVIN; sp\|Q2KIJ6\|UBXN6_BOVIN | 23.926 | NaN | EV fraction only | 2.10E+06 |
| TWF2 protein | tr\|A2VDX0\|A2VDX0_BOVIN | 23.932 | NaN | EV fraction only | 8.40E+05 |
| Uncharacterized protein | tr\|F1MK10\|F1MK10_BOVIN | 23.936 | NaN | EV fraction only | 1.30E+06 |
| ACP1 protein | tr\|A5PK96\|A5PK96_BOVIN; sp\|P11064\|PPAC_BOVIN | 23.940 | NaN | EV fraction only | 2.40E+07 |
| Tubulin-folding cofactor B | sp\|Q5E951\|TBCB_BOVIN | 23.958 | NaN | EV fraction only | 7.20E+06 |
| Serine/arginine-rich splicing factor 2 | sp\|Q3MHR5\|SRSF2_BOVIN | 23.961 | NaN | EV fraction only | 1.80E+06 |
| Tubulin alpha-8 chain | sp\|Q2HJB8\|TBA8_BOVIN | 23.962 | NaN | EV fraction only | 7.80E+05 |
| Calmegin | sp\|Q3SYT6\|CLGN_BOVIN | 23.967 | NaN | EV fraction only | 4.70E+05 |
| CD9 antigen (Fragment) | tr\|G8JKX6\|G8JKX6_BOVIN; sp\|P30932\|CD9_BOVIN | 23.980 | NaN | EV fraction only | 2.80E+06 |
| Uncharacterized protein | tr\|F1MLY0\|F1MLY0_BOVIN | 23.986 | NaN | EV fraction only | 1.80E+05 |
| C8G protein | tr\|A8YXZ2\|A8YXZ2_BOVIN | 24.000 | NaN | EV fraction only | 2.20E+07 |
| RPRD1B protein | tr\|A6QLW3\|A6QLW3_BOVIN; sp\|Q0P5J9-2\|RPR1A_BOVIN; sp\|Q0P5J9\|RPR1A_BOVIN | 24.000 | NaN | EV fraction only | 1.20E+06 |
| Uncharacterized protein | tr\|F1MS62\|F1MS62_BOVIN; tr\|G3MZI2\|G3MZI2_BOVIN | 24.004 | NaN | EV fraction only | 1.10E+06 |
| Uncharacterized protein | tr\|F1N2Q9\|F1N2Q9_BOVIN | 24.007 | NaN | EV fraction only | 2.50E+06 |
| Protein Hikeshi | sp\|Q56JY0\|HIKES_BOVIN | 24.016 | NaN | EV fraction only | 3.40E+06 |
| Uncharacterized protein | tr\|E1BDS4\|E1BDS4_BOVIN | 24.024 | NaN | EV fraction only | 1.60E+07 |
| Midkine | tr\|Q9N0E6\|QP9N0E6_BOVIN | 24.039 | NaN | EV fraction only | 2.50E+06 |
| Protein prune homolog | sp\|Q5E9Y6\|PRUNE_BOVIN | 24.040 | NaN | EV fraction only | 7.20E+05 |
| Uncharacterized protein | tr\|F1MS94\|F1MS94_BOVIN | 24.042 | NaN | EV fraction only | 1.40E+06 |
| TBC1 domain family member 24 | tr\|F1N534\|F1N534_BOVIN; sp\|Q29RJ2\|TBC24_BOVIN | 24.046 | NaN | EV fraction only | 6.40E+05 |
| AP2-associated protein kinase 1 (Fragment) | tr\|H2XJE8\|H2XJE8_BOVIN; sp\|F1MH24\|AAK1_BOVIN | 24.075 | NaN | EV fraction only | 4.80E+05 |
| Pre-B-cell leukemia transcription factor-interacting protein 1 | sp\|A6QLY7\|PB1P1_BOVIN | 24.090 | NaN | EV fraction only | 6.40E+05 |
| Uncharacterized protein | tr\|F1MYJ4\|F1MYJ4_BOVIN; tr\|G3X7B5\|G3X7B5_BOVIN; sp\|Q01314\|AKT1_BOVIN | 24.093 | NaN | EV fraction only | 5.60E+06 |
| Isoform 2 of Catechol O-methyltransferase | sp\|A7MBI7-2\|COMT_BOVIN; sp\|A7MBI7\|COMT_BOVIN | 24.106 | NaN | EV fraction only | 1.40E+06 |
| Heterogeneous nuclear ribonucleoprotein H2 | tr\|A5D9B4\|A5D9B4_BOVIN; sp\|Q3SZF3\|HNRH2_BOVIN; tr\|E1BF20\|E1BF20_BOVIN | 24.107 | NaN | EV fraction only | 1.30E+07 |
| Vacuolar protein sorting-associated protein VTA1 homolog | tr\|F1N318\|F1N318_BOVIN; sp\|Q32L63\|VTA1_BOVIN | 24.115 | NaN | EV fraction only | 1.50E+06 |
| Mannose-1-phosphate guanyltransferase beta | tr\|F1N7H5\|F1N7H5_BOVIN; sp\|Q2YDJ9\|GMPPB_BOVIN | 24.124 | NaN | EV fraction only | 1.10E+06 |
| Signal transducer and activator of transcription 5B | sp\|Q9TUM3\|STA5B_BOVIN; sp\|Q95115\|STA5A_BOVIN; tr\|F1MER9\|F1MER9_BOVIN | 24.130 | NaN | EV fraction only | 4.70E+05 |
| Excitatory amino acid transporter 1 | sp\|P46411\|EAA1_BOVIN | 24.145 | NaN | EV fraction only | 1.20E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| GNAI2 protein | tr\|A7MBH9\|A7MBH9_BOVIN; tr\|Q3ZCA7\|Q3ZCA7_BOVIN; sp\|P63097\|GNAI1_BOVIN | 24.153 | NaN | EV fraction only | 1.10E+06 |
| Haloacid dehalogenase-like hydrolase domain containing 1A | tr\|Q2KJ86\|Q2KJ86_BOVIN | 24.160 | NaN | EV fraction only | 1.60E+06 |
| Protein FAM49A | sp\|Q17QT7\|FA49A_BOVIN | 24.161 | NaN | EV fraction only | 1.00E+06 |
| Uncharacterized protein | tr\|F1MMA0\|F1MMA0_BOVIN; sp\|Q08E27\|STRBP_BOVIN | 24.172 | NaN | EV fraction only | 5.30E+05 |
| Uncharacterized protein | tr\|E1BM42\|E1BM42_BOVIN | 24.173 | NaN | EV fraction only | 3.30E+05 |
| MGAT1 protein | tr\|Q5E9I4\|Q5E9I4_BOVIN | 24.181 | NaN | EV fraction only | 9.50E+05 |
| UPF0468 protein C16orf80 homolog | sp\|Q6B857\|CP080_BOVIN | 24.191 | NaN | EV fraction only | 1.60E+06 |
| Uncharacterized protein | tr\|E1BNG8\|E1BNG8_BOVIN; tr\|Q2KJ23\|Q2KJ23_BOVIN | 24.245 | NaN | EV fraction only | 1.90E+06 |
| Uncharacterized protein (Fragment) | tr\|F1MHJ5\|F1MHJ5_BOVIN; tr\|F1MR64\|F1MR64_BOVIN | 24.265 | NaN | EV fraction only | 9.20E+05 |
| ADP-ribosylation factor 1 | sp\|P84080\|ARF1_BOVIN | 24.266 | NaN | EV fraction only | 2.00E+06 |
| Uncharacterized protein (Fragment) | tr\|F1MFT4\|F1MFT4_BOVIN | 24.269 | NaN | EV fraction only | 5.90E+05 |
| Uncharacterized protein | tr\|F1N2D5\|F1N2D5_BOVIN | 24.272 | NaN | EV fraction only | 7.50E+06 |
| Uncharacterized protein | tr\|E1B9H5\|E1B9H5_BOVIN | 24.287 | NaN | EV fraction only | 1.40E+06 |
| PLAA protein | tr\|A7Z055\|A7Z055_BOVIN | 24.288 | NaN | EV fraction only | 4.50E+05 |
| Integrin beta-2 | sp\|P32592\|ITB2_BOVIN | 24.290 | NaN | EV fraction only | 3.80E+06 |
| Very-long-chain (3R)-3-hydroxyacyl-CoA dehydratase 3 | sp\|A7YY55\|HACD3_BOVIN | 24.297 | NaN | EV fraction only | 1.10E+06 |
| Uncharacterized protein | tr\|F1MJ80\|F1MJ80_BOVIN | 24.311 | NaN | EV fraction only | 7.20E+05 |
| MOB1, Mps One Binder kinase activator-like 1B (Yeast) | tr\|Q0VCJ5\|Q0VCJ5_BOVIN; tr\|E1BMG1\|E1BMG1_BOVIN | 24.315 | NaN | EV fraction only | 2.10E+06 |
| Protein FAM49B | sp\|Q2KJI3\|FA49B_BOVIN | 24.332 | NaN | EV fraction only | 1.10E+06 |
| Isoform 2 of Serine/threonine-protein phosphatase 2B catalytic subunit alpha isoform | sp\|P48452-2\|PP2BA_BOVIN; sp\|P48452\|PP2BA_BOVIN; tr\|G3MYK1\|G3MYK1_BOVIN | 24.348 | NaN | EV fraction only | 3.90E+06 |
| Uncharacterized protein | tr\|F1N7U2\|F1N7U2_BOVIN | 24.352 | NaN | EV fraction only | 7.40E+05 |
| FTO protein | tr\|A5D798\|A5D798_BOVIN | 24.363 | NaN | EV fraction only | 7.20E+05 |
| Annexin A2 | sp\|P04272\|ANXA2_BOVIN | 24.372 | NaN | EV fraction only | 9.40E+05 |
| Uncharacterized protein | tr\|F1MX43\|F1MX43_BOVIN | 24.381 | NaN | EV fraction only | 1.80E+06 |
| Uncharacterized Protein | tr\|F2Z4E7\|F2Z4E7_BOVIN | 24.385 | NaN | EV fraction only | 1.20E+06 |
| Protein NDRG3 | sp\|A7MB28\|NDRG3_BOVIN | 24.385 | NaN | EV fraction only | 1.50E+06 |
| Ribosome maturation protein SBDS | sp\|Q3SWZ6\|SBDS_BOVIN | 24.390 | NaN | EV fraction only | 1.30E+06 |
| Uncharacterized protein | tr\|E1BMX0\|E1BMX0_BOVIN; tr\|G3MXH2\|G3MXH2_BOVIN; tr\|A5D7R9\|A5D7R9_BOVIN; tr\|G3N1U2\|G3N1U2_BOVIN | 24.400 | NaN | EV fraction only | 2.50E+06 |
| Uncharacterized protein (Fragment) | tr\|F1MSM4\|F1MSM4_BOVIN | 24.403 | NaN | EV fraction only | 1.10E+06 |
| Transcription elongation factor B polypeptide 1 | sp\|Q2KII4\|ELOC_BOVIN | 24.410 | NaN | EV fraction only | 9.50E+06 |
| Uncharacterized protein | tr\|F6QE33\|F6QE33_BOVIN; tr\|F1MDK0\|F1MDK0_BOVIN | 24.413 | NaN | EV fraction only | 1.50E+06 |
| Uncharacterized protein (Fragment) | tr\|F1MX83\|F1MX83_BOVIN | 24.437 | NaN | EV fraction only | 2.90E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Uncharacterized protein | tr\|E1B763\|E1B763_BOVIN | 24.442 | NaN | EV fraction only | 1.00E+06 |
| Monocarboxylate transporter 1 | sp\|Q3MHW6\|MOT1_BOVIN | 24.442 | NaN | EV fraction only | 1.60E+06 |
| >P07477 SWISS-PROT: P07477 Tax_Id = 9606 Gene_Symbol = PRSS1 Trypsin-1 precursor | CON_P07477 | 24.461 | NaN | EV fraction only | 9.50E+06 |
| Uncharacterized protein (Fragment) | tr\|F1N025\|F1N025_BOVIN | 24.470 | NaN | EV fraction only | 8.00E+05 |
| Uncharacterized protein (Fragment) | tr\|F1N6Y7\|F1N6Y7_BOVIN | 24.476 | NaN | EV fraction only | 4.60E+05 |
| BLVRA protein | tr\|A5D7K0\|A5D7K0_BOVIN | 24.486 | NaN | EV fraction only | 1.50E+06 |
| RAB10 protein | tr\|A6QLS9\|A6QLS9_BOVIN | 24.489 | NaN | EV fraction only | 7.00E+06 |
| Uncharacterized protein | tr\|F1N7F4\|F1N7F4_BOVIN | 24.520 | NaN | EV fraction only | 1.20E+07 |
| Prolargin | tr\|F1MX63\|F1MX63_BOVIN; sp\|Q9GKN8\|PRELP_BOVIN | 24.537 | NaN | EV fraction only | 7.30E+06 |
| NHP2-like protein 1 | sp\|Q3B8S0\|NH2L1_BOVIN | 24.547 | NaN | EV fraction only | 3.10E+06 |
| Tubulin-specific chaperone E | sp\|Q32KS0\|TBCE_BOVIN | 24.561 | NaN | EV fraction only | 2.10E+06 |
| Uncharacterized protein | tr\|F1MUP9\|F1MUP9_BOVIN | 24.563 | NaN | EV fraction only | 3.60E+06 |
| Lipopolysaccharide-binding protein | tr\|F1MNN7\|F1MNN7_BOVIN; sp\|Q2TBI0\|LBP_BOVIN | 24.572 | NaN | EV fraction only | 1.30E+06 |
| Uncharacterized protein | tr\|F1MX60\|F1MX60_BOVIN; tr\|E1BN47\|E1BN47_BOVIN | 24.590 | NaN | EV fraction only | 3.70E+05 |
| CaM kinase-like vesicle-associated | tr\|Q08DK8\|Q08DK8_BOVIN | 24.623 | NaN | EV fraction only | 3.10E+06 |
| Uncharacterized protein | tr\|F1MYK4\|F1MYK4_BOVIN | 24.632 | NaN | EV fraction only | 1.80E+06 |
| Uncharacterized protein | tr\|E1BBK6\|E1BBK6_BOVIN | 24.636 | NaN | EV fraction only | 4.30E+06 |
| T-complex protein 1 subunit alpha | tr\|G5E531\|G5E531_BOVIN; sp\|Q32L40\|TCPA_BOVIN | 24.637 | NaN | EV fraction only | 5.90E+06 |
| Uncharacterized protein | tr\|E1BDM8\|E1BDM8_BOVIN | 24.650 | NaN | EV fraction only | 9.40E+05 |
| Septin-6 | sp\|Q3SZN0\|SEPT6_BOVIN; sp\|A2VE99\|SEP11_BOVIN | 24.677 | NaN | EV fraction only | 4.40E+06 |
| ATP synthase subunit alpha | tr\|F1MLB8\|F1MLB8_BOVIN; sp\|P19483\|ATPA_BOVIN | 24.685 | NaN | EV fraction only | 8.70E+05 |
| TIP41, TOR signaling pathway regulator-like (*S. cerevisiae*) | tr\|Q29RT7\|Q29RT7_BOVIN | 24.690 | NaN | EV fraction only | 6.50E+06 |
| Leucine carboxyl methyltransferase 1 | sp\|Q3T0H0\|LCMT1_BOVIN | 24.694 | NaN | EV fraction only | 3.40E+06 |
| Isoform 2 of Reticulon-3 | sp\|Q08D83-2\|RTN3_BOVIN; tr\|G3X7U3\|G3X7U3_BOVIN; tr\|G8JKY8\|G8JKY8_BOVIN; sp\|Q08D83\|RTN3_BOVIN | 24.695 | NaN | EV fraction only | 4.50E+06 |
| Ras-related protein Rab-6B | sp\|A6QR46\|RAB6B_BOVIN | 24.697 | NaN | EV fraction only | 2.10E+06 |
| Monocyte differentiation antigen CD14 | sp\|Q95122\|CD14_BOVIN; tr\|A6QNL0\|A6QNL0_BOVIN | 24.698 | NaN | EV fraction only | 4.30E+06 |
| Coronin | tr\|A2VDN8\|A2VDN8_BOVIN; tr\|G3MWI5\|G3MWI5_BOVIN | 24.698 | NaN | EV fraction only | 5.00E+06 |
| KH domain containing, RNA binding, signal transduction associated 1 | tr\|Q29RQ2\|Q29RQ2_BOVIN | 24.706 | NaN | EV fraction only | 1.70E+07 |
| Plexin domain containing 2 | tr\|A0JN47\|A0JN47_BOVIN | 24.707 | NaN | EV fraction only | 8.50E+06 |
| Annexin | tr\|F6QVC9\|F6QVC9_BOVIN; sp\|P81287\|ANXA5_BOVIN | 24.710 | NaN | EV fraction only | 1.20E+06 |
| AP-2 complex subunit beta | sp\|P63009\|AP2B1_BOVIN; sp\|Q08DS7\|AP1B1_BOVIN; tr\|G3X7G4\|G3X7G4_BOVIN | 24.715 | NaN | EV fraction only | 1.40E+06 |
| Uncharacterized protein (Fragment) | tr\|E1BLV6\|E1BLV6_BOVIN | 24.716 | NaN | EV fraction only | 6.10E+05 |
| Basigin | tr\|Q3ZBX0\|Q3ZBX0_BOVIN | 24.718 | NaN | EV fraction only | 1.80E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| RAB2A, member RAS oncogene family | tr\|Q148J4\|Q148J4_BOVIN | 24.722 | NaN | EV fraction only | 9.30E+06 |
| Asparagine-tRNA ligase, cytoplasmic | tr\|F1MKH6\|F1MKH6_BOVIN; sp\|Q2KJG3\|SYNC_BOVIN; tr\|G3MXW8\|G3MXW8_BOVIN | 24.730 | NaN | EV fraction only | 3.80E+06 |
| 11-cis retinol dehydrogenase | sp\|Q27979\|RDH1_BOVIN | 24.740 | NaN | EV fraction only | 1.60E+06 |
| Uncharacterized protein (Fragment) | tr\|F1MW66\|F1MW66_BOVIN | 24.742 | NaN | EV fraction only | 5.20E+06 |
| Ubiquitin-like modifier-activating enzyme 5 | sp\|A7MAZ3\|UBA5_BOVIN | 24.742 | NaN | EV fraction only | 1.70E+06 |
| cAMP-dependent protein kinase type II-beta regulatory subunit | tr\|F6Q9S4\|F6Q9S4_BOVIN; sp\|P31322\|KAP3_BOVIN | 24.761 | NaN | EV fraction only | 1.20E+06 |
| Uncharacterized protein | tr\|F1MZK4\|F1MZK4_BOVIN; tr\|A6H7D7\|A6H7D7_BOVIN | 24.788 | NaN | EV fraction only | 1.00E+06 |
| Suppressor of G2 allele of SKP1 homolog | sp\|Q2KIK0\|SUGT1_BOVIN; tr\|G1K147\|G1K147_BOVIN | 24.807 | NaN | EV fraction only | 3.50E+06 |
| Uncharacterized protein | tr\|E1BPN4\|E1BPN4_BOVIN | 24.822 | NaN | EV fraction only | 4.60E+06 |
| Uncharacterized protein | tr\|F1MZT1\|F1MZT1_BOVIN | 24.834 | NaN | EV fraction only | 5.60E+06 |
| Adenylosuccinate lyase | tr\|F1MHP6\|F1MHP6_BOVIN; sp\|A3KN12\|PUR8_BOVIN | 24.837 | NaN | EV fraction only | 1.80E+06 |
| Ganglioside-induced differentiation-associated protein 1-like 1 | tr\|Q1JPF3\|Q1JPF3_BOVIN | 24.858 | NaN | EV fraction only | 1.50E+06 |
| Rhophilin-2 | tr\|F1MZ22\|F1MZ22_BOVIN; sp\|A4FUC9\|RHPN2_BOVIN | 24.878 | NaN | EV fraction only | 7.70E+05 |
| Ubiquitin-conjugating enzyme E2 variant 1 | sp\|Q3SZ52\|UB2V1_BOVIN | 24.885 | NaN | EV fraction only | 4.80E+07 |
| Cell division control protein 42 homolog | sp\|Q2KJ93\|CDC42_BOVIN; tr\|F1MND1\|F1MND1_BOVIN; tr\|Q1RMI2\|Q1RMI2_BOVIN; tr\|E1BLE9\|E1BLE9_BOVIN; tr\|F1MK42\|F1MK42_BOVIN; tr\|A4FV20\|A4FV20_BOVIN | 24.895 | NaN | EV fraction only | 1.10E+07 |
| Uncharacterized protein | tr\|E1B820\|E1B820_BOVIN | 24.916 | NaN | EV fraction only | 7.40E+05 |
| Annexin | tr\|F1N650\|F1N650_BOVIN; sp\|P46193\|ANXA1_BOVIN | 24.954 | NaN | EV fraction only | 1.60E+06 |
| Voltage-dependent anion-selective channel protein 1 | sp\|P45879\|VDAC1_BOVIN; tr\|F1MIN1\|F1MIN1_BOVIN | 24.961 | NaN | EV fraction only | 1.90E+06 |
| Actin-related protein 2/3 complex subunit 3 | sp\|Q3T035\|ARPC3_BOVIN | 24.975 | NaN | EV fraction only | 1.70E+07 |
| Uncharacterized protein (Fragment) | tr\|F1MPZ9\|F1MPZ9_BOVIN | 24.976 | NaN | EV fraction only | 5.70E+05 |
| Replication protein A1, 70 kDa | tr\|Q0VCV0\|Q0VCV0_BOVIN | 24.994 | NaN | EV fraction only | 1.00E+06 |
| Twinfilin-1 | sp\|Q56JV6\|TWF1_BOVIN | 24.996 | NaN | EV fraction only | 1.50E+06 |
| Ras-related protein Rab-5A | sp\|Q0IIG7\|RAB5A_BOVIN; tr\|G3N2V0\|G3N2V0_BOVIN | 25.008 | NaN | EV fraction only | 3.10E+06 |
| DEK protein | tr\|A5PJQ1\|A5PJQ1_BOVIN | 25.025 | NaN | EV fraction only | 1.60E+06 |
| Tripartite motif-containing protein 2 | sp\|A4IF63\|TRIM2_BOVIN | 25.033 | NaN | EV fraction only | 2.60E+06 |
| ADP-dependent glucokinase | sp\|A2VE47\|ADPGK_BOVIN | 25.035 | NaN | EV fraction only | 2.00E+06 |
| Uncharacterized protein | tr\|F1MYD0\|F1MYD0_BOVIN; tr\|G3N0Q3\|G3N0Q3_BOVIN | 25.050 | NaN | EV fraction only | 7.60E+05 |
| ADP-ribosylation factor-like protein 1 | sp\|Q2YDM1\|ARL1_BOVIN | 25.058 | NaN | EV fraction only | 3.90E+06 |
| Uncharacterized protein | tr\|G5E631\|G5E631_BOVIN; tr\|D3IVZ2\|D3IVZ2_BOVIN | 25.069 | NaN | EV fraction only | 9.00E+05 |
| Proteasome (Prosome, macropain) activator subunit 1 (PA28 alpha) | tr\|Q2KJE7\|Q2KJE7_BOVIN; sp\|Q4U5R3\|PSME1_BOVIN | 25.072 | NaN | EV fraction only | 6.70E+06 |
| Uncharacterized protein | tr\|E1BIP3\|E1BIP3_BOVIN | 25.072 | NaN | EV fraction only | 4.20E+06 |
| Synaptobrevin homolog YKT6 | sp\|Q3T000\|YKT6_BOVIN | 25.077 | NaN | EV fraction only | 2.40E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Uncharacterized protein | tr\|F1MM57\|F1MM57_BOVIN | 25.108 | NaN | EV fraction only | 1.30E+06 |
| Serine/threonine-protein kinase PAK 1 | sp\|Q08E52\|PAK1_BOVIN | 25.123 | NaN | EV fraction only | 1.40E+06 |
| ADP-ribosylation factor-like protein 8B | tr\|F2Z4I5\|F2Z4I5_BOVIN; sp\|Q2KI07\|ARL8B_BOVIN | 25.134 | NaN | EV fraction only | 3.30E+06 |
| Uncharacterized protein | tr\|F1N5K2\|F1N5K2_BOVIN | 25.194 | NaN | EV fraction only | 1.10E+06 |
| Cyclin-dependent kinase 5 | sp\|Q02399\|CDK5_BOVIN; tr\|G3N0Y1\|G3N0Y1_BOVIN; sp\|Q5E9Y0\|CDK2_BOVIN; sp\|Q32KY4\|CDK4_BOVIN; tr\|A5PJJ9\|A5PJJ9_BOVIN; tr\|E1BC36\|E1BC36_BOVIN; sp\|Q5EAB2\|CDK9_BOVIN; tr\|A3KMY7\|A3KMY7_BOVIN; tr\|A6QR30\|A6QR30_BOVIN; tr\|F1MN42\|F1MN42_BOVIN; sp\|E1BB50\|CDK12_BOVIN; tr\|G5E518\|G5E518_BOVIN; sp\|E1BB52\|CDK13_BOVIN | 25.224 | NaN | EV fraction only | 8.30E+06 |
| Uncharacterized protein (Fragment) | tr\|F1MJ53\|F1MJ53_BOVIN; tr\|G3MXD5\|G3MXD5_BOVIN; tr\|F1N061\|F1N061_BOVIN | 25.248 | NaN | EV fraction only | 1.30E+06 |
| COP9 signalosome complex subunit 4 | sp\|Q3SZA0\|CSN4_BOVIN | 25.275 | NaN | EV fraction only | 3.10E+06 |
| KIF1-binding protein | sp\|Q3SYS9\|KBP_BOVIN | 25.297 | NaN | EV fraction only | 1.30E+06 |
| ADP/ATP translocase 2 | sp\|Q8SQH5\|ADT2_BOVIN; sp\|P02722\|ADT1_BOVIN; tr\|G3N3W3\|G3N3W3_BOVIN; sp\|P32007\|ADT3_BOVIN; tr\|F1MDK8\|F1MDK8_BOVIN; sp\|Q2YDD9\|ADT4_BOVIN | 25.320 | NaN | EV fraction only | 2.10E+06 |
| Uncharacterized protein | tr\|G3N3N1\|G3N3N1_BOVIN | 25.322 | NaN | EV fraction only | 5.20E+06 |
| Uncharacterized protein | tr\|G5E6L2\|G5E6L2_BOVIN | 25.323 | NaN | EV fraction only | 9.60E+06 |
| Calcium/calmodulin-dependent protein kinase II delta | tr\|A5D9F0\|A5D9F0_BOVIN; sp\|Q2HJF7\|KCC2D_BOVIN; tr\|Q08E45\|Q08E45_BOVIN | 25.326 | NaN | EV fraction only | 6.20E+06 |
| Uncharacterized protein | tr\|F6RWK1\|F6RWK1_BOVIN | 25.327 | NaN | EV fraction only | 1.50E+06 |
| Uncharacterized protein | tr\|F1N7B5\|F1N7B5_BOVIN | 25.336 | NaN | EV fraction only | 2.00E+06 |
| Uncharacterized protein | tr\|E1B7J7\|E1B7J7_BOVIN | 25.346 | NaN | EV fraction only | 3.60E+06 |
| Neurocalcin-delta | sp\|P61602\|NCALD_BOVIN; sp\|Q4PL64\|HPCA_BOVIN; sp\|P29105\|HPCL1_BOVIN | 25.370 | NaN | EV fraction only | 7.10E+06 |
| Epoxide hydrolase 1, microsomal (Xenobiotic) | tr\|Q3ZCJ6\|Q3ZCJ6_BOVIN | 25.388 | NaN | EV fraction only | 1.50E+06 |
| Uncharacterized protein (Fragment) | tr\|F1MDV3\|F1MDV3_BOVIN | 25.400 | NaN | EV fraction only | 1.30E+06 |
| Uncharacterized protein | tr\|F1ME38\|F1ME38_BOVIN | 25.408 | NaN | EV fraction only | 7.80E+05 |
| Isoform Cytoplasmic + peroxisomal of Peroxiredoxin-5, mitochondrial | sp\|Q9BGI1-2\|PRDX5_BOVIN; sp\|Q9BGI1\|PRDX5_BOVIN | 25.417 | NaN | EV fraction only | 1.10E+07 |
| Phosphatidylinositol transfer protein beta isoform | sp\|Q9TR36\|PIPNB_BOVIN | 25.423 | NaN | EV fraction only | 2.50E+06 |
| AP-3 complex subunit delta-1 | sp\|Q865S1\|AP3D1_BOVIN | 25.448 | NaN | EV fraction only | 8.30E+05 |
| Ribose-phosphate pyrophosphokinase 1 | sp\|Q2HJ58\|PRPS1_BOVIN; tr\|G3MY14\|G3MY14_BOVIN; tr\|F6RJ91\|F6RJ91_BOVIN | 25.452 | NaN | EV fraction only | 1.20E+07 |
| Uncharacterized protein | tr\|E1BBG4\|E1BBG4_BOVIN | 25.483 | NaN | EV fraction only | 7.80E+06 |
| Fibulin 5 | tr\|Q2KJ89\|Q2KJ89_BOVIN; sp\|Q5EA62\|FBLN5_BOVIN | 25.499 | NaN | EV fraction only | 5.00E+06 |
| Prostamide/prostaglandin F synthase | sp\|Q58CY6\|PGFS_BOVIN | 25.510 | NaN | EV fraction only | 4.80E+06 |
| Sulfotransferase family 4A, member 1 | tr\|Q17QV7\|Q17QV7_BOVIN | 25.526 | NaN | EV fraction only | 1.60E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Ubiquitin-conjugating enzyme E2 K | sp\|P61085\|UBE2K_BOVIN | 25.541 | NaN | EV fraction only | 4.10E+06 |
| MTHFD1 protein | tr\|A4FUD0\|A4FUD0_BOVIN | 25.548 | NaN | EV fraction only | 9.60E+05 |
| Guanylate cyclase soluble subunit alpha-1 | sp\|P19687\|GCYA1_BOVIN | 25.553 | NaN | EV fraction only | 1.30E+06 |
| Beta-galactoside alpha-2,6-sialyltransferase 2 | sp\|A5D7T4\|SIAT2_BOVIN | 25.587 | NaN | EV fraction only | 4.70E+06 |
| ATP-dependent RNA helicase DDX1 | sp\|Q0IIK5\|DDX1_BOVIN | 25.590 | NaN | EV fraction only | 1.80E+06 |
| AMPH protein | tr\|A5D783\|A5D783_BOVIN | 25.593 | NaN | EV fraction only | 3.00E+06 |
| Zinc finger Ran-binding domain-containing protein 2 | tr\|A7YWH2\|A7YWH2_BOVIN | 25.596 | NaN | EV fraction only | 2.80E+06 |
| Uncharacterized protein | tr\|E1BQ15\|E1BQ15_BOVIN; tr\|E1BGU2\|E1BGU2_BOVIN; tr\|G3N2Y5\|G3N2Y5_BOVIN | 25.678 | NaN | EV fraction only | 1.20E+06 |
| DDX17 protein | tr\|A7E307\|A7E307_BOVIN | 25.702 | NaN | EV fraction only | 2.90E+06 |
| DCLK1 protein | tr\|A8E644\|A8E644_BOVIN; tr\|G3MYK0\|G3MYK0_BOVIN; tr\|E1BBU3\|E1BBU3_BOVIN | 25.711 | NaN | EV fraction only | 5.80E+06 |
| Interferon-inducible double-stranded RNA-dependent protein kinase activator A | sp\|Q2HJ92\|PRKRA_BOVIN | 25.780 | NaN | EV fraction only | 6.40E+06 |
| Beta-soluble NSF attachment protein | sp\|P81126\|SNAB_BOVIN | 25.785 | NaN | EV fraction only | 5.70E+06 |
| Uncharacterized protein (Fragment) | tr\|F1MP10\|F1MP10_BOVIN | 25.809 | NaN | EV fraction only | 3.30E+06 |
| Sorting nexin-2 | tr\|F1MZN7\|F1MZN7_BOVIN; sp\|Q2TBW7\|SNX2_BOVIN; tr\|F1MYH6\|F1MYH6_BOVIN; tr\|F1N399\|F1N399_BOVIN; sp\|Q05B62\|SNX1_BOVIN | 25.824 | NaN | EV fraction only | 2.20E+06 |
| Uncharacterized protein (Fragment) | tr\|F1MC86\|F1MC86_BOVIN | 25.825 | NaN | EV fraction only | 2.80E+06 |
| Serine/threonine-protein phosphatase 2A 55 kDa regulatory subunit B | tr\|F1MG56\|F1MG56_BOVIN; sp\|Q5E9Q7\|2ABB_BOVIN; tr\|F1MY94\|F1MY94_BOVIN | 25.848 | NaN | EV fraction only | 4.60E+06 |
| Canx protein | tr\|A7Z066\|A7Z066_BOVIN | 25.849 | NaN | EV fraction only | 1.90E+06 |
| Ataxin-10 | tr\|F1MH20\|F1MH20_BOVIN; sp\|Q2TBW0\|ATX10_BOVIN | 25.850 | NaN | EV fraction only | 3.50E+06 |
| Endoplasmin | sp\|Q95M18\|ENPL_BOVIN | 25.859 | NaN | EV fraction only | 3.50E+06 |
| TBCD protein | tr\|A7MB50\|A7MB50_BOVIN; sp\|Q28205\|TBCD_BOVIN | 25.865 | NaN | EV fraction only | 1.40E+06 |
| Sorting nexin-3 | sp\|Q1RMH8\|SNX3_BOVIN | 25.870 | NaN | EV fraction only | 8.90E+06 |
| 6-phosphofructokinase | tr\|E1BCW3\|E1BCW3_BOVIN | 25.876 | NaN | EV fraction only | 1.90E+06 |
| Histidine triad nucleotide-binding protein 2, mitochondrial | sp\|Q8SQ21\|HINT2_BOVIN | 25.896 | NaN | EV fraction only | 1.60E+07 |
| Uncharacterized protein | tr\|F6R173\|F6R173_BOVIN; tr\|F1MDA8\|F1MDA8_BOVIN | 25.896 | NaN | EV fraction only | 3.50E+06 |
| GTP-binding protein SAR1a | sp\|Q3T0D7\|SAR1A_BOVIN | 25.911 | NaN | EV fraction only | 6.30E+06 |
| MAP2K4 protein | tr\|A5PJP8\|A5PJP8_BOVIN | 25.913 | NaN | EV fraction only | 2.70E+06 |
| MAP2K2 protein | tr\|Q17QH2\|Q17QH2_BOVIN | 25.915 | NaN | EV fraction only | 6.40E+06 |
| ARF5 protein | tr\|A4IFP7\|A4IFP7_BOVIN | 25.923 | NaN | EV fraction only | 1.40E+07 |
| 55 kDa erythrocyte membrane protein | sp\|Q17QN6\|EM55_BOVIN | 25.958 | NaN | EV fraction only | 4.10E+06 |
| Guanylate cyclase soluble subunit beta-1 | tr\|G3N145\|G3N145_BOVIN; sp\|P16068\|GCYB1_BOVIN | 25.974 | NaN | EV fraction only | 2.40E+06 |
| Serine/threonine-protein phosphatase 2A 56 kDa regulatory subunit epsilon isoform | sp\|A4FV68\|2A5E_BOVIN; tr\|Q08DP7\|Q08DP7_BOVIN | 25.990 | NaN | EV fraction only | 6.10E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Guanine nucleotide-binding protein G(o) subunit alpha | sp\|P08239\|GNAO_BOVIN; tr\|G8JKZ5\|G8JKZ5_BOVIN; tr\|F1N461\|F1N461_BOVIN; sp\|P04896-2\|GNAS2_BOVIN; sp\|P04896\|GNAS2_BOVIN | 26.064 | NaN | EV fraction only | 1.00E+07 |
| T-complex protein 1 subunit theta | sp\|Q3ZCI9\|TCPQ_BOVIN; tr\|G3X861\|G3X861_BOVIN | 26.065 | NaN | EV fraction only | 8.30E+06 |
| Uncharacterized protein | tr\|E1BFC3\|E1BFC3_BOVIN | 26.093 | NaN | EV fraction only | 5.90E+06 |
| Eukaryotic initiation factor 4A-I | sp\|Q3SZ54\|IF4A1_BOVIN | 26.121 | NaN | EV fraction only | 1.10E+07 |
| V-type proton ATPase subunit C 1 | sp\|P21282\|VATC1_BOVIN | 26.189 | NaN | EV fraction only | 4.10E+06 |
| Uncharacterized protein (Fragment) | tr\|F6RJG0\|F6RJG0_BOVIN | 26.224 | NaN | EV fraction only | 4.70E+06 |
| Uncharacterized protein (Fragment) | tr\|E1BEI0\|E1BEI0_BOVIN | 26.229 | NaN | EV fraction only | 7.20E+06 |
| Annexin A6 | sp\|P79134\|ANXA6_BOVIN | 26.312 | NaN | EV fraction only | 1.90E+06 |
| tRNA-splicing ligase RtcB homolog | sp\|Q5E9T9\|RTCB_BOVIN | 26.380 | NaN | EV fraction only | 3.60E+06 |
| Uncharacterized protein (Fragment) | tr\|F1MU05\|F1MU05_BOVIN | 26.380 | NaN | EV fraction only | 2.70E+06 |
| Histone H2A.J | sp\|Q3ZBX9\|H2AJ_BOVIN; tr\|G8JL00\|G8JL00_BOVIN; tr\|F2Z4J1\|F2Z4J1_BOVIN; tr\|F2Z4G5\|F2Z4G5_BOVIN; tr\|A4IFU5\|A4IFU5_BOVIN; sp\|P0C0S9\|H2A1_BOVIN; sp\|A1A4R1\|H2A2C_BOVIN; tr\|F2Z4I6\|F2Z4I6_BOVIN; tr\|Q17QG8\|Q17QG8_BOVIN; sp\|Q32LA7\|H2AV_BOVIN; sp\|P0C0S4\|H2AZ_BOVIN; tr\|F1MLQ1\|F1MLQ1_BOVIN; tr\|F1MRN2\|F1MRN2_BOVIN; tr\|E1BH22\|E1BH22_BOVIN; tr\|F1MT45\|F1MT45_BOVIN | 26.413 | NaN | EV fraction only | 3.10E+07 |
| Uncharacterized protein | tr\|E1BGE5\|E1BGE5_BOVIN; tr\|E1B8Q9\|E1B8Q9_BOVIN | 26.421 | NaN | EV fraction only | 5.40E+06 |
| COP9 signalosome complex subunit 3 | sp\|A6H7B5\|CSN3_BOVIN | 26.440 | NaN | EV fraction only | 5.10E+06 |
| RAP1 GTPase activating protein | tr\|Q08E64\|Q08E64_BOVIN; tr\|F1N2P1\|F1N2P1_BOVIN | 26.453 | NaN | EV fraction only | 5.10E+06 |
| Galactokinase | sp\|A6H768\|GALK1_BOVIN; tr\|G1K1R6\|G1K1R6_BOVIN | 26.458 | NaN | EV fraction only | 6.60E+06 |
| NDRG family member 4 | tr\|Q0VCK8\|Q0VCK8_BOVIN | 26.527 | NaN | EV fraction only | 9.10E+06 |
| Glutamate--cysteine ligase regulatory subunit | sp\|Q2T9Y6\|GSH0_BOVIN | 26.568 | NaN | EV fraction only | 1.10E+07 |
| AHA1, activator of heat shock 90 kDa protein ATPase homolog 1 (Yeast) | tr\|Q3T0G3\|Q3T0G3_BOVIN | 26.574 | NaN | EV fraction only | 1.30E+07 |
| Uncharacterized protein | tr\|E1BIN5\|E1BIN5_BOVIN | 26.776 | NaN | EV fraction only | 3.90E+06 |
| Uncharacterized protein | tr\|F1N102\|F1N102_BOVIN; tr\|F1MX86\|F1MX86_BOVIN | 26.837 | NaN | EV fraction only | 1.00E+07 |
| RPE-retinal G protein-coupled receptor | sp\|P47803\|RGR_BOVIN | 26.918 | NaN | EV fraction only | 1.80E+07 |
| Solute carrier family 2, facilitated glucose transporter member 1 | sp\|P27674\|GTR1_BOVIN | 26.928 | NaN | EV fraction only | 1.10E+07 |
| Uncharacterized protein | tr\|G3N2N1\|G3N2N1_BOVIN | 26.929 | NaN | EV fraction only | 9.30E+06 |
| Histone H2B | tr\|F1N453\|F1N453_BOVIN;tr\|E1BGW2\|E1BGW2_BOVIN; tr\|G8JL06\|G8JL06_BOVIN; tr\|E1B8G9\|E1B8G9_BOVIN; tr\|Q32S29\|Q32S29_BOVIN; tr\|Q2KII5\|Q2KII5_BOVIN; tr\|F2Z4F9\|F2Z4F9_BOVIN; tr\|F2Z4E8\|F2Z4E8_BOVIN; tr\|F1MUD2\|F1MUD2_BOVIN; sp\|Q2M2T1\|H2B1K_BOVIN; sp\|P62808\|H2B1_BOVIN; tr\|G3N080\|G3N080_BOVIN; tr\|G3N0F3\|G3N0F3_BOVIN; | 26.997 | NaN | EV fraction only | 2.90E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| >P35908 SWISS-PROT: P35908 Tax_Id = 9606 Gene_Symbol = KRT2 Keratin, type II cytoskeletal 2 epidermal | tr\|F1MIF8\|F1MIF8_BOVIN; tr\|G5E6I9\|G5E6I9_BOVIN; tr\|G3N3L9\|G3N3L9_BOVIN; tr\|G3N1C9\|G3N1C9_BOVIN; tr\|G3N068\|G3N068_BOVIN; tr\|G3N011\|G3N011_BOVIN; tr\|G3MYV4\|G3MYV4_BOVIN; tr\|G3MWH4\|G3MWH4_BOVIN; tr\|F1MUU9\|F1MUU9_BOVIN; sp\|Q32L48\|H2B1N_BOVIN; tr\|G3N053\|G3N053_BOVIN; tr\|E1BK75\|E1BK75_BOVIN; tr\|G3MXP6\|G3MXP6_BOVIN; tr\|F1MV26\|F1MV26_BOVIN; tr\|A6QQ28\|A6QQ28_BOVIN; tr\|G3MZL8\|G3MZL8_BOVIN; tr\|G3MX03\|G3MX03_BOVIN; tr CON_P35908; CON_Q7Z794; tr\|G3X8G9\|G3X8G9_BOVIN; sp\|P05786\|K2C8_BOVIN; CON_Q9H552; CON_Q9R0H5; tr\|G3MYU2\|G3MYU2_BOVIN; sp\|P04262\|K2CB_BOVIN; sp\|P04261\|K2C3_BOVIN; sp\|P04260\|K2C4_BOVIN; tr\|A4IFN4\|A4IFN4_BOVIN; tr\|E1BIX9\|E1BIX9_BOVIN; tr\|F1MU12\|F1MU12_BOVIN; CON_Q14CN4-1; CON_Q6IME9; CON_Q3SY84; sp\|Q148H8\|K2C72_BOVIN; sp\|Q148H5\|K2C71_BOVIN; CON_Q7RTS7; CON_Q32MB2; sp\|A3KN27\|K2C74_BOVIN; tr\|E1B991\|E1B991_BOVIN; tr\|G3MZ71\|G3MZ71_BOVIN | 27.001 | NaN | EV fraction only | 4.50E+06 |
| General vesicular transport factor p115 | sp\|P41541\|USO1_BOVIN | 27.009 | NaN | EV fraction only | 3.10E+07 |
| Histone H4 (Fragment) | tr\|G3X807\|G3X807_BOVIN; tr\|E1BLC2\|E1BLC2_BOVIN; sp\|P62803\|H4_BOVIN; tr\|E1BBP7\|E1BBP7_BOVIN; tr\|G3N2B8\|G3N2B8_BOVIN; tr\|E1B9M9\|E1B9M9_BOVIN; tr\|E1B7N2\|E1B7N2_BOVIN; tr\|G3N081\|G3N081_BOVIN; tr\|G3MYX0\|G3MYX0_BOVIN | 27.033 | NaN | EV fraction only | 4.10E+07 |
| Uncharacterized protein | tr\|F1MZX2\|F1MZX2_BOVIN | 27.040 | NaN | EV fraction only | 9.70E+06 |
| Signal transducer and activator of transcription | tr\|B0JYL6\|B0JYL6_BOVIN | 27.060 | NaN | EV fraction only | 4.60E+06 |
| Uncharacterized protein | tr\|E1BPK6\|E1BPK6_BOVIN | 27.067 | NaN | EV fraction only | 3.40E+06 |
| Uncharacterized protein (Fragment) | tr\|E1BB36\|E1BB36_BOVIN | 27.135 | NaN | EV fraction only | 8.70E+06 |
| Aspartate--tRNA ligase, cytoplasmic | tr\|F1MTX7\|F1MTX7_BOVIN | 27.282 | NaN | EV fraction only | 5.30E+06 |
| Uncharacterized protein | tr\|F1MBF6\|F1MBF6_BOVIN; tr\|G3X7D3\|G3X7D3_BOVIN; tr\|F1MX39\|F1MX39_BOVIN | 27.330 | NaN | EV fraction only | 4.60E+07 |
| Sodium/potassium-transporting ATPase subunit alpha-1 | tr\|F1MI32\|F1MI32_BOVIN; sp\|Q08DA1\|AT1A1_BOVIN; sp\|A2VDL6\|AT1A2_BOVIN; tr\|F1MR06\|F1MR06_BOVIN; tr\|E1B8N5\|E1B8N5_BOVIN; tr\|F1N1K4\|F1N1K4_BOVIN; tr\|G3N2I3\|G3N2I3_BOVIN; tr\|F1MXW4\|F1MXW4_BOVIN | 27.405 | NaN | EV fraction only | 3.90E+06 |
| Uncharacterized protein | tr\|F1MIF2\|F1MIF2_BOVIN | 27.572 | NaN | EV fraction only | 4.50E+06 |
| Tubulin beta-2B chain | sp\|Q6B856\|TBB2B_BOVIN; tr\|G3N1W7\|G3N1W7_BOVIN | 27.788 | NaN | EV fraction only | 1.20E+07 |
| Microfibrillar-associated protein 2 | tr\|F1MWK6\|F1MWK6_BOVIN; sp\|P27424\|MFAP2_BOVIN | 28.384 | NaN | EV fraction only | 4.00E+08 |
| Cystatin-C | sp\|P01035\|CYTC_BOVIN | 28.772 | NaN | EV fraction only | 1.20E+08 |
| Estradiol 17-beta-dehydrogenase 12 | tr\|A6H7H3\|A6H7H3_BOVIN | 29.508 | NaN | EV fraction only | 4.80E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/whole vitreous Log2 difference | iBAQ |
|---|---|---|---|---|---|
| Uncharacterized protein | tr\|E1BDX8\|E1BDX8_BOVIN | 30.705 | NaN | EV fraction only | 6.90E+06 |
| Protein FAM188A | sp\|Q0IIH8\|F188A_BOVIN | NaN | 19.040 | Total vitreous | 4.80E+05 |
| Coagulation factor V | tr\|F1N0I3\|F1N0I3_BOVIN; sp\|Q28107\|FA5_BOVIN; CON_Q28107 | NaN | 19.050 | Total vitreous | 9.30E+04 |
| Fructose-2,6-bisphosphatase TIGAR | sp\|Q1JQA7\|TIGAR_BOVIN | NaN | 19.685 | Total vitreous | 8.10E+05 |
| Non-histone chromosomal protein HMG-17 | tr\|F2Z4H2\|F2Z4H2_BOVIN; sp\|P02313\|HMGN2_BOVIN | NaN | 19.875 | Total vitreous | 6.50E+06 |
| Heterochromatin protein 1-binding protein 3 | sp\|Q08DU9\|HP1B3_BOVIN | NaN | 20.120 | Total vitreous | 7.70E+05 |
| Uncharacterized protein | tr\|E1B9Y0\|E1B9Y0_BOVIN | NaN | 20.142 | Total vitreous | 6.20E+05 |
| Protein pelota homolog | sp\|Q58DV0\|PELO_BOVIN | NaN | 20.144 | Total vitreous | 7.40E+05 |
| Eukaryotic initiation factor 4A-III | sp\|Q2NL22\|IF4A3_BOVIN | NaN | 20.172 | Total vitreous | 9.40E+05 |
| Calpain small subunit 1 | sp\|P13135\|CPNS1_BOVIN | NaN | 20.247 | Total vitreous | 1.50E+06 |
| Calsequestrin | tr\|Q3MHM1\|Q3MHM1_BOVIN | NaN | 20.279 | Total vitreous | 1.00E+06 |
| Protein mago nashi homolog | sp\|Q3ZBV3\|MGN_BOVIN; sp\|Q0VC92\|MGN2_BOVIN | NaN | 20.303 | Total vitreous | 1.70E+06 |
| TNFRSF6B protein | tr\|A6QPW7\|A6QPW7_BOVIN | NaN | 20.341 | Total vitreous | 1.80E+06 |
| Uncharacterized protein | tr\|E1BMN6\|E1BMN6_BOVIN | NaN | 20.347 | Total vitreous | 6.20E+05 |
| Uncharacterized protein | tr\|E1BJW3\|E1BJW3_BOVIN | NaN | 20.404 | Total vitreous | 4.30E+05 |
| Uncharacterized protein | tr\|F1MIZ7\|F1MIZ7_BOVIN | NaN | 20.453 | Total vitreous | 6.70E+05 |
| U6 snRNA-associated Sm-like protein LSm4 | sp\|Q3ZBK6\|LSM4_BOVIN | NaN | 20.459 | Total vitreous | 2.20E+06 |
| DnaJ homolog subfamily A member 1 | sp\|Q5E954\|DNJA1_BOVIN; tr\|A6QM13\|A6QM13_BOVIN | NaN | 20.497 | Total vitreous | 1.00E+06 |
| Uncharacterized protein | tr\|E1BIG6\|E1BIG6_BOVIN | NaN | 20.501 | Total vitreous | 6.20E+05 |
| 15 kDa selenoprotein | sp\|A8YXY3\|SEP15_BOVIN | NaN | 20.564 | Total vitreous | 2.80E+06 |
| FAM151B protein | tr\|A5PKK0\|A5PKK0_BOVIN | NaN | 20.600 | Total vitreous | 1.80E+06 |
| Uncharacterized protein | tr\|F1MBQ8\|F1MBQ8_BOVIN | NaN | 20.626 | Total vitreous | 6.80E+05 |
| PC4 and SFRS1-interacting protein | tr\|E1BP00\|E1BP00_BOVIN; sp\|Q8MJG1\|PSIP1_BOVIN | NaN | 20.661 | Total vitreous | 7.20E+05 |
| Uncharacterized protein (Fragment) | tr\|F1N3R6\|F1N3R6_BOVIN | NaN | 20.729 | Total vitreous | 6.00E+05 |
| Septin-8 | sp\|Q0VCP4\|SEPT8_BOVIN; tr\|F1MDV8\|F1MDV8_BOVIN; sp\|Q2KJB1\|SEP10_BOVIN | NaN | 20.732 | Total vitreous | 1.40E+06 |
| Uncharacterized protein | tr\|F1MHX0\|F1MHX0_BOVIN | NaN | 20.784 | Total vitreous | 6.10E+05 |
| Costars family protein ABRACL | sp\|Q3ZBN0\|ABRAL_BOVIN | NaN | 20.795 | Total vitreous | 4.90E+06 |
| ADAM23 protein | tr\|A4FUX7\|A4FUX7_BOVIN | NaN | 20.803 | Total vitreous | 7.10E+05 |
| Cholinesterase | sp\|P32749\|CHLE_BOVIN | NaN | 20.809 | Total vitreous | 8.80E+05 |
| Uncharacterized protein (Fragment) | tr\|F1MG74\|F1MG74_BOVIN | NaN | 20.840 | Total vitreous | 1.20E+06 |
| Phosphorylase | tr\|F1MJ28\|F1MJ28_BOVIN; sp\|P79334\|PYGM_BOVIN | NaN | 20.874 | Total vitreous | 7.40E+05 |
| CRISPLD1 protein | tr\|A6QR60\|A6QR60_BOVIN | NaN | 20.886 | Total vitreous | 1.00E+06 |
| Adenylosuccinate synthetase isozyme 2 | sp\|A7MBG0\|PURA2_BOVIN | NaN | 20.926 | Total vitreous | 1.30E+06 |
| Uncharacterized protein | tr\|E1BIS6\|E1BIS6_BOVIN | NaN | 20.968 | Total vitreous | 3.30E+05 |
| Uncharacterized protein (Fragment) | tr\|F1N0C0\|F1N0C0_BOVIN | NaN | 20.980 | Total vitreous | 4.60E+05 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Uncharacterized protein | tr\|F1MU85\|F1MU85_BOVIN | NaN | 20.992 | Total vitreous | 1.70E+06 |
| Ubiquitin-like protein 5 | tr\|G3MY86\|G3MY86_BOVIN; sp\|Q3T0Z3\|UBL5_BOVIN | NaN | 21.003 | Total vitreous | 7.10E+06 |
| Metallo-beta-lactamase domain-containing protein 1 | tr\|F1MBD2\|F1MBD2_BOVIN; sp\|Q2HJB0\|MBLC1_BOVIN | NaN | 21.006 | Total vitreous | 2.60E+06 |
| Uncharacterized protein | tr\|G3X7R5\|G3X7R5_BOVIN; tr\|F1MBI6\|F1MBI6_BOVIN; tr\|G3N2N4\|G3N2N4_BOVIN; tr\|F1MS84\|F1MS84_BOVIN | NaN | 21.007 | Total vitreous | 1.50E+06 |
| Uncharacterized protein (Fragment) | tr\|F1MZD0\|F1MZD0_BOVIN | NaN | 21.013 | Total vitreous | 2.30E+05 |
| Uncharacterized protein | tr\|E1BL29\|E1BL29_BOVIN | NaN | 21.026 | Total vitreous | 1.10E+06 |
| CHMP4B protein | tr\|Q08E32\|Q08E32_BOVIN | NaN | 21.035 | Total vitreous | 2.10E+06 |
| UBX domain-containing protein 1 | sp\|Q32KW2\|UBXN1_BOVIN | NaN | 21.040 | Total vitreous | 1.90E+06 |
| Cathepsin S | sp\|P25326\|CATS_BOVIN | NaN | 21.193 | Total vitreous | 2.50E+06 |
| Signal-regulatory protein delta | tr\|Q2TA28\|Q2TA28_BOVIN | NaN | 21.207 | Total vitreous | 2.20E+06 |
| Ecdysoneless homolog (*Drosophila*) | tr\|Q2KI67\|Q2KI67_BOVIN | NaN | 21.234 | Total vitreous | 1.00E+06 |
| Uncharacterized protein (Fragment) | tr\|F1MC13\|F1MC13_BOVIN | NaN | 21.243 | Total vitreous | 2.00E+05 |
| Uncharacterized protein | tr\|E1BPZ4\|E1BPZ4_BOVIN | NaN | 21.267 | Total vitreous | 5.70E+06 |
| NHL repeat-containing protein 2 | sp\|A4IF69\|NHLC2_BOVIN | NaN | 21.281 | Total vitreous | 1.40E+06 |
| Lambda-crystallin homolog | sp\|Q8SPX7\|CRYL1_BOVIN | NaN | 21.296 | Total vitreous | 2.10E+06 |
| Complexin-1 | sp\|Q0IIL7\|CPLX1_BOVIN | NaN | 21.304 | Total vitreous | 7.00E+06 |
| Uncharacterized protein (Fragment) | tr\|F1MZ93\|F1MZ93_BOVIN | NaN | 21.308 | Total vitreous | 9.70E+05 |
| Transcription elongation factor A protein 1 (Fragment) | tr\|F1MIT2\|F1MIT2_BOVIN; sp\|Q29RL9\|TCEA1_BOVIN; sp\|Q148K0\|TCEA2_BOVIN; tr\|G1K224\|G1K224_BOVIN | NaN | 21.313 | Total vitreous | 2.20E+06 |
| FBXO22 protein | tr\|A5PJX0\|A5PJX0_BOVIN | NaN | 21.319 | Total vitreous | 2.10E+06 |
| Uncharacterized protein | tr\|F1MIX9\|F1MIX9_BOVIN | NaN | 21.322 | Total vitreous | 8.80E+05 |
| Uncharacterized protein (Fragment) | tr\|F1MFY9\|F1MFY9_BOVIN | NaN | 21.328 | Total vitreous | 2.20E+06 |
| Regakine-1 | sp\|P82943\|REG1 _BOVIN | NaN | 21.358 | Total vitreous | 6.00E+06 |
| CHN1 protein | tr\|A7Z037\|A7Z037_BOVIN; tr\|Q0VD41\|Q0VD41_BOVIN | NaN | 21.367 | Total vitreous | 1.50E+06 |
| Uncharacterized protein | tr\|E1BGJ4\|E1BGJ4_BOVIN | NaN | 21.372 | Total vitreous | 7.00E+05 |
| Uncharacterized protein (Fragment) | tr\|F1MFI5\|F1MFI5_BOVIN | NaN | 21.388 | Total vitreous | 4.70E+05 |
| Iron-sulfur cluster scaffold homolog (*E. coli*) | tr\|Q17QE6\|Q17QE6_BOVIN | NaN | 21.403 | Total vitreous | 3.10E+06 |
| Splicing factor 1 | tr\|A2VDM7\|A2VDM7_BOVIN | NaN | 21.424 | Total vitreous | 2.40E+06 |
| Uncharacterized protein | tr\|F1MG94\|F1MG94_BOVIN; tr\|A7Z085\|A7Z085_BOVIN | NaN | 21.429 | Total vitreous | 2.60E+06 |
| Polyadenylate-binding protein 1 | sp\|P61286\|PABP1 _BOVIN; tr\|A4IFC3\|A4IFC3_BOVIN | NaN | 21.441 | Total vitreous | 1.10E+06 |
| Alanyl-tRNA-editing protein Aarsd1 | tr\|F1MZR1\|F1MZR1_BOVIN; sp\|Q32LK1\|AASD1_BOVIN; tr\|E1BP20\|E1BP20_BOVIN | NaN | 21.453 | Total vitreous | 1.70E+06 |
| Uncharacterized protein | tr\|F1N761\|F1N761_BOVIN | NaN | 21.491 | Total vitreous | 2.70E+06 |
| PKIB protein | tr\|Q0VCK2\|Q0VCK2_BOVIN | NaN | 21.521 | Total vitreous | 1.00E+07 |
| WD repeat-containing protein 44 | tr\|G3X7E3\|G3X7E3_BOVIN; sp\|Q9XSC3\|WDR44_BOVIN | NaN | 21.539 | Total vitreous | 7.80E+05 |
| Rap1 GTPase-GDP dissociation stimulator 1 | sp\|Q04173\|GDS1_BOVIN | NaN | 21.539 | Total vitreous | 1.50E+06 |
| Uncharacterized protein | tr\|F1MDD8\|F1MDD8_BOVIN | NaN | 21.544 | Total | 1.80E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| (Fragment) | | | | vitreous | |
| Transforming growth factor-beta-induced protein ig-h3 (Fragment) | tr\|F1MBS3\|F1MBS3_BOVIN | NaN | 21.564 | Total vitreous | 1.30E+06 |
| Phytanoyl-CoA hydroxylase-interacting protein | sp\|Q0VD34\|PHYIP_BOVIN | NaN | 21.577 | Total vitreous | 2.60E+06 |
| Ubiquitin carboxyl-terminal hydrolase | tr\|G5E630\|G5E630_BOVIN | NaN | 21.594 | Total vitreous | 3.80E+05 |
| Selenide, water dikinase 1 | sp\|Q0VC82\|SPS1_BOVIN | NaN | 21.598 | Total vitreous | 3.80E+06 |
| Collagen alpha-1(IV) chain (Fragment) | sp\|Q7SIB2\|CO4A1_BOVIN; tr\|G1K238\|G1K238_BOVIN | NaN | 21.604 | Total vitreous | 4.80E+06 |
| Uncharacterized protein (Fragment) | tr\|G3N286\|G3N286_BOVIN | NaN | 21.606 | Total vitreous | 1.10E+07 |
| Chitinase-3-like protein 1 | sp\|P30922\|CH3L1_BOVIN; tr\|G3X7D2\|G3X7D2_BOVIN | NaN | 21.609 | Total vitreous | 2.10E+06 |
| FAS-associated death domain protein | sp\|Q645M6\|FADD_BOVIN | NaN | 21.614 | Total vitreous | 3.60E+06 |
| Uncharacterized protein | tr\|F1N4Y5\|F1N4Y5_BOVIN | NaN | 21.617 | Total vitreous | 2.30E+06 |
| Epsilon-sarcoglycan | tr\|F1MYZ0\|F1MYZ0_BOVIN; sp\|Q29S03\|SGCE_BOVIN | NaN | 21.618 | Total vitreous | 2.20E+06 |
| Protein dpy-30 homolog | sp\|Q2NKU6\|DPY30_BOVIN | NaN | 21.625 | Total vitreous | 1.10E+07 |
| Adenosine deaminase-like protein | tr\|F1N1T1\|F1N1T1_BOVIN; sp\|Q0VC13\|ADAL_BOVIN | NaN | 21.632 | Total vitreous | 2.60E+06 |
| Cytosol aminopeptidase | tr\|G3N0I4\|G3N0I4_BOVIN; sp\|P0727-2\|AMPL_BOVIN; sp\|P00727\|AMPL_BOVIN | NaN | 21.638 | Total vitreous | 1.60E+06 |
| Uncharacterized protein | tr\|F1N7G0\|F1N7G0_BOVIN | NaN | 21.659 | Total vitreous | 1.90E+06 |
| Calpastatin | tr\|G3N2N7\|G3N2N7_BOVIN; tr\|F1MD74\|F1MD74_BOVIN; sp\|P20811\|ICAL_BOVIN; tr\|F1N161\|F1N161_BOVIN; tr\|F1MR96\|F1MR96_BOVIN | NaN | 21.663 | Total vitreous | 2.20E+06 |
| Leucine zipper transcription factor-like protein 1 (Fragment) | tr\|F1MNG7\|F1MNG7_BOVIN; sp\|Q3ZBL4\|LZTL1_BOVIN | NaN | 21.667 | Total vitreous | 3.60E+06 |
| MARCKS-related protein | tr\|G3MZA0\|G3MZA0_BOVIN; sp\|Q0VBZ9\|MRP_BOVIN; tr\|G3MY11\|G3MY11_BOVIN | NaN | 21.683 | Total vitreous | 6.50E+06 |
| Uncharacterized protein | tr\|F1MX44\|F1MX44_BOVIN; tr\|E1BGC0\|E1BGC0_BOVIN; sp\|Q28035\|GSTA1_BOVIN; sp\|O18879\|GSTA2_BOVIN | NaN | 21.692 | Total vitreous | 4.20E+06 |
| Uncharacterized protein | tr\|F1N1F8\|F1N1F8_BOVIN | NaN | 21.692 | Total vitreous | 2.40E+05 |
| Carbonyl reductase 3 | tr\|Q0VC97\|Q0VC97_BOVIN | NaN | 21.697 | Total vitreous | 3.10E+06 |
| Uncharacterized protein (Fragment) | tr\|F1N5W4\|F1N5W4_BOVIN | NaN | 21.708 | Total vitreous | 3.10E+06 |
| Aspartate aminotransferase, mitochondrial | sp\|P12344\|AATM_BOVIN | NaN | 21.715 | Total vitreous | 1.80E+06 |
| Integrin-linked kinase-associated serine/threonine phosphatase 2C | sp\|Q0IIF0\|ILKAP_BOVIN | NaN | 21.723 | Total vitreous | 2.20E+06 |
| Uroporphyrinogen decarboxylase | tr\|E1BEX4\|E1BEX4_BOVIN | NaN | 21.723 | Total vitreous | 3.10E+06 |
| Heterogeneous nuclear ribonucleoprotein A/B | tr\|Q3ZC44\|Q3ZC44_BOVIN | NaN | 21.734 | Total vitreous | 3.60E+06 |
| ARSB protein | tr\|A6QLZ3\|A6QLZ3_BOVIN | NaN | 21.751 | Total vitreous | 1.70E+06 |
| Uncharacterized protein | tr\|E1BCU8\|E1BCU8_BOVIN | NaN | 21.755 | Total vitreous | 3.20E+06 |
| Uncharacterized protein | tr\|E1BGE9\|E1BGE9_BOVIN | NaN | 21.803 | Total vitreous | 4.50E+06 |
| Uncharacterized protein | tr\|E1BKX1\|E1BKX1_BOVIN | NaN | 21.817 | Total vitreous | 7.50E+05 |
| Uncharacterized protein | tr\|F6PZ08\|F6PZ08_BOVIN | NaN | 21.838 | Total vitreous | 4.20E+06 |
| Uncharacterized protein | tr\|F1N1A3\|F1N1A3_BOVIN; tr\|Q95M59\|Q95M59_BOVIN | NaN | 21.849 | Total vitreous | 3.90E+06 |
| Desmocollin-3 (Fragment) | tr\|F1N5L6\|F1N5L6_BOVIN; sp\|Q28060-2\|DSC3_BOVIN; tr\|E1BB21\|E1BB21_BOVIN; | NaN | 21.851 | Total vitreous | 1.10E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| | tr\|F1MXJ3\|F1MXJ3_BOVIN; sp\|Q28060\|DSC3_BOVIN | | | | |
| Uncharacterized protein | tr\|F1MB84\|F1MB84_BOVIN | NaN | 21.879 | Total vitreous | 3.10E+06 |
| Endothelial differentiation-related factor 1 | sp\|Q3T0V7\|EDF1_BOVIN | NaN | 21.892 | Total vitreous | 5.80E+06 |
| Xaa-Pro aminopeptidase 1 | sp\|Q1JPJ2\|XPP1_BOVIN | NaN | 21.901 | Total vitreous | 1.60E+06 |
| Follistatin-related protein 3 | sp\|Q1LZB9\|FSTL3_BOVIN | NaN | 21.904 | Total vitreous | 4.80E+06 |
| Catalase | sp\|P00432\|CATA_BOVIN | NaN | 21.913 | Total vitreous | 1.80E+06 |
| Calcium regulated heat stable protein 1, 24 kDa | tr\|Q2NKU4\|Q2NKU4_BOVIN | NaN | 21.921 | Total vitreous | 7.70E+06 |
| Semaphorin-4A | tr\|F1MY79\|F1MY79_BOVIN; sp\|Q5EA85\|SEM4A_BOVIN | NaN | 21.922 | Total vitreous | 1.90E+06 |
| Tissue specific transplantation antigen P35B | tr\|Q2KIT8\|Q2KIT8_BOVIN | NaN | 21.937 | Total vitreous | 3.60E+06 |
| Craniofacial development protein 2 | tr\|F1MS40\|F1MS40_BOVIN; sp\|O02751\|CFDP2_BOVIN | NaN | 21.955 | Total vitreous | 1.50E+06 |
| Eukaryotic translation initiation factor 6 | sp\|Q9TU47\|IF6_BOVIN | NaN | 21.967 | Total vitreous | 6.10E+06 |
| Vacuolar protein sorting-associated protein 4B | sp\|Q0VD48\|VPS4B_BOVIN | NaN | 21.969 | Total vitreous | 2.30E+06 |
| N(G),N(G)-dimethylarginine dimethylaminohydrolase 2 | sp\|Q3SX44\|DDAH2_BOVIN | NaN | 21.969 | Total vitreous | 3.30E+06 |
| Uncharacterized protein (Fragment) | tr\|E1BKZ1\|E1BKZ1_BOVIN | NaN | 21.969 | Total vitreous | 3.10E+06 |
| Uncharacterized protein (Fragment) | tr\|F1N048\|F1N048_BOVIN | NaN | 21.979 | Total vitreous | 2.10E+06 |
| Nascent polypeptide-associated complex subunit alpha | sp\|Q5E9A1\|NACA_BOVIN | NaN | 21.997 | Total vitreous | 9.40E+06 |
| Malignant T-cell-amplified sequence | tr\|A6QLG1\|A6QLG1_BOVIN; sp\|Q2KIE4\|MCTS1_BOVIN | NaN | 21.997 | Total vitreous | 5.60E+06 |
| Alpha-2,8-sialyltransferase ST8Sia II | tr\|A2BCP4\|A2BCP4_BOVIN | NaN | 22.004 | Total vitreous | 2.80E+06 |
| Homeodomain-only protein | sp\|Q8MJD5\|HOP_BOVIN | NaN | 22.006 | Total vitreous | 1.90E+07 |
| Uncharacterized protein | tr\|F1MXN8\|F1MXN8_BOVIN | NaN | 22.007 | Total vitreous | 3.30E+06 |
| Non-histone chromosomal protein HMG-14 | sp\|P02316\|HMGN1_BOVIN | NaN | 22.015 | Total vitreous | 1.40E+07 |
| Uncharacterized protein | tr\|F1MVS4\|F1MVS4_BOVIN | NaN | 22.015 | Total vitreous | 6.40E+06 |
| Uncharacterized protein (Fragment) | tr\|E1BJV1\|E1BJV1_BOVIN | NaN | 22.059 | Total vitreous | 2.90E+05 |
| ATP-citrate synthase | sp\|Q32PF2\|ACLY_BOVIN | NaN | 22.059 | Total vitreous | 1.50E+06 |
| Selenium-binding protein 1 | sp\|Q2KJ32\|SBP1_BOVIN | NaN | 22.060 | Total vitreous | 1.90E+06 |
| Uncharacterized protein (Fragment) | tr\|F1MYC4\|F1MYC4_BOVIN; sp\|O62829\|PPM1A_BOVIN | NaN | 22.066 | Total vitreous | 3.50E+06 |
| 78 kDa glucose-regulated protein | sp\|Q0VCX2\|GRP78_BOVIN; tr\|F1N614\|F1N614_BOVIN | NaN | 22.071 | Total vitreous | 2.10E+06 |
| Alpha-aminoadipic semialdehyde dehydrogenase | tr\|E1BFG0\|E1BFG0_BOVIN; sp\|Q2KJC9\|AL7A1_BOVIN | NaN | 22.088 | Total vitreous | 2.40E+06 |
| Poly(ADP-ribose) glycohydrolase ARH3 | tr\|F1MWJ3\|F1MWJ3_BOVIN; sp\|Q3SYV9\|ARHL2_BOVIN | NaN | 22.100 | Total vitreous | 4.00E+06 |
| LOX protein | tr\|A5D7S7\|A5D7S7_BOVIN; sp\|P33072\|LYOX_BOVIN | NaN | 22.109 | Total vitreous | 3.10E+06 |
| Proteasome subunit beta type-4 | sp\|Q3T108\|PSB4_BOVIN | NaN | 22.127 | Total vitreous | 5.60E+06 |
| Glutamate decarboxylase 1 | sp\|Q0VCA1\|DCE1_BOVIN | NaN | 22.132 | Total vitreous | 2.60E+06 |
| Uncharacterized protein | tr\|E1BHY6\|E1BHY6_BOVIN | NaN | 22.140 | Total vitreous | 2.50E+06 |
| TOM1L2 protein | tr\|A5PK10\|A5PK10_BOVIN | NaN | 22.144 | Total vitreous | 3.90E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Uncharacterized protein | tr\|E1BIU8\|E1BIU8_BOVIN | NaN | 22.159 | Total vitreous | 7.50E+05 |
| Pro-cathepsin H | sp\|Q3T0I2\|CATH_BOVIN | NaN | 22.167 | Total vitreous | 3.70E+06 |
| A disintegrin and metalloproteinase with thrombospondin motifs 5 | tr\|F1MRZ2\|F1MRZ2_BOVIN | NaN | 22.171 | Total vitreous | 1.10E+06 |
| NmrA-like family domain-containing protein 1 | sp\|Q0VCN1\|NMRL1_BOVIN | NaN | 22.178 | Total vitreous | 4.20E+06 |
| Uncharacterized protein | tr\|F1MHF7\|F1MHF7_BOVIN | NaN | 22.186 | Total vitreous | 9.20E+06 |
| Mitochondrial fission 1 protein | sp\|Q3T0I5\|FIS1_BOVIN | NaN | 22.209 | Total vitreous | 1.00E+07 |
| Proteasome activator complex subunit 2 | sp\|Q5E9G3\|PSME2_BOVIN; tr\|F1MU19\|F1MU19_BOVIN | NaN | 22.212 | Total vitreous | 5.40E+06 |
| F-actin-capping protein subunit alpha-1 | sp\|A4FUA8\|CAZA1_BOVIN | NaN | 22.221 | Total vitreous | 5.10E+06 |
| Proteasome subunit alpha type-2 | sp\|Q3T0Y5\|PSA2_BOVIN | NaN | 22.238 | Total vitreous | 5.10E+06 |
| Uncharacterized protein (Fragment) | tr\|F1N4I2\|F1N4I2_BOVIN; tr\|Q08DL9\|Q08DL9_BOVIN | NaN | 22.246 | Total vitreous | 4.40E+06 |
| GFRA1 protein | tr\|A7YY41\|A7YY41_BOVIN | NaN | 22.258 | Total vitreous | 3.40E+06 |
| Uncharacterized protein | tr\|E1BKZ9\|E1BKZ9_BOVIN | NaN | 22.263 | Total vitreous | 2.10E+06 |
| Cystatin-B | sp\|P25417\|CYTB_BOVIN | NaN | 22.266 | Total vitreous | 1.10E+07 |
| Uncharacterized protein | tr\|E1B9D4\|E1B9D4_BOVIN; tr\|A2VDV0\|A2VDV0_BOVIN | NaN | 22.271 | Total vitreous | 7.90E+06 |
| Uncharacterized protein | tr\|E1BE14\|E1BE14_BOVIN | NaN | 22.277 | Total vitreous | 6.90E+06 |
| Protein phosphatase 1G | sp\|P79126\|PPM1G_BOVIN | NaN | 22.279 | Total vitreous | 3.00E+06 |
| Superoxide dismutase [Mn], mitochondrial | sp\|P41976\|SODM_BOVIN | NaN | 22.280 | Total vitreous | 8.60E+06 |
| Target of myb1 | tr\|Q5BIP4\|Q5BIP4_BOVIN | NaN | 22.285 | Total vitreous | 3.30E+06 |
| Uncharacterized protein (Fragment) | tr\|E1BAK6\|E1BAK6_BOVIN | NaN | 22.295 | Total vitreous | 7.70E+06 |
| Prefoldin subunit 2 | sp\|A1A4P5\|PFD2_BOVIN | NaN | 22.295 | Total vitreous | 6.90E+06 |
| Uncharacterized protein | tr\|E1BBU4\|E1BBU4_BOVIN | NaN | 22.299 | Total vitreous | 2.00E+06 |
| Harmonin (Fragment) | tr\|E1BK26\|E1BK26_BOVIN; tr\|F1MIQ5\|F1MIQ5_BOVIN; sp\|Q3MHQ0\|USH1C_BOVIN | NaN | 22.308 | Total vitreous | 1.20E+06 |
| Beta-enolase | sp\|Q3ZC09\|ENOB_BOVIN | NaN | 22.310 | Total vitreous | 3.50E+06 |
| Hornerin | CON_Q86YZ3 | NaN | 22.313 | Total vitreous | 1.10E+06 |
| Uncharacterized protein (Fragment) | tr\|E1B8G8\|E1B8G8_BOVIN; tr\|G3N3S9\|G3N3S9_BOVIN | NaN | 22.322 | Total vitreous | 1.20E+06 |
| Protein phosphatase 1B | sp\|O62830\|PPM1B_BOVIN | NaN | 22.324 | Total vitreous | 3.10E+06 |
| Dihydrofolate reductase | sp\|P00376\|DYR_BOVIN | NaN | 22.324 | Total vitreous | 5.90E+06 |
| Uncharacterized protein (Fragment) | tr\|F1MX14\|F1MX14_BOVIN | NaN | 22.342 | Total vitreous | 1.50E+06 |
| Uncharacterized protein | tr\|F1MBV2\|F1MBV2_BOVIN | NaN | 22.346 | Total vitreous | 5.70E+06 |
| Uncharacterized protein | tr\|E1BDI4\|E1BDI4_BOVIN | NaN | 22.349 | Total vitreous | 9.50E+05 |
| 3-phosphoadenosine 5-phosphosulfate synthase 1 | tr\|Q3T0J0\|Q3T0J0_BOVIN | NaN | 22.353 | Total vitreous | 2.30E+06 |
| Uncharacterized protein | tr\|E1BPX9\|E1BPX9_BOVIN | NaN | 22.392 | Total vitreous | 8.20E+05 |
| Uncharacterized protein (Fragment) | tr\|G3N019\|G3N019_BOVIN | NaN | 22.403 | Total vitreous | 1.40E+06 |
| Growth factor receptor-bound protein 2 | tr\|Q3T0F9\|Q3T0F9_BOVIN | NaN | 22.419 | Total vitreous | 5.40E+06 |
| Density-regulated protein | sp\|Q2HJ47\|DENR_BOVIN; tr\|E1BIK7\|E1BIK7_BOVIN | NaN | 22.428 | Total vitreous | 8.50E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Probable tRNA N6-adenosine threonylcarbamoyltransferase | sp\|Q0VCI1\|OSGEP_BOVIN | NaN | 22.429 | Total vitreous | 5.10E+06 |
| Uncharacterized protein | tr\|F1MLU5\|F1MLU5_BOVIN | NaN | 22.440 | Total vitreous | 1.20E+06 |
| similar to Pregnancy zone protein, partial | CON_ENSEMBL: ENSBTAP00000037665 | NaN | 22.440 | Total vitreous | 2.70E+06 |
| Uncharacterized protein | tr\|F1N611\|F1N611_BOVIN | NaN | 22.447 | Total vitreous | 1.80E+06 |
| Uncharacterized protein (Fragment) | tr\|E1BEI7\|E1BEI7_BOVIN | NaN | 22.451 | Total vitreous | 3.90E+06 |
| Ras-related protein Rab-5C | sp\|Q58DS9\|RAB5C_BOVIN | NaN | 22.455 | Total vitreous | 7.90E+06 |
| Cathepsin Z | tr\|F1MW68\|F1MW68_BOVIN; sp\|P05689\|CATZ_BOVIN | NaN | 22.461 | Total vitreous | 7.10E+06 |
| Neuropeptide-like protein C4orf48 homolog | sp\|A0JNN8\|CD048_BOVIN | NaN | 22.466 | Total vitreous | 1.10E+07 |
| Fibroblast growth factor receptor | tr\|A4IFL5\|A4IFL5_BOVIN | NaN | 22.477 | Total vitreous | 2.30E+06 |
| Sialyltransferase 4A | tr\|A5D960\|A5D960_BOVIN | NaN | 22.496 | Total vitreous | 4.40E+06 |
| 26S proteasome non-ATPase regulatory subunit 2 | sp\|P56701\|PSMD2_BOVIN | NaN | 22.499 | Total vitreous | 1.60E+06 |
| Uncharacterized protein (Fragment) | tr\|F1MZC0\|F1MZC0_BOVIN; tr\|F1N6I4\|F1N6I4_BOVIN | NaN | 22.499 | Total vitreous | 7.50E+06 |
| Uncharacterized protein | tr\|E1BIT8\|E1BIT8_BOVIN | NaN | 22.502 | Total vitreous | 2.50E+06 |
| Protein disulfide-isomerase | tr\|A6H7J6\|A6H7J6_BOVIN; sp\|P05307\|PDIA1_BOVIN | NaN | 22.518 | Total vitreous | 2.50E+06 |
| U6 snRNA-associated Sm-like protein LSm3 | sp\|Q32PE9\|LSM3_BOVIN | NaN | 22.525 | Total vitreous | 2.70E+07 |
| GATS-like protein 3 | sp\|Q0V8A3\|GATL3_BOVIN | NaN | 22.532 | Total vitreous | 8.20E+06 |
| Translation machinery-associated protein 7 | sp\|A1A4Q4\|TMA7_BOVIN | NaN | 22.542 | Total vitreous | 4.10E+07 |
| Nucleobindin 2 | tr\|Q0IIH5\|Q0IIH5_BOVIN | NaN | 22.549 | Total vitreous | 3.90E+06 |
| Uncharacterized protein | tr\|E1BIR7\|E1BIR7_BOVIN | NaN | 22.550 | Total vitreous | 6.60E+06 |
| Optineurin | tr\|Q3ZC32\|Q3ZC32_BOVIN | NaN | 22.552 | Total vitreous | 2.50E+06 |
| Uncharacterized protein (Fragment) | tr\|G3MXA7\|G3MXA7_BOVIN | NaN | 22.558 | Total vitreous | 2.80E+07 |
| Hepatocyte growth factor receptor | tr\|Z4YHD9\|Z4YHD9_BOVIN; sp\|Q769I5\|MET_BOVIN | NaN | 22.567 | Total vitreous | 1.20E+06 |
| cAMP-dependent protein kinase type I-alpha regulatory subunit | sp\|P00514\|KAP0_BOVIN | NaN | 22.576 | Total vitreous | 4.70E+06 |
| GSTM1 protein | tr\|A4IFG0\|A4IFG0_BOVIN | NaN | 22.585 | Total vitreous | 5.30E+06 |
| Uncharacterized protein | tr\|F1MMW5\|F1MMW5_BOVIN | NaN | 22.587 | Total vitreous | 1.60E+06 |
| Moesin | sp\|Q2HJ49\|MOES_BOVIN | NaN | 22.595 | Total vitreous | 2.60E+06 |
| mRNA cap guanine-N7 methyltransferase | tr\|F1MHQ5\|F1MHQ5_BOVIN | NaN | 22.617 | Total vitreous | 3.90E+06 |
| Uncharacterized protein | tr\|F1MBV6\|F1MBV6_BOVIN; tr\|Q3ZCA8\|Q3ZCA8_BOVIN; tr\|E1BE76\|E1BE76_BOVIN | NaN | 22.631 | Total vitreous | 1.30E+07 |
| Serine/threonine-protein phosphatase | tr\|Q2KIC7\|Q2KIC7_BOVIN | NaN | 22.648 | Total vitreous | 5.50E+06 |
| Septin-2 | sp\|Q2NKY7\|SEPT2_BOVIN; tr\|E1BKU2\|E1BKU2_BOVIN | NaN | 22.653 | Total vitreous | 4.80E+06 |
| CHST10 protein | tr\|A5D799\|A5D799_BOVIN | NaN | 22.666 | Total vitreous | 5.60E+06 |
| Uncharacterized protein | tr\|G5E5H2\|G5E5H2_BOVIN | NaN | 22.709 | Total vitreous | 1.80E+07 |
| Uncharacterized protein | tr\|E1BFZ0\|E1BFZ0_BOVIN; tr\|E1BIC8\|E1BIC8_BOVIN | NaN | 22.712 | Total vitreous | 4.10E+06 |
| Bucentaur-2 | tr\|A0JBZ9\|A0JBZ9_BOVIN | NaN | 22.726 | Total vitreous | 2.50E+06 |
| Twisted gastrulation | tr\|Q0VD44\|Q0VD44_BOVIN | NaN | 22.736 | Total | 9.40E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| homolog 1 (*Drosophila*) | | | | vitreous | |
| Aldose 1-epimerase | sp\|Q5EA79\|GALM_BOVIN | NaN | 22.746 | Total vitreous | 5.90E+06 |
| Cation-independent mannose-6-phosphate receptor | tr\|F1MIE6\|F1MIE6_BOVIN; sp\|P08169\|MPRI_BOVIN | NaN | 22.776 | Total vitreous | 7.90E+05 |
| Inositol monophosphatase 3 | sp\|Q2KJ53\|IMPA3_BOVIN | NaN | 22.778 | Total vitreous | 7.80E+06 |
| Reticulon (Fragment) | tr\|E1BP30\|E1BP30_BOVIN | NaN | 22.801 | Total vitreous | 3.20E+06 |
| S-methyl-5-thioadenosine phosphorylase | sp\|Q3MHF7\|MTAP_BOVIN; tr\|H9KUV2\|H9KUV2_BOVIN | NaN | 22.802 | Total vitreous | 5.50E+06 |
| Calpain-2 catalytic subunit | sp\|Q27971\|CAN2_BOVIN | NaN | 22.804 | Total vitreous | 3.60E+06 |
| TSC22 domain family protein 1 | sp\|Q3MHL6\|T22D1_BOVIN; tr\|E1BCC2\|E1BCC2_BOVIN | NaN | 22.805 | Total vitreous | 1.40E+07 |
| Uncharacterized protein | tr\|F1MEG3\|F1MEG3_BOVIN | NaN | 22.808 | Total vitreous | 6.50E+05 |
| Uncharacterized protein | tr\|F1MUH4\|F1MUH4_BOVIN; tr\|E1B7G3\|E1B7G3_BOVIN | NaN | 22.812 | Total vitreous | 4.70E+06 |
| GDNF family receptor alpha-2 | tr\|F1MF66\|F1MF66_BOVIN; sp\|Q5E9X0\|GFRA2_BOVIN | NaN | 22.814 | Total vitreous | 4.50E+06 |
| Uncharacterized protein | tr\|E1BLR9\|E1BLR9_BOVIN | NaN | 22.833 | Total vitreous | 1.90E+06 |
| Acidic leucine-rich nuclear phosphoprotein 32 family member B | sp\|Q3SZC6\|AN32B_BOVIN; tr\|F1MZ46\|F1MZ46_BOVIN | NaN | 22.845 | Total vitreous | 1.00E+07 |
| Inhibin beta A chain | sp\|P07995\|INHBA_BOVIN | NaN | 22.849 | Total vitreous | 4.10E+06 |
| Uncharacterized protein | tr\|F1MLR4\|F1MLR4_BOVIN | NaN | 22.850 | Total vitreous | 6.00E+06 |
| Uncharacterized protein | tr\|E1BA13\|E1BA13_BOVIN; sp\|P62894\|CYC_BOVIN; CON_P62894 | NaN | 22.854 | Total vitreous | 1.70E+07 |
| Uncharacterized protein | tr\|F2Z4H3\|F2Z4H3_BOVIN | NaN | 22.857 | Total vitreous | 1.10E+07 |
| Uncharacterized protein | tr\|E1BMJ0\|E1BMJ0_BOVIN | NaN | 22.860 | Total vitreous | 6.10E+06 |
| Lysosomal Pro-X carboxypeptidase | tr\|F1MAU4\|F1MAU4_BOVIN; sp\|Q2TA14\|PCP_BOVIN | NaN | 22.868 | Total vitreous | 5.90E+06 |
| Uncharacterized protein (Fragment) | tr\|F1MDE4\|F1MDE4_BOVIN | NaN | 22.870 | Total vitreous | 5.40E+06 |
| PCDHGC3 protein | tr\|A5D7F4\|A5D7F4_BOVIN | NaN | 22.872 | Total vitreous | 2.30E+06 |
| Complement C1q subcomponent subunit B | sp\|Q2KIV9\|C1QB_BOVIN | NaN | 22.874 | Total vitreous | 7.00E+06 |
| Cellular nucleic acid-binding protein | sp\|Q3T0Q6\|CNBP_BOVIN | NaN | 22.876 | Total vitreous | 8.70E+06 |
| Cadherin 11, type 2, OB-cadherin (Osteoblast) | tr\|A2VDQ6\|A2VDQ6_BOVIN | NaN | 22.877 | Total vitreous | 2.80E+06 |
| Uveal autoantigen with coiled-coil domains and ankyrin repeats protein | tr\|F1MKQ9\|F1MKQ9_BOVIN; sp\|Q8HYY4\|UACA_BOVIN; tr\|F1N101\|F1N101_BOVIN | NaN | 22.878 | Total vitreous | 1.20E+06 |
| Glucosidase 2 subunit beta | sp\|Q28034\|GLU2B_BOVIN | NaN | 22.881 | Total vitreous | 5.50E+06 |
| Uncharacterized protein | tr\|F1MJU6\|F1MJU6_BOVIN | NaN | 22.897 | Total vitreous | 3.40E+06 |
| Peptidyl-prolyl cis-trans isomerase (Fragment) | tr\|E1B9G4\|E1B9G4_BOVIN | NaN | 22.902 | Total vitreous | 9.60E+06 |
| Uncharacterized protein | tr\|F1MME1\|F1MME1_BOVIN | NaN | 22.908 | Total vitreous | 1.70E+06 |
| Uncharacterized protein (Fragment) | tr\|F1N0M5\|F1N0M5_BOVIN | NaN | 22.946 | Total vitreous | 7.80E+06 |
| Prefoldin subunit 1 | sp\|Q3SZE2\|PFD1_BOVIN | NaN | 22.966 | Total vitreous | 1.40E+07 |
| Uncharacterized protein | tr\|F1N0F7\|F1N0F7_BOVIN | NaN | 22.986 | Total vitreous | 5.10E+06 |
| T-cell surface protein tactile | tr\|F1N360\|F1N360_BOVIN; sp\|Q3MHP9\|TACT_BOVIN | NaN | 22.988 | Total vitreous | 4.00E+06 |
| Uncharacterized protein | tr\|E1BEC6\|E1BEC6_BOVIN | NaN | 22.997 | Total vitreous | 4.20E+06 |
| Uncharacterized protein | tr\|F1MW03\|F1MW03_BOVIN | NaN | 23.001 | Total vitreous | 1.90E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Phosphotriesterase-related protein | sp\|A6QLJ8\|PTER_BOVIN | NaN | 23.003 | Total vitreous | 6.00E+06 |
| Glycylpeptide N-tetradecanoyltransferase | tr\|F1MZK0\|F1MZK0_BOVIN; sp\|P31717\|NMT1_BOVIN; sp\|Q9N181\|NMT2_BOVIN; tr\|G3N0U1\|G3N0U1_BOVIN | NaN | 23.004 | Total vitreous | 5.40E+06 |
| Serine-threonine kinase receptor-associated protein | sp\|Q5E959\|STRAP_BOVIN | NaN | 23.009 | Total vitreous | 5.40E+06 |
| HMT1 hnRNP methyltransferase-like 2 isoform 3 | tr\|Q5E949\|Q5E949_BOVIN; tr\|F1MP07\|F1MP07_BOVIN | NaN | 23.011 | Total vitreous | 5.30E+06 |
| NPC1 protein | tr\|B0JYK2\|B0JYK2_BOVIN | NaN | 23.015 | Total vitreous | 3.00E+06 |
| Microtubule-associated proteins 1A/1B light chain 3B | sp\|O41515\|MLP3B_BOVIN | NaN | 23.036 | Total vitreous | 2.90E+07 |
| Paraoxonase 1 | tr\|Q2KIW1\|Q2KIW1_BOVIN | NaN | 23.049 | Total vitreous | 6.90E+06 |
| Small acidic protein | sp\|Q3MHL8\|SMAP_BOVIN | NaN | 23.055 | Total vitreous | 2.40E+07 |
| Corticosteroid-binding globulin | sp\|E1BF81\|CBG_BOVIN; CON_ENSEMBL: ENSBTAP00000023402 | NaN | 23.056 | Total vitreous | 5.70E+06 |
| Uncharacterized protein | tr\|F1MPJ7\|F1MPJ7_BOVIN | NaN | 23.069 | Total vitreous | 1.50E+07 |
| Uncharacterized protein | tr\|F1MBT2\|F1MBT2_BOVIN; tr\|G3N1F0\|G3N1F0_BOVIN | NaN | 23.074 | Total vitreous | 5.40E+06 |
| Cocaine- and amphetamine-regulated transcript protein | sp\|Q68RJ9\|CART_BOVIN | NaN | 23.079 | Total vitreous | 2.40E+07 |
| UDP-Gal:betaGlcNAc beta 1,4-galactosyltransferase, polypeptide 4 | tr\|Q32LF7\|Q32LF7_BOVIN | NaN | 23.079 | Total vitreous | 7.70E+06 |
| Phosphoinositide-3-kinase-interacting protein 1 | sp\|Q1RMT9\|P3IP1_BOVIN | NaN | 23.083 | Total vitreous | 1.70E+07 |
| Heme-binding protein 1 | sp\|Q148C9\|HEBP1_BOVIN; tr\|G5E6G2\|G5E6G2_BOVIN | NaN | 23.086 | Total vitreous | 1.00E+07 |
| Carbonic anhydrase-related protein 10 | sp\|A0JN41\|CAH10_BOVIN | NaN | 23.088 | Total vitreous | 9.30E+06 |
| ATPase, H+ transporting, lysosomal 13 kDa, V1 subunit G2 | tr\|Q0VCV6\|Q0VCV6_BOVIN; sp\|P79251\|VATG1_BOVIN | NaN | 23.097 | Total vitreous | 1.70E+07 |
| Uncharacterized protein | tr\|F1MJM5\|F1MJM5_BOVIN; tr\|F1N444\|F1N444_BOVIN | NaN | 23.107 | Total vitreous | 2.10E+06 |
| Heat shock factor-binding protein 1 | sp\|Q3ZC22\|HSBP1_BOVIN | NaN | 23.129 | Total vitreous | 2.50E+07 |
| Uncharacterized protein | tr\|F1N381\|F1N381_BOVIN | NaN | 23.147 | Total vitreous | 3.00E+06 |
| Uncharacterized protein | tr\|F1MHT1\|F1MHT1_BOVIN | NaN | 23.161 | Total vitreous | 1.40E+06 |
| Serine/threonine-protein phosphatase | tr\|F1N719\|F1N719_BOVIN | NaN | 23.171 | Total vitreous | 4.60E+06 |
| Uncharacterized protein | tr\|F1N4K1\|F1N4K1_BOVIN | NaN | 23.177 | Total vitreous | 2.50E+06 |
| Uncharacterized protein | tr\|E1BDS6\|E1BDS6_BOVIN | NaN | 23.181 | Total vitreous | 1.50E+06 |
| Uncharacterized protein | tr\|F1MC76\|F1MC76_BOVIN; sp\|A3KMX8\|CF211_BOVIN | NaN | 23.185 | Total vitreous | 5.40E+06 |
| Uncharacterized protein (Fragment) | tr\|G3MXB5\|G3MXB5_BOVIN | NaN | 23.187 | Total vitreous | 2.60E+07 |
| Uncharacterized protein | tr\|E1BA44\|E1BA44_BOVIN; tr\|G3MZT8\|G3MZT8_BOVIN | NaN | 23.192 | Total vitreous | 1.90E+06 |
| Uncharacterized protein (Fragment) | tr\|F1MHR6\|F1MHR6_BOVIN | NaN | 23.194 | Total vitreous | 3.90E+06 |
| Uncharacterized protein | tr\|F1N7G8\|F1N7G8_BOVIN | NaN | 23.214 | Total vitreous | 1.80E+06 |
| Procollagen-lysine,2-oxoglutarate 5-dioxygenase 1 | sp\|O77588\|PLOD1_BOVIN; tr\|G8JKV7\|G8JKV7_BOVIN | NaN | 23.225 | Total vitreous | 3.30E+06 |
| Thimet oligopeptidase | sp\|Q1JPJ8\|THOP1_BOVIN | NaN | 23.238 | Total vitreous | 3.70E+06 |
| Thy-1 cell surface antigen | tr\|Q3SX33\|Q3SX33_BOVIN | NaN | 23.245 | Total vitreous | 1.90E+07 |
| Uncharacterized protein (Fragment) | tr\|G5E5K5\|G5E5K5_BOVIN | NaN | 23.247 | Total vitreous | 2.20E+07 |

TABLE 3-continued

| Protein Name | Protein IDs | LFQ intensity vitreous-EV | LFQ intensity total vitreous | EV/ whole vitreous Log2 difference | iBAQ |
|---|---|---|---|---|---|
| Proteins expressed in the extracellular vesicles fraction and the cell free vitreous fraction. | | | | | |
| LSM2 protein | tr\|A6QQV3\|A6QQV3_BOVIN | NaN | 23.248 | Total vitreous | 2.30E+07 |
| Uncharacterized protein (Fragment) | tr\|F1N764\|F1N764_BOVIN | NaN | 23.255 | Total vitreous | 7.50E+06 |
| U6 snRNA-associated Sm-like protein LSm8 | sp\|Q3ZCE0\|LSM8_BOVIN | NaN | 23.258 | Total vitreous | 1.90E+07 |
| Beta-hexosaminidase subunit alpha | sp\|Q0V8R6\|HEXA_BOVIN | NaN | 23.282 | Total vitreous | 6.40E+06 |
| Cysteine-rich protein 2 | sp\|Q0VFX8\|CRIP2_BOVIN | NaN | 23.283 | Total vitreous | 1.50E+07 |
| Uncharacterized protein | tr\|F1N2Y8\|F1N2Y8_BOVIN | NaN | 23.299 | Total vitreous | 3.10E+06 |
| Proteasome subunit beta type-2 | sp\|Q5E9K0\|PSB2_BOVIN | NaN | 23.305 | Total vitreous | 1.40E+07 |
| Melanoma inhibitory activity protein 3 (Fragment) | tr\|G5E5L5\|G5E5L5_BOVIN; sp\|Q0VC16\|MIA3_BOVIN | NaN | 23.319 | Total vitreous | 1.30E+06 |
| Uncharacterized protein | tr\|E1B7B0\|E1B7B0_BOVIN | NaN | 23.334 | Total vitreous | 4.80E+06 |
| Glucosamine-6-phosphate isomerase 1 | sp\|A4FV08\|GNPI1_BOVIN; sp\|Q17QL1\|GNPI2_BOVIN | NaN | 23.338 | Total vitreous | 8.90E+06 |
| Uncharacterized protein | tr\|E1BEG2\|E1BEG2_BOVIN | NaN | 23.343 | Total vitreous | 8.10E+06 |
| Peptidyl-prolyl cis-trans isomerase-like 1 | sp\|Q5E992\|PPIL1_BOVIN | NaN | 23.349 | Total vitreous | 1.80E+07 |
| Hepatocyte growth factor-regulated tyrosine kinase substrate | sp\|Q0V8S0\|HGS_BOVIN | NaN | 23.349 | Total vitreous | 6.60E+06 |
| Mitochondrial peptide methionine sulfoxide reductase | sp\|P54149\|MSRA_BOVIN | NaN | 23.358 | Total vitreous | 9.70E+06 |
| Syntaxin-1B | sp\|P61267\|STX1B_BOVIN | NaN | 23.379 | Total vitreous | 9.20E+06 |
| Uridine diphosphate glucose pyrophosphatase | sp\|Q05B60\|NUD14_BOVIN | NaN | 23.381 | Total vitreous | 1.30E+07 |
| Prosaposin | sp\|P26779\|SAP_BOVIN; tr\|F1MXP8\|F1MXP8_BOVIN | NaN | 23.382 | Total vitreous | 5.30E+06 |
| Serine protease 23 | sp\|Q1LZE9\|PRS23_BOVIN | NaN | 23.390 | Total vitreous | 6.40E+06 |
| Neuron specific gene family member 1 | tr\|Q08DZ1\|Q08DZ1_BOVIN | NaN | 23.394 | Total vitreous | 1.50E+07 |
| Gamma-aminobutyric acid receptor-associated protein-like 2 | tr\|F1MFF1\|F1MFF1_BOVIN; sp\|P60519\|GBRL2_BOVIN | NaN | 23.395 | Total vitreous | 2.00E+07 |
| Insulin-like growth factor-binding protein 4 | sp\|Q05716\|IBP4_BOVIN | NaN | 23.399 | Total vitreous | 1.20E+07 |
| Uncharacterized protein | tr\|F1N4K6\|F1N4K6_BOVIN | NaN | 23.421 | Total vitreous | 1.60E+06 |
| Prefoldin subunit 3 | tr\|G5E5K1\|G5E5K1_BOVIN; sp\|Q2TBX2\|PFD3_BOVIN | NaN | 23.433 | Total vitreous | 1.00E+07 |
| Uncharacterized protein | tr\|G3MYZ3\|G3MYZ3_BOVIN; CON_REFSEQ: XP_585019 | NaN | 23.445 | Total vitreous | 4.70E+06 |
| Uncharacterized protein (Fragment) | tr\|F1N3V8\|F1N3V8_BOVIN | NaN | 23.467 | Total vitreous | 3.10E+07 |
| 3-hydroxybutyrate dehydrogenase type 2 | tr\|F1MLA4\|F1MLA4_BOVIN; sp\|Q3T046\|BDH2_BOVIN | NaN | 23.471 | Total vitreous | 1.30E+07 |
| Glypican-1 | sp\|G3X745\|GPC1_BOVIN | NaN | 23.483 | Total vitreous | 5.90E+06 |
| Uncharacterized protein (Fragment) | tr\|F1MXM6\|F1MXM6_BOVIN | NaN | 23.518 | Total vitreous | 1.10E+07 |
| Purkinje cell protein 4-like protein 1 | sp\|A8R4Q8\|PC4L1_BOVIN | NaN | 23.528 | Total vitreous | 4.10E+07 |
| Beta-1,3-N-acetylglucosaminyltransferase lunatic fringe | sp\|Q2KJ92\|LFNG_BOVIN | NaN | 23.550 | Total vitreous | 8.70E+06 |
| Uncharacterized protein | tr\|E1B8P9\|E1B8P9_BOVIN | NaN | 23.552 | Total vitreous | 1.20E+07 |
| Uncharacterized protein | tr\|F1N3N6\|F1N3N6_BOVIN | NaN | 23.567 | Total vitreous | 7.30E+06 |
| Uncharacterized protein (Fragment) | tr\|G5E5W4\|G5E5W4_BOVIN; tr\|F1MYL5\|F1MYL5_BOVIN; tr\|F1MES2\|F1MES2_BOVIN | NaN | 23.568 | Total vitreous | 3.00E+06 |

TABLE 3-continued

| Protein Name | Protein IDs | LFQ intensity vitreous-EV | LFQ intensity total vitreous | EV/ whole vitreous Log2 difference | iBAQ |
|---|---|---|---|---|---|
| Proteins expressed in the extracellular vesicles fraction and the cell free vitreous fraction. | | | | | |
| Drebrin-like protein | sp\|A6H7G2\|DBNL_BOVIN | NaN | 23.586 | Total vitreous | 8.10E+06 |
| Uncharacterized protein | tr\|F6PZ29\|F6PZ29_BOVIN | NaN | 23.587 | Total vitreous | 2.40E+07 |
| Uncharacterized protein | tr\|G3N0B6\|G3N0B6_BOVIN | NaN | 23.604 | Total vitreous | 6.10E+06 |
| Uncharacterized protein | tr\|F1N789\|F1N789_BOVIN | NaN | 23.644 | Total vitreous | 2.70E+06 |
| Uncharacterized protein (Fragment) | tr\|F1MXN4\|F1MXN4_BOVIN; tr\|E1BFN8\|E1BFN8_BOVIN | NaN | 23.645 | Total vitreous | 8.00E+06 |
| 2-deoxynucleoside 5-phosphate N-hydrolase 1 | tr\|E1BM28\|E1BM28_BOVIN | NaN | 23.656 | Total vitreous | 2.00E+07 |
| Integral membrane protein 2B | tr\|F1N026\|F1N026_BOVIN; sp\|Q3T0P7\|ITM2B_BOVIN | NaN | 23.664 | Total vitreous | 1.30E+07 |
| Uncharacterized protein (Fragment) | tr\|F1MC06\|F1MC06_BOVIN; tr\|G3MYW6\|G3MYW6_BOVIN | NaN | 23.673 | Total vitreous | 1.60E+07 |
| Uncharacterized protein | tr\|F1MUE3\|F1MUE3_BOVIN | NaN | 23.678 | Total vitreous | 7.90E+06 |
| Proteasome subunit alpha type-4 | sp\|Q3ZCK9\|PSA4_BOVIN | NaN | 23.681 | Total vitreous | 1.40E+07 |
| Neural cell adhesion molecule 1 (Fragment) | tr\|F1N1W7\|F1N1W7_BOVIN | NaN | 23.683 | Total vitreous | 5.00E+06 |
| Microtubule-associated proteins 1A/1B light chain 3A | sp\|Q2HJ23\|MLP3A_BOVIN | NaN | 23.687 | Total vitreous | 4.60E+07 |
| Lysyl oxidase homolog 1 | sp\|Q95L39\|LOXL1_BOVIN; tr\|A0JNB6\|A0JNB6_BOVIN | NaN | 23.690 | Total vitreous | 6.80E+06 |
| Calcium-binding protein 39 | sp\|Q29RI6\|CAB39_BOVIN | NaN | 23.690 | Total vitreous | 1.10E+07 |
| Histidine--tRNA ligase, cytoplasmic | sp\|Q2KI84\|SYHC_BOVIN | NaN | 23.696 | Total vitreous | 6.10E+06 |
| LIM and SH3 domain protein 1 | sp\|Q3B7M5\|LASP1_BOVIN | NaN | 23.696 | Total vitreous | 1.30E+07 |
| NAD(P)H dehydrogenase, quinone 2 | tr\|Q3SZT2\|Q3SZT2_BOVIN | NaN | 23.700 | Total vitreous | 1.40E+07 |
| Uncharacterized protein | tr\|F1MET0\|F1MET0_BOVIN | NaN | 23.705 | Total vitreous | 4.30E+06 |
| Prefoldin subunit 5 | sp\|Q8HYI9\|PFD5_BOVIN | NaN | 23.717 | Total vitreous | 2.40E+07 |
| Collectin-12 | sp\|A6QP79\|COL12_BOVIN | NaN | 23.739 | Total vitreous | 5.10E+06 |
| Chromosome 10 open reading frame 116 ortholog | tr\|Q2NKR5\|Q2NKR5_BOVIN | NaN | 23.740 | Total vitreous | 6.30E+07 |
| Dynamin-2 | sp\|A6H7I5\|DYN2_BOVIN; tr\|F1MW91\|F1MW91_BOVIN | NaN | 23.755 | Total vitreous | 4.70E+06 |
| RAN binding protein 6 | tr\|Q3B7N3\|Q3B7N3_BOVIN | NaN | 23.757 | Total vitreous | 8.30E+06 |
| Uncharacterized protein | tr\|E1BER5\|E1BER5_BOVIN; tr\|F1MHZ5\|F1MHZ5_BOVIN | NaN | 23.759 | Total vitreous | 3.70E+06 |
| Uncharacterized protein | tr\|G3N3R5\|G3N3R5_BOVIN; tr\|G3MWN4\|G3MWN4_BOVIN; tr\|E1BAB5\|E1BAB5_BOVIN | NaN | 23.772 | Total vitreous | 5.90E+06 |
| Alpha-synuclein | sp\|Q3T0G8\|SYUA_BOVIN | NaN | 23.786 | Total vitreous | 3.30E+07 |
| Uncharacterized protein | tr\|G3N1H5\|G3N1H5_BOVIN; tr\|G3N1R1\|G3N1R1_BOVIN; tr\|G3MWT1\|G3MWT1_BOVIN; tr\|G3N148\|G3N148_BOVIN | NaN | 23.805 | Total vitreous | 2.80E+07 |
| Hexokinase 1 | tr\|Q5W5U3\|Q5W5U3_BOVIN; tr\|F1MZV1\|F1MZV1_BOVIN; sp\|P27595\|HXK1_BOVIN; tr\|E1BME6\|E1BME6_BOVIN; tr\|F1MIM3\|F1MIM3_BOVIN | NaN | 23.808 | Total vitreous | 4.20E+06 |
| Transketolase | sp\|Q6B855\|TKT_BOVIN | NaN | 23.812 | Total vitreous | 7.40E+06 |
| Uncharacterized protein (Fragment) | tr\|E1BCE0\|E1BCE0_BOVIN | NaN | 23.829 | Total vitreous | 1.70E+07 |
| Translin | sp\|Q08DM8\|TSN_BOVIN | NaN | 23.838 | Total vitreous | 1.80E+07 |
| Fas apoptotic inhibitory molecule 1 | sp\|Q0IIF6\|FAIM1_BOVIN | NaN | 23.840 | Total vitreous | 2.00E+07 |
| ST6 (Alpha-N-acetyl-neuraminyl-2,3-beta- | tr\|Q148L9\|Q148L9_BOVIN | NaN | 23.846 | Total vitreous | 2.10E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| galactosyl-1,3)-N-acetylgalactosaminide alpha-2,6-sialyltransferase 2 | | | | | |
| DUSP3 protein | tr\|A7YY43\|A7YY43_BOVIN; tr\|Q2T9T7\|Q2T9T7_BOVIN | NaN | 23.858 | Total vitreous | 2.70E+07 |
| Secretagogin | tr\|F1N1I2\|F1N1I2_BOVIN; sp\|A5PJN0\|SEGN_BOVIN | NaN | 23.859 | Total vitreous | 1.30E+07 |
| Uncharacterized protein | tr\|E1BNX1\|E1BNX1_BOVIN | NaN | 23.865 | Total vitreous | 2.00E+07 |
| Complement factor properdin | tr\|Q17QC8\|Q17QC8_BOVIN | NaN | 23.866 | Total vitreous | 1.30E+07 |
| Isoform Tau-E of Microtubule-associated protein tau | sp\|P29172-5\|TAU_BOVIN; sp\|P29172-4\|TAU_BOVIN; sp\|P29172-10\|TAU_BOVIN; sp\|P29172-16\|TAU_BOVIN; sp\|P29172-8\|TAU_BOVIN; tr\|G3N2J1\|G3N2J1_BOVIN; sp\|P29172-7\|TAU_BOVIN; sp\|P29172-13\|TAU_BOVIN; sp\|P29172-12\|TAU_BOVIN; sp\|P29172-2\|TAU_BOVIN; sp\|P29172-19\|TAU_BOVIN; sp\|P29172\|TAU_BOVIN; sp\|P29172-18\|TAU_BOVIN; sp\|P29172-9\|TAU_BOVIN; sp\|P29172-15\|TAU_BOVIN | NaN | 23.887 | Total vitreous | 1.10E+07 |
| UPF0454 protein C12orf49 homolog | sp\|Q17QN8\|CL049_BOVIN | NaN | 23.889 | Total vitreous | 2.10E+07 |
| Poliovirus receptor-related 2 (Herpesvirus entry mediator B) | tr\|Q17QC7\|Q17QC7_BOVIN | NaN | 23.898 | Total vitreous | 8.20E+06 |
| Actin-related protein 2/3 complex subunit 4 | sp\|Q148J6\|ARPC4_BOVIN | NaN | 23.899 | Total vitreous | 2.70E+07 |
| Uncharacterized protein | tr\|E1BL59\|E1BL59_BOVIN | NaN | 23.902 | Total vitreous | 3.70E+06 |
| Putative phospholipase B-like 2 | tr\|F1MIH9\|F1MIH9_BOVIN; sp\|Q2KIY5\|PLBL2_BOVIN | NaN | 23.903 | Total vitreous | 7.30E+06 |
| Endoplasmic reticulum resident protein 44 | sp\|Q3T0L2\|ERP44_BOVIN | NaN | 23.904 | Total vitreous | 1.10E+07 |
| Cysteine and histidine-rich domain-containing protein 1 | sp\|Q29RL2\|CHRD1_BOVIN | NaN | 23.912 | Total vitreous | 1.60E+07 |
| Uncharacterized protein | tr\|F1N0D3\|F1N0D3_BOVIN | NaN | 23.915 | Total vitreous | 5.80E+06 |
| Glucose-6-phosphate 1-dehydrogenase | tr\|F1MMK2\|F1MMK2_BOVIN; REV_tr\|E1BIG2\|E1BIG2_BOVIN | NaN | 23.918 | Total vitreous | 6.90E+06 |
| Maturin | sp\|A7MBJ1\|MTURN_BOVIN | NaN | 23.920 | Total vitreous | 7.30E+07 |
| Tyrosine-tRNA ligase, cytoplasmic | tr\|F1MHM5\|F1MHM5_BOVIN; sp\|Q29465\|SYYC_BOVIN | NaN | 23.927 | Total vitreous | 5.80E+06 |
| Uncharacterized protein (Fragment) | tr\|E1BIB8\|E1BIB8_BOVIN | NaN | 23.928 | Total vitreous | 3.40E+07 |
| Coagulation factor IX | tr\|F1MBC5\|F1MBC5_BOVIN; sp\|P00741\|FA9_BOVIN; tr\|F1MFL4\|F1MFL4_BOVIN | NaN | 23.934 | Total vitreous | 1.60E+07 |
| SH3 domain-binding glutamic acid-rich-like protein 2 | sp\|A4IFC4\|SH3L2_BOVIN; tr\|F1MR08\|F1MR08_BOVIN | NaN | 23.935 | Total vitreous | 5.50E+07 |
| Uncharacterized protein | tr\|E1BCA0\|E1BCA0_BOVIN | NaN | 23.942 | Total vitreous | 3.50E+06 |
| Peptidase inhibitor 16 | sp\|Q58D34\|PI16_BOVIN | NaN | 23.952 | Total vitreous | 9.10E+06 |
| Thymosin beta-10 | sp\|P21752\|TYB10_BOVIN; CON_P21752 | NaN | 24.003 | Total vitreous | 1.10E+08 |
| Kininogen-1 | sp\|P01044\|KNG1_BOVIN; CON_P01044-1; sp\|P01044-2\|KNG1_BOVIN | NaN | 24.017 | Total vitreous | 6.50E+06 |
| Cadherin-13 (Fragment) | tr\|F1MKP6\|F1MKP6_BOVIN; sp\|Q3B7N0\|CAD13_BOVIN | NaN | 24.022 | Total vitreous | 7.70E+06 |
| CD59 molecule, complement regulatory protein | tr\|Q32PA1\|Q32PA1_BOVIN | NaN | 24.028 | Total vitreous | 5.90E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Dentin matrix acidic phosphoprotein 1 | tr\|F1MJM1\|F1MJM1_BOVIN | NaN | 24.028 | Total vitreous | 8.90E+06 |
| Uncharacterized protein | tr\|F6S1Q0\|F6S1Q0_BOVIN | NaN | 24.037 | Total vitreous | 1.10E+07 |
| Protein S100-A12 | sp\|P79105\|S10AC_BOVIN; tr\|G3N2H5\|G3N2H5_BOVIN | NaN | 24.043 | Total vitreous | 3.90E+07 |
| Parvalbumin alpha | sp\|Q0VCG3\|PRVA_BOVIN | NaN | 24.044 | Total vitreous | 2.90E+07 |
| Biotinidase | tr\|F1MJM4\|F1MJM4_BOVIN; sp\|A6QQ07\|BTD_BOVIN | NaN | 24.051 | Total vitreous | 1.10E+07 |
| SCRG1 protein | tr\|A6QPC2\|A6QPC2_BOVIN | NaN | 24.054 | Total vitreous | 3.90E+07 |
| Uncharacterized protein | tr\|F1MZX8\|F1MZX8_BOVIN | NaN | 24.063 | Total vitreous | 8.20E+06 |
| Vitamin K-dependent protein C (Fragment) | sp\|P00745\|PROC_BOVIN | NaN | 24.069 | Total vitreous | 8.30E+06 |
| Proteasome subunit beta type-5 | sp\|Q32KL2\|PSB5_BOVIN | NaN | 24.086 | Total vitreous | 1.50E+07 |
| Acyl-CoA-binding domain-containing protein 7 | sp\|Q3SZF0\|ACBD7_BOVIN | NaN | 24.090 | Total vitreous | 4.00E+07 |
| Cortactin | tr\|Q1RMR3\|Q1RMR3_BOVIN | NaN | 24.097 | Total vitreous | 8.60E+06 |
| Uncharacterized protein | tr\|F1ME46\|F1ME46_BOVIN | NaN | 24.102 | Total vitreous | 1.20E+07 |
| Procollagen C-endopeptidase enhancer | tr\|Q2HJB6\|Q2HJB6_BOVIN | NaN | 24.113 | Total vitreous | 1.20E+07 |
| Proline synthase co-transcribed bacterial homolog protein | sp\|Q3T0G5\|PROSC_BOVIN | NaN | 24.120 | Total vitreous | 1.80E+07 |
| Putative uncharacterized protein MGC139448 | tr\|A1A4H7\|A1A4H7_BOVIN | NaN | 24.121 | Total vitreous | 1.00E+07 |
| Uncharacterized protein | tr\|E1BJ82\|E1BJ82_BOVIN | NaN | 24.123 | Total vitreous | 1.20E+08 |
| Uncharacterized protein (Fragment) | tr\|F1N104\|F1N104_BOVIN; tr\|G3X7N7\|G3X7N7_BOVIN; tr\|F6Q4B1\|F6Q4B1_BOVIN | NaN | 24.124 | Total vitreous | 1.10E+07 |
| Uncharacterized protein | tr\|E1BD36\|E1BD36_BOVIN | NaN | 24.135 | Total vitreous | 5.00E+06 |
| Uncharacterized protein | tr\|F2Z4F5\|F2Z4F5_BOVIN | NaN | 24.136 | Total vitreous | 6.50E+06 |
| Uncharacterized protein | tr\|F1MX87\|F1MX87_BOVIN | NaN | 24.138 | Total vitreous | 9.50E+06 |
| Cadherin-3 | tr\|E1BGT1\|E1BGT1_BOVIN | NaN | 24.150 | Total vitreous | 7.40E+06 |
| Alpha-amylase | tr\|F1MJQ3\|F1MJQ3_BOVIN; CON_Q3MHH8; tr\|F1MP21\|F1MP21_BOVIN | NaN | 24.152 | Total vitreous | 1.00E+07 |
| Isoamyl acetate-hydrolyzing esterase 1 homolog | sp\|Q3SZ16\|IAH1_BOVIN | NaN | 24.155 | Total vitreous | 2.10E+07 |
| Tripeptidyl-peptidase 1 | tr\|F1MK08\|F1MK08_BOVIN; sp\|Q0V8B6\|TPP1_BOVIN | NaN | 24.158 | Total vitreous | 1.10E+07 |
| Uncharacterized protein | tr\|E1B7S3\|E1B7S3_BOVIN; tr\|F1MCU7\|F1MCU7_BOVIN; sp\|Q9N179\|41_BOVIN; tr\|F1MCU4\|F1MCU4_BOVIN | NaN | 24.174 | Total vitreous | 5.50E+06 |
| Uncharacterized protein (Fragment) | tr\|E1B805\|E1B805_BOVIN | NaN | 24.175 | Total vitreous | 3.10E+06 |
| Chemokine (C-C motif) ligand 14 | tr\|Q29RR9\|Q29RR9_BOVIN | NaN | 24.175 | Total vitreous | 4.30E+07 |
| Desmocollin-2 | tr\|F1MZF2\|F1MZF2_BOVIN; sp\|P33545-2\|DSC2_BOVIN; sp\|P33545\|DSC2_BOVIN | NaN | 24.192 | Total vitreous | 6.30E+06 |
| Uncharacterized protein (Fragment) | tr\|F1N6H1\|F1N6H1_BOVIN | NaN | 24.216 | Total vitreous | 1.10E+06 |
| Angiopoietin-related protein 7 | sp\|Q5EA66\|ANGL7_BOVIN | NaN | 24.249 | Total vitreous | 1.80E+07 |
| Small glutamine-rich tetratricopeptide repeat-containing protein alpha | sp\|Q32LM2\|SGTA_BOVIN | NaN | 24.254 | Total vitreous | 2.10E+07 |
| Pyridoxine-5-phosphate oxidase | sp\|Q5E9K3\|PNPO_BOVIN | NaN | 24.254 | Total vitreous | 2.20E+07 |
| Cathepsin L2 | sp\|Q5E998\|CATL2_BOVIN; sp\|P25975\|CATL1_BOVIN; sp\|Q5E968\|CATK_BOVIN; tr\|A4IFS7\|A4IFS7_BOVIN | NaN | 24.270 | Total vitreous | 1.50E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Heat shock protein 105 kDa | sp\|Q0IIM3\|HS105_BOVIN | NaN | 24.278 | Total vitreous | 5.80E+06 |
| Glutathione peroxidase 1 | sp\|P00435\|GPX1_BOVIN | NaN | 24.291 | Total vitreous | 1.90E+07 |
| Ubiquitin-conjugating enzyme E2 D3 | sp\|Q3ZCF7\|UB2D3_BOVIN; sp\|Q1RMX2\|UB2D2_BOVIN; tr\|G3MZ57\|G3MZ57_BOVIN; tr\|G3MY62\|G3MY62_BOVIN; tr\|G3MXY4\|G3MXY4_BOVIN | NaN | 24.303 | Total vitreous | 7.60E+07 |
| Glandular kallikrein | tr\|Q6H320\|Q6H320_BOVIN | NaN | 24.317 | Total vitreous | 3.10E+07 |
| CD166 antigen | tr\|F1MHN8\|F1MHN8_BOVIN; sp\|Q9BH13\|CD166_BOVIN | NaN | 24.321 | Total vitreous | 9.10E+06 |
| Uncharacterized protein (Fragment) | tr\|F1N554\|F1N554_BOVIN; tr\|F1MLM4\|F1MLM4_BOVIN | NaN | 24.324 | Total vitreous | 1.00E+07 |
| Beta-mannosidase | tr\|A6QLB0\|A6QLB0_BOVIN; sp\|Q29444\|MANBA_BOVIN | NaN | 24.330 | Total vitreous | 6.00E+06 |
| Uncharacterized protein (Fragment) | tr\|G3N2S8\|G3N2S8_BOVIN | NaN | 24.333 | Total vitreous | 7.60E+07 |
| Proteasome subunit alpha type | tr\|G5E5C3\|G5E5C3_BOVIN; sp\|Q2YDE4\|PSA6_BOVIN | NaN | 24.334 | Total vitreous | 1.70E+07 |
| Proteasome subunit alpha type-3 | sp\|Q58DU5\|PSA3_BOVIN | NaN | 24.345 | Total vitreous | 2.20E+07 |
| Diphosphoinositol polyphosphate phosphohydrolase 1 | sp\|A2VE79\|NUDT3_BOVIN | NaN | 24.347 | Total vitreous | 3.20E+07 |
| Uncharacterized protein | tr\|F6QD94\|F6QD94_BOVIN | NaN | 24.349 | Total vitreous | 7.20E+07 |
| FXYD domain-containing ion transport regulator 6 | sp\|Q3MHZ5\|FXYD6_BOVIN | NaN | 24.351 | Total vitreous | 7.20E+07 |
| Adiponectin | sp\|Q3Y5Z3\|ADIPO_BOVIN; CON_Q3Y5Z3 | NaN | 24.360 | Total vitreous | 2.30E+07 |
| Uncharacterized protein (Fragment) | tr\|F1MYZ4\|F1MYZ4_BOVIN | NaN | 24.365 | Total vitreous | 7.70E+06 |
| Programmed cell death protein 5 | sp\|Q2HJH9\|PDCD5_BOVIN | NaN | 24.371 | Total vitreous | 2.90E+07 |
| Nucleosome assembly protein 1-like 1 | sp\|A6H767\|NP1L1_BOVIN; tr\|G3X7M5\|G3X7M5_BOVIN | NaN | 24.378 | Total vitreous | 2.30E+07 |
| Gelsolin | tr\|F1MJH1\|F1MJH1_BOVIN; sp\|Q3SX14\|GELS_BOVIN | NaN | 24.387 | Total vitreous | 9.50E+06 |
| Fatty acid-binding protein, brain | sp\|Q09139\|FABP7_BOVIN | NaN | 24.388 | Total vitreous | 3.70E+07 |
| Phosphatidylinositol-glycan-specific phospholipase D | sp\|P80109\|PHLD_BOVIN | NaN | 24.398 | Total vitreous | 7.90E+06 |
| Uncharacterized protein | tr\|G1K1Z9\|G1K1Z9_BOVIN; sp\|Q2TA21\|CN037_BOVIN | NaN | 24.405 | Total vitreous | 1.50E+07 |
| Protein disulfide-isomerase | tr\|A5D7E8\|A5D7E8_BOVIN; sp\|P38657\|PDIA3_BOVIN | NaN | 24.415 | Total vitreous | 9.70E+06 |
| Peptidyl-prolyl cis-trans isomerase NIMA-interacting 1 | sp\|Q5BIN5\|PIN1_BOVIN | NaN | 24.420 | Total vitreous | 3.00E+07 |
| Serotransferrin | tr\|G3X6N3\|G3X6N3_BOVIN | NaN | 24.431 | Total vitreous | 9.50E+06 |
| Uncharacterized protein | tr\|F1MZK8\|F1MZK8_BOVIN | NaN | 24.455 | Total vitreous | 8.20E+06 |
| Plasminogen | sp\|P06868\|PLMN_BOVIN; CON_P06868 | NaN | 24.472 | Total vitreous | 6.30E+06 |
| G protein-coupled receptor 37 (Endothelin receptor type B-like) | tr\|Q0VD43\|Q0VD43_BOVIN | NaN | 24.482 | Total vitreous | 1.10E+07 |
| Uncharacterized protein | tr\|F1N2I5\|F1N2I5_BOVIN | NaN | 24.490 | Total vitreous | 2.40E+07 |
| Receptor-type tyrosine-protein phosphatase F | sp\|A7MBJ4\|PTPRF_BOVIN | NaN | 24.494 | Total vitreous | 3.20E+06 |
| Uncharacterized protein | tr\|F1N0N6\|F1N0N6_BOVIN; sp\|Q32P66\|CA123_BOVIN | NaN | 24.501 | Total vitreous | 3.20E+07 |
| Uncharacterized protein | tr\|F1N678\|F1N678_BOVIN | NaN | 24.514 | Total vitreous | 1.50E+07 |
| Prothymosin alpha | sp\|P01252\|PTMA_BOVIN | NaN | 24.524 | Total vitreous | 1.10E+08 |
| 72 kDa type IV collagenase | tr\|F1MKH8\|F1MKH8_BOVIN; sp\|Q9GLE5\|MMP2_BOVIN | NaN | 24.532 | Total vitreous | 1.10E+07 |
| Uncharacterized protein (Fragment) | tr\|F1MCM7\|F1MCM7_BOVIN | NaN | 24.540 | Total vitreous | 6.60E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| F-actin-capping protein subunit alpha-2 | sp\|Q5E997\|CAZA2_BOVIN | NaN | 24.542 | Total vitreous | 2.80E+07 |
| Heterogeneous nuclear ribonucleoproteins A2/B1 | sp\|Q2HJ60\|ROA2_BOVIN | NaN | 24.547 | Total vitreous | 1.80E+07 |
| Proteasome subunit alpha type-1 | sp\|Q3T0X5\|PSA1_BOVIN | NaN | 24.575 | Total vitreous | 2.00E+07 |
| 121 kDa protein | CON_ENSEMBL:ENSBTAP00000031900 | NaN | 24.575 | Total vitreous | 6.60E+06 |
| N-acetylglucosamine-6-sulfatase | tr\|F1MXZ0\|F1MXZ0_BOVIN; sp\|Q1LZH9\|GNS_BOVIN | NaN | 24.576 | Total vitreous | 1.50E+07 |
| Proteasome subunit alpha type-7 | sp\|Q3ZBG0\|PSA7_BOVIN; tr\|E1BD83\|E1BD83_BOVIN | NaN | 24.579 | Total vitreous | 2.40E+07 |
| Cochlin | tr\|F1N103\|F1N103_BOVIN; sp\|Q5EA64\|COCH_BOVIN | NaN | 24.586 | Total vitreous | 1.20E+07 |
| Inactive serine protease 35 | sp\|Q5E9X7\|PRS35_BOVIN | NaN | 24.591 | Total vitreous | 1.90E+07 |
| Histidine-rich glycoprotein (Fragments) | sp\|P33433\|HRG_BOVIN | NaN | 24.628 | Total vitreous | 1.90E+07 |
| Parathymosin | sp\|P08814\|PTMS_BOVIN | NaN | 24.639 | Total vitreous | 1.20E+08 |
| DNA damage-binding protein 1 | sp\|A1A4K3\|DDB1_BOVIN | NaN | 24.640 | Total vitreous | 6.40E+06 |
| Heat shock protein beta-6 | sp\|Q148F8\|HSPB6_BOVIN | NaN | 24.641 | Total vitreous | 5.00E+07 |
| Uncharacterized protein (Fragment) | tr\|F1N1R9\|F1N1R9_BOVIN | NaN | 24.643 | Total vitreous | 1.60E+07 |
| Guanine nucleotide-binding protein G(T) subunit gamma-T1 | sp\|P02698\|GBG1_BOVIN | NaN | 24.660 | Total vitreous | 1.20E+08 |
| Coactosin-like protein | sp\|Q2HJ57\|COTL1_BOVIN | NaN | 24.677 | Total vitreous | 4.00E+07 |
| Prolyl endopeptidase (Fragment) | tr\|F6QHN4\|F6QHN4_BOVIN; sp\|Q9XTA2\|PPCE_BOVIN | NaN | 24.681 | Total vitreous | 7.90E+06 |
| Cathepsin D | sp\|P80209\|CATD_BOVIN | NaN | 24.683 | Total vitreous | 2.00E+07 |
| Legumain | sp\|Q95M12\|LGMN_BOVIN | NaN | 24.688 | Total vitreous | 2.00E+07 |
| Retinol-binding protein 3 | tr\|F1MLW4\|F1MLW4_BOVIN | NaN | 24.691 | Total vitreous | 6.90E+06 |
| Gamma-aminobutyric acid receptor-associated protein-like 1 | sp\|Q8HYB6\|GBRL1_BOVIN; sp\|Q9GJW7\|GBRAP_BOVIN | NaN | 24.697 | Total vitreous | 1.20E+08 |
| Ran-specific GTPase-activating protein | sp\|Q3T0M7\|RANG_BOVIN; tr\|G5E582\|G5E582_BOVIN; tr\|G3MX11\|G3MX11_BOVIN | NaN | 24.699 | Total vitreous | 4.60E+07 |
| Serpin A3-2 | sp\|A2I7M9\|SPA32_BOVIN | NaN | 24.706 | Total vitreous | 2.10E+07 |
| Uncharacterized protein (Fragment) | tr\|F1MJR2\|F1MJR2_BOVIN | NaN | 24.713 | Total vitreous | 4.20E+06 |
| Ras-related C3 botulinum toxin substrate 1 | sp\|P62998\|RAC1_BOVIN; tr\|F1MNG3\|F1MNG3_BOVIN; sp\|Q9TU25\|RAC2_BOVIN; tr\|F1MCR0\|F1MCR0_BOVIN | NaN | 24.722 | Total vitreous | 5.40E+07 |
| Retinoic acid receptor responder protein 2 | sp\|Q29RS5\|RARR2_BOVIN | NaN | 24.731 | Total vitreous | 4.70E+07 |
| S-adenosylmethionine synthase | tr\|A7E3T7\|A7E3T7_BOVIN; tr\|G5E5U7\|G5E5U7_BOVIN; sp\|Q2KJC6\|METK1_BOVIN | NaN | 24.757 | Total vitreous | 2.20E+07 |
| NSFL1 cofactor p47 | sp\|Q3SZC4\|NSF1C_BOVIN | NaN | 24.767 | Total vitreous | 1.80E+07 |
| Acetylcholinesterase | sp\|P23795\|ACES_BOVIN; sp\|P23795-2\|ACES_BOVIN; tr\|F1MIM4\|F1MIM4_BOVIN | NaN | 24.773 | Total vitreous | 1.50E+07 |
| Uncharacterized protein | tr\|E1BL08\|E1BL08_BOVIN | NaN | 24.777 | Total vitreous | 8.60E+06 |
| Threonine--tRNA ligase, cytoplasmic | sp\|Q3ZBV8\|SYTC_BOVIN | NaN | 24.788 | Total vitreous | 9.60E+06 |
| Thioredoxin reductase 1, cytoplasmic | tr\|G1K1Q2\|G1K1Q2_BOVIN; sp\|O62768\|TRXR1_BOVIN; tr\|G3MWU1\|G3MWU1_BOVIN; tr\|F1MN10\|F1MN10_BOVIN; sp\|Q9N2I8\|TRXR2_BOVIN | NaN | 24.793 | Total vitreous | 1.60E+07 |
| Calsyntenin-3 | sp\|Q0VCN6\|CSTN3_BOVIN | NaN | 24.802 | Total vitreous | 1.10E+07 |
| Tropomyosin alpha-1 chain | tr\|G3X7S7\|G3X7S7_BOVIN; sp\|Q5KR47- | NaN | 24.804 | Total | 3.00E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| (Fragment) | 2\|TPM3_BOVIN; tr\|A6QR15\|A6QR15_BOVIN; sp\|Q5KR49\|TPM1_BOVIN; sp\|Q5KR48-2\|TPM2_BOVIN; sp\|Q5KR48\|TPM2_BOVIN; sp\|Q5KR47\|TPM3_BOVIN; CON_Q3SX28; tr\|F1MV90\|F1MV90_BOVIN | | | vitreous | |
| Eukaryotic translation initiation factor 4H | tr\|A7MBG9\|A7MBG9_BOVIN; sp\|Q1JPH61\|IF4H_BOVIN | NaN | 24.805 | Total vitreous | 3.30E+07 |
| Fibroblast growth factor 1 | sp\|P03968\|FGF1_BOVIN | NaN | 24.808 | Total vitreous | 5.00E+07 |
| Uncharacterized protein | tr\|F1MGN0\|F1MGN0_BOVIN | NaN | 24.810 | Total vitreous | 9.80E+06 |
| Uncharacterized protein | tr\|F1N468\|F1N468_BOVIN; tr\|F1MX22\|F1MX22_BOVIN | NaN | 24.814 | Total vitreous | 2.30E+07 |
| Putative GTP cyclohydrolase 1 type 2 NIF3L1 | sp\|Q051389\|GTPC1_BOVIN | NaN | 24.831 | Total vitreous | 2.20E+07 |
| Uncharacterized protein | tr\|F1MLW8\|F1MLW8_BOVIN | NaN | 24.831 | Total vitreous | 4.00E+07 |
| High mobility group nucleosome-binding domain-containing protein 3 | sp\|Q3ZBV4\|HMGN3_BOVIN | NaN | 24.836 | Total vitreous | 1.40E+08 |
| Metallothionein | tr\|Q2NKV6\|Q2NKV6_BOVIN; tr\|Q17QH0\|Q17QH0_BOVIN; sp\|P68301\|MT2_BOVIN; sp\|P67983\|MT1A_BOVIN; sp\|P58280\|MT1_BOVIN; sp\|P55943\|MT2H_BOVIN; sp\|P55942\|MT1H_BOVIN; CON_P67983 | NaN | 24.860 | Total vitreous | 1.40E+08 |
| Uncharacterized protein (Fragment) | tr\|F1MU84\|F1MU84_BOVIN | NaN | 24.873 | Total vitreous | 1.40E+07 |
| Mth938 domain-containing protein | sp\|Q32PA8\|AAMDC_BOVIN | NaN | 24.928 | Total vitreous | 4.80E+07 |
| Complement component C6 | tr\|F1MM86\|F1MM86_BOVIN; sp\|Q29RU4\|CO6_BOVIN | NaN | 24.934 | Total vitreous | 8.30E+06 |
| Serpin A3-6 | sp\|A2I7N2\|SPA36_BOVIN | NaN | 24.971 | Total vitreous | 3.10E+07 |
| Uncharacterized protein | tr\|E1B919\|E1B919_BOVIN; tr\|G3MWU4\|G3MWU4_BOVIN | NaN | 24.988 | Total vitreous | 9.10E+06 |
| Proteasome subunit beta type | tr\|G5E589\|G5E589_BOVIN; sp\|Q2TBX6\|PSB1_BOVIN | NaN | 24.997 | Total vitreous | 3.50E+07 |
| Uncharacterized protein (Fragment) | tr\|F1MVT9\|F1MVT9_BOVIN | NaN | 24.999 | Total vitreous | 3.20E+07 |
| Glia maturation factor beta | sp\|P60984\|GMFB_BOVIN; sp\|Q56JZ9\|GMFG_BOVIN | NaN | 25.014 | Total vitreous | 5.20E+07 |
| Peroxiredoxin-4 | sp\|Q9BGI2\|PRDX4_BOVIN | NaN | 25.020 | Total vitreous | 3.10E+07 |
| Protein phosphatase inhibitor 2 | tr\|F1MTZ0\|F1MTZ0_BOVIN; sp\|Q3SZX2\|IPP2_BOVIN | NaN | 25.029 | Total vitreous | 6.70E+07 |
| Farnesyl pyrophosphate synthase | sp\|Q8WMY2\|FPPS_BOVIN; tr\|F1N431\|F1N431_BOVIN; tr\|F1N0Q7\|F1N0Q7_BOVIN; tr\|G3MZT9\|G3MZT9_BOVIN | NaN | 25.044 | Total vitreous | 3.20E+07 |
| Glial fibrillary acidic protein | sp\|Q28115\|GFAP_BOVIN | NaN | 25.065 | Total vitreous | 1.70E+07 |
| PGM2 protein (Fragment) | tr\|A6QQ11\|A6QQ11_BOVIN | NaN | 25.091 | Total vitreous | 1.50E+07 |
| UV excision repair protein RAD23 homolog A | sp\|A3KMV2\|RD23A_BOVIN | NaN | 25.108 | Total vitreous | 3.80E+07 |
| Uncharacterized protein | tr\|E1B8P3\|E1B8P3_BOVIN | NaN | 25.123 | Total vitreous | 4.50E+07 |
| Uncharacterized protein (Fragment) | tr\|F1MY31\|F1MY31_BOVIN | NaN | 25.129 | Total vitreous | 1.30E+07 |
| Leukotriene A-4 hydrolase | sp\|Q3SZH7\|LKHA4_BOVIN | NaN | 25.152 | Total vitreous | 1.50E+07 |
| Major prion protein | sp\|P10279\|PRIO_BOVIN | NaN | 25.169 | Total vitreous | 4.20E+07 |
| Neurofilament medium polypeptide | tr\|F1MDZ2\|F1MDZ2_BOVIN; sp\|O77788\|NFM_BOVIN | NaN | 25.170 | Total vitreous | 1.10E+07 |
| G1 to S phase transition 1 | tr\|F6Q087\|F6Q087_BOVIN | NaN | 25.184 | Total vitreous | 1.80E+07 |
| Uncharacterized protein | tr\|F1MRZ5\|F1MRZ5_BOVIN; tr\|F1MRZ6\|F1MRZ6_BOVIN | NaN | 25.188 | Total vitreous | 5.90E+06 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Branched-chain-amino-acid aminotransferase | tr\|A4IFQ7\|A4IFQ7_BOVIN | NaN | 25.204 | Total vitreous | 2.90E+07 |
| Isopentenyl-diphosphate Delta-isomerase 1 | sp\|Q1LZ95\|IDI1_BOVIN; sp\|Q1LZ95-2\|IDI1_BOVIN | NaN | 25.216 | Total vitreous | 4.00E+07 |
| Pikachurin | tr\|F1N606\|F1N606_BOVIN; sp\|A3KN33\|EGFLA_BOVIN | NaN | 25.218 | Total vitreous | 1.20E+07 |
| Argininosuccinate lyase | tr\|F1MTV7\|F1MTV7_BOVIN; sp\|Q3SZJ0\|ARLY_BOVIN | NaN | 25.218 | Total vitreous | 2.10E+07 |
| Lysosomal-associated membrane protein 2 | tr\|Q3SZJ7\|Q3SZJ7_BOVIN; tr\|G3MXJ5\|G3MXJ5_BOVIN | NaN | 25.219 | Total vitreous | 3.30E+07 |
| Uncharacterized protein | tr\|E1BPC9\|E1BPC9_BOVIN | NaN | 25.224 | Total vitreous | 1.10E+07 |
| 45 kDa calcium-binding protein | sp\|Q3ZBZ1\|CAB45_BOVIN; tr\|F1MKI5\|F1MK15_BOVIN | NaN | 25.230 | Total vitreous | 3.10E+07 |
| Epiphycan | sp\|P79119\|EPYC_BOVIN | NaN | 25.231 | Total vitreous | 4.40E+07 |
| Reticulon | tr\|F1N405\|F1N405_BOVIN; tr\|Q7YRW9\|Q7YRW9_BOVIN; tr\|Q1RMR8\|Q1RMR8_BOVIN | NaN | 25.232 | Total vitreous | 1.50E+07 |
| Mannose-6-phosphate isomerase | tr\|F1N327\|F1N327_BOVIN; sp\|Q3SZI0\|MPI_BOVIN | NaN | 25.232 | Total vitreous | 2.40E+07 |
| Uncharacterized protein | tr\|F1MS23\|F1MS23_BOVIN | NaN | 25.239 | Total vitreous | 5.30E+07 |
| RNASET2 protein (Fragment) | tr\|Q0III8\|Q0III8_BOVIN | NaN | 25.240 | Total vitreous | 3.10E+07 |
| Enolase-phosphatase E1 | sp\|Q0VD27\|ENOPH_BOVIN | NaN | 25.264 | Total vitreous | 4.60E+07 |
| Copper transport protein ATOX1 | sp\|Q3T0E0\|ATOX1_BOVIN | NaN | 25.284 | Total vitreous | 1.40E+08 |
| Tyrosine-protein phosphatase non-receptor type substrate 1 | sp\|O46631\|SHPS1_BOVIN; tr\|F1MD75\|F1MD75_BOVIN; tr\|F1MRG6\|F1MRG6_BOVIN; tr\|G3X6M9\|G3X6M9_BOVIN | NaN | 25.289 | Total vitreous | 2.40E+07 |
| Uncharacterized protein | tr\|E1BGX4\|E1BGX4_BOVIN | NaN | 25.292 | Total vitreous | 5.20E+07 |
| Insulin-like growth factor II | sp\|P07456\|IGF2_BOVIN | NaN | 25.309 | Total vitreous | 6.20E+07 |
| Uncharacterized protein | tr\|F1MWN3\|F1MWN3_BOVIN | NaN | 25.311 | Total vitreous | 9.20E+06 |
| Kininogen-2 | sp\|P01045\|KNG2_BOVIN; CON_P01045-1; sp\|P01045-2\|KNG2_BOVIN | NaN | 25.315 | Total vitreous | 1.80E+07 |
| ECM1 protein | tr\|A5PJT7\|A5PJT7_BOVIN | NaN | 25.317 | Total vitreous | 1.90E+07 |
| Complement component 1, r subcomponent | tr\|A5D9E9\|A5D9E9_BOVIN; tr\|Q3SYT3\|Q3SYT3_BOVIN; tr\|F1N0N3\|F1N0N3_BOVIN | NaN | 25.326 | Total vitreous | 1.60E+07 |
| Uncharacterized protein | tr\|E1BA06\|E1BA06_BOVIN | NaN | 25.329 | Total vitreous | 4.10E+07 |
| Ezrin | sp\|P31976\|EZRI_BOVIN; tr\|F1MJJ8\|F1MJJ8_BOVIN; sp\|Q32LP2\|RADI_BOVIN | NaN | 25.380 | Total vitreous | 1.90E+07 |
| Uncharacterized protein | tr\|F1N6Y1\|F1N6Y1_BOVIN | NaN | 25.390 | Total vitreous | 1.20E+07 |
| Angiotensin-converting enzyme (Fragment) | tr\|F1MQJ0\|F1MQJ0_BOVIN | NaN | 25.391 | Total vitreous | 9.00E+06 |
| Uncharacterized protein | tr\|F6QJQ2\|F6QJQ2_BOVIN | NaN | 25.408 | Total vitreous | 1.40E+07 |
| Peptidyl-prolyl cis-trans isomerase D | sp\|P26882\|PPID_BOVIN | NaN | 25.408 | Total vitreous | 2.60E+07 |
| Uncharacterized protein | tr\|E1BKN2\|E1BKN2_BOVIN | NaN | 25.452 | Total vitreous | 1.10E+07 |
| Uncharacterized protein | tr\|E1BP81\|E1BP81_BOVIN | NaN | 25.455 | Total vitreous | 1.20E+07 |
| Complement factor H (Fragment) | tr\|F1MC45\|F1MC45_BOVIN | NaN | 25.455 | Total vitreous | 1.50E+07 |
| Complement factor D | sp\|Q3T0A3\|CFAD_BOVIN; tr\|G3N1I8\|G3N1I8_BOVIN | NaN | 25.463 | Total vitreous | 4.50E+07 |
| Uncharacterized protein | tr\|F1MNS8\|F1MNS8_BOVIN | NaN | 25.470 | Total vitreous | 9.00E+07 |
| Uncharacterized protein | tr\|F1MND9\|F1MND9_BOVIN | NaN | 25.474 | Total vitreous | 1.30E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Galectin-1 | sp\|P11116\|LEG1_BOVIN | NaN | 25.496 | Total vitreous | 8.10E+07 |
| F-box only protein 2 | sp\|Q17QK6\|FBX2_BOVIN; tr\|F1MFN6\|F1MFN6_BOVIN | NaN | 25.505 | Total vitreous | 5.40E+07 |
| Collagen alpha-1(XI) chain | tr\|F1N0K0\|F1N0K0_BOVIN | NaN | 25.510 | Total vitreous | 7.00E+06 |
| Neurofilament light polypeptide | sp\|P02548\|NFL_BOVIN | NaN | 25.566 | Total vitreous | 1.80E+07 |
| Serpin peptidase inhibitor, clade A (Alpha-1 antiproteinase, antitrypsin), member 7 | tr\|Q3SYR0\|Q3SYR0_BOVIN; sp\|Q9TT36\|THBG_BOVIN; CON_Q9TT36 | NaN | 25.570 | Total vitreous | 3.20E+07 |
| Uncharacterized protein | tr\|Q3T0Z0\|Q3T0Z0_BOVIN; tr\|G3MX65\|G3MX65_BOVIN | NaN | 25.572 | Total vitreous | 8.40E+07 |
| Proliferation-associated 2G4, 38 kDa | tr\|Q3ZBH5\|Q3ZBH5_BOVIN | NaN | 25.574 | Total vitreous | 3.10E+07 |
| RAB1A, member RAS oncogene family | tr\|A1L528\|A1L528_BOVIN; tr\|Q3ZBD1\|Q3ZBD1_BOVIN; tr\|G3MYN4\|G3MYN4_BOVIN; sp\|Q1RMR4\|RAB15_BOVIN | NaN | 25.578 | Total vitreous | 4.70E+07 |
| Complexin-3 | tr\|F1MWQ0\|F1MWQ0_BOVIN; sp\|Q0IIE0\|CPLX3_BOVIN | NaN | 25.594 | Total vitreous | 7.60E+07 |
| Serpin A3-4 | sp\|A2I7N0\|SPA34_BOVIN; CON_A2I7N0; sp\|Q3ZEJ6\|SPA33_BOVIN | NaN | 25.613 | Total vitreous | 3.50E+07 |
| Small ubiquitin-related modifier 2 (Fragment) | tr\|G5E5Y5\|G5E5Y5_BOVIN; sp\|P61955\|SUMO2_BOVIN; sp\|Q17QV3\|SUMO3_BOVIN; tr\|G3N303\|G3N303_BOVIN | NaN | 25.619 | Total vitreous | 3.50E+08 |
| Uncharacterized protein | tr\|E1BIM6\|E1BIM6_BOVIN | NaN | 25.630 | Total vitreous | 3.30E+07 |
| Myristoylated alanine-rich C-kinase substrate | tr\|F1N2N5\|F1N2N5_BOVIN; sp\|P12624\|MARCS_BOVIN; tr\|E1B916\|E1B916_BOVIN | NaN | 25.648 | Total vitreous | 5.10E+07 |
| DNA-(apurinic or apyrimidinic site) lyase | sp\|P23196\|APEX1_BOVIN | NaN | 25.656 | Total vitreous | 5.10E+07 |
| Coagulation factor X | sp\|P00743\|FA10_BOVIN | NaN | 25.658 | Total vitreous | 3.40E+07 |
| Phospholysine phosphohistidine inorganic pyrophosphate phosphatase | sp\|Q0VD18\|LHPP_BOVIN | NaN | 25.670 | Total vitreous | 5.10E+07 |
| Tubulin polymerization-promoting protein | sp\|Q27957\|TPPP_BOVIN | NaN | 25.671 | Total vitreous | 6.10E+07 |
| Oligodendrocyte myelin glycoprotein | tr\|Q0IIH3\|Q0IIH3_BOVIN | NaN | 25.672 | Total vitreous | 3.80E+07 |
| Phosphoglycolate phosphatase | sp\|Q2T9S4\|PGP_BOVIN | NaN | 25.676 | Total vitreous | 3.90E+07 |
| Follistatin-related protein 1 | sp\|Q58D84\|FSTL1_BOVIN | NaN | 25.678 | Total vitreous | 3.30E+07 |
| ADM | sp\|O62827\|ADML_BOVIN | NaN | 25.688 | Total vitreous | 6.10E+07 |
| Nuclear transport factor 2 | sp\|Q32KP9\|NTF2_BOVIN | NaN | 25.690 | Total vitreous | 1.00E+08 |
| Insulin-like growth factor-binding protein 2 | sp\|P13384\|IBP2_BOVIN; tr\|F1N2P8\|F1N2P8_BOVIN | NaN | 25.691 | Total vitreous | 4.60E+07 |
| Glutaminyl-peptide cyclotransferase | tr\|Q0P598\|Q0P598_BOVIN; sp\|Q28120\|QPCT_BOVIN | NaN | 25.702 | Total vitreous | 4.30E+07 |
| Uncharacterized protein (Fragment) | tr\|F1MQJ3\|F1MQJ3_BOVIN | NaN | 25.706 | Total vitreous | 3.20E+07 |
| Uncharacterized protein | tr\|G3MYU9\|G3MYU9_BOVIN | NaN | 25.729 | Total vitreous | 3.30E+07 |
| Beta-crystallin A3 | tr\|F1N5Q6\|F1N5Q6_BOVIN | NaN | 25.742 | Total vitreous | 6.90E+07 |
| Ubiquitin-conjugating enzyme E2 L3 (Fragment) | tr\|F1MC72\|F1MC72_BOVIN; sp\|Q3MHP1\|UB2L3_BOVIN | NaN | 25.764 | Total vitreous | 9.80E+07 |
| NAD(P)H dehydrogenase, quinone 1 | tr\|Q3ZBH2\|Q3ZBH2_BOVIN | NaN | 25.774 | Total vitreous | 5.50E+07 |
| Uncharacterized protein (Fragment) | tr\|F1MUA1\|F1MUA1_BOVIN | NaN | 25.774 | Total vitreous | 6.50E+07 |
| Heterogeneous nuclear ribonucleoprotein A1 | sp\|P09867\|ROA1_BOVIN; tr\|G5E5V7\|G5E5V7_BOVIN; tr\|F1MH29\|F1MH29_BOVIN; tr\|F1MTY3\|F1MTY3_BOVIN | NaN | 25.815 | Total vitreous | 4.40E+07 |
| UMP-CMP kinase | sp\|Q2KIW9\|KCY_BOVIN | NaN | 25.869 | Total vitreous | 7.60E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Destrin | sp\|Q5E9D5\|DEST_BOVIN | NaN | 25.880 | Total vitreous | 8.00E+07 |
| Uncharacterized protein (Fragment) | tr\|F1MCF1\|F1MCF1_BOVIN; tr\|F1N7I0\|F1N7I0_BOVIN | NaN | 25.902 | Total vitreous | 1.20E+08 |
| Methionine adenosyltransferase 2 subunit beta | sp\|Q29RI9\|MAT2B_BOVIN | NaN | 25.906 | Total vitreous | 4.50E+07 |
| NEDD8 (Fragment) | tr\|G8JKV8\|G8JKV8_BOVIN; sp\|P61282\|NEDD8_BOVIN | NaN | 25.913 | Total vitreous | 2.80E+08 |
| PCSK1N protein | tr\|A4IFR2\|A4IFR2_BOVIN | NaN | 25.914 | Total vitreous | 7.10E+07 |
| Uncharacterized protein | tr\|E1BI82\|E1BI82_BOVIN; CON_Q2HJF0 | NaN | 25.928 | Total vitreous | 2.30E+07 |
| Uncharacterized protein | tr\|F1MCF8\|F1MCF8_BOVIN | NaN | 25.932 | Total vitreous | 1.20E+08 |
| C—X—C motif chemokine 16 | sp\|Q29RT9\|CXL16_BOVIN | NaN | 25.941 | Total vitreous | 1.10E+08 |
| Uncharacterized protein (Fragment) | tr\|F1MYW3\|F1MYW3_BOVIN | NaN | 25.959 | Total vitreous | 2.10E+07 |
| Uncharacterized protein (Fragment) | tr\|G3MXG6\|G3MXG6_BOVIN; CON_ENSEMBL: ENSBTAP00000033053; tr\|G3MZH0\|G3MZH0_BOVIN; CON_ENSEMBL: ENSBTAP00000011227; tr\|G3MXD9\|G3MXD9_BOVIN; tr\|G3N3Q3\|G3N3Q3_BOVIN | NaN | 25.967 | Total vitreous | 1.30E+08 |
| Apolipoprotein A-II | sp\|P81644\|APOA2_BOVIN; CON_P81644 | NaN | 25.973 | Total vitreous | 1.80E+08 |
| Cystatin-B | tr\|F6QEL0\|F6QEL0_BOVIN | NaN | 25.978 | Total vitreous | 2.20E+08 |
| Serpin A3-8 | sp\|A6QPQ2\|SPA38_BOVIN | NaN | 26.000 | Total vitreous | 3.50E+07 |
| Uncharacterized protein | tr\|F1MIQ2\|F1MIQ2_BOVIN | NaN | 26.033 | Total vitreous | 2.10E+07 |
| Uncharacterized protein (Fragment) | tr\|F1MF04\|F1MF04_BOVIN | NaN | 26.035 | Total vitreous | 2.80E+07 |
| Tubulin-specific chaperone A | sp\|P48427\|TBCA_BOVIN | NaN | 26.060 | Total vitreous | 1.60E+08 |
| Stathmin | sp\|Q3T0C7\|STMN1_BOVIN; tr\|F1N1C2\|F1N1C2_BOVIN; tr\|Q3MHJ8\|Q3MHJ8_BOVIN | NaN | 26.062 | Total vitreous | 1.10E+08 |
| Neurosecretory protein VGF | tr\|F2Z4E0\|F2Z4E0_BOVIN; sp\|P86435\|VGF_BOVIN | NaN | 26.085 | Total vitreous | 3.40E+07 |
| Uncharacterized protein | tr\|E1BLA8\|E1BLA8_BOVIN | NaN | 26.102 | Total vitreous | 4.00E+07 |
| Peptidyl-prolyl cis-trans isomerase FKBP1A | sp\|P18203\|FKB1A_BOVIN; tr\|Q2NKS8\|Q2NKS8_BOVIN | NaN | 26.137 | Total vitreous | 3.30E+08 |
| Uncharacterized protein (Fragment) | tr\|F1MPD1\|F1MPD1_BOVIN | NaN | 26.161 | Total vitreous | 1.80E+07 |
| Ephrin-A1 | sp\|Q3ZC64\|EFNA1_BOVIN | NaN | 26.169 | Total vitreous | 1.10E+08 |
| 14 kDa phosphohistidine phosphatase | sp\|Q32PA4\|PHP14_BOVIN | NaN | 26.169 | Total vitreous | 1.10E+08 |
| Profilin | tr\|E1BHJ0\|E1BHJ0_BOVIN; sp\|P02584\|PROF1_BOVIN; CON_P02584 | NaN | 26.169 | Total vitreous | 1.10E+08 |
| Uncharacterized protein (Fragment) | tr\|F6QDM0\|F6QDM0_BOVIN | NaN | 26.197 | Total vitreous | 9.40E+07 |
| Heterogeneous nuclear ribonucleoprotein D | tr\|A5D9H5\|A5D9H5_BOVIN; tr\|A6H6Y0\|A6H6Y0_BOVIN; tr\|F1N2T0\|F1N2T0_BOVIN | NaN | 26.209 | Total vitreous | 7.50E+07 |
| Isoform ACY1 of Acylphosphatase-1 | sp\|P41500-2\|ACYP1_BOVIN; sp\|P41500\|ACYP1_BOVIN | NaN | 26.220 | Total vitreous | 1.50E+08 |
| Mast/stem cell growth factor receptor Kit | sp\|P43481\|KIT_BOVIN | NaN | 26.233 | Total vitreous | 2.00E+07 |
| Uncharacterized protein (Fragment) | tr\|F1MFJ3\|F1MFJ3_BOVIN; tr\|G3MXS7\|G3MXS7_BOVIN | NaN | 26.239 | Total vitreous | 1.80E+07 |
| Myotrophin | sp\|Q3T0F7\|MTPN_BOVIN | NaN | 26.249 | Total vitreous | 2.00E+08 |
| Uncharacterized protein (Fragment) | tr\|E1BE12\|E1BE12_BOVIN | NaN | 26.260 | Total vitreous | 2.40E+07 |
| Uncharacterized protein | tr\|F1N739\|F1N739_BOVIN; tr\|F1N279\|F1N279_BOVIN | NaN | 26.290 | Total vitreous | 1.50E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| MSLN protein | tr\|A6QP39\|A6QP39_BOVIN | NaN | 26.293 | Total vitreous | 5.10E+07 |
| Uncharacterized protein | tr\|F1MDC2\|F1MDC2_BOVIN | NaN | 26.318 | Total vitreous | 2.80E+07 |
| Aldehyde dehydrogenase | tr\|F1N015\|F1N015_BOVIN; sp\|P30907\|AL3A1_BOVIN | NaN | 26.320 | Total vitreous | 5.60E+07 |
| Similar to hemopexin | CON_Q3SZV7 | NaN | 26.325 | Total vitreous | 5.90E+07 |
| Uncharacterized protein (Fragment) | tr\|F1MNL4\|F1MNL4_BOVIN | NaN | 26.329 | Total vitreous | 1.90E+07 |
| Interphotoreceptor matrix proteoglycan 1 | sp\|Q9GMS5\|IMPG1_BOVIN; tr\|G3N2H2\|G3N2H2_BOVIN; tr\|F1MY68\|F1MY68_BOVIN | NaN | 26.419 | Total vitreous | 3.10E+07 |
| SH3 domain-binding glutamic acid-rich-like protein 3 | sp\|Q3ZCL8\|SH3L3_BOVIN; tr\|G3X6S5\|G3X6S5_BOVIN | NaN | 26.432 | Total vitreous | 3.10E+08 |
| Uncharacterized protein | tr\|F1MEH3\|F1MEH3_BOVIN | NaN | 26.438 | Total vitreous | 6.50E+07 |
| Uncharacterized protein | tr\|G3MYP5\|G3MYP5_BOVIN; tr\|F1N3M8\|F1N3M8_BOVIN | NaN | 26.441 | Total vitreous | 9.50E+06 |
| LMAN2 protein | tr\|A6QP36\|A6QP36_BOVIN | NaN | 26.464 | Total vitreous | 6.30E+07 |
| Uncharacterized protein | tr\|F1MGK5\|F1MGK5_BOVIN | NaN | 26.486 | Total vitreous | 1.60E+07 |
| Retinol-binding protein 1 | sp\|P02694\|RET1_BOVIN | NaN | 26.519 | Total vitreous | 1.40E+08 |
| Beta-crystallin B1 | sp\|P07318\|CRBB1_BOVIN; tr\|E1BFK5\|E1BFK5_BOVIN | NaN | 26.545 | Total vitreous | 8.30E+07 |
| CALR protein | tr\|A5D7J6\|A5D7J6_BOVIN; sp\|P52193\|CALR_BOVIN | NaN | 26.599 | Total vitreous | 6.00E+07 |
| Pantetheinase | sp\|Q58CQ9\|VNN1_BOVIN | NaN | 26.609 | Total vitreous | 6.90E+07 |
| Ester hydrolase C11orf54 homolog | sp\|Q2HJH3\|CK054_BOVIN | NaN | 26.615 | Total vitreous | 9.90E+07 |
| Uncharacterized protein | tr\|E1BBM1\|E1BBM1_BOVIN | NaN | 26.636 | Total vitreous | 6.70E+07 |
| Cadherin-6 | sp\|Q3SWX5\|CADH6_BOVIN | NaN | 26.638 | Total vitreous | 4.50E+07 |
| Fatty acid-binding protein, heart | sp\|P10790\|FABPH_BOVIN; tr\|F1MHQ4\|F1MHQ4_BOVIN; sp\|P48035\|FABP4_BOVIN; sp\|P02690\|MYP2_BOVIN | NaN | 26.657 | Total vitreous | 1.50E+08 |
| Uncharacterized protein (Fragment) | tr\|G3N3P6\|G3N3P6_BOVIN | NaN | 26.674 | Total vitreous | 3.20E+08 |
| CSTB protein | tr\|A6QPZ0\|A6QPZ0_BOVIN; sp\|P35478\|CYTX_BOVIN | NaN | 26.695 | Total vitreous | 2.40E+08 |
| Uncharacterized protein (Fragment) | tr\|H9GW42\|H9GW42_BOVIN | NaN | 26.697 | Total vitreous | 1.60E+08 |
| Alpha-N-acetylgalactosaminidase | tr\|Q1RMM9\|Q1RMM9_BOVIN; sp\|Q58DH9\|NAGAB_BOVIN | NaN | 26.701 | Total vitreous | 6.40E+07 |
| Arylsulfatase A | sp\|Q08DD1\|ARSA_BOVIN | NaN | 26.726 | Total vitreous | 1.40E+08 |
| Malic enzyme | tr\|F1N3V0\|F1N3V0_BOVIN | NaN | 26.785 | Total vitreous | 4.90E+07 |
| Uncharacterized protein | tr\|G8JKW3\|G8JKW3_BOVIN; sp\|P62326\|TYB4_BOVIN | NaN | 26.866 | Total vitreous | 8.20E+08 |
| Uncharacterized protein | tr\|F1N1S2\|F1N1S2_BOVIN | NaN | 26.883 | Total vitreous | 1.70E+07 |
| Zinc-alpha-2-glycoprotein | sp\|Q3ZCH5\|ZA2G_BOVIN | NaN | 26.958 | Total vitreous | 1.50E+08 |
| Dihydropteridine reductase | sp\|Q3T0Z7\|DHPR_BOVIN | NaN | 26.975 | Total vitreous | 1.30E+08 |
| Isocitrate dehydrogenase [NADP] cytoplasmic | sp\|Q9XSG3\|IDHC_BOVIN; sp\|Q04467\|IDHP_BOVIN | NaN | 26.978 | Total vitreous | 6.60E+07 |
| CD44 antigen | tr\|F1MHC3\|F1MHC3_BOVIN; sp\|Q29423\|CD44_BOVIN; tr\|Q0VD03\|Q0VD03_BOVIN; tr\|F1MQT9\|F1MQT9_BOVIN | NaN | 26.984 | Total vitreous | 9.90E+07 |
| Gastrin-releasing peptide | sp\|Q863C3\|GRP_BOVIN | NaN | 27.001 | Total vitreous | 2.30E+08 |
| Uncharacterized protein | tr\|E1BF00\|E1BF00_BOVIN | NaN | 27.036 | Total vitreous | 2.70E+07 |
| Carbonic anhydrase 2 (Fragment) | tr\|F1N0H3\|F1N0H3_BOVIN | NaN | 27.060 | Total vitreous | 1.30E+08 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| Uncharacterized protein | tr\|F1MET4\|F1MET4_BOVIN | NaN | 27.065 | Total vitreous | 4.70E+07 |
| SPARC | sp\|P13213\|SPRC_BOVIN | NaN | 27.081 | Total vitreous | 1.50E+08 |
| Transaldolase | tr\|G5E5C8\|G5E5C8_BOVIN; sp\|Q2TBL6\|TALDO_BOVIN; tr\|Q58DR3\|Q58DR3_BOVIN | NaN | 27.122 | Total vitreous | 1.10E+08 |
| Uncharacterized protein | tr\|F1MSA4\|F1MSA4_BOVIN | NaN | 27.173 | Total vitreous | 4.30E+07 |
| Translationally-controlled tumor protein | sp\|Q5E984\|TCTP_BOVIN | NaN | 27.189 | Total vitreous | 2.90E+08 |
| Brain ribonuclease | sp\|P39873\|RNBR_BOVIN; sp\|P61823\|RNAS1_BOVIN; sp\|P00669\|RNS_BOVIN | NaN | 27.196 | Total vitreous | 3.50E+08 |
| Uncharacterized protein | tr\|F1MEW6\|F1MEW6_BOVIN | NaN | 27.211 | Total vitreous | 1.40E+08 |
| Isoform Tau-F of Microtubule-associated protein tau | sp\|P29172-6\|TAU_BOVIN; sp\|P29172-11\|TAU_BOVIN; sp\|P29172-17\|TAU_BOVIN; sp\|P29172-14\|TAU_BOVIN; sp\|P29172-3\|TAU_BOVIN; sp\|P29172-20\|TAU_BOVIN | NaN | 27.221 | Total vitreous | 1.20E+08 |
| Ribonuclease 4 | tr\|Q58DP6\|Q58DP6_BOVIN; sp\|P15467\|RNAS4_BOVIN | NaN | 27.227 | Total vitreous | 3.00E+08 |
| Uncharacterized protein (Fragment) | tr\|F1MVK1\|F1MVK1_BOVIN; tr\|F1MP09\|F1MP09_BOVIN | NaN | 27.246 | Total vitreous | 2.70E+07 |
| Purine nucleoside phosphorylase | sp\|P55859\|PNPH_BOVIN; tr\|G3X8C8\|G3X8C8_BOVIN | NaN | 27.287 | Total vitreous | 1.40E+08 |
| Secretogranin V (7B2 protein) | tr\|Q2HJG0\|Q2HJG0_BOVIN | NaN | 27.306 | Total vitreous | 2.50E+08 |
| Serpin B6 | tr\|F1N2A2\|F1N2A2_BOVIN; sp\|O02739\|SPB6_BOVIN; tr\|F1N0T3\|F1N0T3_BOVIN | NaN | 27.312 | Total vitreous | 1.00E+08 |
| CDKL1 protein | tr\|A6QLF0\|A6QLF0_BOVIN | NaN | 27.312 | Total vitreous | 1.10E+08 |
| Protein S100-A4 | sp\|P35466\|S10A4_BOVIN | NaN | 27.327 | Total vitreous | 3.80E+08 |
| Thioredoxin (Fragment) | tr\|G8JKZ8\|G8JKZ8_BOVIN; sp\|O97680\|THIO_BOVIN | NaN | 27.383 | Total vitreous | 3.40E+08 |
| Primary amine oxidase, liver isozyme | sp\|Q29437\|AOCX_BOVIN; tr\|E1BC10\|E1BC10_BOVIN; sp\|Q9TTK6\|AOC3_BOVIN; tr\|E1BD43\|E1BD43_BOVIN; sp\|Q9TTK6-2\|AOC3_BOVIN; tr\|E1BJN3\|E1BJN3_BOVIN; sp\|O46406\|AOCY_BOVIN; tr\|G3MX04\|G3MX04_BOVIN; tr\|E1BC09\|E1BC09_BOVIN | NaN | 27.383 | Total vitreous | 7.40E+07 |
| Creatine kinase M-type | sp\|Q9XSC6\|KCRM_BOVIN | NaN | 27.408 | Total vitreous | 1.50E+08 |
| Cell adhesion molecule 1 | tr\|Q2TBL2\|Q2TBL2_BOVIN | NaN | 27.419 | Total vitreous | 1.10E+08 |
| SPOCK2 protein | tr\|A7MB04\|A7MB04_BOVIN | NaN | 27.445 | Total vitreous | 1.10E+08 |
| Purkinje cell protein 4 | sp\|Q148C4\|PCP4_BOVIN | NaN | 27.504 | Total vitreous | 6.40E+08 |
| Heat shock 70 kDa protein 1A | sp\|Q27975\|HS71A_BOVIN; sp\|Q27965\|HS71B_BOVIN | NaN | 27.529 | Total vitreous | 7.70E+07 |
| Isoform 2 of Hydroxyacylglutathione hydrolase, mitochondrial | sp\|Q3B7M2-2\|GLO2_BOVIN; sp\|Q3B7M2\|GLO2_BOVIN | NaN | 27.535 | Total vitreous | 1.90E+08 |
| Neurotrimin | sp\|Q58DA5\|NTRI_BOVIN | NaN | 27.541 | Total vitreous | 1.50E+08 |
| Uncharacterized protein | tr\|E1BPW7\|E1BPW7_BOVIN | NaN | 27.620 | Total vitreous | 1.80E+08 |
| Beta-synuclein | tr\|F1MS41\|F1MS41_BOVIN; sp\|P33567\|SYUB_BOVIN | NaN | 27.637 | Total vitreous | 4.70E+08 |
| Uncharacterized protein | tr\|G5E5V1\|G5E5V1_BOVIN | NaN | 27.673 | Total vitreous | 7.20E+08 |
| Seizure 6-like protein 2 | sp\|Q29RN8\|SE6L2_BOVIN | NaN | 27.699 | Total vitreous | 1.10E+08 |
| Uncharacterized protein | tr\|F1MZ78\|F1MZ78_BOVIN | NaN | 27.701 | Total | 6.30E+07 |

TABLE 3-continued

Proteins expressed in the extracellular vesicles fraction and the cell free vitreous fraction.

| Protein Name | Protein IDs | LFQ intensity vitreous-EV | LFQ intensity total vitreous | EV/ whole vitreous Log2 difference | iBAQ |
|---|---|---|---|---|---|
| (Fragment) | | | | vitreous | |
| Protein HP-25 homolog 2 | sp\|Q2KIU3\|HP252_BOVIN; CON_Q2KIU3 | NaN | 27.760 | Total vitreous | 4.00E+08 |
| Secretogranin-1 | sp\|P23389\|SCG1_BOVIN | NaN | 27.817 | Total vitreous | 9.40E+07 |
| Alcohol dehydrogenase [NADP(+)] | sp\|Q3ZCJ2\|AK1A1_BOVIN | NaN | 27.873 | Total vitreous | 1.40E+08 |
| Acidic leucine-rich nuclear phosphoprotein 32 family member A | sp\|P51122\|AN32A_BOVIN | NaN | 27.880 | Total vitreous | 3.70E+08 |
| Uncharacterized protein (Fragment) | tr\|G3X7F3\|G3X7F3_BOVIN | NaN | 27.882 | Total vitreous | 1.00E+08 |
| Protein HP-25 homolog 1 | sp\|Q2KIX7\|HP251_BOVIN | NaN | 27.902 | Total vitreous | 4.80E+08 |
| Tubulin alpha-1D chain | sp\|Q2HJ86\|TBA1D_BOVIN | NaN | 28.087 | Total vitreous | 2.30E+08 |
| Aldo-keto reductase family 1, member B1 | tr\|Q5E962\|Q5E962_BOVIN; sp\|P16116\|ALDR_BOVIN; tr\|E1BNW1\|E1BNW1_BOVIN | NaN | 28.196 | Total vitreous | 2.10E+08 |
| Carbonic anhydrase 3 | sp\|Q3SZX4\|CAH3_BOVIN | NaN | 28.197 | Total vitreous | 2.60E+08 |
| Uncharacterized protein | tr\|F1MPP2\|F1MPP2_BOVIN | NaN | 28.290 | Total vitreous | 3.00E+08 |
| Uncharacterized protein | tr\|E1BAU6\|E1BAU6_BOVIN | NaN | 28.323 | Total vitreous | 1.70E+08 |
| Insulin-like growth factor-binding protein 5 | sp\|Q05717\|IBP5_BOVIN | NaN | 28.330 | Total vitreous | 3.80E+08 |
| Uncharacterized protein | tr\|E1BNR9\|E1BNR9_BOVIN | NaN | 28.337 | Total vitreous | 1.40E+08 |
| Tetranectin | sp\|Q2KIS7\|TETN_BOVIN; CON_Q2KIS7 | NaN | 28.373 | Total vitreous | 5.20E+08 |
| Epididymal secretory protein E1 | sp\|P79345\|NPC2_BOVIN | NaN | 28.512 | Total vitreous | 5.70E+08 |
| Beta-crystallin B3 | sp\|P19141\|CRBB3_BOVIN | NaN | 28.584 | Total vitreous | 4.50E+08 |
| Acyl-CoA-binding protein | sp\|P07107\|ACBP_BOVIN | NaN | 28.692 | Total vitreous | 1.20E+09 |
| Zeta-crystallin | sp\|O97764\|QOR_BOVIN | NaN | 28.709 | Total vitreous | 3.00E+08 |
| Nucleobindin-1 | sp\|Q0P569\|NUCB1_BOVIN | NaN | 28.771 | Total vitreous | 2.20E+08 |
| GLO1 protein | tr\|A4FUZ1\|A4FUZ1_BOVIN | NaN | 28.857 | Total vitreous | 6.00E+08 |
| >P00761 SWISS-PROT: P00761 | CON_P00761 | NaN | 29.035 | Total vitreous | 1.20E+09 |
| >P31096 SWISS-PROT: P31096 Osteopontin-*Bos taurus* (Bovine). | CON_P31096; tr\|F1MI46\|F1MI46_BOVIN; sp\|P31096\|OSTP_BOVIN; sp\|P31098\|OSTK_BOVIN; tr\|Q58DM6\|Q58DM6_BOVIN | NaN | 29.081 | Total vitreous | 7.30E+08 |
| Myoglobin | sp\|P02192\|MYG_BOVIN | NaN | 29.235 | Total vitreous | 9.50E+08 |
| Uncharacterized protein | tr\|F6QLF1\|F6QLF1_BOVIN; tr\|F1N2J5\|F1N2J5_BOVIN | NaN | 29.258 | Total vitreous | 3.90E+08 |
| Alpha-1B-glycoprotein | sp\|Q2KJF1\|A1BG_BOVIN; CON_Q2KJF1 | NaN | 29.537 | Total vitreous | 5.90E+08 |
| Secretogranin-2 | sp\|P20616\|SCG2_BOVIN | NaN | 29.797 | Total vitreous | 3.60E+08 |
| Aldehyde dehydrogenase 18 family, member A1 | tr\|Q2KJH7\|Q2KJH7_BOVIN | NaN | 29.803 | Total vitreous | 2.60E+08 |
| Secretogranin-3 | sp\|A6QLI2\|SCG3_BOVIN | NaN | 30.079 | Total vitreous | 6.50E+08 |
| Chromogranin-A | sp\|P05059\|CMGA_BOVIN | NaN | 30.124 | Total vitreous | 5.30E+08 |
| 14-3-3 protein sigma | sp\|Q0VC36\|1433S_BOVIN | NaN | 30.380 | Total vitreous | 1.10E+09 |

What is claimed is:

1. A composition comprising:

one or more isolated, aqueous humor and/or vitreous humor extracellular vesicle bodies, wherein said extracellular vesicle bodies are modified in vitro to contain one or more exogenous agents, wherein endogenous contents of said extracellular vesicle bodies are removed, wherein said extracellular vesicle bodies are from 100 to 6,000 nanometers in diameter, wherein the composition is at least 75% free of cell or cellular debris, and wherein said extracellular vesicle bodies are modified to display a eukaryotic cell-specific targeting molecule on the vesicle surface so that the composition mediates uptake of the one or more exogenous agents by the eukaryotic cells, wherein the eukaryotic cells are selected from the group consisting of human skin cells, human retinal cells, human ciliary cells, and human corneal cells.

2. The composition of claim 1, wherein the one or more exogenous agents is selected from the group consisting of a nucleic acid molecule, a protein or polypeptide, a small molecule, a hormone, and any combination thereof.

3. The composition of claim 1, wherein the one or more exogenous agents comprise one or more nucleic acid molecules selected from the group consisting of a ribonucleic acid, a small RNA molecule, a complementary RNA, a non-coding RNA molecule, a siRNA, a pi-RNA molecule, a micro-RNA molecule, a sno-RNA molecule, a long non-coding RNA molecule, a messenger RNA molecule, a ribosomal RNA molecule, an antisense nucleic acid molecule, a Locked Nucleic Acid (LNA), an antagomir, a CRISPR/Cas gene editing RNA, a trans-activating crRNA (tracrRNA), a short synthetic RNA composed of a "scaffold" sequence (gRNA), a Small Cajal body-specific RNAs (scaRNA), a natural cis-antisense siRNAs (cis-nat-siRNAs), a trans-acting siRNA (tasiRNA), a repeat associated small interfering RNA (rasiRNA), a 7SK RNA, a transfer-messenger RNA (tmRNA), a transfer RNA (tRNA), a 7SL RNA, a signal recognition particle RNA (SRP), and any combination thereof.

4. The composition of claim 1, wherein the one or more exogenous agents comprise one or more of a small deoxyribonucleic acid (DNA) molecule, a cDNA molecule, an oligonucleotide, a locked Nucleic Acid (LNA), a deoxyribonucleic acid aptamer, a deoxyribonucleic acidzyme, and any combination thereof.

5. The composition of claim 1, wherein the one or more exogenous agents are naked or packaged in a viral vector, a bacterial vector, a plasmid vector, or any combination thereof.

6. The composition of claim 1, wherein the composition comprises a pharmaceutically acceptable carrier.

7. The composition of claim 1, wherein said composition is formulated in a slow or sustained release material.

8. The composition of claim 1, wherein the exogenous agent is a therapeutic agent.

9. The composition of claim 1, wherein the exogenous agent is a diagnostic agent.

10. The composition of claim 1, wherein the one or more extracellular vesicle bodies are isolated from mammalian vitreous humor and/or aqueous humor.

11. The composition of claim 1, wherein the one or more extracellular vesicle bodies are isolated from human vitreous humor and/or aqueous humor.

* * * * *